US007959926B2

(12) United States Patent
Buechler et al.

(10) Patent No.: US 7,959,926 B2
(45) Date of Patent: Jun. 14, 2011

(54) METHODS FOR EXPRESSION AND PURIFICATION OF RECOMBINANT HUMAN GROWTH HORMONE MUTANTS

(75) Inventors: Ying Buechler, Carlsbad, CA (US); Ricky Lieu, San Diego, CA (US); Michael Ong, San Diego, CA (US); Stuart Bussell, Carlsbad, CA (US); Nick Knudsen, San Diego, CA (US); Ho Sung Cho, San Diego, CA (US)

(73) Assignee: Ambrx, Inc., La Jolla, CA (US)

( * ) Notice: Subject to any disclaimer, the term of this patent is extended or adjusted under 35 U.S.C. 154(b) by 0 days.

(21) Appl. No.: 11/874,068

(22) Filed: Oct. 17, 2007

(65) Prior Publication Data
US 2008/0085538 A1    Apr. 10, 2008

Related U.S. Application Data

(63) Continuation of application No. 11/315,752, filed on Dec. 21, 2005.

(60) Provisional application No. 60/727,968, filed on Oct. 17, 2005, provisional application No. 60/680,977, filed on May 13, 2005, provisional application No. 60/655,744, filed on Feb. 23, 2005, provisional application No. 60/638,616, filed on Dec. 22, 2004.

(51) Int. Cl.
*A61K 39/00*    (2006.01)
*A61K 38/02*    (2006.01)
*A61K 38/27*    (2006.01)
*C12P 21/00*    (2006.01)
*C07K 1/16*     (2006.01)
*C07H 21/00*    (2006.01)

(52) U.S. Cl. .................. 424/200.1; 424/198.1; 424/124; 536/23.51; 514/11.4; 435/7.6; 435/69.1; 530/417

(58) Field of Classification Search .................. None
See application file for complete search history.

(56) References Cited

U.S. PATENT DOCUMENTS

| | | | |
|---|---|---|---|
| 3,773,919 A | 11/1973 | Boswell et al. |
| 4,289,872 A | 9/1981 | Denkewalter et al. |
| 4,412,989 A | 11/1983 | Iwashita et al. |
| 4,414,148 A | 11/1983 | Jansen et al. |
| 4,446,235 A | 5/1984 | Seeburg |
| 4,485,045 A | 11/1984 | Regen |
| 4,511,502 A | 4/1985 | Builder et al. |
| 4,511,503 A | 4/1985 | Olson et al. |
| 4,512,922 A | 4/1985 | Jones et al. |
| 4,544,545 A | 10/1985 | Ryan et al. |
| 4,551,433 A | 11/1985 | DeBoer |
| 4,569,789 A | 2/1986 | Blattler et al. |
| 4,601,980 A | 7/1986 | Goeddel et al. |
| 4,604,359 A | 8/1986 | Goeddel et al. |
| 4,619,794 A | 10/1986 | Hauser |
| 4,634,677 A | 1/1987 | Goeddel et al. |
| 4,658,021 A | 4/1987 | Goeddel et al. |
| 4,659,839 A | 4/1987 | Nicolotti et al. |
| 4,665,180 A | 5/1987 | Oude Alink |
| 4,670,393 A | 6/1987 | Seeburg |
| 4,670,417 A | 6/1987 | Iwasaki et al. |
| 4,671,958 A | 6/1987 | Rodwell et al. |
| 4,680,338 A | 7/1987 | Sundoro |
| 4,689,406 A | 8/1987 | Banks et al. |
| 4,699,784 A | 10/1987 | Shih et al. |
| 4,738,921 A | 4/1988 | Belagaje et al. |
| 4,755,465 A | 7/1988 | Gray et al. |
| 4,837,148 A | 6/1989 | Cregg |
| 4,859,600 A | 8/1989 | Gray et al. |
| 4,876,197 A | 10/1989 | Burke et al. |
| 4,880,734 A | 11/1989 | Burke et al. |
| 4,898,830 A | 2/1990 | Goeddel et al. |
| 4,902,502 A | 2/1990 | Nitecki et al. |
| 4,904,584 A | 2/1990 | Shaw |
| 4,929,555 A | 5/1990 | Cregg et al. |
| 4,963,495 A | 10/1990 | Chang et al. |
| 5,021,234 A | 6/1991 | Ehrenfeld |
| 5,057,417 A | 10/1991 | Hammonds et al. |
| 5,063,158 A | 11/1991 | Schoner et al. |
| 5,089,398 A | 2/1992 | Rosenberg et al. |
| 5,122,614 A | 6/1992 | Zalipsky |
| 5,162,601 A | 11/1992 | Slightom |
| 5,183,660 A | 2/1993 | Ikeda et al. |

(Continued)

FOREIGN PATENT DOCUMENTS

DE    3218121 A1    11/1983

(Continued)

OTHER PUBLICATIONS

Fuh, G et al. "Rational design of potent antagonists to the human growth hormone receptor," Science Jun. 19, 1992;256(5064):1677-80.

Gent, J et al. "Ligand-independent growth hormone receptor dimerization occurs in the endoplasmic reticulum and is required for ubiquitin system-dependent endocytosis," Proc Natl Acad Sci U S A. Jul. 23, 2002;99(15):9858-63. Epub Jul. 8, 2002.

Gertler, A et al. "Real-time kinetic measurements of the interactions between lactogenic hormones and prolactin-receptor extracellular domains from several species support the model of hormone-induced transient receptor dimerization," J Biol Chem. Oct. 4, 1996;271(40):24482-91.

Godowski, PJ et al. "Characterization of the human growth hormone receptor gene and demonstration of a partial gene deletion in two patients with Laron-type dwarfism," Proc Natl Acad Sci U S A. Oct. 1989;86(20):8083-7.

(Continued)

*Primary Examiner* — Elly-Gerald Stoica
(74) *Attorney, Agent, or Firm* — John W. Wallen, III; Kristin S. Eaton

(57) ABSTRACT

The present invention relates generally to the production, purification, and isolation of human growth hormone (hGH). More particularly, the invention relates to the production, purification, and isolation of substantially purified hGH comprising non-naturally encoded amino acids and hGH from recombinant host cells or culture medium including, for example, yeast, insect, mammalian and bacterial host cells. The process of the present invention is also useful for purification of hGH linked to polymers or other molecules.

4 Claims, 5 Drawing Sheets

U.S. PATENT DOCUMENTS

| | | | |
|---|---|---|---|
| 5,192,669 A | 3/1993 | Schoner et al. | |
| 5,219,564 A | 6/1993 | Zalipsky et al. | |
| 5,229,490 A | 7/1993 | Tam | |
| 5,231,178 A | 7/1993 | Holtz et al. | |
| 5,252,714 A | 10/1993 | Harris et al. | |
| 5,262,322 A | 11/1993 | Liu et al. | |
| 5,281,698 A | 1/1994 | Nitecki | |
| 5,290,686 A | 3/1994 | Kendal et al. | |
| 5,324,639 A | 6/1994 | Brierley et al. | |
| 5,324,844 A | 6/1994 | Zalipsky | |
| 5,350,836 A | 9/1994 | Kopchick et al. | |
| 5,382,657 A | 1/1995 | Karasiewicz et al. | |
| 5,446,090 A | 8/1995 | Harris | |
| 5,468,478 A | 11/1995 | Saifer et al. | |
| 5,473,034 A | 12/1995 | Yasui et al. | |
| 5,476,653 A | 12/1995 | Pitt et al. | |
| 5,516,657 A | 5/1996 | Murphy et al. | |
| 5,516,673 A | 5/1996 | Margel et al. | |
| 5,532,142 A | 7/1996 | Johnston et al. | |
| 5,534,617 A | 7/1996 | Cunningham et al. | |
| 5,559,213 A | 9/1996 | Hakimi et al. | |
| 5,571,709 A | 11/1996 | Devauchelle et al. | |
| 5,580,723 A | 12/1996 | Wells et al. | |
| 5,583,023 A | 12/1996 | Cerutti et al. | |
| 5,602,034 A | 2/1997 | Tekamp-Olson | |
| 5,605,827 A | 2/1997 | Jackwood et al. | |
| 5,612,460 A | 3/1997 | Zalipsky | |
| 5,629,203 A | 5/1997 | Shuster | |
| 5,629,384 A | 5/1997 | Veronese et al. | |
| 5,643,575 A | 7/1997 | Martinez et al. | |
| 5,650,234 A | 7/1997 | Dolence et al. | |
| 5,672,662 A | 9/1997 | Harris et al. | |
| 5,674,706 A | 10/1997 | Shuster | |
| 5,681,809 A | 10/1997 | Kopchick et al. | |
| 5,688,666 A | 11/1997 | Bass et al. | |
| 5,688,763 A | 11/1997 | Hammonds, Jr. et al. | |
| RE35,749 E | 3/1998 | Rosenberg et al. | |
| 5,736,625 A | 4/1998 | Callstrom et al. | |
| 5,739,208 A | 4/1998 | Harris | |
| 5,747,646 A | 5/1998 | Hakimi et al. | |
| 5,750,373 A | 5/1998 | Garrard et al. | |
| 5,753,220 A | 5/1998 | Suzuki et al. | |
| 5,762,939 A | 6/1998 | Smith et al. | |
| 5,766,885 A | 6/1998 | Carrington et al. | |
| 5,795,745 A | 8/1998 | Goeddel et al. | |
| 5,808,096 A | 9/1998 | Zalipsky | |
| 5,824,778 A | 10/1998 | Ishikawa et al. | |
| 5,824,784 A | 10/1998 | Kinstler et al. | |
| 5,834,250 A | 11/1998 | Wells et al. | |
| 5,834,594 A | 11/1998 | Hakimi et al. | |
| 5,834,598 A | 11/1998 | Lowman et al. | |
| 5,843,733 A | 12/1998 | Estes | |
| 5,849,535 A | 12/1998 | Cunningham et al. | |
| 5,849,860 A | 12/1998 | Hakimi et al. | |
| 5,854,026 A | 12/1998 | Cunningham et al. | |
| 5,858,368 A | 1/1999 | Smith et al. | |
| 5,861,279 A | 1/1999 | Zhang et al. | |
| 5,871,986 A | 2/1999 | Boyce | |
| 5,891,676 A | 4/1999 | Estes | |
| 5,900,461 A | 5/1999 | Harris | |
| 5,932,462 A | 8/1999 | Harris et al. | |
| 5,939,285 A | 8/1999 | Devauchelle et al. | |
| 5,955,346 A | 9/1999 | Wells et al. | |
| 5,962,411 A | 10/1999 | Rosen et al. | |
| 5,965,393 A | 10/1999 | Hasnain et al. | |
| 5,980,948 A | 11/1999 | Goedemoed et al. | |
| 5,989,868 A | 11/1999 | Harrison et al. | |
| 5,990,237 A | 11/1999 | Bentley et al. | |
| 6,004,573 A | 12/1999 | Rathi et al. | |
| 6,004,931 A | 12/1999 | Cunningham et al. | |
| 6,013,433 A | 1/2000 | Pellett et al. | |
| 6,013,478 A | 1/2000 | Wells et al. | |
| 6,017,731 A | 1/2000 | Tekamp-Olson et al. | |
| 6,022,711 A | 2/2000 | Cunningham et al. | |
| 6,057,292 A | 5/2000 | Cunningham et al. | |
| 6,083,723 A | 7/2000 | Tekamp-Olson | |
| 6,096,304 A | 8/2000 | McCutchen | |
| 6,126,944 A | 10/2000 | Pellett et al. | |
| 6,129,912 A | 10/2000 | Hortin et al. | |
| 6,136,563 A | 10/2000 | Cunningham et al. | |
| 6,143,523 A | 11/2000 | Cunningham et al. | |
| 6,160,089 A | 12/2000 | Honjo et al. | |
| 6,168,932 B1 | 1/2001 | Uckun et al. | |
| 6,183,985 B1 | 2/2001 | Shuster | |
| 6,183,987 B1 | 2/2001 | van de Wiel et al. | |
| 6,201,072 B1 | 3/2001 | Rathi et al. | |
| 6,214,966 B1 | 4/2001 | Harris | |
| 6,225,060 B1 | 5/2001 | Clark et al. | |
| 6,245,528 B1 | 6/2001 | Chao | |
| 6,261,805 B1 | 7/2001 | Wood | |
| RE37,343 E | 8/2001 | Tekamp-Olson | |
| 6,281,211 B1 | 8/2001 | Cai et al. | |
| 6,306,821 B1 | 10/2001 | Mikos et al. | |
| 6,312,923 B1 | 11/2001 | Tekamp-Olson | |
| 6,337,191 B1 | 1/2002 | Swartz et al. | |
| 6,338,846 B1 | 1/2002 | Kang et al. | |
| 6,342,216 B1 | 1/2002 | Fidler et al. | |
| 6,361,969 B1 | 3/2002 | Galeotti | |
| 6,368,825 B1 | 4/2002 | Chao | |
| 6,420,339 B1 | 7/2002 | Gegg et al. | |
| 6,423,685 B1 | 7/2002 | Drummond et al. | |
| 6,428,954 B1 | 8/2002 | Wells et al. | |
| 6,436,386 B1 * | 8/2002 | Roberts et al. | 424/78.17 |
| 6,436,674 B1 | 8/2002 | Honjo et al. | |
| 6,451,346 B1 | 9/2002 | Shah et al. | |
| 6,451,561 B1 | 9/2002 | Wells et al. | |
| 6,461,603 B2 | 10/2002 | Bentley et al. | |
| 6,515,100 B2 | 2/2003 | Harris | |
| 6,521,427 B1 | 2/2003 | Evans | |
| 6,552,167 B1 | 4/2003 | Rose | |
| 6,566,328 B1 | 5/2003 | Rosen et al. | |
| 6,586,207 B2 | 7/2003 | Tirrell et al. | |
| 6,602,498 B2 | 8/2003 | Shen | |
| 6,608,183 B1 | 8/2003 | Cox | |
| 6,610,281 B2 | 8/2003 | Harris | |
| 6,638,500 B1 | 10/2003 | El-Tayar et al. | |
| 6,639,055 B1 * | 10/2003 | Carter et al. | 530/387.3 |
| 6,646,110 B2 | 11/2003 | Nissen et al. | |
| 6,927,042 B2 | 8/2005 | Schultz et al. | |
| 7,045,337 B2 * | 5/2006 | Schultz et al. | 435/252.3 |
| 7,083,970 B2 | 8/2006 | Schultz et al. | |
| 2001/0021763 A1 | 9/2001 | Harris | |
| 2001/0044526 A1 | 11/2001 | Shen | |
| 2001/0056171 A1 | 12/2001 | Kozlowski | |
| 2002/0002250 A1 | 1/2002 | Bentley et al. | |
| 2002/0037949 A1 | 3/2002 | Harris et al. | |
| 2002/0040076 A1 | 4/2002 | Harris et al. | |
| 2002/0042097 A1 | 4/2002 | Tirrell et al. | |
| 2002/0052009 A1 | 5/2002 | Hornauer et al. | |
| 2002/0052430 A1 | 5/2002 | Harris et al. | |
| 2002/0055169 A1 | 5/2002 | Tekamp-Olson | |
| 2002/0072573 A1 | 6/2002 | Bentley et al. | |
| 2002/0081660 A1 | 6/2002 | Swartz et al. | |
| 2002/0082345 A1 | 6/2002 | Kozlowski et al. | |
| 2002/0086939 A1 | 7/2002 | Kozlowski | |
| 2002/0099133 A1 | 7/2002 | Kozlowski | |
| 2002/0156047 A1 | 10/2002 | Zhao | |
| 2003/0023023 A1 | 1/2003 | Harris et al. | |
| 2003/0082575 A1 | 5/2003 | Schultz et al. | |
| 2003/0105224 A1 | 6/2003 | Roberts et al. | |
| 2003/0105275 A1 | 6/2003 | Bentley et al. | |
| 2003/0108885 A1 | 6/2003 | Schultz et al. | |
| 2003/0114647 A1 | 6/2003 | Harris et al. | |
| 2003/0143596 A1 | 7/2003 | Bentley et al. | |
| 2003/0153003 A1 | 8/2003 | Wells et al. | |
| 2003/0158333 A1 | 8/2003 | Roberts et al. | |
| 2003/0162949 A1 | 8/2003 | Cox | |
| 2003/0171285 A1 * | 9/2003 | Finn et al. | 514/12 |
| 2003/0220447 A1 | 11/2003 | Harris | |
| 2003/0228274 A1 | 12/2003 | Rose | |
| 2004/0001838 A1 | 1/2004 | Zhao et al. | |
| 2004/0013637 A1 | 1/2004 | Bentley et al. | |
| 2004/0038242 A1 | 2/2004 | Edmonds et al. | |
| 2004/0058849 A1 * | 3/2004 | Sleeman et al. | 514/1 |
| 2004/0138106 A1 | 7/2004 | Schultz et al. | |
| 2004/0198637 A1 | 10/2004 | Schultz et al. | |
| 2005/0009049 A1 | 1/2005 | Chin et al. | |

| | | | |
|---|---|---|---|
| 2005/0085619 A1 | 4/2005 | Wilson et al. | |
| 2005/0170404 A1 | 8/2005 | Cho et al. | |
| 2005/0220762 A1 | 10/2005 | Cho et al. | |

FOREIGN PATENT DOCUMENTS

| | | |
|---|---|---|
| EP | 036 676 A1 | 9/1981 |
| EP | 036 776 A2 | 9/1981 |
| EP | 052 322 A2 | 5/1982 |
| EP | 058 481 A1 | 8/1982 |
| EP | 073 657 A1 | 3/1983 |
| EP | 102 324 A2 | 3/1984 |
| EP | 121 775 A1 | 10/1984 |
| EP | 127 839 A2 | 12/1984 |
| EP | 133 988 A2 | 3/1985 |
| EP | 143 949 A1 | 6/1985 |
| EP | 154 316 A2 | 9/1985 |
| EP | 155 476 A1 | 9/1985 |
| EP | 164 556 A2 | 12/1985 |
| EP | 183 503 A2 | 6/1986 |
| EP | 188 256 A2 | 7/1986 |
| EP | 229 108 B1 | 7/1987 |
| EP | 244 234 A2 | 11/1987 |
| EP | 267 851 A2 | 5/1988 |
| EP | 284 044 A1 | 9/1988 |
| EP | 324 274 A1 | 7/1989 |
| EP | 329 203 A1 | 8/1989 |
| EP | 340 986 A2 | 11/1989 |
| EP | 400 472 A2 | 12/1990 |
| EP | 402 378 B1 | 12/1990 |
| EP | 439 508 B1 | 8/1991 |
| EP | 480 480 A2 | 4/1992 |
| EP | 510 356 A1 | 10/1992 |
| EP | 605 963 A1 | 7/1994 |
| EP | 732 403 A1 | 9/1996 |
| EP | 809 996 A2 | 12/1997 |
| EP | 921 131 A1 | 6/1999 |
| EP | 946 736 B1 | 10/1999 |
| EP | 1219636 A2 | 7/2002 |
| GB | 2426521 A2 | 11/2006 |
| GB | 2426762 A2 | 12/2006 |
| GB | 2429207 A2 | 2/2007 |
| JP | 83-118008 A | 1/1985 |
| WO | 88/07082 A1 | 9/1988 |
| WO | 89/01037 A1 | 2/1989 |
| WO | 89/01038 A1 | 2/1989 |
| WO | 90/01556 A1 | 2/1990 |
| WO | 90/02186 A1 | 3/1990 |
| WO | 90/02566 A1 | 3/1990 |
| WO | 90/05785 A1 | 5/1990 |
| WO | 90/10078 A1 | 9/1990 |
| WO | 90/10277 A1 | 9/1990 |
| WO | 90/13540 A1 | 11/1990 |
| WO | 90/14428 A1 | 11/1990 |
| WO | 91/00357 A1 | 1/1991 |
| WO | WO 91/05853 | 5/1991 |
| WO | 92/01801 A1 | 2/1992 |
| WO | 92/02628 A1 | 2/1992 |
| WO | 92/16619 A1 | 2/1992 |
| WO | 92/16555 A1 | 10/1992 |
| WO | 92/16619 A1 | 10/1992 |
| WO | WO 92/19736 | 11/1992 |
| WO | 93/15189 A1 | 8/1993 |
| WO | 93/21259 A1 | 10/1993 |
| WO | 94/04193 A1 | 3/1994 |
| WO | 94/09027 A1 | 4/1994 |
| WO | 94/14758 A1 | 7/1994 |
| WO | 94/15625 A1 | 7/1994 |
| WO | 94/17039 A1 | 8/1994 |
| WO | 94/18247 A1 | 8/1994 |
| WO | 94/28024 A1 | 12/1994 |
| WO | 95/00162 A1 | 1/1995 |
| WO | 95/06058 A1 | 3/1995 |
| WO | 95/11924 A1 | 5/1995 |
| WO | 95/13090 A1 | 5/1995 |
| WO | 95/13312 A1 | 5/1995 |
| WO | 95/20672 A1 | 8/1995 |
| WO | WO 95/20398 | 8/1995 |
| WO | 95/33490 A1 | 12/1995 |
| WO | 96/00080 A1 | 1/1996 |
| WO | 96/06161 A1 | 2/1996 |
| WO | 96/07670 A1 | 3/1996 |
| WO | 96/21469 A1 | 7/1996 |
| WO | 96/25496 A1 | 8/1996 |
| WO | 96/29400 A1 | 9/1996 |
| WO | 96/40791 A1 | 12/1996 |
| WO | 96/41813 A2 | 12/1996 |
| WO | 97/03106 A1 | 1/1997 |
| WO | 97/18832 A1 | 5/1997 |
| WO | 97/26332 A1 | 7/1997 |
| WO | 97/32607 A2 | 9/1997 |
| WO | 98/05363 A2 | 2/1998 |
| WO | 98/26080 A1 | 6/1998 |
| WO | 98/32466 A1 | 7/1998 |
| WO | 98/37208 A1 | 8/1998 |
| WO | 98/41562 A1 | 9/1998 |
| WO | 98/48837 A1 | 11/1998 |
| WO | 99/03887 A1 | 1/1999 |
| WO | 99/05297 A1 | 2/1999 |
| WO | 99/07862 A1 | 2/1999 |
| WO | 99/09193 A1 | 2/1999 |
| WO | 99/10515 A1 | 3/1999 |
| WO | 99/31257 A2 | 6/1999 |
| WO | 99/32134 A1 | 7/1999 |
| WO | 99/32139 A1 | 7/1999 |
| WO | 99/32140 A1 | 7/1999 |
| WO | 99/45130 A1 | 9/1999 |
| WO | 99/51721 A1 | 10/1999 |
| WO | 99/67291 A2 | 12/1999 |
| WO | WO 00/17361 A2 | 3/2000 |
| WO | 00/20032 A1 | 4/2000 |
| WO | 00/26354 A1 | 5/2000 |
| WO | 00/55345 A2 | 9/2000 |
| WO | 00/55353 A1 | 9/2000 |
| WO | WO 00/68387 A2 | 11/2000 |
| WO | 01/05956 A2 | 1/2001 |
| WO | 01/27301 A2 | 4/2001 |
| WO | 01/90390 A1 | 11/2001 |
| WO | 02/06305 A1 | 1/2002 |
| WO | 02/085923 A2 | 10/2002 |
| WO | 02/086075 A2 | 10/2002 |
| WO | WO 02/085923 A2 | 10/2002 |
| WO | WO 03/062276 | 7/2003 |
| WO | WO 03/089582 | 10/2003 |
| WO | 03/101972 A1 | 12/2003 |
| WO | 2004/035605 A2 | 4/2004 |
| WO | 2004/035743 A2 | 4/2004 |
| WO | 2004/058946 A2 | 7/2004 |
| WO | 2004/094593 A2 | 11/2004 |
| WO | WO 2004/094593 A2 | 11/2004 |
| WO | 2005/007624 A2 | 1/2005 |
| WO | 2005/007870 A2 | 1/2005 |
| WO | WO 2005/003294 A2 | 1/2005 |
| WO | 2005/019415 A2 | 3/2005 |
| WO | 2005/035727 A2 | 4/2005 |
| WO | 2005/074524 A2 | 8/2005 |
| WO | 2005/074546 A2 | 8/2005 |
| WO | 2005/074650 A2 | 8/2005 |
| WO | WO 2005/074524 A2 | 8/2005 |
| WO | WO 2005/074546 A2 | 8/2005 |
| WO | WO 2005/074650 A2 | 8/2005 |

OTHER PUBLICATIONS

Goeddel, DV et al. "Direct expression in *Escherichia coli* of a DNA sequence coding for human growth hormone" Nature Oct. 18, 1979;281(5732):544-8.

Gomez-Orellana, I et al. "Thermodynamic characterization of an intermediate state of human growth hormone," Protein Sci. Jun. 1998;7(6):1352-8.

Gout, PW et al. "Prolactin-stimulated growth of cell cultures established from malignant Nb rat lymphomas," Cancer Res. Jul. 1980;40(7):2433-6.

Hill, CP et al. "The Structure of Granulocyte-Colony-Stimulating Factor and its Relationship to Other Growth Factors," Proc. Natl. Acad. Sci. USA (1993); 90:5167-71.

Hughes, JP and HG Friesen. "The nature and regulation of the receptors for pituitary growth hormone," Annu Rev Physiol. 1985;47:469-82.

Igout, A, et al. "Expression and secretion of the human placental growth hormone in *Escherichia coli*," Nucleic Acids Res. May 25, 1989;17(10):3998.

Isaksson, OG, et al. "Mode of action of pituitary growth hormone on target cells," Annu Rev Physiol. 1985;47:483-99.

Johnston, LB et al. "Analysis of the intracellular signalling domain of the human growth hormone receptor in children with idiopathic short stature," Clin Endocrinol (Oxf). Apr. 2000;52(4):463-9.

Kasukawa, Y et al. "Evidence that sensitivity to growth hormone (GH) is growth period and tissue type dependent: studies in GH-deficient lit/lit mice," Endocrinology. Sep. 2003;144(9):3950-7.

Khan, RH et al. "Solubilization of recombinant ovine growth hormone with retention of native-like secondary structure and its refolding from the inclusion bodies of *Escherichia coli*," Biotechnol Prog. Sep.-Oct. 1998;14(5):722-8.

Klaus, W et al. "The three-dimensional high resolution structure of human interferon alpha-2a determined by heteronuclear NMR spectroscopy in solution," J Mol Biol. Dec. 12, 1997;274(4):661-75.

Kopchick, JJ et al. "Growth hormone receptor antagonists: discovery, development, and use in patients with acromegaly," Endocr Rev. Oct. 2002;23(5):623-46.

Kostyo, JL et al. "Biological characterization of purified native 20-kDa human growth hormone," Biochim Biophys Acta. Sep. 11, 1987;925(3):314-24.

Krawczak, M et al. "Evolution of the proximal promoter region of the mammalian growth hormone gene," Gene Sep. 3, 1999;237(1):143-51.

Lee, N et al. "Interferon-alpha 2 variants in the human genome," J Interferon Cytokine Res. Apr. 1995;15(4):341-9.

Leung, DW et al. "Growth hormone receptor and serum binding protein: purification, cloning and expression," Nature Dec. 10-16, 1987;330(6148):537-43.

Trahair, JF et al. "Use of transgenic mice to study the routing of secretory proteins in intestinal epithelial cells: analysis of human growth hormone compartmentalization as a function of cell type and differentiation," J Cell Biol. Dec. 1989;109(6 Pt 2):3231-42.

Tsunekawa, B et al. "The binding between the stem regions of human growth hormone (GH) receptor compensates for the weaker site 1 binding of 20-kDa human GH (hGH) than that of 22-kDa hGH," J Biol Chem. May 26, 2000;275 (21):15652-6.

Ultsch, MH et al. "The crystal structure of affinity-matured human growth hormone at 2 A resolution," J Mol Biol. Feb. 11, 1994;236(1):286-99.

Urbanek, M et al. "Functional characterization of the alternatively spliced, placental human growth hormone receptor," J Biol Chem. Sep. 5, 1993;268(25):19025-32.

Van Der Lely, AJ et al. "Long-term treatment of acromegaly with pegvisomant, a growth hormone receptor antagonist," Lancet Nov. 24, 2001;358(9295):1754-9.

Wada, M. et al. "The 20-kilodalton (kDa) human growth hormone (hGH) differs from the 22-kDa hGH in the complex formation with cell surface hGH receptor and hGH-binding protein circulating in human plasma," Mol Endocrinol. Jan. 1998;12(1):146-56.

Walsh, STR et al. "Site2 binding energetics of the regulatory step of growth hormone-induced receptor homodimerization," Protein Sci. Sep. 2003;12(9):1960-70.

Walter, MR et al. "Three-dimensional structure of recombinant human granulocyte-macrophage colony-stimulating factor," J Mol Biol. Apr. 20, 1992;224(4):1075-85.

Wang, X et al. "A 40-amino acid segment of the growth hormone receptor cytoplasmic domain is essential for GH-induced tyrosine-phosphorylated cytosolic proteins," J Biol Chem. Mar. 17, 1995;270(11):6261-6.

Weiss, GA et al. "Rapid mapping of protein functional epitopes by combinatorial alanine scanning," Proc Natl Acad Sci U S A. Aug. 1, 2000;97(16):8950-4.

Wells, JA. "Binding in the growth hormone receptor complex," Proc Natl Acad Sci U S A. Jan. 9, 1996;93(1):1-6.

Wen, D et al. "Erythropoietin structure-function relationships. Identification of functionally important domains," J. Biol. Chem. 1994; 269(36):22839-22846.

Zink, T et al. "Secondary structure of human granulocyte colony-stimulating factor derived from NMR spectroscopy," FEBS Lett. Dec. 21, 1992;314(3):435-9.

Zink, T et al. "Structure and dynamics of the human granulocyte colony-stimulating factor determined by NMR spectroscopy. Loop mobility in a four-helix-bundle protein," Biochemistry Jul. 19, 1994;33(28):8453-63.

Kappelgaard, A-M et al. "Liquid growth hormone: preservatives and buffers," Horm Res. 2004;62 Suppl 3:98-103.

Karlsson, G et al. "Separation of oxidized and deamidated human growth hormone variants by isocratic reversed-phase high-performance liquid chromatography," J Chromatogr A. Sep. 3, 1999;855(1):147-55.

Karlsson, G et al. "Usage of nonporous polymeric particles for reversed-phase high-performance liquid chromatography of oxidized and deamidated forms of recombinant human growth hormone," J Chromatogr Sci. Jul. 2004;42(6):285-7.

Kasimova, MR et al. "NMR studies of the backbone flexibility and structure of human growth hormone: a comparison of high and low pH conformations," J Mol Biol. May 3, 2002;318(3):679-95.

Kasimova, MR et al. "The conformational equilibrium of human growth hormone," J Mol Biol. Mar. 27, 1998;277 (2):409-18.

Kasraian, K et al. "Sustained in vivo activity of recombinant bovine granulocyte colony stimulating factor (rbG-CSF) using HEPES buffer," Pharm Dev Technol. Aug. 2001;6(3):441-7.

Katakam, M et al. "Effect of surfactants on the physical stability of recombinant human growth hormone," J Pharm Sci. Jun. 1995;84(6):713-6.

Kim, He et al. "Microencapsulation of dissociable human growth hormone aggregates within poly(D,L-lactic-co-glycolic acid) microparticles for sustained release," Intl J of Pharm 2001; 229:107-16.

Kunitani, M et al. "On-line characterization of polyethylene-glycol modified proteins," J Chromatogr. 1991;588:125-137.

Lai, MC et al. "Chemical stability of peptides in polymers. 2. Discriminating between solvent and plasticizing effects of water on peptide deamidation in poly(vinylpyrrolidone)," J Pharm Sci. Oct. 1999;88(10):1081-9.

Liu, JL et al. "In vitro methionine oxidation of recombinant human leptin," Pharm Res. Apr. 1998;15(4):632-40.

Maa, Y-F et al. "Spray-drying of air-liquid interface sensitive recombinant human growth hormone," J Pharm Sci. Feb. 1998;87(2):152-9-F et al. "Spray-drying of air-liquid interface sensitive recombinant human growth hormone," J Pharm Sci. Feb. 1998;87(2):152-9.

Maisano, F et al. "Immobilized metal-ion affinity chromatography of human growth hormone," J Chromatogr. Jun. 23, 1989;472(2):422-7.

Manning, MC et al. "Stability of protein pharmaceuticals," Pharm Res. Nov. 1989;6(11):903-18.

Mukhija, R et al. "High-level production and one-step purification of biologically active human growth hormone in *Escherichia coli*," Gene. Nov. 20, 1995;165(2):303-6.

Naglak, TJ et Hy Wang. "Recovery of a foreign protein from the periplasm of *Escherichia coli* by chemical permeabilization," Enzyme Microb Technol. Aug. 1990;12(8):603-11.

Olson, KC et al. "Purified human growth hormone from *E. coli* is biologically active," Nature. Oct. 1, 1981;293 (5831):408-11.

Pan, F-M et W-C Chang. "Purification of growth hormones by reversed-phase high-performance liquid chromatography," J Chromatogr. Apr. 2, 1993;613(2):326-9.

Panda, AK. "Bioprocessing of therapeutic proteins from the inclusion bodies of *Escherichia coli*," Adv Biochem Eng Biotechnol. 2003;85:43-93.

Patience, RL and LH Rees. "Comparison of reversed-phase and anion-exchange high-performance liquid chromatography for the analysis of human growth hormones," J Chromatogr. Feb. 21, 1986;352:241-53.

Lewis, UJ et al. "A naturally occurring structural variant of human growth hormone," J Biol Chem. Apr. 25, 1978;253(8):2679-87.

Lewis, UJ et al. "An interchain disulfide dimer of human growth hormone," J Biol Chem. Jun. 10, 1977;252(11):3697-702.

Lewis, UJ et al. "Altered proteolytic cleavage of human growth hormone as a result of deamidation," J Biol Chem. Nov. 25, 1981;256(22):11645-50.

Li, CH, "Human growth hormone: 1974-1981," Mol Cell Biochem. Jul. 7, 1982;46(1):31-41.

Linzer, Dih et F. Talamantes. "Nucleotide sequence of mouse prolactin and growth hormone mRNAs and expression of these mRNAs during pregnancy," J Biol Chem. Aug. 15, 1985;260(17):9574-9.

Liu, JC et al. "Episodic evolution of growth hormone in primates and emergence of the species specificity of human growth hormone receptor," Mol Biol Evol. Jun. 2001;18(6):945-53.

MacGillivray, MH et al. "Outcome of a four-year randomized study of daily versus three times weekly somatropin treatment in prepubertal naive growth hormone-deficient children. Genentech Study Group." J Clin Endocrinol Metab. May 1996;81(5):1806-9.

Mathews, LS et al. "Regulation of rat growth hormone receptor gene expression," J Biol Chem. Jun. 15, 1989;264(17):9905-10.

Matthews, DJ et al. "A sequential dimerization mechanism for erythropoietin receptor activation," Proc Natl Acad Sci U S A. Sep. 3, 1996;93(18):9471-6.

McFarland, KC et al. "Lutropin-choriogonadotropin receptor: an unusual member of the G protein-coupled receptor family," Science Aug. 4, 1989;245(4917):494-9.

Milburn, MV et al. "A novel dimer configuration revealed by the crystal structure at 2.4 A resolution of human interleukin-5" Nature 1993; 363:172-176.

Mills, JB, et al. "Fragments of human growth hormone produced by digestion with thrombin: chemistry and biological properties," Endocrinology Aug. 1980;107(2):391-9.

Mordenti, J et al. "Interspecies scaling of clearance and volume of distribution data for five therapeutic proteins," Pharm Res. Nov. 1991;8(11):1351-9.

Mott, HR and ID Campbell. "Four-helix bundle growth factors and their receptors: protein-protein interactions," Curr Opin Struct Biol. Feb. 1995;5(1):114-21.

Murgolo, NJ et al. "A homology model of human interferon alpha-2," Proteins Sep. 1993;17(1):62-74.

Oliva, A et al. "Comparative study of protein molecular weights by size-exclusion chromatography and laser-light scattering," J Pharm Biomed Anal. Jul. 2001;25(5-6):833-41.

Pal, G et al. "The functional binding epitope of a high affinity variant of human growth hormone mapped by shotgun alanine-scanning mutagenesis: insights into the mechanisms responsible for improved affinity," J Mol Biol. Sep. 5, 2003;332(1):195-204.

Pantel, J et al. "Species-specific alternative splice mimicry at the growth hormone receptor locus revealed by the lineage of retroelements during primate evolution," J Biol Chem. Jun. 23, 2000;275(25):18664-9.

Paonessa, G et al. "Two distinct and independent sites on IL-6 trigger gp 130 dimer formation and signaling," EMBO J. May 1, 1995;14(9):1942-51.

Pearce, KH et al. "Growth hormone binding affinity for its receptor surpasses the requirements for cellular activity," Biochemistry. Jan. 5, 1999;38(1):81-9.

Pearlman, R et T Nguyen. "Pharmaceutics of protein drugs," J Pharm Pharmacol. Feb. 1992;44 Suppl 1:178-85.

Pikal, MJ et al. "The effects of formulation variables on the stability of freeze-dried human growth hormone," Pharm Res. Apr. 1991;8(4):427-36.

Rathore, AS et al. "Optimization of an osmotic shock procedure for isolation of a protein product expressed in E. coli," Biotechnol Prog. Sep.-Oct. 2003;19(5):1541-6.

Reddy, KR. "Controlled-release, pegylation, liposomal formulations: new mechanisms in the delivery of injectable drugs," Ann Pharmacother. Jul.-Aug. 2000;34(7-8):915-23.

Remmele, RL et al. "Interleukin-1 receptor (IL-1R) liquid formulation development using differential scanning calorimetry," Pharm Res. Feb. 1998;15(2):200-8.

Riggin, RM et al. "High-performance size-exclusion chromatographic determination of the potency of biosynthetic human growth hormone products," J Chromatogr. Jan. 8, 1988;435(2):307-18.

Riggin, RM et al. "A reversed-phase high-performance liquid chromatographic method for characterization of biosynthetic human growth hormone," Anal Biochem. Nov. 15, 1987;167(1):199-209.

Sharma, VK et DS Kalonia. "Polyethylene glycol-induced precipitation of interferon alpha-2a followed by vacuum drying: development of a novel process for obtaining a dry, stable powder," AAPS PharmSci. Jan. 26, 2004;6(1):E4.

Takahashi, Y et al. "Brief report: short stature caused by a mutant growth hormone," N Engl J Med. Feb. 15, 1996;334 (7):432-6.

Tang, X et MJ Pikal. "Design of freeze-drying processes for pharmaceuticals: practical advice," Pharm Res. Feb. 2004;21(2):191-200.

Tatford, OC et al. "Analytical techniques for the evaluation of liquid protein therapeutics," Biotechnol Appl Biochem. Aug. 2004;40(Pt 1):67-81.

Tkac, J et al. "Evaluation of disruption methods for the release of intracellular recombinant protein from Escherichia coli for analytical purposes," Biotechnol Appl Biochem. Aug. 2004;40(Pt 1):83-8.

Treuheit, MJ et al. "Inverse relationship of protein concentration and aggregation," Pharm Res. Apr. 2002;19(4):511-6.

Tsubery, H et al. "Prolonging the action of protein and peptide drugs by a novel approach of reversible polyethylene glycol modification," J Biol Chem. Sep. 10, 2004;279(37):38118-24. Epub Jun. 8, 2004.

Wang, W. "Instability, stabilization, and formulation of liquid protein pharmaceuticals," Int J Pharm. Aug. 20, 1999;185(2):129-88.

Welinder, BS et al. "Reversed-phase high-performance liquid chromatography of human growth hormone," J Chromatogr. Jul. 10, 1987;398:309-16.

Wu, SL et al. "Application of high-performance hydrophobic-interaction chromatography to the characterization of recombinant DNA-derived human growth hormone," J Chromatogr. Feb. 2, 1990;500:595-606.

Yan, Y-B et al. "Protein thermal aggregation involves distinct regions: sequential events in the heat-induced unfolding and aggregation of hemoglobin," Biophys J. Mar. 2004;86(3):1682-90.

Yang, T-H et al. "Use of Infrared Spectroscopy to Assess Secondary Structure of Human Growth Hormone within Biodegradable Microspheres," J Pharm Sci Feb. 1999; 88(2):161-165.

Pearce, KH et al. "Structural and mutational analysis of affinity-inert contact residues at the growth hormone-receptor interface," Biochemistry. Aug. 13, 1996;35(32)10300-7.

Powers, R et al. "Three-dimensional solution structure of human interleukin-4 by multidimensional heteronuclear magnetic resonance spectroscopy," Science Jun. 19, 1992;256(5064):1673-7.

Radhakrishnan, R et al. "Zinc mediated dimer of human interferon-alpha 2b revealed by X-ray crystallography," Structure Dec. 15, 1996;4(12):1453-63.

Redfield, C et al. "Secondary structure and topology of human interleukin 4 in solution," Biochemistry Nov. 19, 1991;30(46):11029-35.

Ross, RJM et al. "Binding and functional studies with the growth hormone receptor antagonist, B2036-PEG (pegvisomant), reveal effects of pegylation and evidence that it binds to a receptor dimer," J Clin Endocrinol Metab. Apr. 2001;86(4):1716-23.

Rottman, JN et JI Gordon. "Comparison of the patterns of expression of rat intestinal fatty acid binding protein/human growth hormone fusion genes in cultured intestinal epithelial cell lines and in the gut epithelium of transgenic mice," J Biol Chem. Jun. 5, 1993;268(16):11994-2002.

Rowland, JE et al. "A novel bioassay for human somatogenic activity in serum samples supports the clinical reliability of immunoassays," Clin Endocrinol (Oxf). Apr. 2002;56(4):475-85.

Schiffer, C et al. "Structure of a phage display-derived variant of human growth hormone complexed to two copies of the extracellular domain of its receptor: evidence for strong structural coupling between receptor binding sites," J Mol Biol. Feb. 15, 2002;316(2):277-89.

Schoner, BE et al. "Role of mRNA translational efficiency in bovine growth hormone expression in Escherichia coli," Proc Natl Acad Sci U S A. Sep. 1984;81(17):5403-7.

Seeburg, PH. "The human growth hormone gene family: nucleotide sequences show recent divergence and predict a new polypeptide hormone," DNA 1982;1(3):239-49.

Silva, CM et al. "Characterization and cloning of STAT5 from IM-9 cells and its activation by growth hormone," Mol Endocrinol. May 1996;10(5):508-18.

Sobrier, ML et al. "Expression and binding properties of two isoforms of the human growth hormone receptor," FEBS Lett. Mar. 15, 1993;319(1-2):16-20.

Sobrier, ML et al. "Nine novel growth hormone receptor gene mutations in patients with Laron syndrome," J Clin Endocrinol Metab. Feb. 1997;82(2):435-7.

Souza, SC et al. "A single arginine residue determines species specificity of the human growth hormone receptor," Proc Natl Acad Sci U S A. Feb. 14, 1995;92(4):959-63.

Spencer, SA et al. "Rabbit liver growth hormone receptor and serum binding protein. Purification, characterization, and sequence," J Biol Chem. Jun. 5, 1988;263(16):7862-7.

Stallings-Mann, ML et al. "Alternative splicing of exon 3 of the human growth hormone receptor is the result of an unusual genetic polymorphism," Proc Natl Acad Sci U S A. Oct. 29, 1996;93(22):12394-9.

Sundstrom, M et al. "Crystal structure of an antagonist mutant of human growth hormone, G120R, in complex with its receptor at 2.9 A resolution," J Biol Chem. Dec. 13, 1996;271(50):32197-203.

Syed, RS et al. "Efficiency of signalling through cytokine receptors depends critically on receptor orientation," Nature. Oct. 1, 1998;395(6701):511-6.

Talamantes, F et R Ortiz. "Structure and regulation of expression of the mouse GH receptor," J Endocrinol. Oct. 2002;175(1):55-9.

Teh, LC et al. "Methionine oxidation in human growth hormone and human chorionic somatomammotropin. Effects on receptor binding and biological activities," J Biol Chem. May 15, 1987;262(14):6472-7.

Cleland, JL et al. "The development of stable protein formulations: a close look at protein aggregation, deamidation, and oxidation," Crit Rev Ther Drug Carrier Syst. 1993;10(4):307-77.

Costantino, HR et al. "Effect of excipients on the stability and structure of lyophilized recombinant human growth hormone," J Pharm Sci. Nov. 1998;87(11):1412-20.

Costantino, HR et al. "Protein spray freeze drying. 2. Effect of formulation variables on particle size and stability," J Pharm Sci. Feb. 2002;91(2):388-95.

Cueto, M et al. "New approach to stability assessment of protein solution formulations by differential scanning calorimetry," Int J Pharm. Feb. 18, 2003;252(1-2):159-66.

Cunico, RL et al. "Characterization of polyethylene glycol modified proteins using charge-reversed capillary electrophoresis," J Chromatogr 1991; 559:467-477.

Dalboge, H et al. "A novel enzymatic method for production of authentic hGH from an *Eschericia coli* produced hGH-precursor," Bio/Technology 1987; 5:161-164.

De Oliveira, JE et al. "High-yield purification of biosynthetic human growth hormone secreted in *Escherichia coli* periplasmic space," J Chromatogr A. Aug. 13, 1999;852(2):441-50.

Defelippis, MR et al. "Evidence for a self-associating equilibrium intermediate during folding of human growth hormone," Biochemistry. Feb. 16, 1993;32(6):1555-62.

Dong, A et al. "Infrared spectroscopic studies of lyophilization- and temperature-induced protein aggregation," J Pharm Sci. Apr. 1995;84(4):415-24.

Eckhardt, BM et al. "Effect of freezing on aggregation of human growth hormone," Pharm Res. Nov. 1991;8 (11):1360-4.

Fee, CJ. "Size-exclusion reaction chromatography (SERC): a new technique for protein PEGylation," Biotechnol Bioeng. Apr. 20, 2003;82(2):200-6.

Filikov, AV et al. "Computational stabilization of human growth hormone," Protein Sci. Jun. 2002;11(6):1452-61.

Flodh, H. "Human growth hormone produced with recombinant DNA technology: development and production," Acta Paediatr Scand Suppl. 1986;325:1-9.

Gellerfors, P et al. "Separation and identification of growth hormone variants with high performance liquid chromatography techniques," Acta Paediatr Scand Suppl. 1990;370:93-100.

Haro, LS et al. "Divalent metal cation chelators enhance chromatographic separation of structurally similar macromolecules: separation of human growth hormone isoforms," J Chromatogr B Biomed Sci Appl. Dec. 11, 1998;720(1-2):39-47.

Ikeda, M et al. "A novel bioassay based on human growth hormone (hGH) receptor mediated cell proliferation: measurement of 20K-hGH and its modified forms," Growth Horm IGF Res. Oct. 2000;10(5):248-55.

Jespersen, AM et al. "Characterisation of a trisulphide derivative of biosynthetic human growth hormone produced in *Escherichia coli*," Eur J Biochem. Jan. 15, 1994;219(1-2):365-73.

Johnson, BA et al. "Formation of isoaspartate at two distinct sites during in vitro aging of human growth hormone," J Biol Chem. Aug. 25, 1989;264(24):14262-71.

Jones, RL et al. "Large-scale preparation of highly purified pyrogen-free human growth hormone for clinical use," J Endocrinol. Jul. 1979;82(1):77-86.

Jorgensen, TK et al. "Quantifying biosynthetic human growth hormone in *Escherichia coli* with capillary electrophoresis under hydrophobic conditions," J Chromatogr A. Aug. 21, 1998;817(1-2):205-14.

Alam, KS et al. "Expression and purification of a mutant human growth hormone that is resistant to proteolytic cleavage by thrombin, plasmin and human plasma in vitro," J Biotechnol. Oct. 27, 1998;65(2-3):183-90.

Alves Dos Santos, CM et al. "The signal transduction of the growth hormone receptor is regulated by the ubiquitin/proteasome system and continues after endocytosis," J Biol Chem. Apr. 6, 2001;276(14):10839-46. Epub Jan. 10, 2001.

Amit, T et al. "A membrane-fixed, truncated isoform of the human growth hormone receptor," J Clin Endocrinol Metab. Nov. 1997;82(11):3813-7.

Appa Rao, KBC et al. "High-level expression of ovine growth hormone in *Escherichia coli*: single-step purification and characterization," Protein Expr Purif. Nov. 1997;11(2):201-8.

Atwell, S et al. "Structural plasticity in a remodeled protein-protein interface," Science. Nov. 7, 1997;278(5340):1125-8.

Barazzone, P et al. "Binding, internalization, and lysosomal association of 125I-human growth hormone in cultured human lymphocytes: a quantitative morphological and biochemical study," J Cell Biol. Nov. 1980;87(2 Pt 1):360-9.

Bass, SH et al. "A systematic mutational analysis of hormone-binding determinants in the human growth hormone receptor," Proc Natl Acad Sci U S A. May 15, 1991;88(10):4498-502.

Baumann, G. "Growth hormone heterogeneity: genes, isohormones, variants, and binding proteins," Endocr Rev. Nov. 1991;12(4):424-49.

Bazan, JF. "Haemopoietic receptors and helical cytokines," Immunology Today (1990); 11: 350-354.

Bazan, JF. "Structural design and molecular evolution of a cytokine receptor superfamily," Proc Natl Acad Sci U S A. Sep. 1990;87(18):6934-8.

Bazan, JF et DB McKay. "Unraveling the structure of IL-2," Science. Jul. 17, 1992;257(5068):410-3.

Becker, GW et al. "Isolation and characterization of a sulfoxide and a desamido derivative of biosynthetic human growth hormone," Biotechnol Appl Biochem. Aug. 1988;10(4):326-37.

Behncken, SN et al. "Growth hormone (GH)-independent dimerization of GH receptor by a leucine zipper results in constitutive activation," J Biol Chem. Jun. 2, 2000;275(22):17000-7.

Bell, JA et al. "Crystallization and preliminary x-ray characterization of bovine growth hormone. Purification of bovine prolactin and growth hormone," J Biol Chem. Jul. 15, 1985;260(14):8520-5.

Bernat, B et al. "Determination of the energetics governing the regulatory step in growth hormone-induced receptor homodimerization," Proc Natl Acad Sci U S A. Feb. 4, 2003;100(3):952-7. Epub Jan. 27, 2003.

Bewley, TA et al. "Human pituitary growth hormone. Physicochemical investigations of the native and reduced-alkylated protein," Biochemistry Dec. 1969;8(12):4701-8.

Bieth, E et al. "Human growth hormone receptor: cloning and expression of the full-length complementary DNA after site-directed inactivation ion of a cryptic bacterial promoter," Gene Jul. 18, 1997;194(1):97-105.

Bignon, C et al. "Preparation of the extracellular domain of the rabbit prolactin receptor expressed in *Escherichia coli* and its interaction with lactogenic hormones," J Biol Chem. Feb. 4, 1994;269(5):3318-24.

Boutin, JM, et al. "Cloning and expression of the rat prolactin receptor, a member of the growth hormone/prolactin receptor gene family," Cell Apr. 8, 1988;53(1):69-77.

Brostedt, P and P Roos. "Isolation of dimeric forms of human pituitary growth hormone," Prep Biochem. 1989;19(3):217-29.

Bam, NB et al. "Tween protects recombinant human growth hormone against agitation-induced damage via hydrophobic interactions," J Pharm Sci. Dec. 1998;87(12):1554-9.

Bam, NB et al. "Molten globule intermediate of recombinant human growth hormone: stabilization with surfactants," Biotechnol Prog. Nov.-Dec. 1996;12(6):801-9.

Bam, NB et al. "Stability of protein formulations: investigation of surfactant effects by a novel EPR spectroscopic technique," Pharm Res. Jan. 1995;12(1):2-11.

Battersby, JE et al. "Affinity purification and microcharacterization of recombinant DNA-derived human growth hormone isolated from an in vivo model," Anal Chem. Jan. 15, 1995;67(2):447-55.

Battersby, JE et al. "Diketopiperazine formation and N-terminal degradation in recombinant human growth hormone," Int J Pept Protein Res. Sep. 1994;44(3):215-22.

Becker, GW et JM Hsiung. "Expression, secretion and folding of human growth hormone in *Escherichia coli*. Purification and characterization," FEBS Lett. Aug. 11, 1986;204(1):145-50.

Bedu-Addo, F et al. "Preformulation development of recombinant pegylated staphylokinase SY161 using statistical design," AAPS PharmSci. 2002;4(4):E19.

Bondos, SE et A Bicknell. "Detection and prevention of protein aggregation before, during, and after purification," Anal Biochem. May 15, 2003;316(2):223-31.

Brems, DN et al. "Equilibrium denaturation of human growth hormone and its cysteine-modified forms," J Biol Chem. Apr. 5, 1990;265(10):5504-11.

Callahan, WJ et al. "Sodium chloride enhances the storage and conformational stability of BDNF and PEG-BDNF," Pharm Res. Mar. 2001;18(3):261-6.

Capan, Y et al. "Preparation and characterization of poly(D,L-lactide-co-glycolide) microspheres for controlled release of human growth hormone," AAPS PharmSciTech. 2003;4(2):E28.

Carpenter, JF et al. "Application of infrared spectroscopy to development of stable lyophilized protein formulations," Eur J Pharm Biopharm. May 1998;45(3):231-8.

Chang, JYH et al. "Periplasmic secretion of human growth hormone by *Escherichia coli*," Biochem Soc Trans. Apr. 1989;17(2):335-7.

Chapman, GE et al. "The 20,000 molecular weight variant of human growth hormone. Preparation and some physical and chemical properties," J Biol Chem. Mar. 10, 1981;256(5):2395-401.

Charman, SA et al. "Techniques for assessing the effects of pharmaceutical excipients on the aggregation of porcine growth hormone," Pharm Res. Jul. 1993;10(7):954-62.

Cheah, K-C et al. "Secretion of eukaryotic growth hormones in *Escherichia coli* is influenced by the sequence of the mature proteins," Gene. Jan. 28, 1994;138(1-2):9-15.

Chi, EY et al. "Physical stability of proteins in aqueous solution: mechanism and driving forces in nonnative protein aggregation," Pharm Res. Sep. 2003;20(9):1325-36.

Chi, EY et al. "Roles of conformational stability and colloidal stability in the aggregation of recombinant human granulocyte colony-stimulating factor," Protein Sci. May 2003;12(5):903-13.

Cholewinski, M et al. "Degradation pathways, analytical characterization and formulation strategies of a peptide and a protein. Calcitonine and human growth hormone in comparison," Pharm Acta Helv. Dec. 1996;71(6):405-19.

Clackson, T et JA Wells. "A hot spot of binding energy in a hormone-receptor interface," Science. Jan. 20, 1995;267(5196):383-6.

Chang, CN et al. "High-level secretion of human growth hormone by *Escherichia coli*" Gene 1987;55(2-3):189-96.

Chawla, RK et al. "Structural variants of human growth hormone: biochemical, genetic, and clinical aspects," Annu Rev Med. 1983;34:519-47.

Chen, C et al. "The role of receptor dimerization domain residues in growth hormone signaling," J Biol Chem. Feb. 21, 1997;272(8):5133-40.

Chiba, T et al. "Tryptophan residue of Trp-Ser-X-Trp-Ser motif in extracellular domains of erythropoietin receptor is essential for signal transduction," Biochim. Biophys. Res. Comm. (1992);184: 485-490.

Chihara, K et al. "Short stature caused by a natural growth hormone antagonist," Horm Res. 1998;49 Suppl 1:41-5.

Conte, F et al. "Identification of a region critical for proteolysis of the human growth hormone receptor," Biochem Biophys Res Commun. Jan. 18, 2002;290(2):851-7.

Cunningham, BC et JA Wells. "High-resolution epitope mapping of hGH-receptor interactions by alanine-scanning mutagenesis," Science Jun. 2, 1989;244(4908):1081-5.

Cunningham, BC et al. "Receptor and antibody epitopes in human growth hormone identified by homolog-scanning mutagenesis," Science Mar. 10, 1989;243(4896):1330-6.

Cunningham, BC and JA Wells. "Rational design of receptor-specific variants of human growth hormone," Proc Natl Acad Sci U S A. Apr. 15, 1991;88(8):3407-11.

Cunningham, BC et al. "Dimerization of the extracellular domain of the human growth hormone receptor by a single hormone molecule," Science Nov. 8, 1991;254(5033):821-5.

Cunningham, BC et JA Wells. "Comparison of a structural and a functional epitope," J. Mol Biol. Dec. 5, 1993;234(3):554-63.

Dastot, F et al. "Alternatively spliced in the cytoplasmic domain of the human growth hormone (GH) receptor regulate its ability to generate a soluble GH-binding protein," Proc Natl Acad Sci U S A. Oct. 1, 1996;93(20):10723-8.

Dattani, MT et al. "G120R, a human growth hormone antagonist, shows zinc-dependent agonist and antagonist activity on Nb2 cells," J Biol Chem. Apr. 21, 1995;270(16):9222-6.

Mott et al., "Four-helix Bundle Growth Factors and Their Receptors: Protein-Protein Interactions" Current Opinion in Structural Biology, May 1995:114-121.

Deiters et al., "Site-specific PEGylation of Proteins Containing Unnatural Amino Acids", Bioorganic & Medicinal Chemistry Letters, Dec. 6, 2004, 14(23):5743-5745.

E.A. Cornish, "Probing Protein Structure and Function with Expanded Genetic Code", Angew. Chem. Int. Ed. Eng, 1995 34:621-633.

Tondelli, L. et al. "Poly(ethylene Glycol) Imidazolyl Formates as Oligomeric Drug-Binding Matrices," J. Controlled Release 1985;1(4):251-7.

Tornoe, CW et al., "Peptidotriazoles on solid phase: [1,2,3]-triazoles by regiospecific copper(i)-catalyzed 1,3-dipolar cycloadditions of terminal alkynes to azides," J Org Chem. May 3, 2002;67(9):3057-64.

Trotter, KM and HA Wood, "Transfection techniques for producing recombinant baculoviruses," in Methods in Molecular Biology—Baculovirus Expression Protocols, vol. 39 (1995); Ed. C.D. Richardson, 97-107.

Tschumper, G. et al., "Sequence of a yeast DNA fragment containing a chromosomal replicator and the TRP1 gene," Gene 1980; 10(2):157-66.

Turcatti, G et al. "Probing the structure and function of the tachykinin neurokinin-2 receptor through biosynthetic incorporation of fluorescent amino acids at specific sites," J Biol Chem. Aug. 16, 1996;271(33):19991-8.

Van Den Berg, JA et al., "Kluyveromyces as a host for heterologous gene expression: expression and secretion of prochymosin," Biotechnology (N Y). Feb. 1990;8(2):135-9.

Van Hest, JC and DA Tirrell, "Efficient introduction of alkene functionality into proteins in vivo," FEBS Lett. May 22, 1998;428(1-2):68-70.

Debinski, W et al. "A wide range of human cancers express interleukin 4 (IL4) receptors that can be targeted with chimeric toxin composed of IL4 and Pseudomonas exotoxin," J Biol Chem. Jul. 5, 1993;268(19):14065-70.

Deiters, A., et al., "Adding Amino Acids with Novel Reactivity to the Genetic Code of *Saccharomyces cerevisiae*," J. Am. Chem. Soc. 2003; 125(39):11782-11783.

Delgado, C et al., "The uses and properties of PEG-linked proteins," Crit Rev Ther Drug Carrier Syst. 1992;9(3-4):249-304.

Dennis, MS et al., "Albumin binding as a general strategy for improving the pharmacokinetics of proteins," J Biol Chem. Sep. 20, 2002;277(38):35035-43. Epub Jul. 15, 2002.

Dolphin, CT et al., "Missense mutation in flavin-containing monooxygenase 3 gene, FMO3, underlies fish-odour syndrome," Nat Genet. Dec. 1997;17(4):491-4.

Doring, V et al., "Enlarging the amino acid set of *Escherichia coli* by infiltration of the valine coding pathway," Science. Apr. 20, 2001;292(5516):501-4.

Dougherty, DA. "Unnatural amino acids as probes of protein structure and function," Curr Opin Chem Biol. Dec. 2000;4(6):645-52.

Duewel, H et al., "Incorporation of trifluoromethionine into a phage lysozyme: implications and a new marker for use in protein 19F NMR," Biochemistry. Mar. 18, 1997;36(11):3404-16.

Eghtedarzadeh MK & S Henikoff "Use of oligonucleotides to generate large deletions" Nucleic Acids Res. Jun. 25, 1986;14(12):5115.

Elling L et MR Kula., "Immunoaffinity partitioning: synthesis and use of polyethylene glycol-oxirane for coupling to bovine serum albumin and monoclonal antibodies," Biotechnol Appl Biochem. Jun. 1991;13(3):354-62.

Elliott, S et al., "Yeast-derived recombinant human insulin-like growth factor I: production, purification, and structural characterization," J Protein Chem. Feb. 1990;9(1):95-104.

Ellman, J.A., Mendel, D., Anthony-Cahill, S., Noren, C.J., Schultz, P.G. "Biosynthetic method for introducing unnatural amino acids site-specifically into proteins," Methods in Enz., 1992; 202:301-336.

Ellman, JA, et al. "Site-specific incorporation of novel backbone structures into proteins," Science. Jan. 10, 1992;255(5041):197-200.

England, P. M., et al., "Backbone mutations in transmembrane domains of a ligand-gated ion channel: implications for the mechanism of gating," Cell. Jan. 8, 1999;96(1):89-98.

Eppstein et al., "Biological Activity of Liposome-Encapsulated Murine Interferon is Mediated by a Cell Membrane Receptor," Proc. Natl. Acad. Sci. U.S.A.(1985); 82: 3688-3692.

Fieschko, JC et al., "Controlled expression and purification of human immune interferon from high-cell-density fermentations of *Saccharomyces cerevisiae*," Biotech. Bioeng. (1987) 29(9):1113-21.

Forster, AC et al., " Programming peptidomimetic syntheses by translating genetic codes designed de novo," Proc Natl Acad Sci U S A. May 27, 2003;100(11):6353-7. Epub May 16, 2003.

Frankel, A et al., "Encodamers: unnatural peptide oligomers encoded in RNA," Chem Biol. Nov. 2003;10(11):1043-50.

Fraser, MJ et al., "Expression of eucaryotic genes in insect cell cultures," In Vitro Cell. Dev. Biol. 1989; 25:225-235.

Friedman, O.M. & R. Chatterrji. "Synthesis of Derivatives of Glutamine as Model Substrates for Anti-Tumor Agents," J. Am. Chem. Soc. 1959; 81(14):3750-3752.

Fritz HJ et al., "Oligonucleotide-directed construction of mutations: a gapped duplex DNA procedure without enzymatic reactions in vitro," Nucleic Acids Res. Jul. 25, 1988;16(14B):6987-99.

Fromm, M. et al., "Expression of Genes Transferred into Monocot and Dicot Plant Cells by Electroporation," Proc. Natl. Acad. Sci. USA (1985) 82:5824-8.

Furter, R. "Expansion of the genetic code: site-directed p-fluorophenylalanine incorporation in *Escherichia coli*," Protein Sci. Feb. 1998;7(2):419-26.

Gaertner, HF et al., "Construction of protein analogues by site-specific condensation of unprotected fragments," Bioconjug Chem. May-Jun. 1992;3(3):262-8.

Gaertner, HF et al., "Chemo-enzymic backbone engineering of proteins. Site-specific incorporation of synthetic peptides that mimic the 64-74 disulfide loop of granulocyte colony-stimulating factor," J Biol Chem. Mar. 11, 1994;269 (10):7224-30.

Gallivan, JP et al., "Site-specific incorporation of biotinylated amino acids to identify surface-exposed residues in integral membrane proteins," Chem Biol. Oct. 1997;4(10):739-49.

Gellissen, G et al., "Heterologous protein production in yeast," Antonie Van Leeuwenhoek. Aug. 1992;62(1-2):79-93.

Geoghegan, KF and JG Stroh, "Site-directed conjugation of nonpeptide groups to peptides and proteins via periodate oxidation of a 2-amino alcohol. Application to modification at N-terminal serine," Bioconjug Chem. Mar.-Apr. 1992;3(2):138-46.

Gillam, S. & M Smith, "Site-specific mutagenesis using synthetic oligodeoxyribonucleotide primers: I. Optimum conditions and minimum oligodeoxyribonucleotide length," Gene 1979; 8(1):81-97.

Gleeson, MA et al., "Transformation of the methylotrophic yeast hansenula polymorphica," J. Gen. Microbiol. (1986) 132:3459-3465.

Goeddel, DV, "Systems for heterologous gene expression," Methods Enzymol. 1990;185:3-7.

Goeddel, DV et al., "Synthesis of human fibroblast interferon by *E. coli*," Nucleic Acids Res. Sep. 25, 1980;8(18):4057-74.

Goodson RJ et NV Katre. "Site-directed pegylation of recombinant interleukin-2 at its glycosylation site," Biotechnology (N Y). Apr. 1990;8(4):343-6.

Graves, SW et al., "Expression, purification, and initial kinetic characterization of the large subunit of the human mitochondrial DNA polymerase," Biochemistry. Apr. 28, 1998;37(17):6050-8.

Griffin, BA et al., "Specific Covalent Labeling of Recombinant Protein Molecules Inside Live Cells," Science (1998) 281:269-272.

Grundström T et al., "Oligonucleotide-directed mutagenesis by microscale 'shot-gun' gene synthesis," Nucleic Acids Res. May 10, 1985;13(9):3305-16.

Guckian, KM and ET Kool, "Highly Precise Shape Mimicry by a Difluorotoluene Deoxynucleoside, a Replication-Competent Substitute for Thymidine," Angew. Chem. Int. Ed. Engl (1998) 36(24):2825-8.

Hamano-Takaku, F et al., "A mutant *Escherichia coli* tyrosyl-tRNA synthetase utilizes the unnatural amino acid azatyrosine more efficiently than tyrosine," J Biol Chem. Dec. 22, 2000;275(51):40324-8.

Hang, HC and CR Bertozzi, "Chemoselective approaches to glycoprotein assembly," Acc Chem Res. Sep. 2001;34 (9):727-36.

Harris, JM et al. "Synthesis and Characterization of Poly(ethylene Glycol) Derivatives," J. Polym. Sci. Chem. Ed. 1984; 22:341-352.

Harris, JM. "Laboratory Synthesis of Polyethylene Glycol Derivatives," JMS-Rev. Macromol. Chem. Phys. 1985;C25(3): 325-373.

Hendrickson, WA et al., "Selenomethionyl proteins produced for analysis by multiwavelength anomalous diffraction (MAD): a vehicle for direct determination of three-dimensional structure," EMBO J. May 1990;9(5):1665-72.

Henikoff, S and JG Henikoff "Amino Acid Substitution Matrices from Protein Blocks," Proc. Natl. Acad. Sci. USA 1992; 89:10915-9.

Hess, B. et al., "Cooperation of glycolytic enzymes," J. Adv. Enzyme Reg. (1969) 7:149-67.

Hinnen, A et al., "Transformation of yeast," Proc Nati Acad Sci U S A. Apr. 1978;75(4):1929-33.

Hirao, I et al., "An unnatural base pair for incorporating amino acid analogues into proteins," Nat Biotechnol. Feb. 2002;20(2):177-82.

Hitzeman, RA et al., "Isolation and characterization of the yeast 3-phosphoglycerokinase gene (PGK) by an immunological screening technique," J. Biol Chem. Dec. 25, 1980;255(24):12073-80.

Hofmann, K., et H. Bohn. "Studies on polypeptides. XXXVI. The effect of pyrazole-imidazole replacements on the S-protein activating potency of an S-peptide fragment," J. Am Chem, (1966); 88(24):5914-5919.

Hohsaka, T et al., "Efficient Incorporation of Nonnatural Amino Acids with Large Aromatic Groups into Streptavidin in in Vitro Protein Synthesizing Systems," J. Am. Chem. Soc. 1999; 121(1); 34-40.

Hohsaka, T et al., "Incorporation of Two Different Nonnatural Amino Acids Independently into a Single Protein through Extension of the Genetic Code," J. Am. Chem. Soc. 1999; 121(51):12194-12195.

Liu, H. et al. "A Method for the Generation of Glycoprotein Mimetics," J. Am. Chem. Soc. 2003 125(7): 1702-1703.

Liu, D.R. & Schultz, P.G. "Progress toward the evolution of an organism with an expanded genetic code," Proc Natl Acad Sci U S A. Apr. 27, 1999;96(9):4780-5.

Lorimer, I. A. et I. Pastan, "Random recombination of antibody single chain Fv sequences after fragmentation with DNaseI in the presence of Mn2+," Nucleic Acids Res. Aug. 11, 1995;23(15):3067-8.

Lu, T. et al. "Probing ion permeation and gating in a K +channel with backbone mutations in the selectivity filter," Nature Neurosci. Mar. 2001;4(3):239-246.

Luckow, VA and MD Summers, "High level expression of nonfused foreign genes with Autographa californica nuclear polyhedrosis virus expression vectors," Virology. May 1989;170(1):31-9.

Ma, C et al., "In vitro protein engineering using synthetic tRNA(Ala) with different anticodons," Biochemistry. Aug. 10, 1993;32(31):7939-45.

Magliery, TJ et al. "Expanding the Genetic Code: Selection of Efficient Suppressors of Four-base Codons and Identification of "Shifty" Four-base Codons with a Library Approach in *Escherichia coli*," J Mol Biol. Mar. 30, 2001;307(3):755-69.

Mahal, L. K., et al., "Engineering chemical reactivity on cell surfaces through oligosaccharide biosynthesis," Science. May 16, 1997;276(5315):1125-8.

Makrides, SC et al., "Extended in vivo half-life of human soluble complement receptor type 1 fused to a serum albumin-binding receptor," J Pharmacol Exp Ther. Apr. 1996;277(1):534-42.

Mamot, C, et al., "Epidermal growth factor receptor (EGFR)-targeted immunoliposomes mediate specific and efficient drug delivery to EGFR- and EGFRvIII-overexpressing tumor cells," Cancer Res. Jun. 15, 2003;63(12):3154-61.

Mandecki, W. Oligonucleotide-directed double-strand break repair in plasmids of *Escherichia coli*: a method for site-specific mutagenesis, Proc Natl Acad Sci U S A. Oct. 1986;83(19):7177-81.

Mann, SG and LA King, "Efficient transfection of insect cells with baculovirus DNA using electroporation," J Gen Virol. Dec. 1989;70 (Pt 12):3501-5.

Matsoukas, JM et al., "Differences in backbone structure between angiotensin II agonists and type I antagonists," J Med Chem. Nov. 10, 1995;38(23):4660-9.

McMinn, DL et al., "Efforts toward Expansion of the Genetic Alphabet: DNA Polymerase Recognition of a Highly Stable, Self-Pairing Hydrophobic Base," J. Am. Chem. Soc. 1999; 121(49):11585-6.

Meggers, E et al., "A Novel Copper-Mediated DNA Base Pair," J. Am. Chem. Soc. 2000; 122(43):10714-10715.

Mehvar, R.,"Modulation of the pharmacokinetics and pharmacodynamics of proteins by polyethylene glycol conjugation" J Pharm Pharm Sci. Jan.-Apr. 2000;3(1):125-36.

Mendel, D, et al. "Site-directed mutagenesis with an expanded genetic code," Annu Rev Biophys Biomol Struct. 1995;24:435-62.

Miller, LK, "Baculoviruses as gene expression vectors," Ann. Rev. Microbiol. 1988; 42:177-99.

Miller, LK. "Insect baculoviruses: powerful gene expression vectors," Bioessays. Oct. 1989;11(4):91-5.

Miller, JC et al. "Flash decaging of tyrosine sidechains in an ion channel," Neuron. Apr. 1998;20(4):619-24.

Minks, C. et al., Noninvasive tracing of recombinant proteins with "fluorophenylalanine-fingers," Anal Biochem. Aug. 15, 2000;284(1):29-34.

Miyanohara, A et al., "Expression of hepatitis B surface antigen gene in yeast," Proc Natl Acad Sci U S A. Jan. 1983;80(1):1-5.

Moore, B. et al., "Quadruplet codons: implications for code expansion and the specification of translation step size," J. Mol. Biol. 2000; 298(2):195-209.

Mosbach, K. et al., "Formation of proinsulin by immobilized *Bacillus subtilis*," Nature Apr. 1983; 302:543-545.

Nakamaye, KL & Eckstein F, "Inhibition of restriction endonuclease Nci I cleavage by phosphorothioate groups and its application to oligonucleotide-directed mutagenesis" Nucleic Acids Res. Dec. 22, 1986;14(24):9679-98.

Nakatsuka, T., et al. "Peptide segment coupling catalyzed by the semisynthetic enzyme thiosubtilisin," J Am Chem Soc, 1987; 109(12): 3808-3810.

Nambiar, KP et al., "Total synthesis and cloning of a gene coding for the ribonuclease S protein," Science (1984) 223: 1299-1301.

Needleman, SB and Wunsch CD, "A general method applicable to the search for similarities in the amino acid sequence of two proteins," J Mol Biol. Mar. 1970;48(3):443-53.

Neet, KE et al. "Properties of thiol-subtilisin. The consequences of converting the active serine residue to cysteine in a serine protease," J Biol Chem. Dec. 25, 1968;243(24):6392-401.

Nielsen, UB, et al., "Therapeutic efficacy of anti-ErbB2 immunoliposomes targeted by a phage antibody selected for cellular endocytosis," Biochim Biophys Acta. Aug. 19, 2002;1591(1-3):109-118.

Nomura, T. et al., "Purification, cDNA Cloning, and Expression of UDP-Gal: Glucosylceramide-1,4-Galactosyltransferase from Rat Brain," J. Biol. Chem. 1998; 273(22):13570-7.

Noren, CJ et al. "A general method for site-specific incorporation of unnatural amino acids into proteins," Science. Apr. 14, 1989;244(4901):182-8.

Nowak, MW et al., "Nicotinic receptor binding site probed with unnatural amino acid incorporation in intact cells," Science. Apr. 21, 1995;268(5209):439-42.

Ogawa, AK et al., "Efforts toward the Expansion of the Genetic Alphabet: Information Storage and Replication with Unnatural Hydrophobic Base Pairs," J. Am. Chem. Soc. 2000; 122(14):3274-3287.

Ogawa, AK et al., "Rational Design of an Unnatural Base Pair with Increased Kinetic Selectivity," J. Am. Chem. Soc. 2000; 122(36); 8803-8804.

Ohtsuka, E et al., "An alternative approach to deoxyoligonucleotides as hybridization probes by insertion of deoxyinosine at ambiguous codon positions," J Biol Chem. Mar. 10, 1985;260(5):2605-8.

Olson et al. "Preparation and Characterization of Poly(ethylene glycol)yated Human Growth Hormone Antagonist," in Poly(ethylene glycol) Chemistry & Biological Applications, 1997; Eds. JM Harris & S. Zalipsky; ACS, Washington, D.C., 170-181.

Padwa, A. "Intermolecular 1,3-Dipolar Cycloadditions," in Comprehensive Organic Synthesis, vol. 4, (1991) Ed. Trost, B. M.; Pergamon, Oxford, 1069-1109.

Palva, I et al., "Secretion of interferon by *Bacillus subtilis*," Gene. May-Jun. 1983;22(2-3):229-35.

Park, JW, et al., "Development of anti-p185HER2 immunoliposomes for cancer therapy," Proc Natl Acad Sci U S A. Feb. 28, 1995;92(5):1327-31.

Park, JW, et al., "Anti-HER2 immunoliposomes: enhanced efficacy attributable to targeted delivery," Clin Cancer Res. Apr. 2002;8(4):1172-81.

Patnaik, R. R and JR Swartz, "*E. coli*-based in vitro transcription/translation: in vivo-specific synthesis rates and high yields in a batch system," Biotechniques. May 1998;24(5):862-8.

Pearson, WR and DJ Lipman, "Improved tools for biological sequence comparison," Proc Natl Acad Sci U S A. Apr. 1988;85(8):2444-8.

Pepinsky, RB., et al., "Improved pharmacokinetic properties of a polyethylene glycol-modified form of interferon-beta-1a with preserved in vitro bioactivity," J Pharmacol Exp Ther. Jun. 2001;297(3):1059-66.

Piccirilli, JA et al., "Enzymatic incorporation of a new base pair into DNA and RNA extends the genetic alphabet," Nature 1990; 343:33-37.

Pintar, A et al. "CX, an algorithm that identifies protruding atoms in proteins," Bioinformatics. Jul. 2002;18(7):980-4.

Pitha, J et al. "Detergents linked to polysaccharides: preparation and effects on membranes and cells," Eur J Biochem. Feb. 15, 1979;94(1):11-8.

Polgar, L. and ML Bender. "A new enzyme containing a synthetically formed active site. Thiol-subtilisin." J. Am Chem Soc., 1966; 88(13): 3153-3154.

Pollack, SJ et al. "Introduction of nucleophiles and spectroscopic probes into antibody combining sites," Science. Nov. 18, 1988;242(4881):1038-40.

Preneta, AZ. "Separation on the basis of size: gel permeation chromatography," in Protein Purification Methods, a practical approach, 1989; Eds. Harris & Angal; IRL Press, Oxford; 293-306.

Holland, MJ et JP Holland., "Isolation and identification of yeast messenger ribonucleic acids coding for enolase, glyceraldehyde-3-phosphate dehydrogenase, and phosphoglycerate kinase," Biochemistry. Nov. 14, 1978;17(23):4900-7.

Holland, MJ et al., "The primary structures of two yeast enolase genes. Homology between the 5' noncoding flanking regions of yeast enolase and glyceraldehyde-3-phosphate dehydrogenase genes," J Biol Chem. Feb. 10, 1981;256(3):1385-95.

Hsiao, CL et J Carbon, "High-frequency transformation of yeast by plasmids containing the cloned yeast ARG4 gene," Proc Natl Acad Sci U S A. Aug. 1979;76(8):3829-33.

Huisgen, R. in 1,3-Dipolar Cycloaddition Chemistry, vol. 1, 1984; Ed. Padwa A.; John Wiley and Sons, New York, p. 1-176.

Hwang, KJ et al., "Hepatic uptake and degradation of unilamellar sphingomyelin/cholesterol liposomes: a kinetic study," Proc Natl Acad Sci U S A. Jul. 1980;77(7):4030-4.

Ibba, M et al., "Substrate specificity is determined by amino acid binding pocket size in *Escherichia coli* phenylalanyl-tRNA synthetase," Biochemistry. Jun. 14, 1994;33(23):7107-12.

Ibba, M and H Hennecke, "Relaxing the substrate specificity of an aminoacyl-tRNA synthetase allows in vitro and in vivo synthesis of proteins containing unnatural amino acids," FEBS Lett. May 15, 1995;364(3):272-5.

Ito, H. et al., "Transformation of intact yeast cells treated with alkali cations," J. Bacteriol. 1983; 153(1):163-8.

Jackson, DY et al. "A designed peptide ligase for total synthesis of ribonuclease A with unnatural catalytic residues," Science. Oct. 14, 1994;266(5183):243-7.

Jakobsson, PJ et al., "Identification and characterization of a novel human microsomal glutathione S-transferase with leukotriene C4 synthase activity and significant sequence identity to 5-lipoxygenase-activating protein and leukotriene C4 synthase," J Biol Chem. Sep. 6, 1996;271(36):22203-10.

Jencks, W.P., "Studies on the Mechanism of Oxime and Semicarbazone Formation," J. Am. Chem. Soc.; 1959; 81(2):475-481.

Joppich, M. et al. "Peptides Flanked by Two Polymer Chains, 1; Synthesis of Glycyl-L-tryptophylglycine Substituted by Poly(ethylene oxide) at both the Carboxy and the Amino End Groups," Makromol. Chem. 1979;180:1381-4.

Kaiser, ET. "Synthetic approaches to biologically active peptides and proteins including enzymes," Acc Chem Res, (1989); 22(2):47-54.

Kaiser, ET et al. "The chemical modification of enzymatic specificity," Annu Rev Biochem. 1985;54:565-95.

Kaiser, ET and DS Lawrence. "Chemical mutation of enzyme active sites," Science. Nov. 2, 1984;226(4674):505-11.

Karlin, S and SF Altschul "Applications and statistics for multiple high-scoring segments in molecular sequences," Proc Natl Acad Sci U S A. Jun. 15, 1993;90(12):5873-7.

Kayser, B., et al., "Alkyne bridged alpha-amino acids by palladium mediated coupling of alkynes with N-t-Boc-4-iodo-phenylalanine methyl ester," Tetrahedron (1997); 53(7): 2475-2484.

Kelly, JM and MJ Hynes, "Transformation of *Aspergillus niger* by the amdS gene of *Aspergillus nidulans*," EMBO J. 1985; 4(2):475-479.

Kiick, K. L. and D. A. Tirrell, "Protein Engineering by in Vivo Incorporation of Non-Natural Amino Acids: Control of Incorporation of Methionine Analogues by Methionyl-tRNA Synthetase," Tetrahedron (2000), 56:9487-9493.

Kiick, KL et al., "Incorporation of azides into recombinant proteins for chemoselective modification by the Staudinger ligation," Proc Natl Acad Sci U S A. Jan. 8, 2002;99(1):19-24. Epub Dec. 18, 2001.

Kim, DM and JR Swartz, "Regeneration of adenosine triphosphate from glycolytic intermediates for cell-free protein synthesis," Biotechnol Bioeng. Aug. 20, 2001;74(4):309-16.

Kim, DM and JR Swartz, "Oxalate improves protein synthesis by enhancing ATP supply in a cell-free system derived from *Escherichia coli*," Biotechnology Letters, 2000; 22:1537-1542.

Kim, DM, and JR Swartz, "Prolonging cell-free protein synthesis by selective reagent additions," Biotechnol Prog. May-Jun. 2000;16(3):385-90.

Kim, DM, and JR Swartz, "Prolonging cell-free protein synthesis with a novel ATP regeneration system," Biotechnol Bioeng. 1999;66(3):180-8.

King, F.E. & Kidd, D.A.A. "A New Synthesis of Glutamine and of gamma-Dipeptides of Glutamic Acid from Phthylated Intermediates," J. Chem. Soc. 1949; 3315-3319.

Kingsman, AJ et al., "Replication in *Saccharomyces cerevisiae* of plasmid pBR313 carrying DNA from the yeast trpl region," Gene. Oct. 1979;7(2):141-52.

Kitts, PA et al. "Linearization of baculovirus DNA enhances the recovery of recombinant virus expression vectors," Nucleic Acids Res. Oct. 11, 1990;18(19):5667-72.

Klein, TM et al., "High-velocity microprojectiles for delivering nucleic acids into living cells," Nature 1987; 327(6117):70-73.

Kobayashi, T. et al., "Structural basis for orthogonal tRNA specificities of tyrosyl-tRNA synthetases for genetic code expansion," Nature Structural Biology (2003); 10(6):425-432.

Kogan, TP. "The synthesis of substituted methoxy-poly(ethyleneglycol) derivatives suitable for selective protein modification," Synthetic Comm. 1992; 22(16):2417-24.

Kool, ET. "Synthetically modified DNAs as substrates for polymerases," Curr Opin Chem Biol. Dec. 2000;4(6):602-8.

Koskinen, A.M.P. & Rapoport, H. "Synthesis of 4-Substituted Prolines as Conformationally Constrained Amino Acid Analogues," J. Org. Chem. (1989) 54(8):1859-1866.

Kost, TA et al., "Production of a urokinase plasminogen activator-IgG fusion protein (uPA-IgG) in the baculovirus expression system," Gene. Apr. 29, 1997;190(1):139-44.

Kramer, W et al., "The gapped duplex DNA approach to oligonucleotide-directed mutation construction," Nucleic Acids Res. Dec. 21, 1984;12(24):9441-56.

Kramer, W & Fritz HJ. "Oligonucleotide-directed construction of mutations via gapped duplex DNA" Methods Enzymol. 1987;154:350-67.

Kramer, W. et al., "Improved enzymatic in vitro reactions in the gapped duplex DNA approach to oligonucleotide-directed construction of mutations," Nucleic Acids Res. Jul. 25, 1988;16(14B):7207.

Kramer, B. et al., "Different base/base mismatches are corrected with different efficiencies by the methyl-directed DNA mismatch-repair system of *E. coli*," Cell. Oct. 1984;38(3):879-87.

Kreitman, RJ and I. Pastan "Purification and characterization of IL6-PE4E, a recombinant fusion of interleukin 6 with Pseudomonas exotoxin," Bioconjug Chem. Nov.-Dec. 1993;4(6):581-5.

Krieg, UC, et al. "Photocrosslinking of the signal sequence of nascent preprolactin to the 54-kilodalton polypeptide of the signal recognition particle," Proc Natl Acad Sci U S A. Nov. 1986;83(22):8604-8.

Kunitani, M. et al., "Reversed-phase chromatography of interleukin-2 muteins," J Chromatogr. May 30, 1986;359:391-402.

Kunkel, "The efficiency of oligonucleotide directed mutagenesis," in Nucleic Acids & Molecular Biology 1987; Eckstein, F. and Lilley, D.M.J. eds.; Springer Verlag, Berlin; 124-135.

Kunkel, TA "Rapid and efficient site-specific mutagenesis without phenotypic selection," Proc Natl Acad Sci U S A. Jan. 1985;82(2):488-92.

Kunkel, TA et al., "Rapid and efficient site-specific mutagenesis without phenotypic selection," Methods Enzymol. 1987;154:367-82.

Kunze, G et al., "Transformation of the industrially important yeasts Candida maltosa and Pichia guilliermondii," J. Basic Microbiol. 1985; 25:141-4.

Kurtz et al., "Integrative transformation of Candida albicans, using a cloned Candida ADE2 gene," Mol Cell Biol. Jan. 1986;6(1):142-9.

Kurtzhals, P et al., "Albumin binding of insulins acylated with fatty acids: characterization of the ligand-protein interaction and correlation between binding affinity and timing of the insulin effect in vivo," Biochem J. Dec. 15, 1995;312( Pt 3):725-31.

Langer, R et al., "Biocompatibility of polymeric delivery systems for macromolecules," J Biomed Mater Res. Mar. 1981;15(2):267-77.

Langer, R. "Controlled release of macromolecules," Chem. Tech. 1982; 12: 98-105.

Liebman, JM et al., "When less is more: enhanced baculovirus production of recombinant proteins at very low multiplicities of infection," Biotechniques. Jan. 1999;26(1):36-8, 40, 42.

Ling, MM et al BH Robinson, "Approaches to DNA mutagenesis: an overview" Anal Biochem. Dec. 15, 1997;254(2):157-78.

Van Hest, J. C. et al., "Efficient Incorporation of Unsaturated Methionine Analogues into Proteins in Vivo," J. Am. Chem. Soc.2000 ;122 (7); 1282-1288.

Van Solingen, P. et JB van der Plaat. "Fusion of yeast spheroplasts," J Bacteriol. May 1977;130(2):946-7.

Veronese, FM et al., "Surface modification of proteins. Activation of monomethoxy-polyethylene glycols by phenylchloroformates and modification of ribonuclease and superoxide dismutase," Appl Biochem Biotechnol. Apr. 1985;11(2):141-52.

Vlak, JM et al., "Functional studies on the p10 gene of Autographa californica nuclear polyhedrosis virus using a recombinant expressing a p10-beta-galactosidase fusion gene," J Gen Virol. Apr. 1988;69 (Pt 4):765-76.

Wang, Q., et al., "Bioconjugation by Copper(I)-Catalyzed Azide-Alkyne [3+2] Cycloaddition," J. Am. Chem. Soc. 2003; 125(11):3192-3193.

Wang, L. et al., "Addition of the keto functional group to the genetic code of Escherichia coli," Proc. Natl. Acad. Sci. (2003); 100(1):56-61.

Wang, L et al., "Expanding the genetic code of Escherichia coli," Science. Apr. 20, 2001;292(5516):498-500.

Raibaud, O et M Schwartz. "Positive control of transcription initiation in bacteria," Annu Rev Genet. 1984;18:173-206.

Reverey, H. et al., "Differential Fatty Acid Selection during Biosynthetic S-Acylation of a Transmembrane Protein (HEF) and Other Proteins in Insect Cells (Sf9) and in Mammalian Cells (CV1)," J. Biol. Chem. 1996; 271(39):23607-10.

Rivier, J et R McClintock, "Reversed-phase high-performance liquid chromatography of insulins from different species," J Chromatogr. Sep. 23, 1983;268(1):112-9.

Roberts, et al., "Generation of an antibody with enhanced affinity and specificity for its antigen by protein engineering," Nature 1987;328:731-734.

Roberts, RW and JW Szostak, "RNA-peptide fusions for the in vitro selection of peptides and proteins," Proc Natl Acad Sci U S A. Nov. 11, 1997;94(23):12297-302.

Roggenkamp, R. et al., "Transformation of the methylotrophic yeast Hansenula polymorpha by autonomous replication and integration vectors," MOL. Genetics and Genomics 1986;202(2):302-8.

Romani et al. "Synthesis of unsymmetrical cystine peptides: directed disulfide pairing with the sulfenohydrazide method," in Chemistry of Peptides and Proteins 1984; eds. Voelter, W. et al.; Walter de Gruyter et al., Berlin; vol. 2:29-33.

Romanos, MA et al., "Foreign gene expression in yeast: a review," Yeast. Jun. 1992;8(6):423-88.

Rosenthal, GA. "L-canaline: a potent antimetabolite and anti-cancer agent from leguminous plants," Life Sci.1997;60(19):1635-41.

Rossolini, GM et al., "Use of deoxyinosine-containing primers vs degenerate primers for polymerase chain reaction based on ambiguous sequence information," Mol. Cell. Probes 1994; 8:91-98.

Rostovtsev, VV et al., "A stepwise huisgen cycloaddition process: copper(I)-catalyzed regioselective "ligation" of azides and terminal alkynes," Angew Chem Int Ed Engl Jul. 15, 2002;41(14):2596-9.

Rowles, J et al., "Cloning and characterization of PDK4 on 7q21.3 encoding a fourth pyruvate dehydrogenase kinase isoenzyme in human," J Biol Chem. Sep. 13, 1996;271(37):22376-82.

Sakmar, TP and Khorana HG, "Total synthesis and expression of a gene for the alpha-subunit of bovine rod outer segment guanine nucleotide-binding protein (transducin)" Nucleic Acids Res. Jul. 25, 1988;16(14A):6361-72.

Sandler and Karo, "Polyoxyalkylation of hydroxyl compounds," in Polymer Synthesis, vol. 3, 1980; Academic Press, New York, 138-161.

Sartore, L et al., "Enzyme modification by MPEG with an amino acid or peptide as spacer arms," Appl Biochem Biotechnol. Jan. 1991;27(1):45-54.

Sawhney, AS et al., "Bioerodible Hydrogels Based on Photopolymerized Poly(ethylene glycol)-co-poly(alpha-hydroxy acid) Diacrylate Macromers," Macromolecules 1993; 26(4):581-7.

Saxon, E and C. Bertozzi, "Cell Surface Engineering by a Modified Staudinger Reaction," Science (2000); 287 (5460):2007-2010.

Sayers, Jr et al., "Strand specific cleavage of phosphorothioate-containing DNA by reaction with restriction endonucleases in the presence of ethidium bromide" Nucleic Acids Res. Feb. 11, 1988;16(3):803-14.

Sayers, Jr, et al. "5'-3' exonucleases in phosphorothioate-based oligonucleotide-directed mutagenesis," Nucleic Acids Res. Feb. 11, 1988;16(3):791-802.

Schanbacher, FL et al. "Galactosyltransferase Acceptor Specificity of the Lactose Synthetase a Protein," J. Biol. Chem. 1970; 245(19):5057-5061.

Schmidt, M et al., "Baculovirus-mediated large-scale expression and purification of a polyhistidine-tagged rubella virus capsid protein," Protein Expr Purif. Apr. 1998;12(3):323-30.

Schneider, E., et al., "Functional Purification of a Bacterial ATP-Binding Cassette Transporter Protein (MaIK) from the Cytoplasmic Fraction of an Overproducing Strain," Protein Expr. Purif. 1995; 6(1):10-14.

Schnolzer, M. and SBH Kent. "Constructing proteins by dovetailing unprotected synthetic peptides: backbone-engineered HIV protease," Science. Apr. 10, 1992;256(5054):221-5.

Scouten, WH. "A survey of enzyme coupling techniques," Methods Enzymol. 1987;135:30-65.

Shao, J and JP Tam, "Unprotected Peptides as Building Blocks for the Synthesis of Peptide Dendrimers with Oxime, Hydrazone, and Thiazolidine Linkages," J. Am. Chem. Soc. 1995; 117(14):3893-3899.

Sharma, N. et al., "Efficient introduction of aryl bromide functionality into proteins in vivo," FEBS Lett. Feb. 4, 2000;467(1):37-40.

Shimatake, H et M Rosenberg, "Purified gamma regulatory protein cII positively activates promoters for lysogenic development," Nature Jul. 1981; 292:128-132.

Shine, J and L Dalgarno, "Determinant of cistron specificity in bacterial ribosomes," Nature. Mar. 6, 1975;254(5495):34-8.

Sidman, KR et al., "Controlled release of macromolecules and pharmaceuticals from synthetic polypeptides based on glutamic acid," Biopolymers. Jan. 1983;22(1):547-56.

Sieber, V. et al., "Libraries of hybrid proteins from distantly related sequences," Nature Biotechnology, May 2001;19:456-460.

Siffert, W et al., "Association of a human G-protein beta3 subunit variant with hypertension," Nat Genet. Jan. 1998;18(1):45-8.

Sikorski, RS et al., "A System of Shuttle Vectors and Yeast Host Strains Designed for Efficient Manipulation of DNA in Saccharomyces cerevisiae," Genetics (1989) 122:19-27.

Sisk, WP et al., "High-level expression and purification of secreted forms of herpes simplex virus type 1 glycoprotein gD synthesized by baculovirus-infected insect cells," J Virol. Feb. 1994;68(2):766-75.

Sjolander, A et al., "The serum albumin-binding region of streptococcal protein G: a bacterial fusion partner with carrier-related properties," J Immunol Methods. Feb. 14, 1997;201(1):115-23.

Smith, M. "In vitro mutagenesis" Ann. Rev. Genet. 1985; 19:423-462.

Smith, GE et al., "Production of human beta interferon in insect cells infected with a baculovirus expression vector," Mol Cell Biol. Dec. 1983;3(12):2156-65.

Stanley, SL et al., "The serine-rich Entamoeba histolytica protein is a phosphorylated membrane protein containing O-linked terminal N-acetylglucosamine residues," J Biol Chem. Feb. 24, 1995;270(8):4121-6.

Steitz, JA et al. "Genetic signals and nucleotide sequences in messenger RNA," in Biological Regulation and Development: Gene Expression 1979; ed. R. F. Goldberger; Plenum Press, New York; 349-399.

Stemmer, WPC, "Rapid evolution of a protein in vitro by DNA shuffling," Nature 1994;370(4):389-391.

Stemmer, WP "DNA shuffling by random fragmentation and reassembly: In vitro recombination for molecular evolution," Proc Natl Acad Sci U S A. Oct. 25, 1994;91(22):10747-51.

Studier, FW et BA Moffatt, "Use of bacteriophage T7 RNA polymerase to direct selective high-level expression of cloned genes," J. Mol Biol. May 5, 1986;189(1):113-30.

Subasinghe, N. et al., "Quisqualic acid analogues: synthesis of beta-heterocyclic 2-aminopropanoic acid derivatives and their activity at a novel quisqualate-sensitized site," J Med Chem. Nov. 27, 1992;35(24):4602-7.

Switzer, C et al., "Enzymatic incorporation of a new base pair into DNA and RNA," J. Am. Chem. Soc. 1989; 111(21):8322-8323.

Tabor, S et CC Richardson, "A bacteriophage T7 RNA polymerase/ promoter system for controlled exclusive expression of specific genes," Proc Natl Acad Sci U S A. Feb. 1985;82(4):1074-8.

Tae, EL et al., "Efforts toward Expansion of the Genetic Alphabet: Replication of DNA with Three Base Pairs," J. Am. Chem. Soc. 2001; 123(30):7439-7440.

Tang, Y et al., "Fluorinated Coiled-Coil Proteins Prepared in Vivo Display Enhanced Thermal and Chemical Stability," Angew Chem Int Ed Engl. Apr. 17, 2001;40(8):1494-1496.

Taylor, JW et al., "The use of phosphorothioate-modified DNA in restriction enzyme reactions to prepare nicked DNA," Nucleic Acids Res. Dec. 20, 1985;13(24):8749-64.

Taylor, JW et al., "The rapid generation of oligonucleotide-directed mutations at high frequency using phosphorothioate-modified DNA," Nucleic Acids Res. Dec. 20, 1985;13(24):8765-85.

Tijssen, P. "Overview of principles of hybridization and the strategy of nucleic acid assays," in Laboratory Techniques in Biochemistry and Molecular Biology—Hybridization with Nucleic Probes, Part I, 1993; Elsevier Science Publishers, Amsterdam, 19-78.

Tilburn, J. et al., "Transformation by integration in Aspergillus nidulans," Gene. Dec. 1983;26(2-3):205-21.

Yelton, MM et al., "Transformation of Aspergillus nidulans by using a trpC plasmid," Proc Natl Acad Sci U S A. Mar. 1984;81(5):1470-4.

Yelverton, E et al., "Bacterial synthesis of a novel human leukocyte interferon," Nucleic Acids Res. Feb. 11, 1981;9(3):731-41.

Zalipsky, S et al. "Attachment of drugs to polyethylene glycols," Eur. Polymer Journal. 1983 19(12):1177-83.

Zalipsky, S. "Functionalized poly(ethylene glycol) for preparation of biologically relevant conjugates," Bioconjug Chem. Mar.-Apr. 1995;6(2):150-65.

Zhang, Z., et al. "A new strategy for the site-specific modification of proteins in vivo," Biochemistry. Jun. 10, 2003;42(22):6735-46.

Zoller, MJ & M Smith, "Oligonucleotide-directed mutagenesis using M13-derived vectors: an efficient and general procedure for the production of point mutations in any fragment of DNA" Nucleic Acids Res. Oct. 25, 1982;10(20):6487-500.

Zoller, MJ & M. Smith, "Oligonucleotide-directed mutagenesis of DNA fragments cloned into M13 vectors" Methods Enzymol. 1983;100:468-500.

Wang, L & PG Schultz, "Expanding the genetic code," Chem Commun (Camb). Jan. 7, 2002;1:1-11.

Weissmann, C. "The cloning of interferon and other mistakes." in Interferon Mar. 1981; ed. I. Gresser; Academic Press, London, 101-134.

Wells, JA et al., "Importance of hydrogen-bond formation in stabilizing the transition state of subtilisin," Phil. Trans. R. Soc. Lond. A 1986; 317: 415-423.

Wells, JA et al., "Cassette mutagenesis: an efficient method for generation of multiple mutations at defined sites," Gene. 1985;34(2-3):315-23.

Woghiren, C et al. "Protected thiol-polyethylene glycol: a new activated polymer for reversible protein modification," Bioconjug Chem. Sep.-Oct. 1993;4(5):314-8.

Wong, SS et LJ Wong, "Chemical crosslinking and the stabilization of proteins and enzymes," Enzyme Microb Technol. Nov. 1992;14(11):866-74.

Wright, K. "Biotechnology: Insect virus as super-vector?," Nature (1986) 321(6072):718.

Duncan, R. "The dawning era of polymer therapeutics," Nat Rev Drug Discov May 2003;2(5):347-60.

Gaertner, HF et RE Offord. "Site-specific attachment of functionalized poly(ethylene glycol) to the amino terminus of proteins," Bioconjug Chem Jan.-Feb. 1996;7(1):38-44.

Gu, Z et al. "Chromatographic methods for the isolation of, and refolding of proteins from, Escherichia coli inclusion bodies," Protein Expr Purif. Jun. 2002;25(1):174-9.

Hohsaka, T et M Sisido. "Incorporation of non-natural amino acids into proteins," Curr Opin Chem Biol. Dec. 2002;6(6):809-15.

Lilie, H et al. "Advances in refolding of proteins produced in E. coli," Curr Opin Biotechnol. Oct. 1998;9(5):497-501.

Tsumoto, K et al. "Practical considerations in refolding proteins from inclusion bodies," Protein Expr Purif. Mar. 2003;28(1):1-8.

Wang, W. "Instability, stabilization, and formulation of liquid protein pharmaceuticals," Int J Pharm. Aug. 20, 1999;185(2):129-88.

Zoller, MJ & Smith M, "Oligonucleotide-directed mutagenesis: a simple method using two oligonucleotide primers and a single-stranded DNA template," Methods Enzymol. 1987;154:329-50.

Mehl, RA et al. "Generation of a bacterium with a 21 amino acid genetic code," J Am Chem Soc. Jan. 29, 2003;125(4):935-9.

Santoro, SW et al. "An efficient system for the evolution of aminoacyl-tRNA synthetase specificity," Nat Biotechnol. Oct. 2002;20(10):1044-8. Epub Sep. 16, 2002.

Caliceti, P et FM Veronese. "Pharmacokinetic and biodistribution properties of poly(ethylene glycol)-protein conjugates," Adv Drug Deliv Rev. Sep. 26, 2003;55(10):1261-77.

Clark, EDB, "Refolding of recombinant proteins," Curr Opin Biotechnol Apr. 1, 1998;9(2):157-63.

Clark, EDB, "Protein refolding for industrial processes," Curr Opin Biotechnol Apr. 2001;12(2):202-7.

Davis, GD et al., "New fusion protein systems designed to give soluble expression in Escherichia coli," Biotechnol Bioeng Nov. 20, 1999;65(4):382-8.

Abuchowski, A. et al. "Cancer therapy with chemically modified enzymes. I. Antitumor properties of polyethylene glycol-asparaginase conjugates," Cancer Biochem Biophys. Jun. 1984;7(2):175-86.

Altschul, SF et al. "Gapped BLAST and PSI-BLAST: a new generation of protein database search programs," Nucleic Acids Res. Sep. 1, 1997;25(17):3389-402.

Altschul, SF et al. "Basic local alignment search tool," J Mol Biol. Oct. 5, 1990;215(3):403-10.

Amann, E et al., "Vectors bearing a hybrid trp-lac promoter useful for regulated expression of cloned genes in Escherichia coli," Gene. Nov. 1983;25(2-3):167-78.

Anderson, JC et al., "Exploring the limits of codon and anticodon size," Chem Biol. Feb. 2002;9(2):237-44.

Andresz, H et al. Abstract of "Chemische Synthese verzweigter Polysaccharide, 5; Kopplung von Oligosacchariden und Amylose an verschiedene Träger durch Hydrazonbindung," Makromol. Chem. 1978;179:301 Abstract.

Arnold, FH. "Protein engineering for unusual environments," Curr Opin Biotechnol. Aug. 1993;4(4):450-5.

Azoulay, M., et al. "Glutamine analogues as Potential Antimalarials," Eur. J. Med. Chem. (1991); 26(2):201-5.

Bain, JD, et al. "Biosynthetic site-specific incorporation of a non-natural amino acid into a polypeptide," J. Am Chem Soc 1989;111(20):8013-8014.

Ballance, DJ et al., "Transformation of Aspergillus nidulans by the orotidine-5'-phosphate decarboxylase gene of Neurospora crassa," Biochem Biophys Res Commun. Apr. 15, 1983;112(1):284-9.

Barany, F. et al., "Genetic disease detection and DNA amplification using cloned thermostable ligase," Proc Natl Acad Sci U S A. Jan. 1, 1991;88(1):189-93.

Barton, DHR et al., "Synthesis of Novel alpha-Amino-Acids and Derivatives Using Radical Chemistry: Synthesis of L- and D-alpha-Amino-Adipic Acids, L-alpha-aminopimelic Acid and Appropriate Unsaturated Derivatives," Tetrahedron (1987) 43:4297-4308.

Bass, S et al., "Mutant Trp repressors with new DNA-binding specificities," Science (1988) 242:240-245.

Batzer, MA et al., "Enhanced evolutionary PCR using oligonucleotides with inosine at the 3'-terminus," Nucleic Acids Res. Sep. 25, 1991;19(18):5081.

Beach, D et al., "Functionally homologous cell cycle control genes in budding and fission yeast," Nature Dec. 1982; 300:706-709.

Beauchamp, CO et al., "A new procedure for the synthesis of polyethylene glycol-protein adducts; effects on function, receptor recognition, and clearance of superoxide dismutase, lactoferrin, and alpha 2-macroglobulin," Anal Biochem. May 1983;131(1):25-33.

Bernstein, FC, et al. "The protein data bank: a computer-based archival file for macromolecular structures," J. Mol. Biol. 1977; 112:535-542.

Boissel, JP et al., "Erythropoietin structure-function relationships. Mutant proteins that test a model of tertiary structure," J Biol Chem. Jul. 25, 1993;268(21):15983-93.

Boles, JO et al. "Bio-incorporation of telluromethionine into buried residues of dihydrofolate reductase," Nat Struct Biol. May 1994;1(5):283-4.

Botstein, D et D Shortle, "Strategies and applications of in vitro mutagenesis," Science. Sep. 20, 1985;229(4719):1193-201.

Brunner, J. "New photolabeling and crosslinking methods," Annu Rev Biochem. 1993;62:483-514.

Buchner, J. et al., "A method for increasing the yield of properly folded recombinant fusion proteins: Single-chain immunotoxins from renaturation of bacterial inclusion bodies," Anal. Biochem. 1992; 205(2): 263-270.

Bückmann et al. "Functionalization of Poly(ethylene glycol) and Monomethoxy-Poly(ethylene glycol),"Makromol. Chem. 1981;182:1379-84.

Budisa, N et al. "High-level biosynthetic substitution of methionine in proteins by its analogs 2-aminohexanoic acid, selenomethionine, telluromethionine and ethionine in *Escherichia coli*," Eur J Biochem. Jun. 1, 1995;230(2):788-96.

Budisa, N et al., "Bioincorporation of telluromethionine into proteins: a promising new approach for X-ray structure analysis of proteins," J Mol Biol. Jul. 25, 1997;270(4):616-23.

Budisa, N et al., "Toward the experimental codon reassignment in vivo: protein building with an expanded amino acid repertoire," FASEB J. Jan. 1999;13(1):41-51.

Cai, X-Y et al., "Expression, Purification, and Characterization of an Activated Cytokine-Suppressive Anti-inflammatory Drug-Binding Protein 2 (CSBP2) Kinase from Baculovirus-Infected Insect Cells," Protein Expression and Purification 1997; 10(2):263-74.

Carbonell, LF et al., "Baculovirus-mediated expression of bacterial genes in dipteran and mammalian cells," J Virol. Oct. 1985;56(1):153-60.

Carrasco, M. and R. Brown, "A Versatile Set of Aminooxy Amino Acids for the Synthesis of Neoglycopeptides," J. Org. Chem. (2003); 68(23): 8853-8858.

Carter, P. "Site-directed mutagenesis," Biochem J. Jul. 1, 1986; 237(1):1-7.

Carter, P et al. "Improved oligonucleotide site-directed mutagenesis using M13 vectors" Nucleic Acids Res. Jun. 25, 1985;13(12):4431-43.

Carter, P. "Improved oligonucleotide-directed mutagenesis using M13 vectors" Methods Enzymol. 1987;154:382-403.

Chaiken, IM. "Semisynthetic peptides and proteins," CRC Crit Rev Biochem. 1981;11(3):255-301.

Chin, JW et al., "Addition of p-azido-L-phenylalanine to the genetic code of *E. coli*," J Am Chem Soc. Aug. 7, 2002;124(31):9026-7.

Chin, JW et al., "Addition of a photocrosslinking amino acid to the genetic code of *Escherichia coli*," Proc Natl Acad Sci U S A. Aug. 20, 2002;99(17):11020-4. Epub Aug. 1, 2002.

Chin, JW et al., "An expanded eukaryotic genetic code," Science. Aug. 15, 2003;301(5635):964-7.

Chin, JW & P. G. Schultz, "In vivo photocrosslinking with unnatural amino acid mutagenesis," Chembiochem. Nov. 4, 2002; 3(11): 1135-7.

Christie, B.D. & Rapoport, H. "Synthesis of Optically Pure Pipecolates from L-Asparagine. Application to the Total Synthesis of (+)-Apovincamine through Amino Acid Decarbonylation and Iminium Ion Cyclization," J. Org. Chem. 1985;50(8):1239-1246.

Clark, R et al., "Long-acting growth hormones produced by conjugation with polyethylene glycol," J Biol Chem. Sep. 6, 1996;271(36):21969-77.

Corey, D.R., Schultz, P.G. "Generation of a hybrid sequence-specific single-stranded deoxyribonuclease," Science 1987; 238(4832):1401-1403.

Cornish, VW, et al., "Site-Specific Protein Modification Using a Ketone Handle," J. Am. Chem. Soc. 1996; 118(34):8150-8151.

Cornish, VW et al., "Probing Protein Structure and Function with an Expanded Genetic Code,"Angew Chem Int Ed Engl,1995;34(6):621-33.

Craig, J.C. et al. "Absolute Configuration of the Enantiomers of 7-Chloro-4 [[4-(diethylamino)-1-methylbutyl]amino] quinoline (Chloroquine)," J. Org. Chem. 1988; 53(6):1167-1170.

Cregg, JM et al., "Pichia pastoris as a host system for transformations," Mol Cell Biol. Dec. 1985;5(12):3376-85.

Crick, FHC, et al. "General nature of the genetic code for proteins," Nature. Dec. 30, 1961;192:1227-32.

Dale et al., Oligonucleotide-directed random mutagenesis using the phosphorothioate method, Methods Mol. Biol.1996;57:369-374.

Das, S et al., "Transformation of Kluyveromyces fragilis," J Bacteriol. Jun. 1984;158(3):1165-7.

Dawson, P. E. and S. B. H. Kent, "Synthesis of native proteins by chemical ligation," Annu. Rev. Biochem. 2000;69:923-60.

De Boer, Ha et al., "The tac promoter: a functional hybrid derived from the trp and lac promoters," Proc Natl Acad Sci U S A. Jan. 1983;80(1):21-5.

De Louvencourt, L et al., "Transformation of Kluyveromyces lactis by killer plasmid DNA," J Bacteriol. May 1983;154(2):737-42.

\* cited by examiner hGH Periplasmic Release vs. Homogenization

A. Periplasmic Release

B. Lysis by Microfluidizer linear, 30 kDa monomethoxy-poly(ethylene glycol)-2-aminooxy ethylamine carbamate hydrochloride

SEQUENCE LISTING

```
<160> NUMBER OF SEQ ID NOS: 3

<210> SEQ ID NO 1
<211> LENGTH: 217
<212> TYPE: PRT
<213> ORGANISM: Homo sapiens

<400> SEQUENCE: 1

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60
```

```
Glu Gln Lys Tyr Ser Phe Leu Gln Asn Pro Gln Thr Ser Leu Cys Phe
 65                  70                  75                  80

Ser Glu Ser Ile Pro Thr Pro Ser Asn Arg Glu Glu Thr Gln Gln Lys
                 85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe
    210                 215

<210> SEQ ID NO 2
<211> LENGTH: 191
<212> TYPE: PRT
<213> ORGANISM: Homo sapiens

<400> SEQUENCE: 2

Phe Pro Thr Ile Pro Leu Ser Arg Leu Phe Asp Asn Ala Met Leu Arg
 1               5                  10                  15

Ala His Arg Leu His Gln Leu Ala Phe Asp Thr Tyr Gln Glu Phe Glu
             20                  25                  30

Glu Ala Tyr Ile Pro Lys Glu Gln Lys Tyr Ser Phe Leu Gln Asn Pro
         35                  40                  45

Gln Thr Ser Leu Cys Phe Ser Glu Ser Ile Pro Thr Pro Ser Asn Arg
     50                  55                  60

Glu Glu Thr Gln Gln Lys Ser Asn Leu Glu Leu Leu Arg Ile Ser Leu
 65                  70                  75                  80

Leu Leu Ile Gln Ser Trp Leu Glu Pro Val Gln Phe Leu Arg Ser Val
                 85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190

<210> SEQ ID NO 3
<211> LENGTH: 176
<212> TYPE: PRT
<213> ORGANISM: Homo sapiens
```

```
<400> SEQUENCE: 3

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Asn
            20                  25                  30

Pro Gln Thr Ser Leu Cys Phe Ser Glu Ser Ile Pro Thr Pro Ser Asn
        35                  40                  45

Arg Glu Glu Thr Gln Gln Lys Ser Asn Leu Glu Leu Leu Arg Ile Ser
    50                  55                  60

Leu Leu Leu Ile Gln Ser Trp Leu Glu Pro Val Gln Phe Leu Arg Ser
65                  70                  75                  80

Val Phe Ala Asn Ser Leu Val Tyr Gly Ala Ser Asp Ser Asn Val Tyr
            85                  90                  95

Asp Leu Leu Lys Asp Leu Glu Glu Gly Ile Gln Thr Leu Met Gly Arg
            100                 105                 110

Leu Glu Asp Gly Ser Pro Arg Thr Gly Gln Ile Phe Lys Gln Thr Tyr
        115                 120                 125

Ser Lys Phe Asp Thr Asn Ser His Asn Asp Asp Ala Leu Leu Lys Asn
    130                 135                 140

Tyr Gly Leu Leu Tyr Cys Phe Arg Lys Asp Met Asp Lys Val Glu Thr
145                 150                 155                 160

Phe Leu Arg Ile Val Gln Cys Arg Ser Val Glu Gly Ser Cys Gly Phe
                165                 170                 175
```

METHODS FOR EXPRESSION AND PURIFICATION OF RECOMBINANT HUMAN GROWTH HORMONE MUTANTS

CROSS-REFERENCE TO RELATED APPLICATIONS

This application claims priority to U.S. provisional patent application Ser. No. 60/638,616 filed Dec. 22, 2004, U.S. provisional patent application Ser. No. 60/655,744 filed Feb. 23, 2005, U.S. provisional patent application Ser. No. 60/680,977 filed May 13, 2005, and U.S. provisional patent application Ser. No. 60/727,968 filed Oct. 17, 2005, the specifications of which are incorporated herein in their entirety.

FIELD OF THE INVENTION

The present invention relates generally to the production, purification, and isolation of human growth hormone (hGH). More particularly, the invention relates to the production, purification, and isolation of substantially purified hGH from a recombinant host.

BACKGROUND OF THE INVENTION

The growth hormone (GH) supergene family (Bazan, F. Immunology Today 11: 350-354 (1990); Mott, H. R. and Campbell, I. D. Current Opinion in Structural Biology 5: 114-121 (1995); Silvennoinen, O. and Ihle, J. N. (1996) SIGNALING BY THE HEMATOPOIETIC CYTOKINE RECEPTORS) represents a set of proteins with similar structural characteristics. Each member of this family of proteins comprises a four helical bundle. While there are still more members of the family yet to be identified, some members of the family include the following: growth hormone, prolactin, placental lactogen, erythropoietin (EPO), thrombopoietin (TPO), interleukin-2 (IL-2), IL-3, IL-4, IL-5, IL-6, IL-7, IL-9, IL-10, IL-11, IL-12 (p35 subunit), IL-13, IL-15, oncostatin M, ciliary neurotrophic factor, leukemia inhibitory factor, alpha interferon, beta interferon, gamma interferon, omega interferon, tau interferon, epsilon interferon, granulocyte-colony stimulating factor (G-CSF), granulocyte-macrophage colony stimulating factor (GM-CSF), macrophage colony stimulating factor (M-CSF) and cardiotrophin-1 (CT-1) ("the GH supergene family"). Members of the GH supergene family have similar secondary and tertiary structures, despite the fact that they generally have limited amino acid or DNA sequence identity. The shared structural features allow new members of the gene family to be readily identified.

Human growth hormone participates in much of the regulation of normal human growth and development. This naturally-occurring single-chain pituitary hormone consists of 191 amino acid residues and has a molecular weight of approximately 22 kDa. hGH exhibits a multitude of biological effects, including linear growth (somatogenesis), lactation, activation of macrophages, and insulin-like and diabetogenic effects, among others (Chawla, R., et al, Ann. Rev. Med. 34:519-547 (1983); Isaksson, O., et al., Ann. Rev. Physiol., 47:483-499 (1985); Hughes, J. and Friesen, H., Ann. Rev. Physiol., 47:469-482 (1985)). The structure of hGH is well known (Goeddel, D., et al., Nature 281:544-548 (1979)), and the three-dimensional structure of hGH has been solved by x-ray crystallography (de Vos, A., et al., Science 255:306-312 (1992)). The protein has a compact globular structure, comprising four amphipathic alpha helical bundles, termed A-D beginning from the N-terminus, which are joined by loops. hGH also contains four cysteine residues, which participate in two intramolecular disulfide bonds: C53 is paired with C165 and C182 is paired with C189. The hormone is not glycosylated and has been expressed in a secreted form in E. coli (Chang, C., et al., Gene 55:189-196 (1987)).

A number of naturally occurring mutants of hGH have been identified. These include hGH-V (Seeburg, DNA 1: 239 (1982); U.S. Pat. Nos. 4,446,235, 4,670,393, and 4,665,180, which are incorporated by reference herein) and a 20-kDa hGH containing a deletion of residues 32-46 of hGH (Kostyo et al., Biochem. Biophys. Acta 925: 314 (1987); Lewis, U., et al., J. Biol. Chem., 253:2679-2687 (1978)). In addition, numerous hGH variants, arising from post-transcriptional, post-translational, secretory, metabolic processing, and other physiological processes, have been reported (Baumann, G., Endocrine Reviews 12: 424 (1991)). The biological effects of hGH derive from its interaction with specific cellular receptors. The hormone is a member of a family of homologous proteins that include placental lactogens and prolactins. hGH is unusual among the family members, however, in that it exhibits broad species specificity and binds to either the cloned somatogenic (Leung, D., et al., Nature 330:537-543 (1987)) or prolactin (Boutin, J., et al., Cell 53:69-77 (1988)) receptor. Based on structural and biochemical studies, functional maps for the lactogenic and somatogenic binding domains have been proposed (Cunningham, B. and Wells, J., Proc. Natl. Acad. Sci. 88: 3407 (1991)). The hGH receptor is a member of the hematopoietic/cytokine/growth factor receptor family, which includes several other growth factor receptors, such as the interleukin (IL)-3, -4 and -6 receptors, the granulocyte macrophage colony-stimulating factor (GM-CSF) receptor, the erythropoietin (EPO) receptor, as well as the G-CSF receptor. See, Bazan, Proc. Natl. Acad. Sci. USA 87: 6934-6938 (1990). Members of the cytokine receptor family contain four conserved cysteine residues and a tryptophan-serine-X-tryptophan-serine motif positioned just outside the transmembrane region. The conserved sequences are thought to be involved in protein-protein interactions. See, e.g., Chiba et al., Biochim. Biophys. Res. Comm. 184: 485-490 (1992). The interaction between hGH and extracellular domain of its receptor (hGHbp) is among the most well understood hormone-receptor interactions. High-resolution X-ray crystallographic data (Cunningham, B., et al., Science, 254:821-825 (1991)) has shown that hGH has two receptor binding sites and binds two receptor molecules sequentially using distinct sites on the molecule. The two receptor binding sites are referred to as Site I and Site II. Site I includes the carboxy terminal end of helix D and parts of helix A and the A-B loop, whereas Site II encompasses the amino terminal region of helix A and a portion of helix C. Binding of GH to its receptor occurs sequentially, with Site I binding first. Site II then engages a second GH receptor, resulting in receptor dimerization and activation of the intracellular signaling pathways that lead to cellular responses to the hormone. An hGH mutein in which a G120R substitution has been introduced into site II is able to bind a single hGH receptor, but is unable to dimerize two receptors. The mutein acts as an hGH antagonist in vitro, presumably by occupying receptor sites without activating intracellular signaling pathways (Fuh, G., et al., Science 256:1677-1680 (1992)).

Recombinant hGH is used as a therapeutic and has been approved for the treatment of a number of indications. hGH deficiency leads to dwarfism, for example, which has been successfully treated for more than a decade by exogenous administration of the hormone. Forms of hGH deficiency (GHD) include pediatric GHD, adult GHD of childhood onset, and adult GHD of adult onset. In addition to hGH deficiency, hGH has also been approved for the treatment of renal failure (in children), Turner's Syndrome, and cachexia in AIDS patients. Recently, the Food and Drug Administration (FDA) has approved hGH for the treatment of non-GH-dependent short stature. hGH is also currently under investigation for the treatment of aging, frailty in the elderly, short bowel syndrome, and congestive heart failure. Target populations for hGH treatment include children with idiopathic short stature (ISS) and adults with GHD-like symptoms. Recombinant hGH is currently sold as a daily injectable product, with five major products currently on the market: Humatrope™ (Eli Lilly & Co.), Nutropin™ (Genentech), Norditropin™ (Novo-Nordisk), Genotropin™ (Pfizer) and Saizen/Serostim™ (Serono). A significant challenge to using growth hormone as a therapeutic, however, is that the protein has a short in vivo half-life and, therefore, it must be administered by daily subcutaneous injection for maximum effectiveness (MacGillivray, et al., *J. Clin. Endocrinol. Metab.* 81: 1806-1809 (1996)). Considerable effort is focused on means to improve the administration of hGH agonists and antagonists, by lowering the cost of production, making administration easier for the patient, improving efficacy and safety profile, and creating other properties that would provide a competitive advantage. For example, Genentech and Alkermes formerly marketed Nutropin Depot™, a depot formulation of hGH, for pediatric growth hormone deficiency. While the depot permits less frequent administration (once every 2-3 weeks rather than once daily), it is also associated with undesirable side effects, such as decreased bioavailability and pain at the injection site and was withdrawn from the market in 2004. Another product, Pegvisomant™ (Pfizer), has also recently been approved by the FDA. Pegvisomant™ is a genetically-engineered analogue of hGH that functions as a highly selective growth hormone receptor antagonist indicated for the treatment of acromegaly (van der Lely, et al., *The Lancet* 358: 1754-1759 (2001). Although several of the amino acid side chain residues in Pegvisomant™ are derivatized with polyethylene glycol (PEG) polymers, the product is still administered once-daily, indicating that the pharmaceutical properties are not optimal. In addition to PEGylation and depot formulations, other administration routes, including inhaled and oral dosage forms of hGH, are under early-stage pre-clinical and clinical development and none have yet received approval from the FDA. Accordingly, there is a need for a polypeptide that exhibits growth hormone activity but that also provides a longer serum half-life and, therefore, more optimal therapeutic levels of hGH and an increased therapeutic half-life.

Recently, an entirely new technology in the protein sciences has been reported, which promises to overcome many of the limitations associated with site-specific modifications of proteins such as hGH. Specifically, new components have been added to the protein biosynthetic machinery of the prokaryote *Escherichia coli* (*E. coli*) (e.g., L. Wang, et al., (2001), *Science* 292:498-500) and the eukaryote *Sacchromyces cerevisiae* (*S. cerevisiae*) (e.g., J. Chin et al., *Science* 301:964-7 (2003)), which has enabled the incorporation of non-genetically encoded amino acids to proteins in vivo. Constructs provided to host cells contain a polynucleotide encoding the hGH polypeptide comprising a selector codon and an orthogonal tRNA synthetase and/or an orthogonal tRNA for substituting a non-naturally encoded amino acid into the hGH polypeptide. A number of new amino acids with novel chemical, physical or biological properties, including photoaffinity labels and photoisomerizable amino acids, photocrosslinking amino acids (see, e.g., Chin, J. W., et al. (2002) *Proc. Natl. Acad. Sci. U.S.A.* 99:11020-11024; and, Chin, J. W., et al., (2002) *J. Am. Chem. Soc.* 124:9026-9027), keto amino acids, heavy atom containing amino acids, and glycosylated amino acids have been incorporated efficiently and with high fidelity into proteins in *E. coli* and in yeast in response to the amber codon, TAG, using this methodology. See, e.g., J. W. Chin et al., (2002), *Journal of the American Chemical Society* 124:9026-9027; J. W. Chin, & P. G. Schultz, (2002), *ChemBioChem* 3(11):1135-1137; J. W. Chin, et al., (2002), *PNAS United States of America* 99:11020-11024; and, L. Wang, & P. G. Schultz, (2002), *Chem. Comm.*, 1:1-11. All references are incorporated by reference herein in their entirety. These studies have demonstrated that it is possible to selectively and routinely introduce chemical functional groups that are chemically inert to all of the functional groups found in the 20 common, genetically-encoded amino acids and that may be used to react efficiently and selectively to form stable covalent linkages. The ability to incorporate non-genetically encoded amino acids into proteins permits the introduction of chemical functional groups that could provide valuable alternatives to the naturally-occurring functional groups, such as the epsilon —$NH_2$ of lysine, the sulfhydryl —SH of cysteine, the imino group of histidine, etc. Certain chemical functional groups are known to be inert to the functional groups found in the 20 common, genetically-encoded amino acids but react cleanly and efficiently to form stable linkages.

Covalent attachment of the hydrophilic polymer poly(ethylene glycol), abbreviated PEG, is a method of increasing water solubility, bioavailability, increasing serum half-life, increasing therapeutic half-life, modulating immunogenicity, modulating biological activity, or extending the circulation time of many biologically active molecules, including proteins, peptides, and particularly hydrophobic molecules. PEG has been used extensively in pharmaceuticals, on artificial implants, and in other applications where biocompatibility, lack of toxicity, and lack of immunogenicity are of importance. In order to maximize the desired properties of PEG, the total molecular weight and hydration state of the PEG polymer or polymers attached to the biologically active molecule must be sufficiently high to impart the advantageous characteristics typically associated with PEG polymer attachment, such as increased water solubility and circulating half life, while not adversely impacting the bioactivity of the parent molecule. Any molecular mass for a PEG can be used as practically desired, including but not limited to, from about 100 Daltons (Da) to 100,000 Da or more as desired (including but not limited to, sometimes 0.1-50 kDa or 10-40 kDa). Branched chain PEGs, including but not limited to, PEG molecules with each chain having a MW ranging from 1-100 kDa (including but not limited to, 1-50 kDa or 5-20 kDa) can also be used.

PEG derivatives are frequently linked to biologically active molecules through reactive chemical functionalities, such as lysine, cysteine and histidine residues, the N-terminus and carbohydrate moieties. Proteins and other molecules often have a limited number of reactive sites available for polymer attachment. Often, the sites most suitable for modification via polymer attachment play a significant role in receptor binding, and are necessary for retention of the biological activity of the molecule. As a result, indiscriminate attachment of polymer chains to such reactive sites on a biologically active molecule often leads to a significant reduction or even total loss of biological activity of the polymer-modified molecule. R. Clark et al., (1996), *J. Biol. Chem.*, 271:21969-21977. To form conjugates having sufficient polymer molecular weight for imparting the desired advantages to a target molecule, prior art approaches have typically involved random attachment of numerous polymer arms to the molecule, thereby increasing the risk of a reduction or even total loss in bioactivity of the parent molecule.

Reactive sites that form the loci for attachment of PEG derivatives to proteins are dictated by the protein's structure. Proteins, including enzymes, are composed of various sequences of alpha-amino acids, which have the general structure $H_2N$—CHR—COOH. The alpha amino moiety ($H_2N$—) of one amino acid joins to the carboxyl moiety (—COOH) of an adjacent amino acid to form amide linkages, which can be represented as —(NH—CHR—CO)$_n$—, where the subscript "n" can equal hundreds or thousands. The fragment represented by R can contain reactive sites for protein biological activity and for attachment of PEG derivatives.

For example, in the case of the amino acid lysine, there exists an —$NH_2$ moiety in the epsilon position as well as in the alpha position. The epsilon —$NH_2$ is free for reaction under conditions of basic pH. Much of the art in the field of protein derivatization with PEG has been directed to developing PEG derivatives for attachment to the epsilon —$NH_2$ moiety of lysine residues present in proteins. "Polyethylene Glycol and Derivatives for Advanced PEGylation", Nektar Molecular Engineering Catalog, 2003, pp. 1-17. These PEG derivatives all have the common limitation, however, that they cannot be installed selectively among the often numerous lysine residues present on the surfaces of proteins. This can be a significant limitation in instances where a lysine residue is important to protein activity, existing in an enzyme active site for example, or in cases where a lysine residue plays a role in mediating the interaction of the protein with other biological molecules, as in the case of receptor binding sites.

A second and equally important complication of existing methods for protein PEGylation is that the PEG derivatives can undergo undesired side reactions with residues other than those desired. Histidine contains a reactive imino moiety, represented structurally as —N(H)—, but many chemically reactive species that react with epsilon —$NH_2$ can also react with N(H)—. Similarly, the side chain of the amino acid cysteine bears a free sulfhydryl group, represented structurally as —SH. In some instances, the PEG derivatives directed at the epsilon —$NH_2$ group of lysine also react with cysteine, histidine or other residues. This can create complex, heterogeneous mixtures of PEG-derivatized bioactive molecules and risks destroying the activity of the bioactive molecule being targeted. It would be desirable to develop PEG derivatives that permit a chemical functional group to be introduced at a single site within the protein that would then enable the selective coupling of one or more PEG polymers to the bioactive molecule at specific sites on the protein surface that are both well-defined and predictable.

In addition to lysine residues, considerable effort in the art has been directed toward the development of activated PEG reagents that target other amino acid side chains, including cysteine, histidine and the N-terminus. See, e.g., U.S. Pat. No. 6,610,281 which is incorporated by reference herein, and "Polyethylene Glycol and Derivatives for Advanced PEGylation", Nektar Molecular Engineering Catalog, 2003, pp. 1-17. A cysteine residue can be introduced site-selectively into the structure of proteins using site-directed mutagenesis and other techniques known in the art, and the resulting free sulfhydryl moiety can be reacted with PEG derivatives that bear thiol-reactive functional groups. This approach is complicated, however, in that the introduction of a free sulfhydryl group can complicate the expression, folding and stability of the resulting protein. Thus, it would be desirable to have a means to introduce a chemical functional group into bioactive molecules that enables the selective coupling of one or more PEG polymers to the protein while simultaneously being compatible with (i.e., not engaging in undesired side reactions with) sulfhydryls and other chemical functional groups typically found in proteins.

As can be seen from a sampling of the art, many of these derivatives that have been developed for attachment to the side chains of proteins, in particular, the —$NH_2$ moiety on the lysine amino acid side chain and the —SH moiety on the cysteine side chain, have proven problematic in their synthesis and use. Some form unstable linkages with the protein that are subject to hydrolysis and therefore decompose, degrade, or are otherwise unstable in aqueous environments, such as in the bloodstream. Some form more stable linkages, but are subject to hydrolysis before the linkage is formed, which means that the reactive group on the PEG derivative may be inactivated before the protein can be attached. Some are somewhat toxic and are therefore less suitable for use in vivo. Some are too slow to react to be practically useful. Some result in a loss of protein activity by attaching to sites responsible for the protein's activity. Some are not specific in the sites to which they will attach, which can also result in a loss of desirable activity and in a lack of reproducibility of results. In order to overcome the challenges associated with modifying proteins with poly(ethylene glycol) moieties, PEG derivatives have been developed that are more stable (e.g., U.S. Pat. No. 6,602,498, which is incorporated by reference herein) or that react selectively with thiol moieties on molecules and surfaces (e.g., U.S. Pat. No. 6,610,281, which is incorporated by reference herein). There is clearly a need in the art for PEG derivatives that are chemically inert in physiological environments until called upon to react selectively to form stable chemical bonds.

Therefore, there currently exists an unmet need to provide hGH polypeptide in a substantially pure form suitable for use in human therapeutic applications. In addition, methods for the production of pharmaceutical grade hGH polypeptide are needed that are amenable to large-scale production that are highly efficient and cost productive.

BRIEF SUMMARY OF THE INVENTION

The present invention relates generally to the production and purification of hGH polypeptide from recombinant host cells or culture media. More particularly, the invention relates to the production and purification of substantially purified hGH polypeptide from a recombinant host, including, but not limited to, a prokaryotic host, a bacterial host or an *E. coli* host.

In one embodiment, the present invention provides methods for isolating substantially purified hGH polypeptide comprising the steps of: (a) anion exchange chromatography; and (b) hydrophobic interaction chromatography (HIC). Purification of PEGylated hGH polypeptide includes the following additional steps: (c) reacting hGH polypeptide with PEG to form hGH-PEG conjugates; and (d) isolating said hGH-PEG conjugates by an anion exchange chromatography.

In another embodiment, the present invention provides methods for isolating substantially purified hGH polypeptide comprising the steps of: (a) anion exchange chromatography; (b) hydroxyapatite chromatography; and (c) hydrophobic interaction chromatography (HIC). Purification of PEGylated hGH polypeptide includes the following additional steps: (d) reacting hGH polypeptide with PEG to form hGH-PEG conjugates; and (e) isolating said hGH-PEG conjugates by an anion exchange chromatography.

In one embodiment, the recombinant host is selected from the group consisting of a prokaryotic cell and a eukaryotic cell. In one embodiment, the recombinant host may comprise any host cell that produces an insoluble sub-cellular component, such as inclusion bodies, comprising hGH polypeptide including, for example, yeast cells, mammalian cells, insect cells and bacterial cells, including, for example, *E. coli*.

The hydrophobic interaction chromatography materials suitable for use in the methods of the present invention may include, but are not limited to, alkyl- or aryl-substituted matrices, such as butyl-, hexyl-, octyl- or phenyl-substituted matrices including agarose, cross-linked agarose, sepharose, cellulose, silica, dextran, polystyrene, poly(methacrylate) matrices, and mixed mode resins, including but not limited to, a polyethyleneamine resin or a butyl- or phenyl-substituted poly(methacrylate) matrix. In a specific embodiment, the hydrophobic interaction chromatography material may comprise phenyl sepharose resin.

In one embodiment, the substantially purified hGH polypeptide isolated by the methods described herein may include, but is not limited to, mature hGH, mature hGH variants, hGH polypeptides, hGH polypeptide variants, and hGH conjugated to poly(ethylene glycol).

In yet another embodiment, the substantially purified hGH polypeptide isolated by the methods of the present invention may exhibit at least one biological activity of mature hGH.

In yet another embodiment, the substantially purified hGH polypeptide isolated by the methods of the present invention may be mammalian. In a specific embodiment, the substantially purified hGH polypeptide isolated by the methods of the present invention may be human.

In another embodiment of the present invention, the hGH polypeptide obtained from the HIC step is covalently linked to a water soluble polymer. In some embodiments, the water soluble polymer is poly(ethylene glycol). In another embodiment, the hGH polypeptide comprises one or more non-naturally encoded amino acids.

Expression of hGH polypeptides comprising a non-naturally encoded amino acid and purification of PEGylated forms thereof provide hGH molecules altered in a site-specific manner for therapeutic use. PEGylation of hGH polypeptides at naturally encoded amino acids may result in the PEGylation of hGH polypeptide at undesired sites and/or PEGylation of undesired polypeptides that may be contaminants. Methods utilizing non-naturally encoded amino acids for site-specific PEGylation of hGH polypeptide renders such purification steps unnecessary.

In another embodiment, conjugation of the hGH polypeptide comprising one or more non-naturally occurring amino acids to another molecule, including but not limited to PEG, provides substantially purified hGH polypeptide due to the unique chemical reaction utilized for conjugation to the non-natural amino acid. Conjugation of hGH polypeptide comprising one or more non-naturally encoded amino acids to another molecule, such as PEG, may be performed with other purification techniques performed prior to or following the conjugation step to provide substantially pure hGH polypeptide.

DEFINITIONS

Figure 1:
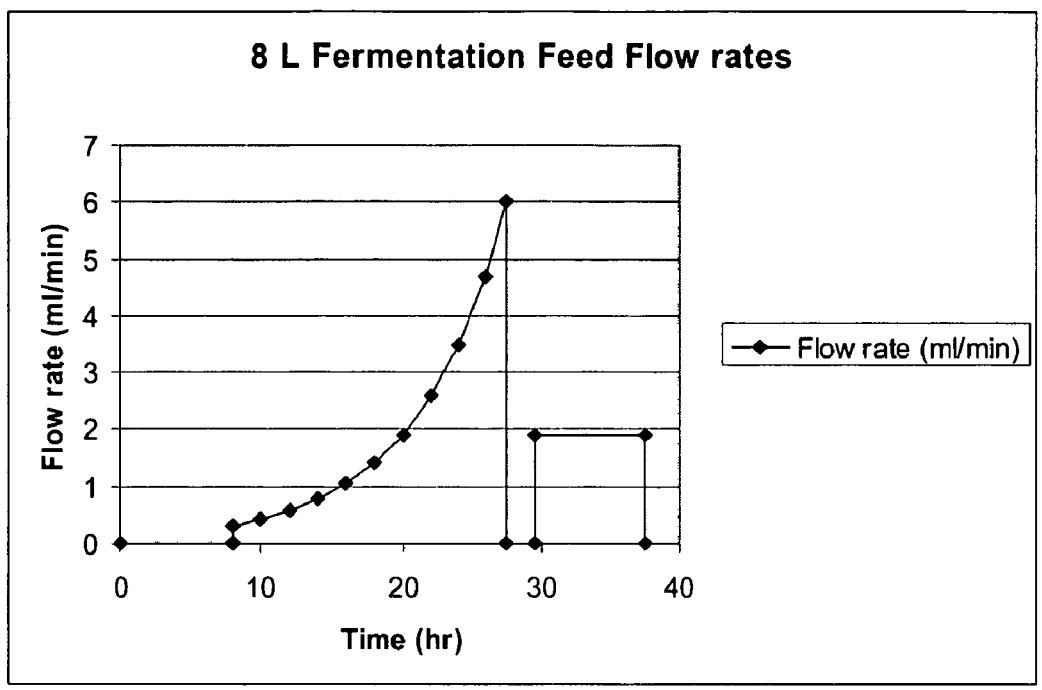
FIG. 1 shows feed flow rates for an 8 liter fermentation.

It is to be understood that this invention is not limited to the particular methodology, protocols, cell lines, constructs, and reagents described herein and as such may vary. It is also to be understood that the terminology used herein is for the purpose of describing particular embodiments only, and is not intended to limit the scope of the present invention, which will be limited only by the appended claims.

As used herein and in the appended claims, the singular forms "a," "an," and "the" include plural reference unless the context clearly indicates otherwise. Thus, for example, reference to a "hGH" is a reference to one or more such proteins and includes equivalents thereof known to those of ordinary skill in the art, and so forth.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices and materials are now described.

All publications and patents mentioned herein are incorporated herein by reference for the purpose of describing and disclosing, for example, the constructs and methodologies that are described in the publications, which might be used in connection with the presently described invention. The publications discussed herein are provided solely for their disclosure prior to the filing date of the present application. Nothing herein is to be construed as an admission that the inventors are not entitled to antedate such disclosure by virtue of prior invention or for any other reason.

U.S. patent application Ser. No. 11/046,432 is incorporated by reference herein in its entirety. U.S. patent application Ser. No. 11/046,432 describes the naturally-occurring amino acid sequences of hGH, site selection for incorporation of non-naturally encoded amino acids, and methods, compositions, techniques and strategies for making, purifying, characterizing, and using non-naturally encoded amino acids, non-naturally encoded amino acid hGH polypeptides, and modified non-naturally encoded amino acid hGH polypeptides.

The term "protein" as used herein, includes a polymer or complex of various polymers of amino acids and does not connote a specific length of a polymer of amino acids. Thus, for example, the terms peptide, oligopeptide, and polypeptide are included within the definition of protein, whether produced using recombinant techniques, chemical or enzymatic synthesis, or naturally occurring. The term also includes peptides, oligopeptides, and polypeptides that have been modified or derivatized, such as by glycosylation, acetylation, phosphorylation, and the like. The term "protein" specifically includes variants, as defined herein. The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally encoded amino acid. As used herein, the terms encompass amino acid chains of any length, including full length proteins, wherein the amino acid residues are linked by covalent peptide bonds.

As used herein, "growth hormone" or "GH" shall include those polypeptides and proteins that have at least one biological activity of a human growth hormone, as well as GH analogs, GH isoforms, GH mimetics, GH fragments, hybrid GH proteins, fusion proteins, oligomers and multimers, homologues, glycosylation pattern variants, variants, splice variants, and muteins, thereof, regardless of the biological activity of same, and further regardless of the method of synthesis or manufacture thereof including, but not limited to, recombinant (whether produced from cDNA, genomic DNA, synthetic DNA or other form of nucleic acid), in vitro, in vivo, by microinjection of nucleic acid molecules, synthetic, transgenic, and gene activated methods. The term "hGH polypeptide" or "hGH" encompasses hGH polypeptides comprising one or more amino acid substitutions, additions or deletions. Exemplary substitutions in a wide variety of amino acid positions in naturally-occurring hGH including substitutions that increase agonist activity, increase protease resistance, convert the polypeptide into an antagonist, modulate immunogenicity, modulate receptor binding, etc. are encompassed by the term "hGH polypeptide."

For the complete full-length naturally-occurring GH amino acid sequence as well as the mature naturally-occurring GH amino acid sequence and naturally occurring mutant, see SEQ ID NO: 1, SEQ ID NO: 2 and SEQ ID NO: 3, respectively, herein. In some embodiments, hGH polypeptides of the invention are substantially identical to SEQ ID NO: 1, or SEQ ID NO: 2, or SEQ ID NO: 3 or any other sequence of a growth hormone polypeptide. A number of naturally occurring mutants of hGH have been identified. These include hGH-V (Seeburg, *DNA* 1: 239 (1982); U.S. Pat. Nos. 4,446,235, 4,670,393, and 4,665,180, which are incorporated by reference herein) and a 20-kDa hGH containing a deletion of residues 32-46 of hGH (Kostyo et al., *Biochem. Biophys. Acta* 925: 314 (1987); Lewis, U., et al., *J. Biol. Chem.*, 253:2679-2687 (1978)). Placental growth hormone is described in Igout, A., et al., *Nucleic Acids Res.* 17(10):3998 (1989)). In addition, numerous hGH variants, arising from post-transcriptional, post-translational, secretory, metabolic processing, and other physiological processes, have been reported including proteolytically cleaved or 2 chain variants (Baumann, G., *Endocrine Reviews* 12: 424 (1991)). Nucleic acid molecules encoding hGH mutants and mutant hGH polypeptides are well known and include, but are not limited to, those disclosed in U.S. Pat. Nos. 5,534,617; 5,580,723; 5,688,666; 5,750,373; 5,834,250; 5,834,598; 5,849,535; 5,854,026; 5,962,411; 5,955,346; 6,013,478; 6,022,711; 6,136,563; 6,143,523; 6,428,954; 6,451,561; 6,780,613 and U.S. Patent Application Publication 2003/0153003; which are incorporated by reference herein. The term ""hGH" may also be used to refer to recombinant human growth hormone with site-directed substitution of a non-naturally encoded amino acid.

All references to amino acid positions in hGH described herein are based on the position in SEQ ID NO: 2, unless otherwise specified (i.e., when it is stated that the comparison is based on SEQ ID NO: 1, 3, or other hGH sequence). Those of skill in the art will appreciate that amino acid positions corresponding to positions in SEQ ID NO: 1, 2, 3, or any other GH sequence can be readily identified in any other hGH molecule such as hGH fusions, variants, fragments, etc. For example, sequence alignment programs such as BLAST can be used to align and identify a particular position in a protein that corresponds with a position in SEQ ID NO: 1, 2, 3, or other GH sequence. Substitutions, deletions or additions of amino acids described herein in reference to SEQ ID NO: 1, 2, 3, or other GH sequence are intended to also refer to substitutions, deletions or additions in corresponding positions in hGH fusions, variants, fragments, etc. described herein or known in the art and are expressly encompassed by the present invention.

Commercial preparations of hGH are sold under the names: Humatrope™ (Eli Lilly & Co.), Nutropin™ (Genentech), Norditropin™ (Novo-Nordisk), Genotropin™ (Pfizer) and Saizen/Serostim™ (Serono).

The term "hGH polypeptide" also includes the pharmaceutically acceptable salts and prodrugs, and prodrugs of the salts, polymorphs, hydrates, solvates, biologically-active fragments, biologically active variants and stereoisomers of the naturally-occurring hGH as well as agonist, mimetic, and antagonist variants of the naturally-occurring hGH and polypeptide fusions thereof. Fusions comprising additional amino acids at the amino terminus, carboxyl terminus, or both, are encompassed by the term "hGH polypeptide." Exemplary fusions include, but are not limited to, e.g., methionyl growth hormone in which a methionine is linked to the N-terminus of hGH resulting from the recombinant expression, fusions for the purpose of purification (including, but not limited to, to poly-histidine or affinity epitopes), fusions with serum albumin binding peptides and fusions with serum proteins such as serum albumin. U.S. Pat. No. 5,750,373, which is incorporated by reference herein, describes a method for selecting novel proteins such as growth hormone and antibody fragment variants having altered binding properties for their respective receptor molecules. The method comprises fusing a gene encoding a protein of interest to the carboxy terminal domain of the gene III coat protein of the filamentous phage M13.

Various references disclose modification of polypeptides by polymer conjugation or glycosylation. The term "hGH polypeptide" includes polypeptides conjugated to a polymer such as PEG and may be comprised of one or more additional derivitizations of cysteine, lysine, or other residues. In addition, the hGH polypeptide may comprise a linker or polymer, wherein the amino acid to which the linker or polymer is conjugated may be a non-natural amino acid according to the present invention, or may be conjugated to a naturally encoded amino acid utilizing techniques known in the art such as coupling to lysine or cysteine.

The present invention provides conjugates of hGH polypeptide having a wide variety of functional groups, substituents or moieties, with other substances including but not limited to a label; a dye; a polymer; a water-soluble polymer; a derivative of polyethylene glycol; a photocrosslinker; a radionuclide; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide; a water-soluble dendrimer; a cyclodextrin; an inhibitory ribonucleic acid; a biomaterial; a nanoparticle; a spin label; a fluorophore, a metal-containing moiety; a radioactive moiety; a novel functional group; a group that covalently or noncovalently interacts with other molecules; a photocaged moiety; a photoisomerizable moiety; biotin; a derivative of biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; a quantum dot, a nanotransmitter, a radionucleotide, a radiotransmitter, a neutron-capture agent, or any combination of the above, or any other desirable compound or substance).

Polymer conjugation of hGH polypeptides has been reported. See, e.g. U.S. Pat. Nos. 5,849,535, 6,136,563 and 6,608,183, which are incorporated by reference herein. U.S. Pat. No. 4,904,584 discloses PEGylated lysine depleted polypeptides, wherein at least one lysine residue has been deleted or replaced with any other amino acid residue. WO 99/67291 discloses a process for conjugating a protein with PEG, wherein at least one amino acid residue on the protein is deleted and the protein is contacted with PEG under conditions sufficient to achieve conjugation to the protein. WO 99/03887 discloses PEGylated variants of polypeptides belonging to the growth hormone superfamily, wherein a cysteine residue has been substituted with a non-essential amino acid residue located in a specified region of the polypeptide. WO 00/26354 discloses a method of producing a glycosylated polypeptide variant with reduced allergenicity, which as compared to a corresponding parent polypeptide comprises at least one additional glycosylation site. U.S. Pat. No. 5,218,092 discloses modification of granulocyte colony stimulating factor (G-CSF) and other polypeptides so as to introduce at least one additional carbohydrate chain as compared to the native polypeptide.

The term "hGH polypeptide" encompasses hGH polypeptides comprising one or more amino acid substitutions, additions or deletions. hGH polypeptides of the present invention may be comprised of modifications with one or more natural amino acids in conjunction with one or more non-natural amino acid modification. Exemplary substitutions in a wide variety of amino acid positions in naturally-occurring hGH polypeptides have been described, including but not limited to substitutions that modulate one or more of the biological activities of the hGH polypeptide, such as but not limited to, increase agonist activity, increase solubility of the polypeptide, convert the polypeptide into an antagonist, decrease protease susceptibility, etc. and are encompassed by the term "hGH polypeptide." In some embodiments, the hGH polypeptides further comprise an addition, substitution or deletion that modulates biological activity of the hGH polypeptide. For example, the additions, substitutions or deletions may modulate affinity for the hGH polypeptide receptor, modulate (including but not limited to, increases or decreases) receptor dimerization, stabilize receptor dimers, modulate circulating half-life, modulate therapeutic half-life, modulate stability of the polypeptide, modulate cleavage by proteases, modulate dose, modulate release or bio-availability, facilitate purification, or improve or alter a particular route of administration.

Similarly, hGH polypeptides may comprise protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification or other traits of the polypeptide. hGH polypeptides may comprise secretion signal sequences. Examples of secretion signal sequences include, but are not limited to, a prokaryotic secretion signal sequence, an eukaryotic secretion signal sequence, an eukaryotic secretion signal sequence 5'-optimized for bacterial expression, a novel secretion signal sequence, pectate lyase secretion signal sequence, Omp A secretion signal sequence, and a phage secretion signal sequence. Examples of secretion signal sequences, include, but are not limited to, STII (prokaryotic), Fd GIII and M13 (phage), Bgl2 (yeast), and the signal sequence bla derived from a transposon.

The term "hGH polypeptide" also encompasses homodimers, heterodimers, homomultimers, and heteromultimers that are linked, including but not limited to those linked directly via non-naturally encoded amino acid side chains, either to the same or different non-naturally encoded amino acid side chains, to naturally-encoded amino acid side chains, or indirectly via a linker. hGH dimers linked directly via Cys-Cys disulfide linkages are described in Lewis, U. J., et al., J. Biol. Chem. 252:3697-3702 (1977); Brostedt, P. and Roos, P., Prep. Biochem. 19:217-229 (1989)). Exemplary linkers including but are not limited to, water soluble polymers such as poly(ethylene glycol) or polydextran or polypeptides of various lengths.

The term "hGH polypeptide" also includes glycosylated hGH, such as but not limited to, polypeptides glycosylated at any amino acid position, N-linked or O-linked glycosylated forms of the polypeptide. Variants containing single nucleotide changes are also considered as biologically active variants of hGH polypeptide. In addition, splice variants are also included. The term "hGH polypeptide" also includes hGH polypeptide heterodimers, homodimers, heteromultimers, or homomultimers of any one or more hGH polypeptides or any other polypeptide, protein, carbohydrate, polymer, small molecule, linker, ligand, or other biologically active molecule of any type, linked by chemical means or expressed as a fusion protein, as well as polypeptide analogues containing, for example, specific deletions or other modifications yet maintain biological activity.

Those of skill in the art will appreciate that amino acid positions corresponding to positions in a particular hGH sequence can be readily identified in any other hGH molecule such as hGH fusions, variants, fragments, etc. For example, sequence alignment programs such as BLAST can be used to align and identify a particular position in a protein that corresponds with a position in a particular GH sequence.

"Native hGH," as used herein, is defined as hGH, including naturally occurring hGH, analogs, and variants thereof, which is properly folded and contains only correct disulfide bonds. hGH also contains four cysteine residues, which participate in two intramolecular disulfide bonds: C53 is paired with C165 and C182 is paired with C189 or the homologs of those amino acid residues in analogs and variants of hGH. Native hGH is biologically active.

"Insoluble hGH" refers to precipitated or aggregated hGH that is produced by recombinant host cells, or is otherwise recombinant host cell associated, and may assume a biologically inactive conformation with possible incorrect or unformed disulfide bonds. Insoluble hGH may be contained in inclusion bodies or refractile bodies, i.e. may or may not be visible under a phase contrast microscope. Insoluble hGH may be produced by rendering soluble hGH insoluble by any method known to one of ordinary skill in the art.

"Improperly folded hGH" refers to hGH which is in a biologically less active conformation with incorrect or unformed disulfide bonds. Improperly folded hGH may be, but need not be, insoluble.

The term "hGH variant," as used herein, includes variants of mature hGH and hGH polypeptides. A "hGH variant" may be created by, and includes, for example, the deletion or addition of one or more amino acids at one or more sites in the mature protein, deletion or addition of one or more amino acids to the N-terminal and/or C-terminal end of the mature protein, and/or substitution of one or more amino acids at one or more sites in the mature protein. For example, a hGH variant may be created by adding or deleting at least 10 amino acids, at least 5 amino acids, at least 3 amino acids, or at least 1 amino acid. hGH variants may also include post-translational modifications including, but not limited to, glycosylation, acetylation, phosphorylation, and the like. The term "hGH variant" specifically includes, but is not limited to, mutants, allelic variants, homologs, and fusions of mature hGH sequences. An hGH variant also includes, but is not limited to, peptide mimics or "peptoids." See WO 91/04282.

The term "substantially purified" refers to hGH polypeptide that may be substantially or essentially free of components that normally accompany or interact with the protein as found in its naturally occurring environment, i.e. a native cell, or host cell in the case of recombinantly produced hGH polypeptide. hGH that may be substantially free of cellular material includes preparations of protein having less than about 30%, less than about 25%, less than about 20%, less than about 15%, less than about 10%, less than about 5%, less than about 4%, less than about 3%, less than about 2%, or less than about 1% (by dry weight) of contaminating protein. When the hGH polypeptide or variant thereof is recombinantly produced by the host cells, the protein may be present at about 30%, about 25%, about 20%, about 15%, about 10%, about 5%, about 4%, about 3%, about 2%, or about 1% or less of the dry weight of the cells. When the hGH polypeptide or variant thereof is recombinantly produced by the host cells, the protein may be present in the culture medium at about 5 g/L, about 4 g/L, about 3 g/L, about 2 g/L, about 1 g/L, about 750 mg/L, about 500 mg/L, about 250 mg/L, about 100 mg/L, about 50 mg/L, about 10 mg/L, or about 1 mg/L or less of the dry weight of the cells. Thus, "substantially purified" hGH polypeptide as produced by the methods of the present invention may have a purity level of at least about 30%, at least about 35%, at least about 40%, at least about 45%, at least about 50%, at least about 55%, at least about 60%, at least about 65%, at least about 70%, specifically, a purity level of at least about 75%, 80%, 85%, and more specifically, a purity level of at least about 90%, a purity level of at least about 95%, a purity level of at least about 99% or greater, as determined by appropriate methods including, but not limited to, SDS/PAGE analysis, RP-HPLC, SEC, and capillary electrophoresis.

A "recombinant host cell" or "host cell" refers to a cell that includes an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome.

As used herein, the term "medium" or "media" includes any culture medium, solution, solid, semi-solid, or rigid support that may support or contain any host cell, including bacterial host cells, eukaryotic host cells, mammalian host cells, yeast host cells, insect host cells, plant host cells, CHO cells, prokaryotic host cells, *E. coli*, or *Pseudomonas* host cells, and cell contents. Thus, the term may encompass medium in which the host cell has been grown, e.g., medium into which the hGH polypeptide has been secreted, including medium either before or after a proliferation step. The term also may encompass buffers or reagents that contain host cell lysates, such as in the case where hGH polypeptides are produced intracellularly and the host cells are lysed or disrupted to release the hGH polypeptide.

"Reducing agent," as used herein with respect to protein refolding, is defined as any compound or material which maintains sulfhydryl groups in the reduced state and reduces intra- or intermolecular disulfide bonds. Suitable reducing agents include, but are not limited to, dithiothreitol (DTT), 2-mercaptoethanol, dithioerythritol, cysteine, cysteamine (2-aminoethanethiol), and reduced glutathione. It is readily apparent to those of ordinary skill in the art that a wide variety of reducing agents are suitable for use in the methods of the present invention.

"Oxidizing agent," as used herein with respect to protein refolding, is defined as any compound or material which is capable of removing an electron from a compound being oxidized. Suitable oxidizing agents include, but are not limited to, oxidized glutathione, cystine, cystamine, oxidized dithiothreitol, oxidized erythreitol, and oxygen. It is readily apparent to those of ordinary skill in the art that a wide variety of oxidizing agents are suitable for use in the methods of the present invention.

"Denaturing agent" or "denaturant," as used herein, is defined as any compound or material which will cause a reversible unfolding of a protein. The strength of a denaturing agent or denaturant will be determined both by the properties and the concentration of the particular denaturing agent or denaturant. Suitable denaturing agents or denaturants may be chaotropes, detergents, organic solvents, water miscible solvents, phospholipids, or a combination of two or more such agents. Suitable chaotropes include, but are not limited to, urea, guanidine, and sodium thiocyanate. Useful detergents may include, but are not limited to, strong detergents such as sodium dodecyl sulfate, or polyoxyethylene ethers (e.g. Tween or Triton detergents), Sarkosyl, mild non-ionic detergents (e.g., digitonin), mild cationic detergents such as N->2, 3-(Dioleyoxy)-propyl-N,N,N-trimethylammonium, mild ionic detergents (e.g. sodium cholate or sodium deoxycholate) or zwitterionic detergents including, but not limited to, sulfobetaines (Zwittergent), 3-(3-chlolamidopropyl)dimethylammonio-1-propane sulfate (CHAPS), and 3-(3-chlolamidopropyl)dimethylammonio-2-hydroxy-1-propane sulfonate (CHAPSO). Organic, water miscible solvents such as acetonitrile, lower alkanols (especially $C_2$-$C_4$ alkanols such as ethanol or isopropanol), or lower alkandiols (especially $C_2$-$C_4$ alkandiols such as ethylene-glycol) may be used as denaturants. Phospholipids useful in the present invention may be naturally occurring phospholipids such as phosphatidylethanolamine, phosphatidylcholine, phosphatidylserine, and phosphatidylinositol or synthetic phospholipid derivatives or variants such as dihexanoylphosphatidylcholine or diheptanoylphosphatidylcholine.

"Refolding," as used herein describes any process, reaction or method which transforms disulfide bond containing polypeptides from an improperly folded or unfolded state to a native or properly folded conformation with respect to disulfide bonds.

"Cofolding," as used herein, refers specifically to refolding processes, reactions, or methods which employ at least two polypeptides which interact with each other and result in the transformation of unfolded or improperly folded polypeptides to native, properly folded polypeptides.

A "non-naturally encoded amino acid" refers to an amino acid that is not one of the 20 common amino acids or pyrrolysine or selenocysteine. Other terms that may be used synonymously with the term "non-naturally encoded amino acid" are "non-natural amino acid," "unnatural amino acid," "non-naturally-occurring amino acid," and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrrolysine and selenocysteine) but are not themselves naturally incorporated into a growing polypeptide chain by the translation complex. Examples of such non-naturally-occurring amino acids include, but are not limited to, N-acetylglucosaminyl-L-serine, N-acetylglucosaminyl-L-threonine, and O-phosphotyrosine.

As used herein, the term "water soluble polymer" refers to any polymer that is soluble in aqueous solvents. Linkage of water soluble polymers to hGH polypeptides can result in changes including, but not limited to, increased or modulated serum half-life, or increased or modulated therapeutic half-life relative to the unmodified form, modulated immunogenicity, modulated physical association characteristics such as aggregation and multimer formation, altered receptor binding, and altered receptor dimerization or multimerization. The water soluble polymer may or may not have its own biological activity, and may be utilized as a linker for attaching hGH to other substances, including but not limited to one or more hGH polypeptides, or one or more biologically active molecules. Suitable polymers include, but are not limited to, polyethylene glycol, polyethylene glycol propionaldehyde, mono C1-C10 alkoxy or aryloxy derivatives thereof (described in U.S. Pat. No. 5,252,714 which is incorporated by reference herein), monomethoxy-polyethylene glycol, polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polypropylene oxide/ethylene oxide copolymer, polyoxyethylated polyol, heparin, heparin fragments, polysaccharides, oligosaccharides, glycans, cellulose and cellulose derivatives, including but not limited to methylcellulose and carboxymethyl cellulose, starch and starch derivatives, polypeptides, polyalkylene glycol and derivatives thereof, copolymers of polyalkylene glycols and derivatives thereof, polyvinyl ethyl ethers, and alpha-beta-poly[(2-hydroxyethyl)-DL-aspartamide, and the like, or mixtures thereof. Examples of such water soluble polymers include, but are not limited to, polyethylene glycol and serum albumin.

An "amino terminus modification group" refers to any molecule that can be attached to the amino terminus of a polypeptide. Similarly, a "carboxy terminus modification group" refers to any molecule that can be attached to the carboxy terminus of a polypeptide. Terminus modification groups include, but are not limited to, various water soluble polymers, peptides or proteins such as serum albumin, or other moieties that increase serum half-life of peptides.

As used herein, the term "polyalkylene glycol" or "poly (alkene glycol)" refers to polyethylene glycol (poly(ethylene glycol)), polypropylene glycol, polybutylene glycol, and derivatives thereof. The term "polyalkylene glycol" encompasses both linear and branched polymers and average molecular weights of between 0.1 kDa and 100 kDa. Other exemplary embodiments are listed, for example, in commercial supplier catalogs, such as Shearwater Corporation's catalog "Polyethylene Glycol and Derivatives for Biomedical Applications" (2001).

The terms "functional group", "active moiety", "activating group", "leaving group", "reactive site", "chemically reactive group" and "chemically reactive moiety" are used in the art and herein to refer to distinct, definable portions or units of a molecule. The terms are somewhat synonymous in the chemical arts and are used herein to indicate the portions of molecules that perform some function or activity and are reactive with other molecules.

The term "linkage" or "linker" is used herein to refer to groups or bonds that normally are formed as the result of a chemical reaction and typically are covalent linkages. Hydrolytically stable linkages means that the linkages are substantially stable in water and do not react with water at useful pH values, including but not limited to, under physiological conditions for an extended period of time, perhaps even indefinitely. Hydrolytically unstable or degradable linkages mean that the linkages are degradable in water or in aqueous solutions, including for example, blood. Enzymatically unstable or degradable linkages mean that the linkage can be degraded by one or more enzymes. As understood in the art, PEG and related polymers may include degradable linkages in the polymer backbone or in the linker group between the polymer backbone and one or more of the terminal functional groups of the polymer molecule. For example, ester linkages formed by the reaction of PEG carboxylic acids or activated PEG carboxylic acids with alcohol groups on a biologically active agent generally hydrolyze under physiological conditions to release the agent. Other hydrolytically degradable linkages include, but are not limited to, carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

The term "biologically active molecule", "biologically active moiety" or "biologically active agent" when used herein means any substance which can affect any physical or biochemical properties of a biological system, pathway, molecule, or interaction relating to an organism, including but not limited to, viruses, bacteria, bacteriophage, transposon, prion, insects, fungi, plants, animals, and humans. In particular, as used herein, biologically active molecules include, but are not limited to, any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes, small molecule drugs, hard drugs, soft drugs, carbohydrates, inorganic atoms or molecules, dyes, lipids, nucleosides, radionuclides, oligonucleotides, toxins, cells, viruses, liposomes, microparticles and micelles. Classes of biologically active agents that are suitable for use with the invention include, but are not limited to, drugs, prodrugs, radionuclides, imaging agents, polymers, antibiotics, fungicides, anti-viral agents, anti-inflammatory agents, anti-tumor agents, cardiovascular agents, anti-anxiety agents, hormones, growth factors, steroidal agents, microbially derived toxins, and the like.

A "bifunctional polymer" refers to a polymer comprising two discrete functional groups that are capable of reacting specifically with other moieties (including but not limited to, amino acid side groups) to form covalent or non-covalent linkages. A bifunctional linker having one functional group reactive with a group on a particular biologically active component, and another group reactive with a group on a second biological component, may be used to form a conjugate that includes the first biologically active component, the bifunctional linker and the second biologically active component. Many procedures and linker molecules for attachment of various compounds to peptides are known. See, e.g., European Patent Application No. 188,256; U.S. Pat. Nos. 4,671, 958, 4,659,839, 4,414,148, 4,699,784; 4,680,338; and 4,569, 789 which are incorporated by reference herein. A "multifunctional polymer" refers to a polymer comprising two or more discrete functional groups that are capable of reacting specifically with other moieties (including but not limited to, amino acid side groups) to form covalent or non-covalent linkages. A bi-functional polymer or multi-functional polymer may be any desired length or molecular weight, and may be selected to provide a particular desired spacing or conformation between one or more molecules linked to hGH.

Where substituent groups are specified by their conventional chemical formulas, written from left to right, they equally encompass the chemically identical substituents that would result from writing the structure from right to left, for example, the structure —$CH_2O$— is equivalent to the structure —$OCH_2$—.

As used herein, the term "modulated serum half-life" means the positive or negative change in circulating half-life of a modified hGH relative to its non-modified form. Serum half-life is measured by taking blood samples at various time points after administration of hGH, and determining the concentration of that molecule in each sample. Correlation of the serum concentration with time allows calculation of the serum half-life. Increased serum half-life desirably has at least about two-fold, but a smaller increase may be useful, for example where it enables a satisfactory dosing regimen or avoids a toxic effect. In some embodiments, the increase is at least about three-fold, at least about five-fold, or at least about ten-fold.

The term "modulated therapeutic half-life" as used herein means the positive or negative change in the half-life of the therapeutically effective amount of hGH polypeptide, relative to its non-modified form. Therapeutic half-life is measured by measuring pharmacokinetic and/or pharmacodynamic properties of the molecule at various time points after administration. Increased therapeutic half-life desirably enables a particular beneficial dosing regimen, a particular beneficial total dose, or avoids an undesired effect. In some embodiments, the increased therapeutic half-life results from increased potency, increased or decreased binding of the modified molecule to its target, increased or decreased breakdown of the molecule by enzymes such as proteases, or an increase or decrease in another parameter or mechanism of action of the non-modified molecule.

The term "isolated," when applied to a nucleic acid or protein, denotes that the nucleic acid or protein is free of at least some of the other cellular components with which it is associated in the natural state, or that the nucleic acid or protein has been concentrated to a level greater than the concentration of its in vivo or in vitro production. It can be in a homogeneous state. Isolated substances can be in either a dry or semi-dry state, or in solution, including but not limited to, an aqueous solution. It can be a component of a pharmaceutical composition that comprises additional pharmaceutically acceptable carriers and/or excipients. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest. The term "purified" denotes that a nucleic acid or protein gives rise to substantially one band in an electrophoretic gel. Particularly, it may mean that the nucleic acid or protein is at least 85% pure, at least 90% pure, at least 95% pure, at least 99% or greater pure.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)).

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine. Amino acid analogs refers to compounds that have the same basic chemical structure as a naturally occurring amino acid, i.e., an α carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of ordinary skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of ordinary skill in the art will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the deletion of an amino acid, addition of an amino acid, or substitution of an amino acid with a chemically similar amino acid. Conservative substitution tables providing functionally similar amino acids are known to those of ordinary skill in the art. Such conservatively modified variants are in addition to and do not exclude polymorphic variants, interspecies homologs, and alleles of the invention.

Conservative substitution tables providing functionally similar amino acids are known to those of ordinary skill in the art. The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins: Structures and Molecular Properties* (W H Freeman & Co.; 2nd edition (December 1993)

The terms "identical" or percent "identity," in the context of two or more nucleic acids or polypeptide sequences, refer to two or more sequences or subsequences that are the same. Sequences are "substantially identical" if they have a percentage of amino acid residues or nucleotides that are the same (i.e., about 60% identity, about 65%, about 70%, about 75%, about 80%, about 85%, about 90%, or about 95% identity over a specified region), when compared and aligned for maximum correspondence over a comparison window, or designated region as measured using one of the following sequence comparison algorithms (or other algorithms available to persons of ordinary skill in the art) or by manual alignment and visual inspection. This definition also refers to the complement of a test sequence. The identity can exist over a region that is at least about 50 amino acids or nucleotides in length, or over a region that is 75-100 amino acids or nucleotides in length, or, where not specified, across the entire sequence of a polynucleotide or polypeptide.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are known to those of ordinary skill in the art. Optimal alignment of sequences for comparison can be conducted, including but not limited to, by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

One example of an algorithm that is suitable for determining percent sequence identity and sequence similarity are the BLAST and BLAST 2.0 algorithms, which are described in Altschul et al. (1997) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1992) *Proc. Natl. Acad. Sci. USA* 89:10915) alignments (B) of 50, expectation (E) of 10, M=5, N=−4, and a comparison of both strands. The BLAST algorithm is typically performed with the "low complexity" filter turned off 1851 The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid may be considered similar to a reference sequence if the smallest sum probability in a comparison of the test nucleic acid to the reference nucleic acid is less than about 0.2, less than about 0.01, or less than about 0.001.

The phrase "selectively (or specifically) hybridizes to" refers to the binding, duplexing, or hybridizing of a molecule only to a particular nucleotide sequence under stringent hybridization conditions when that sequence is present in a complex mixture (including but not limited to, total cellular or library DNA or RNA).

The phrase "stringent hybridization conditions" refers to hybridization of sequences of DNA, RNA, PNA, or other nucleic acid mimics, or combinations thereof under conditions of low ionic strength and high temperature as is known in the art. Typically, under stringent conditions a probe will hybridize to its target subsequence in a complex mixture of nucleic acid (including but not limited to, total cellular or library DNA or RNA) but does not hybridize to other sequences in the complex mixture. Stringent conditions are sequence-dependent and will be different in different circumstances. Longer sequences hybridize specifically at higher temperatures. An extensive guide to the hybridization of nucleic acids is found in Tijssen, *Laboratory Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, typically about 0.01 to 1.0 M sodium ion concentration (or other salts) at pH 7.0 to 8.3 and the temperature is at least about 30° C. for short probes (including but not limited to, 10 to 50 nucleotides) and at least about 60° C. for long probes (including but not limited to, greater than 50 nucleotides). Stringent conditions may also be achieved with the addition of destabilizing agents such as formamide. For selective or specific hybridization, a positive signal may be at least two times background, optionally 10 times background hybridization. Exemplary stringent hybridization conditions can be as following: 50% formamide, 5×SSC, and 1% SDS, incubating at 42° C., or 5×SSC, 1% SDS, incubating at 65° C., with wash in 0.2×SSC, and 0.1% SDS at 65° C. Such washes can be performed for 5, 15, 30, 60, 120, or more minutes.

As used herein, the term "eukaryote" refers to organisms belonging to the phylogenetic domain Eucarya such as animals (including but not limited to, mammals, insects, reptiles, birds, etc.), ciliates, plants (including but not limited to, monocots, dicots, algae, etc.), fungi, yeasts, flagellates, microsporidia, protists, etc.

As used herein, the term "non-eukaryote" refers to non-eukaryotic organisms. For example, a non-eukaryotic organism can belong to the Eubacteria (including but not limited to, *Escherichia coli, Thermus thermophilus, Bacillus stearothermophilus, Pseudomonas fluorescens, Pseudomonas aeruginosa, Pseudomonas putida*, etc.) phylogenetic domain, or the Archaea (including but not limited to, *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix*, etc.) phylogenetic domain.

The term "subject" as used herein, refers to an animal, in some embodiments a mammal, and in other embodiments a human, who is the object of treatment, observation or experiment.

The term "effective amount" as used herein refers to that amount of the non-natural amino acid polypeptide being administered which will relieve to some extent one or more of the symptoms of the disease, condition or disorder being treated. Compositions containing the non-natural amino acid polypeptide described herein can be administered for prophylactic, enhancing, and/or therapeutic treatments.

The terms "enhance" or "enhancing" means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system. When used in a patient, amounts effective for this use will depend on the severity and course of the disease, disorder or condition, previous therapy, the patient's health status and response to the drugs, and the judgment of the treating physician.

The term "modified," as used herein refers to any changes made to a given. polypeptide, such as changes to the length of the polypeptide, the amino acid sequence, chemical structure, co-translational modification, or post-translational modification of a polypeptide. The form "(modified)" term means that the polypeptides being discussed are optionally modified, that is, the polypeptides under discussion can be modified or unmodified.

The term "post-translationally modified" refers to any modification of a natural or non-natural amino acid that occurs to such an amino acid after it has been incorporated into a polypeptide chain. The term encompasses, by way of example only, co-translational in vivo modifications, co-translational in vitro modifications (such as in a cell-free translation system), post-translational in vivo modifications, and post-translational in vitro modifications.

In prophylactic applications, compositions containing the non-natural amino acid polypeptide are administered to a patient susceptible to or otherwise at risk of a particular disease, disorder or condition. Such an amount is defined to be a "prophylactically effective amount." In this use, the precise amounts also depend on the patient's state of health, weight, and the like. It is considered well within the skill of the art for one to determine such prophylactically effective amounts by routine experimentation (e.g., a dose escalation clinical trial).

The term "protected" refers to the presence of a "protecting group" or moiety that prevents reaction of the chemically reactive functional group under certain reaction conditions. The protecting group will vary depending on the type of chemically reactive group being protected. For example, if the chemically reactive group is an amine or a hydrazide, the protecting group can be selected from the group of tert-butyloxycarbonyl (t-Boc) and 9-fluorenylmethoxycarbonyl (Fmoc). If the chemically reactive group is a thiol, the protecting group can be orthopyridyldisulfide. If the chemically reactive group is a carboxylic acid, such as butanoic or propionic acid, or a hydroxyl group, the protecting group can be benzyl or an alkyl group such as methyl, ethyl, or tert-butyl. Other protecting groups known in the art may also be used in or with the methods and compositions described herein, including photolabile groups such as Nvoc and MeNvoc. Other protecting groups known in the art may also be used in or with the methods and compositions described herein.

By way of example only, blocking/protecting groups may be selected from:

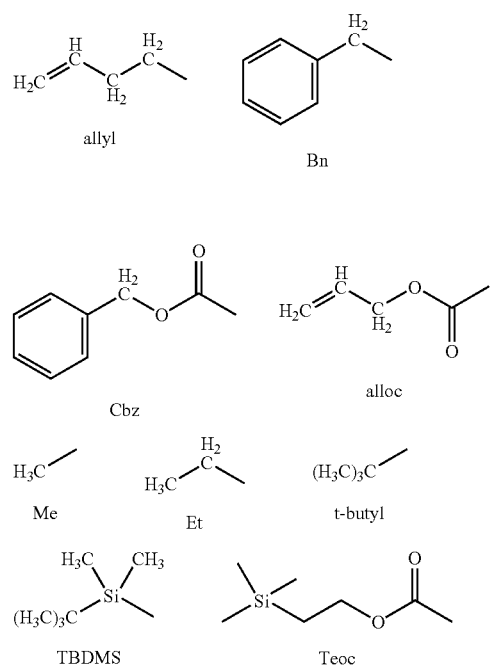

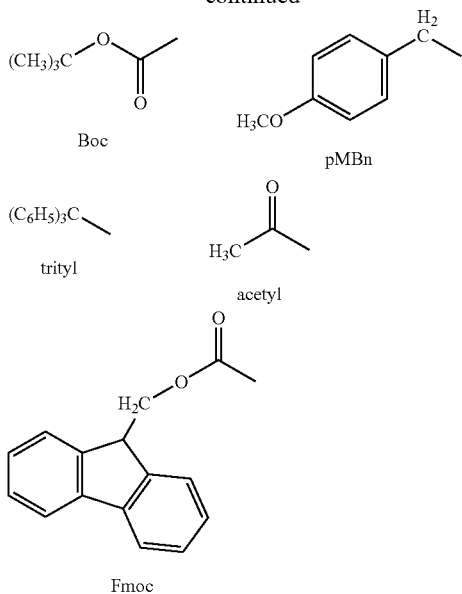

Boc
pMBn
trityl
acetyl
Fmoc

Other protecting groups are described in Greene and Wuts, Protective Groups in Organic Synthesis, 3rd Ed., John Wiley & Sons, New York, N.Y., 1999, which is incorporated herein by reference in its entirety.

In therapeutic applications, compositions containing the (modified) non-natural amino acid polypeptide are administered to a patient already suffering from a disease, condition or disorder, in an amount sufficient to cure or at least partially arrest the symptoms of the disease, disorder or condition. Such an amount is defined to be a "therapeutically effective amount," and will depend on the severity and course of the disease, disorder or condition, previous therapy, the patient's health status and response to the drugs, and the judgment of the treating physician. It is considered well within the skill of the art for one to determine such therapeutically effective amounts by routine experimentation (e.g., a dose escalation clinical trial).

The term "treating" is used to refer to either prophylactic and/or therapeutic treatments.

Non-naturally encoded amino acid polypeptides presented herein may include isotopically-labelled compounds with one or more atoms replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as $^2H$, $^3H$, $^{13}C$, $^{14}C$, $^{15}N$, $^{18}O$, $^{17}O$, $^{35}S$, $^{18}F$, $^{36}Cl$, respectively. Certain isotopically-labelled compounds described herein, for example those into which radioactive isotopes such as $^3H$ and $^{14}C$ are incorporated, may be useful in drug and/or substrate tissue distribution assays. Further, substitution with isotopes such as deuterium, i.e., $^2H$, can afford certain therapeutic advantages resulting from greater metabolic stability, for example increased in vivo half-life or reduced dosage requirements.

All isomers including but not limited to diastereomers, enantiomers, and mixtures thereof are considered as part of the compositions described herein. In additional or further embodiments, the non-naturally encoded amino acid polypeptides are metabolized upon administration to an organism in need to produce a metabolite that is then used to produce a desired effect, including a desired therapeutic effect. In further or additional embodiments are active metabolites of non-naturally encoded amino acid polypeptides.

In some situations, non-naturally encoded amino acid polypeptides may exist as tautomers. In addition, the non-naturally encoded amino acid polypeptides described herein can exist in unsolvated as well as solvated forms with pharmaceutically acceptable solvents such as water, ethanol, and the like. The solvated forms are also considered to be disclosed herein. Those of ordinary skill in the art will recognize that some of the compounds herein can exist in several tautomeric forms. All such tautomeric forms are considered as part of the compositions described herein.

DETAILED DESCRIPTION

I. Introduction hGH molecules comprising at least one unnatural amino acid are provided in the invention. In certain embodiments of the invention, the hGH polypeptide with at least one unnatural amino acid includes at least one post-translational modification. In one embodiment, the at least one post-translational modification comprises attachment of a molecule including but not limited to, a label, a dye, a polymer, a water-soluble polymer, a derivative of polyethylene glycol, a photocrosslinker, a radionuclide, a cytotoxic compound, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, a saccharide, a water-soluble dendrimer, a cyclodextrin, an inhibitory ribonucleic acid, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a photoisomerizable moiety, biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, a small molecule, a quantum dot, a nanotransmitter, a radionucleotide, a radiotransmitter, a neutron-capture agent, or any combination of the above or any other desirable compound or substance, comprising a second reactive group to at least one unnatural amino acid comprising a first reactive group utilizing chemistry methodology that is known to one of ordinary skill in the art to be suitable for the particular reactive groups. In certain embodiments of the modified hGH polypeptide of the present invention, at least one unnatural amino acid (including but not limited to, unnatural amino acid containing a keto functional group) comprising at least one post-translational modification, is used where the at least one post-translational modification comprises a saccharide moiety. In certain embodiments, the post-translational modification is made in vivo in a eukaryotic cell or in a non-eukaryotic cell.

In certain embodiments, the protein includes at least one post-translational modification that is made in vivo by one host cell, where the post-translational modification is not normally made by another host cell type. In certain embodiments, the protein includes at least one post-translational modification that is made in vivo by a eukaryotic cell, where the post-translational modification is not normally made by a non-eukaryotic cell. Examples of post-translational modifications include, but are not limited to, glycosylation, acetylation, acylation, lipid-modification, palmitoylation, palmitate addition, phosphorylation, glycolipid-linkage modification, and the like. In one embodiment, the post-translational modification comprises attachment of an oligosaccharide to an asparagine by a GlcNAc-asparagine linkage (including but not limited to, where the oligosaccharide comprises (GlcNAc-Man)$_2$-Man-GlcNAc-GlcNAc, and the like). In another embodiment, the post-translational modification comprises attachment of an oligosaccharide (including but not limited to, Gal-GalNAc, Gal-GlcNAc, etc.) to a serine or threonine by a GalNAc-serine, a GalNAc-threonine, a GlcNAc-serine, or a GlcNAc-threonine linkage. In certain embodiments, a protein or polypeptide of the invention can comprise a secretion or localization sequence, an epitope tag, a FLAG tag, a polyhistidine tag, a GST fusion, and/or the like. Examples of secretion signal sequences include, but are not limited to, a prokaryotic secretion signal sequence, a eukaryotic secretion signal sequence, a eukaryotic secretion signal sequence 5'-optimized for bacterial expression, a novel secretion signal sequence, pectate lyase secretion signal sequence, Omp A secretion signal sequence, and a phage secretion signal sequence. Examples of secretion signal sequences, include, but are not limited to, STII (prokaryotic), Fd GIII and M13 (phage), Bgl2 (yeast), and the signal sequence bla derived from a transposon.

The protein or polypeptide of interest can contain at least one, at least two, at least three, at least four, at least five, at least six, at least seven, at least eight, at least nine, or ten or more unnatural amino acids. The unnatural amino acids can be the same or different, for example, there can be 1, 2, 3, 4, 5, 6, 7, 8, 9, 10 or more different sites in the protein that comprise 1, 2, 3, 4, 5, 6, 7, 8, 9, 10 or more different unnatural amino acids. In certain embodiments, at least one, but fewer than all, of a particular amino acid present in a naturally occurring version of the protein is substituted with an unnatural amino acid.

The present invention provides methods and compositions based on growth hormone, in particular hGH, comprising at least one non-naturally encoded amino acid. Introduction of at least one non-naturally encoded amino acid into hGH can allow for the application of conjugation chemistries that involve specific chemical reactions, including, but not limited to, with one or more non-naturally encoded amino acids while not reacting with the commonly occurring 20 amino acids. In some embodiments, hGH comprising the non-naturally encoded amino acid is linked or bonded to a water soluble polymer, such as polyethylene glycol (PEG), via the side chain of the non-naturally encoded amino acid. This invention provides a highly efficient method for the selective modification of proteins with PEG derivatives, which involves the selective incorporation of non-genetically encoded amino acids, including but not limited to, those amino acids containing functional groups or substituents not found in the 20 naturally incorporated amino acids, including but not limited to a ketone moiety, into proteins in response to a selector codon and the subsequent modification of those amino acids with a suitably reactive PEG derivative. Once incorporated, the amino acid side chains can then be modified by utilizing chemistry methodologies known to those of ordinary skill in the art to be suitable for the particular functional groups or substituents present in the non-naturally encoded amino acid. Known chemistry methodologies of a wide variety are suitable for use in the present invention to incorporate a water soluble polymer into the protein.

The present invention provides conjugates of hGH polypeptide having a wide variety of functional groups, substituents or moieties, with other substances including but not limited to a label; a dye; a polymer; a water-soluble polymer; a derivative of polyethylene glycol; a photocrosslinker; a radionuclide; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide; a water-soluble dendrimer; a cyclodextrin; an inhibitory ribonucleic acid; a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a photoisomerizable moiety; biotin; a derivative of biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; a quantum dot; a nanotransmitter; a radionuclide; a radiotransmitter; a neutron-capture agent; or any combination of the above, or any other desirable compound or substance.

It is well established in the art that PEG can be used to modify the surfaces of biomaterials (see, e.g., U.S. Pat. No. 6,610,281; Mehvar, R., J. Pharm Pharm Sci., 3(1):125-136 (2000) which are incorporated by reference herein). The PEG derivative can be bonded directly to the polymer via a reactive moiety. Alternatively, the PEG derivative can be prepared by attaching a linking agent that has a reactive moiety at one terminus to a conventional activated polymer so that the resulting polymer has the reactive moiety at its terminus. Alternatively, a water soluble polymer having at least one active nucleophilic or electrophilic moiety undergoes a reaction with a linking agent that has a reactive group at one terminus so that a covalent bond is formed between the PEG polymer and the linking agent and the reactive group is positioned at the terminus of the polymer. Nucleophilic and electrophilic moieties, including amines, thiols, hydrazides, hydrazines, alcohols, carboxylates, aldehydes, ketones, thioesters and the like, are known to those of ordinary skill in the art. The PEG derivatives can be used to modify the properties of surfaces and molecules where biocompatibility, stability, solubility and lack of immunogenicity are important, while at the same time providing a more selective means of attaching the PEG derivatives to proteins than was previously known in the art.

II. Growth Hormone Supergene Family

The following proteins include those encoded by genes of the growth hormone (GH) supergene family (Bazan, F., *Immunology Today* 11: 350-354 (1990); Bazan, J. F. Science 257: 410-413 (1992); Mott, H. R. and Campbell, I. D., *Current Opinion in Structural Biology* 5: 114-121 (1995); Silvennoinen, O. and Ihle, J. N., SIGNALING BY THE HEMATOPOIETIC CYTOKINE RECEPTORS (1996)): growth hormone, prolactin, placental lactogen, erythropoietin (EPO), thrombopoietin (TPO), interleukin-2 (IL-2), IL-3, IL-4, IL-5, IL-6, IL-7, IL-9, IL-10, IL-11, IL-12 (p35 subunit), IL-13, IL-15, oncostatin M, ciliary neurotrophic factor (CNTF), leukemia inhibitory factor (LIF), alpha interferon, beta interferon, epsilon interferon, gamma interferon, omega interferon, tau interferon, granulocyte-colony stimulating factor (G-CSF), granulocyte-macrophage colony stimulating factor (GM-CSF), macrophage colony stimulating factor (M-CSF) and cardiotrophin-1 (CT-1) ("the GH supergene family"). It is anticipated that additional members of this gene family will be identified in the future through gene cloning and sequencing. Members of the GH supergene family have similar secondary and tertiary structures, despite the fact that they generally have limited amino acid or DNA sequence identity. The shared structural features allow new members of the gene family to be readily identified and the non-natural amino acid methods and compositions described herein similarly applied. Given the extent of structural homology among the members of the GH supergene family, non-naturally encoded amino acids may be incorporated into any members of the GH supergene family using the present invention. Each member of this family of proteins comprises a four helical bundle.

Structures of a number of cytokines, including G-CSF (Zink et al:, FEBS Lett. 314:435 (1992); Zink et al., Biochemistry 33:8453 (1994); Hill et al., Proc. Natl. Acad. Sci. USA 90:5167 (1993)), GM-CSF (Diederichs, K., et al. *Science* 154: 1779-1782 (1991); Walter et al., *J. Mol. Biol.* 224:1075-1085 (1992)), IL-2 (Bazan, J. F. and McKay, D. B. *Science* 257: 410-413 (1992), IL-4 (Redfield et al., *Biochemistry* 30: 11029-11035 (1991); Powers et al., *Science* 256:1673-1677 (1992)), and IL-5 (Milbum et al., *Nature* 363: 172-176 (1993)) have been determined by X-ray diffraction and NMR studies and show striking conservation with the GH structure, despite a lack of significant primary sequence homology. IFN is considered to be a member of this family based upon modeling and other studies (Lee et al., J. Interferon Cytokine Res. 15:341 (1995); Murgolo et al., *Proteins* 17:62 (1993); Radhakrishnan et al., *Structure* 4:1453 (1996); Klaus et al., J. Mol. Biol. 274:661 (1997)). EPO is considered to be a member of this family based upon modeling and mutagenesis studies (Boissel et al., *J. Biol. Chem.* 268: 15983-15993 (1993); Wen et al., J. Biol. Chem. 269: 22839-22846 (1994)). All of the above cytokines and growth factors are now considered to comprise one large gene family.

In addition to sharing similar secondary and tertiary structures, members of this family share the property that they must oligomerize cell surface receptors to activate intracellular signaling pathways. Some GH family members, including but not limited to; GH and EPO, bind a single type of receptor and cause it to form homodimers. Other family members, including but not limited to, IL-2, IL-4, and IL-6, bind more than one type of receptor and cause the receptors to form heterodimers or higher order aggregates (Davis et al., (1993), *Science* 260: 1805-1808; Paonessa et al., (1995), EMBO J. 14: 1942-1951; Mott and Campbell, *Current Opinion in Structural Biology* 5: 114-121 (1995)). Mutagenesis studies have shown that, like GH, these other cytokines and growth factors contain multiple receptor binding sites, typically two, and bind their cognate receptors sequentially (Mott and Campbell, *Current Opinion in Structural Biology* 5: 114-121 (1995); Matthews et al., (1996) *Proc. Natl. Acad. Sci. USA* 93: 9471-9476). Like GH, the primary receptor binding sites for these other family members occur primarily in the four alpha helices and the A-B loop. The specific amino acids in the helical bundles that participate in receptor binding differ amongst the family members. Most of the cell surface receptors that interact with members of the GH supergene family are structurally related and comprise a second large multi-gene family. See, e.g. U.S. Pat. No. 6,608,183, which is incorporated by reference herein.

A general conclusion reached from mutational studies of various members of the GH supergene family is that the loops joining the alpha helices generally tend to not be involved in receptor binding. In particular the short B-C loop appears to be non-essential for receptor binding in most, if not all, family members. For this reason, the B-C loop may be substituted with non-naturally encoded amino acids as described herein in members of the GH supergene family. The A-B loop, the C-D loop (and D-E loop of interferon/IL-10-like members of the GH superfamily) may also be substituted with a non-naturally-occurring amino acid. Amino acids proximal to helix A and distal to the final helix also tend not to be involved in receptor binding and also may be sites for introducing non-naturally-occurring amino acids. In some embodiments, a non-naturally encoded amino acid is substituted at any position within a loop structure, including but not limited to, the first 1, 2, 3, 4, 5, 6, 7, or more amino acids of the A-B, B-C, C-D or D-E loop. In some embodiments, one or more non-naturally encoded amino acids are substituted within the last 1, 2, 3, 4, 5, 6, 7, or more amino acids of the A-B, B-C, C-D or D-E loop.

Certain members of the GH family, including but not limited to, EPO, IL-2, IL-3, IL-4, IL-6, G-CSF, GM-CSF, TPO, IL-1, IL-12 p35, IL-13, IL-15 and beta interferon contain N-linked and/or O-linked sugars. The glycosylation sites in the proteins occur almost exclusively in the loop regions and not in the alpha helical bundles. Because the loop regions generally are not involved in receptor binding and because they are sites for the covalent attachment of sugar groups, they may be useful sites for introducing non-naturally-occurring amino acid substitutions into the proteins. Amino acids that comprise the N- and O-linked glycosylation sites in the proteins may be sites for non-naturally-occurring amino acid substitutions because these amino acids are surface-exposed. Therefore, the natural protein can tolerate bulky sugar groups attached to the proteins at these sites and the glycosylation sites tend to be located away from the receptor binding sites.

Additional members of the GH supergene family are likely to be discovered in the future. New members of the GH supergene family can be identified through computer-aided secondary and tertiary structure analyses of the predicted protein sequences, and by selection techniques designed to identify molecules that bind to a particular target. Members of the GH supergene family typically possess four or five amphipathic helices joined by non-helical amino acids (the loop regions). The proteins may contain a hydrophobic signal sequence at their N-terminus to promote secretion from the cell. Such later discovered members of the GH supergene family also are included within this invention. A related application is International Patent Application entitled "Modified Four Helical Bundle Polypeptides and Their Uses" published as WO 05/074650 on Aug. 18, 2005, which is incorporated by reference herein.

Thus, the description of the hGH is provided for illustrative purposes and by way of example only and not as a limit on the scope of the methods, compositions, strategies and techniques described herein. Further, reference to hGH polypeptides in this application is intended to use the generic term as an example of any growth hormone. Thus, it is understood that the modifications and chemistries described herein with reference to hGH polypeptides or protein can be equally applied to any member of the GH supergene family, including those specifically listed herein.

III. Selector Codons

Selector codons of the invention expand the genetic codon framework of protein biosynthetic machinery. For example, a selector codon includes, but is not limited to, a unique three base codon, a nonsense codon, such as a stop codon, including but not limited to, an amber codon (UAG), an ochre codon, or an opal codon (UGA), an unnatural codon, a four or more base codon, a rare codon, or the like. It is readily apparent to those of ordinary skill in the art that there is a wide range in the number of selector codons that can be introduced into a desired gene or polynucleotide, including but not limited to, one or more, two or more, three or more, 4, 5, 6, 7, 8, 9, 10 or more in a single polynucleotide encoding at least a portion of the hGH polypeptide.

In one embodiment, the methods involve the use of a selector codon that is a stop codon for the incorporation of one or more unnatural amino acids in vivo. For example, an O-tRNA is produced that recognizes the stop codon, including but not limited to, UAG, and is aminoacylated by an O-RS with a desired unnatural amino acid. This O-tRNA is not recognized by the naturally occurring host's aminoacyl-tRNA synthetases. Conventional site-directed mutagenesis can be used to introduce the stop codon, including but, not limited to, TAG, at the site of interest in a polypeptide of interest. See, e.g., Sayers, J. R., et al. (1988), 5'-3' *Exonucleases in phosphorothioate-based oligonucleotide-directed mutagenesis. Nucleic Acids Res,* 16:791-802. When the O-RS, O-tRNA and the nucleic acid that encodes the polypeptide of interest are combined in vivo, the unnatural amino acid is incorporated in response to the UAG codon to give a polypeptide containing the unnatural amino acid at the specified position.

The incorporation of unnatural amino acids in vivo can be done without significant perturbation of the eukaryotic host cell. For example, because the suppression efficiency for the UAG codon depends upon the competition between the O-tRNA, including but not limited to, the amber suppressor tRNA, and a eukaryotic release factor (including but not limited to, eRF) (which binds to a stop codon and initiates release of the growing peptide from the ribosome), the suppression efficiency can be modulated by, including but not limited to, increasing the expression level of O-tRNA, and/or the suppressor tRNA.

Unnatural amino acids can also be encoded with rare codons. For example, when the arginine concentration in an in vitro protein synthesis reaction is reduced, the rare arginine codon, AGG, has proven to be efficient for insertion of Ala by a synthetic tRNA acylated with alanine. See, e.g., Ma et al., *Biochemistry,* 32:7939 (1993). In this case, the synthetic tRNA competes with the naturally occurring tRNAArg, which exists as a minor species in *Escherichia coli.* Some organisms do not use all triplet codons. An unassigned codon AGA in *Micrococcus luteus* has been utilized for insertion of amino acids in an in vitro transcription/translation extract. See, e.g., Kowal and Oliver, *Nucl. Acid. Res.,* 25:4685 (1997). Components of the present invention can be generated to use these rare codons in vivo.

Selector codons also comprise extended codons, including but not limited to, four or more base codons, such as, four, five, six or more base codons. Examples of four base codons include, including but are not limited to, AGGA, CUAG, UAGA, CCCU and the like. Examples of five base codons include, but are not limited to, AGGAC, CCCCU, CCCUC, CUAGA, CUACU, UAGGC and the like. A feature of the invention includes using extended codons based on frameshift suppression. Four or more base codons can insert, including but not limited to, one or multiple unnatural amino acids into the same protein. For example, in the presence of mutated O-tRNAs, including but not limited to, a special frameshift suppressor tRNAs, with anticodon loops, for example, with at least 8-10 nt anticodon loops, the four or more base codon is read as single amino acid. In other embodiments, the anticodon loops can decode, including but not limited to, at least a four-base codon, at least a five-base codon, or at least a six-base codon or more. Since there are 256 possible four-base codons, multiple unnatural amino acids can be encoded in the same cell using a four or more base codon. See, Anderson et al., (2002) *Exploring the Limits of Codon and Anticodon Size, Chemistry and Biology,* 9:237-244; Magliery, (2001) *Expanding the Genetic Code: Selection of Efficient Suppressors of Four-base Codons and Identification of "Shifty" Four1-base Codons with a Library Approach in Escherichia coli, J. Mol. Biol.* 307: 755-769.

For example, four-base codons have been used to incorporate unnatural amino acids into proteins using in vitro biosynthetic methods. See, e.g., Ma et al., (1993) *Biochemistry,* 32:7939; and Hohsaka et al., (1999) *J. Am. Chem. Soc.,* 121: 34. CGGG and AGGU were used to simultaneously incorporate 2-naphthylalanine and an NBD derivative of lysine into streptavidin in vitro with two chemically acylated frameshift suppressor tRNAs. See, e.g., Hohsaka et al., (1999) *J. Am. Chem. Soc.,* 121:12194. In an in vivo study, Moore et al. examined the ability of tRNALeu derivatives with NCUA anticodons to suppress UAGN codons (N can be U, A, G, or C), and found that the quadruplet UAGA can be decoded by a tRNALeu with a UCUA anticodon with an efficiency of 13 to 26% with little decoding in the 0 or −1 frame. See, Moore et al., (2000) *J. Mol. Biol.,* 298:195. In one embodiment, extended codons based on rare codons or nonsense codons can be used in the present invention, which can reduce missense readthrough and frameshift suppression at other unwanted sites.

For a given system, a selector codon can also include one of the natural three base codons, where the endogenous system does not use (or rarely uses) the natural base codon. For example, this includes a system that is lacking a tRNA that recognizes the natural three base codon, and/or a system where the three base codon is a rare codon.

Selector codons optionally include unnatural base pairs. These unnatural base pairs further expand the existing genetic alphabet. One extra base pair increases the number of triplet codons from 64 to 125. Properties of third base pairs include stable and selective base pairing, efficient enzymatic incorporation into DNA with high fidelity by a polymerase, and the efficient continued primer extension after synthesis of the nascent unnatural base pair. Descriptions of unnatural base pairs which can be adapted for methods and compositions include, e.g., Hirao, et al., (2002) *An unnatural base pair for incorporating amino acid analogues into protein, Nature Biotechnology,* 20:177-182. See, also, Wu, Y., et al., (2002) *J. Am. Chem. Soc.* 124:14626-14630. Other relevant publications are listed below.

For in vivo usage, the unnatural nucleoside is membrane permeable and is phosphorylated to form the corresponding triphosphate. In addition, the increased genetic information is stable and not destroyed by cellular enzymes. Previous efforts by Benner and others took advantage of hydrogen bonding patterns that are different from those in canonical Watson-Crick pairs, the most noteworthy example of which is the iso-C:iso-G pair. See, e.g., Switzer et al., (1989) *J. Am. Chem. Soc.,* 111:8322; and Piccirilli et al., (1990) *Nature,* 343:33; Kool, (2000) *Curr. Opin. Chem. Biol.,* 4:602. These bases in general mispair to some degree with natural bases and cannot be enzymatically replicated. Kool and co-workers demonstrated that hydrophobic packing interactions between bases can replace hydrogen bonding to drive the formation of base pair. See, Kool, (2000) *Curr. Opin. Chem. Biol.,* 4:602; and Guckian and Kool, (1998) *Angew. Chem. Int. Ed. Engl.,* 36, 2825. In an effort to develop an unnatural base pair satisfying all the above requirements, Schultz, Romesberg and co-workers have systematically synthesized and studied a series of unnatural hydrophobic bases. A PICS:PICS self-pair is found to be more stable than natural base pairs, and can be efficiently incorporated into DNA by Klenow fragment of *Escherichia coli* DNA polymerase I (KF). See, e.g., McMinn et al., (1999) *J. Am. Chem. Soc.,* 121:11585-6; and Ogawa et al., (2000) *J. Am. Chem. Soc.,* 122:3274. A 3MN:3MN self-pair can be synthesized by KF with efficiency and selectivity sufficient for biological function. See, e.g., Ogawa et al., (2000) *J. Am. Chem. Soc.,* 122:8803. However, both bases act as a chain terminator for further replication. A mutant DNA polymerase has been recently evolved that can be used to replicate the PICS self pair. In addition, a 7AI self pair can be replicated. See, e.g., Tae et al., (2001) *J. Am. Chem. Soc.,* 123:7439. A novel metallobase pair, Dipic:Py, has also been developed, which forms a stable pair upon binding Cu(II). See, Meggers et al., (2000) *J. Am. Chem. Soc.,* 122:10714. Because extended codons and unnatural codons are intrinsically orthogonal to natural codons, the methods of the invention can take advantage of this property to generate orthogonal tRNAs for them.

A translational bypassing system can also be used to incorporate an unnatural amino acid in a desired polypeptide. In a translational bypassing system, a large sequence is incorporated into a gene but is not translated into protein. The sequence contains a structure that serves as a cue to induce the ribosome to hop over the sequence and resume translation downstream of the insertion.

In certain embodiments, the protein or polypeptide of interest (or portion thereof) in the methods and/or compositions of the invention is encoded by a nucleic acid. Typically, the nucleic acid comprises at least one selector codon, at least two selector codons, at least three selector codons, at least four selector codons, at least five selector codons, at least six selector codons, at least seven selector codons, at least eight selector codons, at least nine selector codons, ten or more selector codons.

Genes coding for proteins or polypeptides of interest can be mutagenized using methods well-known to one of skill in the art and described herein to include, for example, one or more selector codon for the incorporation of an unnatural amino acid. For example, a nucleic acid for a protein of interest is mutagenized to include one or more selector codon, providing for the incorporation of one or more unnatural amino acids. The invention includes any such variant, including but not limited to, mutant, versions of any protein, for example, including at least one unnatural amino acid. Similarly, the invention also includes corresponding nucleic acids, i.e., any nucleic acid with one or more selector codon that encodes one or more unnatural amino acid.

Nucleic acid molecules encoding a protein of interest such as a hGH polypeptide may be readily mutated to introduce a cysteine at any desired position of the polypeptide. Cysteine is widely used to introduce reactive molecules, water soluble polymers, proteins, or a wide variety of other molecules, onto a protein of interest. Methods suitable for the incorporation of cysteine into a desired position of a polypeptide are known to those of ordinary skill in the art, such as those described in U.S. Pat. No. 6,608,183, which is incorporated by reference herein, and standard mutagenesis techniques.

IV. Non-Naturally Encoded Amino Acids

A very wide variety of non-naturally encoded amino acids are suitable for use in the present invention. Any number of non-naturally encoded amino acids can be introduced into a hGH polypeptide. In general, the introduced non-naturally encoded amino acids are substantially chemically inert toward the 20 common, genetically-encoded amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine). In some embodiments, the non-naturally encoded amino acids include side chain functional groups that react efficiently and selectively with functional groups not found in the 20 common amino acids (including but not limited to, azido, ketone, aldehyde and aminooxy groups) to form stable conjugates.

The generic structure of an alpha-amino acid is illustrated as follows (Formula I):

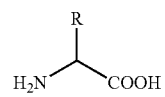

A non-naturally encoded amino acid is typically any structure having the above-listed formula wherein the R group is any substituent other than one used in the twenty natural amino acids, and may be suitable for use in the present invention. Because the non-naturally encoded amino acids of the invention typically differ from the natural amino acids only in the structure of the side chain, the non-naturally encoded amino acids form amide bonds with other amino acids, including but not limited to, natural or non-naturally encoded, in the same manner in which they are formed in naturally occurring polypeptides. However, the non-naturally encoded amino acids have side chain groups that distinguish them from the natural amino acids. For example, R optionally comprises an alkyl-, aryl-, acyl-, keto-, azido-, hydroxyl-, hydrazine, cyano-, halo-, hydrazide, alkenyl, alkynl, ether, thiol, seleno-, sulfonyl-, borate, boronate, phospho, phosphono, phosphine, heterocyclic, enone, imine, aldehyde, ester, thioacid, hydroxylamine, amino group, or the like or any combination thereof. Other non-naturally occurring amino acids of interest that may be suitable for use in the present invention include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, keto-containing amino acids, amino acids comprising polyethylene glycol or polyether, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

Exemplary non-naturally encoded amino acids that may be suitable for use in the present invention and that are useful for reactions with water soluble polymers include, but are not limited to, those with carbonyl, aminooxy, hydrazine, hydrazide, semicarbazide, azide and alkyne reactive groups. In some embodiments, non-naturally encoded amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature—including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

Many of the non-naturally encoded amino acids provided herein are commercially available, e.g., from Sigma-Aldrich (St. Louis, Mo., USA), Novabiochem (a division of EMD Biosciences, Darmstadt, Germany), or Peptech (Burlington, Mass., USA). Those that are not commercially available are optionally synthesized as provided herein or using standard methods known to those of ordinary skill in the art. For organic synthesis techniques, see, e.g., *Organic Chemistry* by Fessendon and Fessendon, (1982, Second Edition, Willard Grant Press, Boston Mass.); *Advanced Organic Chemistry* by March (Third Edition, 1985, Wiley and Sons, New York); and *Advanced Organic Chemistry* by Carey and Sundberg (Third Edition, Parts A and B, 1990, Plenum Press, New York). See, also, U.S. Patent Application Publications 2003/0082575 and 2003/0108885, which are incorporated by reference herein. In addition to unnatural amino acids that contain novel side chains, unnatural amino acids that may be suitable for use in the present invention also optionally comprise modified backbone structures, including but not limited to, as illustrated by the structures of Formula II and III:

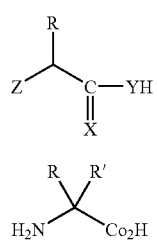

wherein Z typically comprises OH, NH$_2$, SH, NH—R', or S—R'; X and Y, which can be the same or different, typically comprise S or O, and R and R', which are optionally the same or different, are typically selected from the same list of constituents for the R group described above for the unnatural amino acids having Formula I as well as hydrogen. For example, unnatural amino acids of the invention optionally comprise substitutions in the amino or carboxyl group as illustrated by Formulas II and III. Unnatural amino acids of this type include, but are not limited to, α-hydroxy acids, α-thioacids, α-aminothiocarboxylates, including but not limited to, with side chains corresponding to the common twenty natural amino acids or unnatural side chains. In addition, substitutions at the α-carbon optionally include, but are not limited to, L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3, 4, 6, 7, 8, and 9 membered ring proline analogues, β and γ amino acids such as substituted β-alanine and γ-amino butyric acid.

Many unnatural amino acids are based on natural amino acids, such as tyrosine, glutamine, phenylalanine, and the like, and are suitable for use in the present invention. Tyrosine analogs include, but are not limited to, para-substituted tyrosines, ortho-substituted tyrosines, and meta substituted tyrosines, where the substituted tyrosine comprises, including but not limited to, a keto group (including but not limited to, an acetyl group), a benzoyl group, an amino group, a hydrazine, an hydroxyamine, a thiol group, a carboxy group, an isopropyl group, a methyl group, a C$_6$-C$_{20}$ straight chain or branched hydrocarbon, a saturated or unsaturated hydrocarbon, an O-methyl group, a polyether group, a nitro group, an alkynyl group or the like. In addition, multiply substituted aryl rings are also contemplated. Glutamine analogs that may be suitable for use in the present invention include, but are not limited to, α-hydroxy derivatives, γ-substituted derivatives, cyclic derivatives, and amide substituted glutamine derivatives. Example phenylalanine analogs that may be suitable for use in the present invention include, but are not limited to, para-substituted phenylalanines, ortho-substituted phenylalanines, and meta-substituted phenylalanines, where the substituent comprises, including but not limited to, a hydroxy group, a methoxy group, a methyl group, an allyl group, an aldehyde, an azido, an iodo, a bromo, a keto group (including but not limited to, an acetyl group), a benzoyl, an alkynyl group, or the like. Specific examples of unnatural amino acids that may be suitable for use in the present invention include, but are not limited to, a p-acetyl-L-phenylalanine, an O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, and a p-propargyloxy-phenylalanine, and the like. Examples of structures of a variety of unnatural amino acids that may be suitable for use in the present invention are provided in, for example, WO 2002/085923 entitled "In vivo incorporation of unnatural amino acids." See also Kiick et al., (2002) *Incorporation of azides into recombinant proteins for chemoselective modification by the Staudinger ligation, PNAS* 99:19-24, which is incorporated by reference herein, for additional methionine analogs.

In one embodiment, compositions of a hGH polypeptide that include an unnatural amino acid (such as p-(propargyloxy)-phenylalanine) are provided. Various compositions comprising p-(propargyloxy)-phenylalanine and, including but not limited to, proteins and/or cells, are also provided. In one aspect, a composition that includes the p-(propargyloxy)-phenylalanine unnatural amino acid, further includes an orthogonal tRNA. The unnatural amino acid can be bonded (including but not limited to, covalently) to the orthogonal tRNA, including but not limited to, covalently bonded to the orthogonal tRNA though an amino-acyl bond, covalently bonded to a 3'OH or a 2'OH of a terminal ribose sugar of the orthogonal tRNA, etc.

The chemical moieties via unnatural amino acids that can be incorporated into proteins offer a variety of advantages and manipulations of the protein: For example, the unique reactivity of a keto functional group allows selective modification of proteins with any of a number of hydrazine- or hydroxylamine-containing reagents in vitro and in vivo. A heavy atom unnatural amino acid, for example, can be useful for phasing X-ray structure data. The site-specific introduction of heavy atoms using unnatural amino acids also provides selectivity and flexibility in choosing positions for heavy atoms. Photoreactive unnatural amino acids (including but not limited to, amino acids with benzophenone and arylazides (including but not limited to, phenylazide) side chains), for example, allow for efficient in vivo and in vitro photocrosslinking of protein. Examples of photoreactive unnatural amino acids include, but are not limited to, p-azido-phenylalanine and p-benzoyl-phenylalanine. The protein with the photoreactive unnatural amino acids can then be crosslinked at will by excitation of the photoreactive group-providing temporal control. In one example, the methyl group of an unnatural amino can be substituted with an isotopically labeled, including but not limited to, methyl group, as a probe of local structure and dynamics, including but not limited to, with the use of nuclear magnetic resonance and vibrational spectroscopy. Alkynyl or azido functional groups, for example, allow the selective modification of proteins with molecules through a [3+2]cycloaddition reaction.

A non-natural amino acid incorporated into a polypeptide at the amino terminus can be composed of an R group that is any substituent other than one used in the twenty natural amino acids and a $2^{nd}$ reactive group different from the $NH_2$ group normally present in α-amino acids (see Formula I). A similar non-natural amino acid can be incorporated at the carboxyl terminus with a $2^{nd}$ reactive group different from the COOH group normally present in α-amino acids (see Formula I).

The unnatural amino acids of the invention may be selected or designed to provide additional characteristics unavailable in the twenty natural amino acids. For example, unnatural amino acid may be optionally designed or selected to modify the biological properties of a protein, e.g., into which they are incorporated. For example, the following properties may be optionally modified by inclusion of an unnatural amino acid into a protein: toxicity, biodistribution, solubility, stability, e.g., thermal, hydrolytic, oxidative, resistance to enzymatic degradation, and the like, facility of purification and processing, structural properties, spectroscopic properties, chemical and/or photochemical properties, catalytic activity, redox potential, half-life, ability to react with other molecules, e.g., covalently or noncovalently, and the like. U.S. patent application Ser. No. 11/046,432, which is incorporated by reference herein, discusses a number of different non-naturally encoded amino acids.

Chemical Synthesis of Unnatural Amino Acids

Many of the unnatural amino acids suitable for use in the present invention are commercially available, e.g., from Sigma (USA) or Aldrich (Milwaukee, Wis., USA). Those that are not commercially available are optionally synthesized as provided herein or as provided in various publications or using standard methods known to those of ordinary skill in the art. For organic synthesis techniques, see, e.g., *Organic Chemistry* by Fessendon and Fessendon, (1982, Second Edition, Willard Grant Press, Boston Mass.); *Advanced Organic Chemistry* by March (Third Edition, 1985, Wiley and Sons, New York); and *Advanced Organic Chemistry* by Carey and Sundberg (Third Edition, Parts A and B, 1990, Plenum Press, New York). Additional publications describing the synthesis of unnatural amino acids include, e.g., WO 2002/085923 entitled "In vivo incorporation of Unnatural Amino Acids;" Matsoukas et al., (1995) *J. Med. Chem.*, 38, 4660-4669; King, F. E. & Kidd, D. A. A. (1949) *A New Synthesis of Glutamine and of γ-Dipeptides of Glutamic Acid from Phthylated Intermediates. J. Chem. Soc.*, 3315-3319; Friedman, O. M. & Chatterrji, R. (1959) *Synthesis of Derivatives of Glutamine as Model Substrates for Anti-Tumor Agents. J. Am. Chem. Soc.* 81, 3750-3752; Craig, J. C. et al. (1988) *Absolute Configuration of the Enantiomers of 7-Chloro-4[[4-(diethylamino)-1-methylbutyl]amino]quinoline (Chloroquine). J. Org. Chem.* 53, 1167-1170; Azoulay, M., Vilmont, M. & Frappier, F. (1991) *Glutamine analogues as Potential Antimalarials, Eur. J. Med. Chem.* 26, 201-5; Koskinen, A. M. P. & Rapoport, H. (1989) *Synthesis of 4-Substituted Prolines as Conformationally Constrained Amino Acid Analogues. J. Org. Chem.* 54, 1859-1866; Christie, B. D. & Rapoport, H. (1985) *Synthesis of Optically Pure Pipecolates from L-Asparagine. Application to the Total Synthesis of (+)-Apovincamine through Amino Acid Decarbonylation and Iminium Ion Cyclization. J. Org. Chem.* 50:1239-1246; Barton et al., (1987) *Synthesis of Novel alpha-Amino-Acids and Derivatives Using Radical Chemistry: Synthesis of L-and D-alpha-Amino-Adipic Acids, L-alpha-aminopimelic Acid and Appropriate Unsaturated Derivatives. Tetrahedron* 43:4297-4308; and, Subasinghe et al., (1992) *Quisqualic acid analogues: synthesis of beta-heterocyclic 2-aminopropanoic acid derivatives and their activity at a novel quisqualate-sensitized site. J. Med. Chem.* 35:4602-7. See also, U.S. Patent Publication No. US 2004/0198637 entitled "Protein Arrays," which is incorporated by reference.

For example, the synthesis of p-acetyl-(+/−)-phenylalanine and m-acetyl-(+/−)-phenylalanine is described in Zhang, Z., et al., Biochemistry 42: 6735-6746 (2003), which is incorporated by reference herein. Other carbonyl-containing amino acids can be similarly prepared by one of ordinary skill in the art. The carbonyl functionality can be reacted selectively with a hydrazine-, hydrazide-, hydroxylamine-, or semicarbazide-containing reagent under mild conditions in aqueous solution to form the corresponding hydrazone, oxime, or semicarbazone linkages, respectively, that are stable under physiological conditions. See, e.g., Jencks, W. P., *J. Am. Chem. Soc.* 81, 475-481 (1959); Shao, J. and Tam, J. P., *J. Am. Chem. Soc.* 117:3893-3899 (1995). Moreover, the unique reactivity of the carbonyl group allows for selective modification in the presence of the other amino acid side chains. See, e.g., Cornish, V. W., et al., *J. Am. Chem. Soc.* 118:8150-8151 (1996); Geoghegan, K. F. & Stroh, J. G., *Bioconjug. Chem.* 3:138-146 (1992); Mahal, L. K., et al., *Science* 276:1125-1128 (1997).

Biosynthesis of Unnatural Amino Acids

Many biosynthetic pathways already exist in cells for the production of amino acids and other compounds. While a biosynthetic method for a particular unnatural amino acid may not exist in nature, including but not limited to, in a cell, the invention provides such methods. For example, biosynthetic pathways for unnatural amino acids are optionally generated in host cell by adding new enzymes or modifying existing host cell pathways. Additional new enzymes are optionally naturally occurring enzymes or artificially evolved enzymes. For example, the biosynthesis of p-aminophenylalanine (as presented in an example in WO 2002/085923 entitled "In vivo incorporation of unnatural amino acids") relies on the addition of a combination of known enzymes from other organisms. The genes for these enzymes can be introduced into a eukaryotic cell by transforming the cell with a plasmid comprising the genes. The genes, when expressed in the cell, provide an enzymatic pathway to synthesize the desired compound. Examples of the types of enzymes that are optionally added are provided in the examples below. Additional enzymes sequences are found, for example, in Genbank. Artificially evolved enzymes are also optionally added into a cell in the same manner. In this manner, the cellular machinery and resources of a cell are manipulated to produce unnatural amino acids.

A variety of methods are available for producing novel enzymes for use in biosynthetic pathways or for evolution of existing pathways. For example, recursive recombination, including but not limited to, as developed by Maxygen, Inc. (available on the World Wide Web at maxygen.com), is optionally used to develop novel enzymes and pathways. See, e.g., Stemmer (1994), *Rapid evolution of a protein in vitro by DNA shuffling, Nature* 370(4):389-391; and, Stemmer, (1994), *DNA shuffling by random fragmentation and reassembly: In vitro recombination for molecular evolution, Proc. Natl. Acad. Sci. USA.,* 91:10747-10751. Similarly Design-Path™, developed by Genencor (available on the World Wide Web at genencor.com) is optionally used for metabolic pathway engineering, including but not limited to, to engineer a pathway to create O-methyl-L-tyrosine in a cell. This technology reconstructs existing pathways in host organisms using a combination of new genes, including but not limited to, identified through functional genomics, and molecular evolution and design. Diversa Corporation (available on the World Wide Web at diversa.com) also provides technology for rapidly screening libraries of genes and gene pathways, including but not limited to, to create new pathways.

Typically, the unnatural amino acid produced with an engineered biosynthetic pathway of the invention is produced in a concentration sufficient for efficient protein biosynthesis, including but not limited to, a natural cellular amount, but not to, such a degree as to affect the concentration of the other amino acids or exhaust cellular resources. Typical concentrations produced in vivo in this manner are about 10 mM to about 0.05 mM. Once a cell is transformed with a plasmid comprising the genes used to produce enzymes desired for a specific pathway and an unnatural amino acid is generated, in vivo selections are optionally used to further optimize the production of the unnatural amino acid for both ribosomal protein synthesis and cell growth.

Cellular Uptake of Unnatural Amino Acids

Unnatural amino acid uptake by a cell is one issue that is typically considered when designing and selecting unnatural amino acids, including but not limited to, for incorporation into a protein. For example, the high charge density of α-amino acids suggests that these compounds are unlikely to be cell permeable. Natural amino acids are taken up into the eukaryotic cell via a collection of protein-based transport systems. A rapid screen can be done which assesses which unnatural amino acids, if any, are taken up by cells. See, e.g., the toxicity assays in, e.g., U.S. Patent Publication No. US 2004/0198637 entitled "Protein. Arrays," which is incorporated by reference herein; and Liu, D. R. & Schultz, P. G. (1999) *Progress toward the evolution of an organism with an expanded genetic code. PNAS United States* 96:4780-4785. Although uptake is easily analyzed with various assays, an alternative to designing unnatural amino acids that are amenable to cellular uptake pathways is to provide biosynthetic pathways to create amino acids in vivo.

V. Polypeptides with Unnatural Amino Acids

The incorporation of an unnatural amino acid can be done for a variety of purposes, including but not limited to, tailoring changes in protein structure and/or function, changing size, acidity, nucleophilicity, hydrogen bonding, hydrophobicity, accessibility of protease target sites, targeting to a moiety (including but not limited to, for a protein array), adding a biologically active molecule, attaching a polymer, attaching a radionuclide, modulating serum half-life, modulating tissue penetration (e.g. tumors), modulating active transport, modulating tissue, cell or organ specificity or distribution, modulating immunogenicity, modulating protease resistance, etc. Proteins that include an unnatural amino acid can have enhanced or even entirely new catalytic or biophysical properties. For example, the following properties are optionally modified by inclusion of an unnatural amino acid into a protein: toxicity, biodistribution, structural properties, spectroscopic properties, chemical and/or photochemical properties, catalytic ability, half-life (including but not limited to, serum half-life), ability to react with other molecules, including but not limited to, covalently or noncovalently, and the like. The compositions including proteins that include at least one unnatural amino acid are useful for, including but not limited to, novel therapeutics, diagnostics, catalytic enzymes, industrial enzymes, binding proteins (including but not limited to, antibodies), and including but not limited to, the study of protein structure and function. See, e.g., Dougherty, (2000) *Unnatural Amino Acids as Probes of Protein Structure and Function, Current Opinion in Chemical Biology,* 4:645-652.

In one aspect of the invention, a composition includes at least one protein with at least one, including but not limited to, at least two, at least three, at least four, at least five, at least six, at least seven, at least eight, at least nine, or at least ten or more unnatural amino acids. The unnatural amino acids can be the same or different, including but not limited to, there can be 1, 2, 3, 4, 5, 6, 7, 8, 9, or 10 or more different sites in the protein that comprise 1, 2, 3, 4, 5, 6, 7, 8, 9, or 10 or more different unnatural amino acids. In another aspect, a composition includes a protein with at least one, but fewer than all, of a particular amino acid present in the protein is substituted with the unnatural amino acid. For a given protein with more than one unnatural amino acids, the unnatural amino acids can be identical or different (including but not limited to, the protein can include two or more different types of unnatural amino acids, or can include two of the same unnatural amino acid). For a given protein with more than two unnatural amino acids, the unnatural amino acids can be the same, different or a combination of a multiple unnatural amino acid of the same kind with at least one different unnatural amino acid.

Proteins or polypeptides of interest with at least one unnatural amino acid are a feature of the invention. The invention also includes polypeptides or proteins with at least one unnatural amino acid produced using the compositions and methods of the invention. An excipient (including but not limited to, a pharmaceutically acceptable excipient) can also be present with the protein.

By producing proteins or polypeptides of interest with at least one unnatural amino acid in eukaryotic cells, proteins or polypeptides will typically include eukaryotic post-translational modifications. In certain embodiments, a protein includes at least one unnatural amino acid and at least one post-translational modification that is made in vivo by a eukaryotic cell, where the post-translational modification is not made by a prokaryotic cell. For example, the post-translation modification includes, including but not limited to, acetylation, acylation, lipid-modification, palmitoylation, palmitate addition, phosphorylation, glycolipid-linkage modification, glycosylation, and the like. In one aspect, the post-translational modification includes attachment of an oligosaccharide (including but not limited to, (GlcNAc-Man)$_2$-Man-GlcNAc-GlcNAc)) to an asparagine by a GlcNAc-asparagine linkage. See Table 1 which lists some examples of N-linked oligosaccharides of eukaryotic proteins (additional residues can also be present, which are not shown). In another aspect, the post-translational modification includes attachment of an oligosaccharide (including but not limited to, Gal-GalNAc, Gal-GlcNAc, etc.) to a serine or threonine by a GalNAc-serine or GalNAc-threonine linkage, or a GlcNAc-serine or a GlcNAc-threonine linkage.

TABLE 1

Examples of oligosaccharides through GLCNAC-linkage

| Type | Base Structure |
|---|---|
| I. High-mannose | Manα1-6\<br>　　　　＼Manα1-6\<br>Manα1-3／　　　＼Manβ1-4GlcNAcβ1-4GlcNAcβ1-Asn\<br>　　　　Manα1-3／ |
| II. Hybrid | 　　　　　　　Manα1-6\<br>　　　　　　　　　　＼Manβ1-4GlcNAcβ1-4GlcNAcβ1-Asn\<br>GlcNAcβ1-2——Manα1-3／ |
| III. Complex | GlcNAcβ1-2——Manα1-6\<br>　　　　　　　　　　＼Manβ1-4GlcNAcβ1-4GlcNAcβ1-Asn\<br>GlcNAcβ1-2——Manα1-3／ |
| IV. Xylose | Manα1-6\<br>　　　　＼Manβ1-4GlcNAcβ1-4GlcNAcβ1-Asn\<br>Xylβ1-2／ |

In yet another aspect, the post-translation modification includes proteolytic processing of precursors, assembly into a multisubunit protein or macromolecular assembly, translation to another site in the cell (including but not limited to, to organelles, such as the endoplasmic reticulum, the Golgi apparatus, the nucleus, lysosomes, peroxisomes, mitochondria, chloroplasts, vacuoles, etc., or through the secretory pathway). In certain embodiments, the protein comprises a secretion or localization sequence, an epitope tag, a FLAG tag, a polyhistidine tag, a GST fusion, or the like. U.S. Pat. Nos. 4,963,495 and 6,436,674, which are incorporated herein by reference, detail constructs designed to improve secretion of hGH polypeptides.

One advantage of an unnatural amino acid is that it presents additional chemical moieties that can be used to add additional molecules. These modifications can be made in vivo in a eukaryotic or non-eukaryotic cell, or in vitro. Thus, in certain embodiments, the post-translational modification is through the unnatural amino acid. For example, the post-translational modification can be through a nucleophilic-electrophilic reaction. Most reactions currently used for the selective modification of proteins involve covalent bond formation between nucleophilic and electrophilic reaction partners, including but not limited to the reaction of α-haloketones with histidine or cysteine side chains. Selectivity in these cases is determined by the number and accessibility of the nucleophilic residues in the protein. In proteins of the invention, other more selective reactions can be used such as the reaction of an unnatural keto-amino acid with hydrazides or aminooxy compounds, in vitro and in vivo. See, e.g., Cornish, et al., (1996) *J. Am. Chem. Soc.*, 118:8150-8151; Mahal, et al., (1997) *Science*, 276:1125-1128; Wang, et al., (2001) *Science* 292:498-500; Chin, et al., (2002) *J. Am. Chem. Soc.* 124:9026-9027; Chin, et al., (2002) *Proc. Natl. Acad. Sci.*, 99:11020-11024; Wang, et al., (2003) *Proc. Natl. Acad. Sci.*, 100:56-61; Zhang, et al., (2003) *Biochemistry*, 42:6735-6746; and, Chin, et al., (2003) *Science*, 301:964-7, all of which are incorporated by reference herein. This allows the selective labeling of virtually any protein with a host of reagents including fluorophores, crosslinking agents, saccharide derivatives and cytotoxic molecules. See also, U.S. Pat. No. 6,927,042 entitled "Glycoprotein Synthesis," which is incorporated by reference herein. Post-translational modifications, including but not limited to, through an azido amino acid, can also made through the Staudinger ligation (including but not limited to, with triarylphosphine reagents). See, e.g., Kiick et al., (2002) *Incorporation of azides into recombinant proteins for chemoselective modification by the Staudinger ligation, PNAS* 99:19-24.

This invention provides another highly efficient method for the selective modification of proteins, which involves the genetic incorporation of unnatural amino acids. A molecule that can be added to a protein include, but are not limited to, dyes, fluorophores, crosslinking agents, saccharide derivatives, polymers (including but not limited to, derivatives of polyethylene glycol), photocrosslinkers, cytotoxic compounds, affinity labels, derivatives of biotin, resins, beads, a second protein or polypeptide (or more), polynucleotide(s) (including but not limited to, DNA, RNA, etc.), metal chelators, cofactors, fatty acids, carbohydrates, and the like. In one embodiment, the method further includes incorporating into the protein the unnatural amino acid, where the unnatural amino acid comprises a first reactive group; and contacting the protein with a molecule (including but not limited to, a label, a dye, a polymer, a water-soluble polymer, a derivative of polyethylene glycol, a photocrosslinker, a radionuclide, a cytotoxic compound, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, a water-soluble dendrimer, a cyclodextrin, an inhibitory ribonucleic acid, a saccharide, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a photoisomerizable moiety, biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, a small molecule, a quantum dot, a nanotransmitter, a radionucleotide, a radiotransmitter, a neutron-capture agent, or any combination of the above, or any other desirable compound or substance) that comprises a second reactive group.

VI. In Vivo Generation of hGH Polypeptides Comprising Non-Genetically-Encoded Amino Acids The hGH polypeptides of the invention can be generated in vivo using modified tRNA and tRNA synthetases to add to or substitute amino acids that are not encoded in naturally-occurring systems.

Methods for generating tRNAs and tRNA synthetases which use amino acids that are not encoded in naturally-occurring systems are described in, e.g., U.S. Patent Application Publications 2003/0082575 (Ser. No. 10/126,927) and 2003/0108885 (Ser. No. 10/126,931) which are incorporated by reference herein. These methods involve generating a translational machinery that functions independently of the synthetases and tRNAs endogenous to the translation system (and are therefore sometimes referred to as "orthogonal"). Typically, the translation system comprises an orthogonal tRNA (O-tRNA) and an orthogonal aminoacyl tRNA synthetase (O-RS). Typically, the O-RS preferentially aminoacylates the O-tRNA with at least one non-naturally occurring amino acid in the translation system and the O-tRNA recognizes at least one selector codon that is not recognized by other tRNAs in the system. The translation system thus inserts the non-naturally-encoded amino acid into a protein produced in the system, in response to an encoded selector codon, thereby "substituting" an amino acid into a position in the encoded polypeptide.

A wide variety of orthogonal tRNAs and aminoacyl tRNA synthetases have been described in the art for inserting particular synthetic amino acids into polypeptides, and are generally suitable for use in the present invention. For example, keto-specific O-tRNA/aminoacyl-tRNA synthetases are described in Wang, L., et al., *Proc. Natl. Acad. Sci. USA* 100:56-61 (2003) and Zhang, Z. et al., *Biochem.* 42(22): 6735-6746 (2003). Exemplary O-RS, or portions thereof, are encoded by polynucleotide sequences and include amino acid sequences disclosed in U.S. Patent Application Publications 2003/0082575 and 2003/0108885, each incorporated herein by reference. Corresponding O-tRNA molecules for use with the O-RSs are also described in U.S. Patent Application Publications 2003/0082575 (Ser. No. 10/126,927) and 2003/0108885 (Ser. No. 10/126,931) which are incorporated by reference herein.

An example of an azide-specific O-tRNA/aminoacyl-tRNA synthetase system is described in Chin, J. W., et al., *J. Am. Chem. Soc.* 124:9026-9027 (2002). Exemplary O-RS sequences for p-azido-L-Phe include, but are not limited to, nucleotide sequences SEQ ID NOs: 14-16 and 29-32 and amino acid sequences SEQ ID NOs: 46-48 and 61-64 as disclosed in U.S. Patent Application Publication 2003/0108885 (Ser. No. 10/126,931) which is incorporated by reference herein. Exemplary O-tRNA sequences suitable for use in the present invention include, but are not limited to, nucleotide sequences SEQ ID NOs: 1-3 as disclosed in U.S. Patent Application Publication 2003/0108885 (Ser. No. 10/126,931) which is incorporated by reference herein. Other examples of O-tRNA/aminoacyl-tRNA synthetase pairs specific to particular non-naturally encoded amino acids are described in U.S. Patent Application Publication 2003/0082575 (Ser. No. 10/126,927) which is incorporated by reference herein. O-RS and O-tRNA that incorporate both keto- and azide-containing amino acids in *S. cerevisiae* are described in Chin, J. W., et al., *Science* 301:964-967 (2003).

Several other orthogonal pairs have been reported. Glutaminyl (see, e.g., Liu, D. R., and Schultz, P. G. (1999) *Proc. Natl. Acad. Sci. U.S.A.* 96:4780-4785), aspartyl (see, e.g., Pastrnak, M., et al., (2000) *Helv. Chim. Acta* 83:2277-2286), and tyrosyl (see, e.g., Ohno, S., et al., (1998) *J. Biochem.* (Tokyo, Jpn.) 124:1065-1068; and, Kowal, A. K., et al., (2001) *Proc. Natl. Acad. Sci. U.S.A.* 98:2268-2273) systems derived from *S. cerevisiae* tRNA's and synthetases have been described for the potential incorporation of unnatural amino acids in *E. coli*. Systems derived from the *E. coli* glutaminyl (see, e.g., Kowal, A. K., et al., (2001) *Proc. Natl. Acad. Sci. U.S.A.* 98:2268-2273) and tyrosyl (see, e.g., Edwards, H., and Schimmel, P. (1990) *Mol. Cell. Biol.* 10:1633-1641) synthetases have been described for use in *S. cerevisiae*. The *E. coli* tyrosyl system has been used for the incorporation of 3-iodo-L-tyrosine in vivo, in mammalian cells. See, Sakamoto, K., et al., (2002) *Nucleic Acids Res.* 30:4692-4699.

Use of O-tRNA/aminoacyl-tRNA synthetases involves selection of a specific codon which encodes the non-naturally encoded amino acid. While any codon can be used, it is generally desirable to select a codon that is rarely or never used in the cell in which the O-tRNA/aminoacyl-tRNA synthetase is expressed. For example, exemplary codons include nonsense codon such as stop codons (amber, ochre, and opal), four or more base codons and other natural three-base codons that are rarely or unused.

Specific selector codon(s) can be introduced into appropriate positions in the hGH polynucleotide coding sequence using mutagenesis methods known in the art (including but not limited to, site-specific mutagenesis, cassette mutagenesis, restriction selection mutagenesis, etc.).

Methods for generating components of the protein biosynthetic machinery, such as O-RSs, O-tRNAs, and orthogonal O-tRNA/O-RS pairs that can be used to incorporate a non-naturally encoded amino acid are described in Wang, L., et al., *Science* 292: 498-500 (2001); Chin, J. W., et al., *J. Am. Chem. Soc.* 124:9026-9027 (2002); Zhang, Z. et al., *Biochemistry* 42: 6735-6746 (2003): Methods and compositions for the in vivo incorporation of non-naturally encoded amino acids are described in U.S. Patent Application Publication 2003/0082575 (Ser. No. 10/126,927) which is incorporated by reference herein. Methods for selecting an orthogonal tRNA-tRNA synthetase pair for use in in vivo translation system of an organism are also described in U.S. Patent Application Publications 2003/0082575 (Ser. No. 10/126,927) and 2003/0108885 (Ser. No. 10/126,931) which are incorporated by reference herein. PCT Publication No. WO 04/035743 entitled "Site Specific Incorporation of Keto Amino Acids into Proteins," which is incorporated by reference herein in its entirety, describes orthogonal RS and tRNA pairs for the incorporation of keto amino acids. PCT Publication No. WO 04/094593 entitled "Expanding the Eukaryotic Genetic Code," which is incorporated by reference herein in its entirety, describes orthogonal RS and tRNA pairs for the incorporation of non-naturally encoded amino acids in eukaryotic host cells.

Methods for producing at least one recombinant orthogonal aminoacyl-tRNA synthetase (O-RS) comprise: (a) generating a library of (optionally mutant) RSs derived from at least one aminoacyl-tRNA synthetase (RS) from a first organism, including but not limited to, a prokaryotic organism, such as *Methanococcus jannaschii, Methanobacterium thermoautotrophicum, Halobacterium, Escherichia coli, A. fulgidus, P. furiosus, P. horikoshii, A. pernix, T thermophilus*, or the like, or a eukaryotic organism; (b) selecting (and/or screening) the library of RSs (optionally mutant RSs) for members that aminoacylate an orthogonal tRNA (O-tRNA) in the presence of a non-naturally encoded amino acid and a natural amino acid, thereby providing a pool of active (optionally mutant) RSs; and/or, (c) selecting (optionally through negative selection) the pool for active RSs (including but not limited to, mutant RSs) that preferentially aminoacylate the O-tRNA in the absence of the non-naturally encoded amino acid, thereby providing the at least one recombinant O-RS; wherein the at least one recombinant O-RS preferentially aminoacylates the O-tRNA with the non-naturally encoded amino acid.

In one embodiment, the RS is an inactive RS. The inactive RS can be generated by mutating an active RS. For example, the inactive RS can be generated by mutating at least about 1, at least about 2, at least about 3, at least about 4, at least about 5, at least about 6, or at least about 10 or more amino acids to different amino acids, including but not limited to, alanine.

Libraries of mutant RSs can be generated using various techniques known in the art, including but not limited to rational design based on protein three dimensional RS structure, or mutagenesis of RS nucleotides in a random or rational design technique. For example, the mutant RSs can be generated by site-specific mutations, random mutations, diversity generating recombination mutations, chimeric constructs, rational design and by other methods described herein or known in the art.

In one embodiment, selecting (and/or screening) the library of RSs (optionally mutant RSs) for members that are active, including but not limited to, that aminoacylate an orthogonal tRNA (O-tRNA) in the presence of a non-naturally encoded amino acid and a natural amino acid, includes: introducing a positive selection or screening marker, including but not limited to, an antibiotic resistance gene, or the like, and the library of (optionally mutant) RSs into a plurality of cells, wherein the positive selection and/or screening marker comprises at least one selector codon, including but not limited to, an amber, ochre, or opal codon; growing the plurality of cells in the presence of a selection agent; identifying cells that survive (or show a specific response) in the presence of the selection and/or screening agent by suppressing the at least one selector codon in the positive selection or screening marker, thereby providing a subset of positively selected cells that contains the pool of active (optionally mutant) RSs. Optionally, the selection and/or screening agent concentration can be varied.

In one aspect, the positive selection marker is a chloramphenicol acetyltransferase (CAT) gene and the selector codon is an amber stop codon in the CAT gene. Optionally, the positive selection marker is a β-lactamase gene and the selector codon is an amber stop codon in the β-lactamase gene. In another aspect the positive screening marker comprises a fluorescent or luminescent screening marker or an affinity based screening marker (including but not limited to, a cell surface marker).

In one embodiment, negatively selecting or screening the pool for active RSs (optionally mutants) that preferentially aminoacylate the O-tRNA in the absence of the non-naturally encoded amino acid includes: introducing a negative selection or screening marker with the pool of active (optionally mutant) RSs from the positive selection or screening into a plurality of cells of a second organism, wherein the negative selection or screening marker comprises at least one selector codon (including but not limited to, an antibiotic resistance gene, including but not limited to, a chloramphenicol acetyltransferase (CAT) gene); and, identifying cells that survive or show a specific screening response in a first medium supplemented with the non-naturally encoded amino acid and a screening or selection agent, but fail to survive or to show the specific response in a second medium not supplemented with the non-naturally encoded amino acid and the selection or screening agent, thereby providing surviving cells or screened cells with the at least one recombinant O-RS. For example, a CAT identification protocol optionally acts as a positive selection and/or a negative screening in determination of appropriate O-RS recombinants. For instance, a pool of clones is optionally replicated on growth plates containing CAT (which comprises at least one selector codon) either with or without one or more non-naturally encoded amino acid. Colonies growing exclusively on the plates containing non-naturally encoded amino acids are thus regarded as containing recombinant O—RS. In one aspect, the concentration of the selection (and/or screening) agent is varied. In some aspects the first and second organisms are different. Thus, the first and/or second organism optionally comprises: a prokaryote, a eukaryote, a mammal, an *Escherichia coli*, a fungi, a yeast, an archaebacterium, a eubacterium, a plant, an insect, a protist, etc. In other embodiments, the screening marker comprises a fluorescent or luminescent screening marker or an affinity based screening marker.

In another embodiment, screening or selecting (including but not limited to, negatively selecting) the pool for active (optionally mutant) RSs includes: isolating the pool of active mutant RSs from the positive selection step (b); introducing a negative selection or screening marker, wherein the negative selection or screening marker comprises at least one selector codon (including but not limited to, a toxic marker gene, including but not limited to, a ribonuclease barnase gene, comprising at least one selector codon), and the pool of active (optionally mutant) RSs into a plurality of cells of a second organism; and identifying cells that survive or show a specific screening response in a first medium not supplemented with the non-naturally encoded amino acid, but fail to survive or show a specific screening response in a second medium supplemented with the non-naturally encoded amino acid, thereby providing surviving or screened cells with the at least one recombinant O-RS, wherein the at least one recombinant O-RS is specific for the non-naturally encoded amino acid. In one aspect, the at least one selector codon comprises about two or more selector codons. Such embodiments optionally can include wherein the at least one selector codon comprises two or more selector codons, and wherein the first and second organism are different (including but not limited to, each organism is optionally, including but not limited to, a prokaryote, a eukaryote, a mammal, an *Escherichia coli*, a fungi, a yeast, an archaebacteria, a eubacteria, a plant, an insect, a protist, etc.). Also, some aspects include wherein the negative selection marker comprises a ribonuclease barnase gene (which comprises at least one selector codon). Other aspects include wherein the screening marker optionally comprises a fluorescent or luminescent screening marker or an affinity based screening marker. In the embodiments herein, the screenings and/or selections optionally include variation of the screening and/or selection stringency.

In one embodiment, the methods for producing at least one recombinant orthogonal aminoacyl-tRNA synthetase (O-RS) can further comprise: (d) isolating the at least one recombinant O-RS; (e) generating a second set of O-RS (optionally mutated) derived from the at least one recombinant O-RS; and, (f) repeating steps (b) and (c) until a mutated O-RS is obtained that comprises an ability to preferentially aminoacylate the O-tRNA. Optionally, steps (d)-(f) are repeated, including but not limited to, at least about two times. In one aspect, the second set of mutated O-RS derived from at least one recombinant O-RS can be generated by mutagenesis, including but not limited to, random mutagenesis, site-specific mutagenesis, recombination or a combination thereof.

The stringency of the selection/screening steps, including but not limited to, the positive selection/screening step (b), the negative selection/screening step (c) or both the positive and negative selection/screening steps (b) and (c), in the above-described methods, optionally includes varying the selection/screening stringency. In another embodiment, the positive selection/screening step (b), the negative selection/screening step (c) or both the positive and negative selection/screening steps (b) and (c) comprise using a reporter, wherein the reporter is detected by fluorescence-activated cell sorting (FACS) or wherein the reporter is detected by luminescence. Optionally, the reporter is displayed on a cell surface, on a phage display or the like and selected based upon affinity or catalytic activity involving the non-naturally encoded amino acid or an analogue. In one embodiment, the mutated synthetase is displayed on a cell surface, on a phage display or the like.

Methods for producing a recombinant orthogonal tRNA (O-tRNA) include: (a) generating a library of mutant tRNAs derived from at least one tRNA, including but not limited to, a suppressor tRNA, from a first organism; (b) selecting (including but not limited to, negatively selecting) or screening the library for (optionally mutant) tRNAs that are aminoacylated by an aminoacyl-tRNA synthetase (RS) from a second organism in the absence of a RS from the first organism, thereby providing a pool of tRNAs (optionally mutant); and, (c) selecting or screening the pool of tRNAs (optionally mutant) for members that are aminoacylated by an introduced orthogonal RS(O-RS), thereby providing at least one recombinant O-tRNA; wherein the at least one recombinant O-tRNA recognizes a selector codon and is not efficiency recognized by the RS from the second organism and is preferentially aminoacylated by the O—RS. In some embodiments the at least one tRNA is a suppressor tRNA and/or comprises a unique three base codon of natural and/or unnatural bases, or is a nonsense codon, a rare codon, an unnatural codon, a codon comprising at least 4 bases, an amber codon, an ochre codon, or an opal stop codon. In one embodiment, the recombinant O-tRNA possesses an improvement of orthogonality. It will be appreciated that in some embodiments, O-tRNA is optionally imported into a first organism from a second organism without the need for modification. In various embodiments, the first and second organisms are either the same or different and are optionally chosen from, including but not limited to, prokaryotes (including but not limited to, *Methanococcus jannaschii*, *Methanobacterium thermoautotrophicum*, *Escherichia coli*, *Halobacterium*, etc.), eukaryotes, mammals, fungi, yeasts, archaebacteria, eubacteria, plants, insects, protists, etc. Additionally, the recombinant tRNA is optionally aminoacylated by a non-naturally encoded amino acid, wherein the non-naturally encoded amino acid is biosynthesized in vivo either naturally or through genetic manipulation. The non-naturally encoded amino acid is optionally added to a growth medium for at least the first or second organism.

In one aspect, selecting (including but not limited to, negatively selecting) or screening the library for (optionally mutant) tRNAs that are aminoacylated by an aminoacyl-tRNA synthetase (step (b)) includes: introducing a toxic marker gene, wherein the toxic marker gene comprises at least one of the selector codons (or a gene that leads to the production of a toxic or static agent or a gene essential to the organism wherein such marker gene comprises at least one selector codon) and the library of (optionally mutant) tRNAs into a plurality of cells from the second organism; and, selecting surviving cells, wherein the surviving cells contain the pool of (optionally mutant) tRNAs comprising at least one orthogonal tRNA or nonfunctional tRNA. For example, surviving cells can be selected by using a comparison ratio cell density assay.

In another aspect, the toxic marker gene can include two or more selector codons. In another embodiment of the methods, the toxic marker gene is a ribonuclease barnase gene, where the ribonuclease barnase gene comprises at least one amber codon. Optionally, the ribonuclease barnase gene can include two or more amber codons.

In one embodiment, selecting or screening the pool of (optionally mutant) tRNAs for members that are aminoacylated by an introduced orthogonal RS(O-RS) can include: introducing a positive selection or screening marker gene, wherein the positive marker gene comprises a drug resistance gene (including but not limited to, β-lactamase gene, comprising at least one of the selector codons, such as at least one amber stop codon) or a gene essential to the organism, or a gene that leads to detoxification of a toxic agent, along with the O-RS, and the pool of (optionally mutant) tRNAs into a plurality of cells from the second organism; and, identifying surviving or screened cells grown in the presence of a selection or screening agent, including but not limited to, an antibiotic, thereby providing a pool of cells possessing the at least one recombinant tRNA, where the at least one recombinant tRNA is aminoacylated by the O-RS and inserts an amino acid into a translation product encoded by the positive marker gene, in response to the at least one selector codons. In another embodiment, the concentration of the selection and/or screening agent is varied.

Methods for generating specific O-tRNA/O-RS pairs are provided. Methods include: (a) generating a library of mutant tRNAs derived from at least one tRNA from a first organism; (b) negatively selecting or screening the library for (optionally mutant) tRNAs that are aminoacylated by an aminoacyl-tRNA synthetase (RS) from a second organism in the absence of a RS from the first organism, thereby providing a pool of (optionally mutant) tRNAs; (c) selecting or screening the pool of (optionally mutant) tRNAs for members that are aminoacylated by an introduced orthogonal RS(O-RS), thereby providing at least one recombinant O-tRNA. The at least one recombinant O-tRNA recognizes a selector codon and is not efficiency recognized by the RS from the second organism and is preferentially aminoacylated by the O—RS. The method also includes (d) generating a library of (optionally mutant) RSs derived from at least one aminoacyl-tRNA synthetase (RS) from a third organism; (e) selecting or screening the library of mutant RSs for members that preferentially aminoacylate the at least one recombinant O-tRNA in the presence of a non-naturally encoded amino acid and a natural amino, acid, thereby providing a pool of active (optionally mutant) RSs; and, (f) negatively selecting or screening the pool for active (optionally mutant) RSs that preferentially aminoacylate the at least one recombinant O-tRNA in the absence of the non-naturally encoded amino acid, thereby providing the at least one specific O-tRNA/O-RS pair, wherein the at least one specific O-tRNA/O—RS pair comprises at least one recombinant O-RS that is specific for the non-naturally encoded amino acid and the at least one recombinant O-tRNA. Specific O-tRNA/O-RS pairs produced by the methods are included. For example, the specific O-tRNA/O-RS pair can include, including but not limited to, a mutRNATyr-mutTyrRS pair, such as a mutRNATyr-SS12TyrRS pair, a mutRNALeu-mutLeuRS pair, a mutRNAThr-mutThrRS pair, a mutRNAGlu-mutGluRS pair, or the like. Additionally, such methods include wherein the first and third organism are the same (including but not limited to, *Methanococcus jannaschii*).

Methods for selecting an orthogonal tRNA-tRNA synthetase pair for use in an in vivo translation system of a second organism are also included in the present invention. The methods include: introducing a marker gene, a tRNA and an aminoacyl-tRNA synthetase (RS) isolated or derived from a first organism into a first set of cells from the second organism; introducing the marker gene and the tRNA into a duplicate cell set from a second organism; and, selecting for surviving cells in the first set that fail to survive in the duplicate cell set or screening for cells showing a specific screening response that fail to give such response in the duplicate cell set, wherein the first set and the duplicate cell set are grown in the presence of a selection or screening agent, wherein the surviving or screened cells comprise the orthogonal tRNA-tRNA synthetase pair for use in the in the in the in vivo translation system of the second organism. In one embodiment, comparing and selecting or screening includes an in vivo complementation assay. The concentration of the selection or screening agent can be varied.

The organisms of the present invention comprise a variety of organism and a variety of combinations. For example, the first and the second organisms of the methods of the present invention can be the same or different. In one embodiment, the organisms are optionally a prokaryotic organism, including but not limited to, *Methanococcus jannaschii, Methanobacterium thermoautotrophicum, Halobacterium, Escherichia coli, A. fulgidus, P. furiosus, P. horikoshii, A. pernix, T. thermophilus,* or the like. Alternatively, the organisms optionally comprise a eukaryotic organism, including but not limited to, plants (including but not limited to, complex plants such as monocots, or dicots), algae, protists, fungi (including but not limited to, yeast, etc), animals (including but not limited to, mammals, insects, arthropods, etc.), or the like. In another embodiment, the second organism is a prokaryotic organism, including but not limited to, *Methanococcus jannaschii, Methanobacterium thermoautotrophicum, Halobacterium, Escherichia coli, A. fulgidus, Halobacteriuin, P. furiosus, P. horikoshii, A. pernix, T. thermophilus,* or the like. Alternatively, the second organism can be a eukaryotic organism, including but not limited to, a yeast, a animal cell, a plant cell, a fungus, a mammalian cell, or the like. In various embodiments the first and second organisms are different.

VII. Location of Non-Naturally-Occurring Amino Acids in hGH Polypeptides

The present invention contemplates incorporation of one or more non-naturally-occurring amino acids into GH, e.g., hGH polypeptides. One or more non-naturally-occurring amino acids may be incorporated at a particular position which does not disrupt activity of the polypeptide. This can be achieved by making "conservative" substitutions, including but not limited to, substituting hydrophobic amino acids with hydrophobic amino acids, bulky amino acids for bulky amino acids, hydrophilic amino acids for hydrophilic amino acids and/or inserting the non-naturally-occurring amino acid in a location that is not required for activity.

Regions of GH, e.g., hGH can be illustrated as follows, wherein the amino acid positions in hGH are indicated in the middle row (SEQ ID NO: 2):

the art that any position of the polypeptide chain is suitable for selection to incorporate a non-naturally encoded amino acid, and selection may be based on rational design or by random selection for any or no particular desired purpose. Selection of desired sites may be for producing a GH, e.g., hGH molecule having any desired property or activity, including but not limited to, agonists, super-agonists, inverse agonists, antagonists, receptor binding modulators, receptor activity modulators, dimer or multimer formation, no change to activity or property compared to the native molecule, or manipulating any physical or chemical property of the polypeptide such as solubility, aggregation, or stability. For example, locations in the polypeptide required for biological activity of GH, e.g., hGH polypeptides can be identified using point mutation analysis, alanine scanning or homolog scanning methods known in the art. See, e.g., Cunningham, B. and Wells, J., *Science,* 244:1081-1085 (1989) (identifying 14 residues that are critical for GH, e.g., hGH bioactivity) and Cunningham, B., et al. *Science* 243: 1330-1336 (1989) (identifying antibody and receptor epitopes using homolog scanning mutagenesis). U.S. Pat. Nos. 5,580,723; 5,834,250; 6,013,478; 6,428,954; and 6,451,561, which are incorporated by reference herein, describe methods for the systematic analysis of the structure and function of polypeptides such as hGH by identifying active domains which influence the activity of the polypeptide with a target substance. Residues other than those identified as critical to biological activity by alanine or homolog scanning mutagenesis may be good candidates for substitution with a non-naturally encoded amino acid depending on the desired activity sought for the polypeptide. Alternatively, the sites identified as critical to biological activity may also be good candidates for substitution with a non-naturally encoded amino acid, again depending on the desired activity sought for the polypeptide. Another alternative would be to simply make serial substitutions in each position on the polypeptide chain with a non-naturally encoded amino acid and observe the effect on the activities of the polypeptide. It is readily apparent to those of ordinary skill in the art that any means, technique, or method for selecting a position for substitution with a non-natural amino acid into any polypeptide is suitable for use in the present invention.

The structure and activity of naturally-occurring mutants of hGH polypeptides that contain deletions can also be examined to determine regions of the protein that are likely to be tolerant of substitution with a non-naturally encoded amino acid. See, e.g., Kostyo et al., *Biochem. Biophys. Acta,* 925: 314 (1987); Lewis, U., et al., *J. Biol. Chem.,* 253:2679-2687 (1978) for hGH. In a similar manner, protease digestion and monoclonal antibodies can be used to identify regions of hGH that are responsible for binding the hGH receptor. See, e.g., Cunningham, B., et al. *Science* 243: 1330-1336 (1989); Mills, J., et al., *Endocrinology,* 107:391-399 (1980); Li, C., *Mol. Cell. Biochem.,* 46:31-41 (1982) (indicating that amino acids between residues 134-149 can be deleted without a loss of activity). Once residues that are likely to be intolerant to

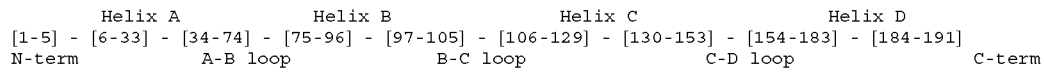

```
        Helix A              Helix B                    Helix C                      Helix D
[1-5] - [6-33] - [34-74] - [75-96] - [97-105] - [106-129] - [130-153] - [154-183] - [184-191]
N-term           A-B loop            B-C loop                       C-D loop                  C-term
```

A variety of biochemical and structural approaches can be employed to select the desired sites for substitution with a non-naturally encoded amino acid within the GH, e.g., hGH polypeptide. It is readily apparent to those of ordinary skill in substitution with non-naturally encoded amino acids have been eliminated, the impact of proposed substitutions at each of the remaining positions can be examined from the three-dimensional crystal structure of the hGH and its binding proteins. See de Vos, A., et al., *Science,* 255:306-312 (1992) for hGH; all crystal structures of hGH are available in the Protein Data Bank (including 3HHR, 1AXI, and 1HWG) (PDB, available on the World Wide Web at rcsb.org), a centralized database containing three-dimensional structural data of large molecules of proteins and nucleic acids. Models may be made investigating the secondary and tertiary structure of polypeptides, if three-dimensional structural data is not available. Thus, those of ordinary skill in the art can readily identify amino acid positions that can be substituted with non-naturally encoded amino acids.

In some embodiments, the GH, e.g., hGH polypeptides of the invention comprise one or more non-naturally occurring amino acids positioned in a region of the protein that does not disrupt the helices or beta sheet secondary structure of the polypeptide.

Exemplary residues of incorporation of a non-naturally encoded amino acid may be those that are excluded from potential receptor binding regions (including but not limited to, Site I and Site II), may be fully or partially solvent exposed, have minimal or no hydrogen-bonding interactions with nearby residues, may be minimally exposed to nearby reactive residues, and may be in regions that are highly flexible (including but not limited to, C-D loop) or structurally rigid (including but not limited to, B helix) as predicted by the three-dimensional, crystal structure, secondary, tertiary, or quaternary structure of hGH, bound or unbound to its receptor.

In some embodiments, one or more non-naturally encoded amino acids are incorporated at any position in one or more of the following regions corresponding to secondary structures in hGH as follows: positions corresponding to 1-5 (N-terminus), 6-33 (A helix), 34-74 (region between A helix and B helix, the A-B loop), 75-96 (B helix), 97-105 (region between B helix and C helix, the B-C loop), 106-129 (C helix), 130-153 (region between C helix and D helix, the C-D loop), 154-183 (D helix), 184-191 (C-terminus) from SEQ ID NO: 2. In other embodiments, GH polypeptides, e.g., hGH polypeptides of the invention comprise at least one non-naturally-occurring amino acid substituted for at least one amino acid located in at least one region of GH, e.g., hGH selected from the group consisting regions corresponding to the N-terminus (1-5), the N-terminal end of the A-B loop (32-46); the B-C loop (97-105), the C-D loop (132-149), and the C-terminus (184-191) of SEQ ID NO: 2. In some embodiments, one or more non-naturally encoded amino acids are incorporated at one or more of the following positions of GH, e.g., hGH corresponding to: before position 1 (i.e. at the N-terminus), 1, 2, 3, 4, 5, 8, 9, 11, 12, 15, 16, 19, 22, 29, 30, 32, 33, 34, 35, 36, 37, 38, 39, 40, 41, 42, 43, 44, 45, 46, 47, 48, 49, 52, 55, 57, 59, 65, 66, 69, 70, 71, 74, 88, 91, 92, 94, 95, 97, 98, 99, 100, 101, 102, 103, 104, 105, 106, 107, 108, 109, 111, 112, 113, 115, 116, 119, 120, 122, 123, 126, 127, 129, 130, 131, 132, 133, 134, 135, 136, 137, 138, 139, 140, 141, 142, 143, 144, 145, 146, 147, 148, 149, 150, 151, 152, 153, 154, 155, 156, 158, 159, 161, 168, 172, 183, 184, 185, 186, 187, 188, 189, 190, 191, 192 (i.e., at the carboxyl terminus of the protein) of SEQ ID NO: 2 or the corresponding amino acids of SEQ ID NO: 1 or 3.

Exemplary sites of incorporation of one or more non-naturally encoded amino acids include sites corresponding to 29, 30, 33, 34, 35, 37, 39, 40, 49, 57, 59, 66, 69, 70, 71, 74, 88, 91, 92, 94, 95, 98, 99, 101, 103, 107, 108, 111, 122, 126, 129, 130, 131, 133, 134, 135, 136, 137, 139, 140, 141, 142, 143, 145, 147, 154, 155, 156, 159, 183, 186, and 187, or any combination thereof from SEQ ID NO: 2 or the corresponding amino acids of SEQ ID NO: 1 or 3.

A subset of exemplary sites for incorporation of one or more non-naturally encoded amino acid include sites corresponding to 29, 33, 35, 37, 39, 49, 57, 69, 70, 71, 74, 88, 91, 92, 94, 95, 98, 99, 101, 103, 107, 108, 111, 129, 130, 131, 133, 134, 135, 136, 137, 139, 140, 141, 142, 143, 145, 147, 154, 155, 156, 186, and 187, or any combination thereof from SEQ ID NO: 2 or the corresponding amino acids of SEQ ID NO: 1 or 3. An examination of the crystal structure of GH, e.g., hGH and its interactions with the GH, e.g., hGH receptor indicates that the side chains of these amino acid residues are fully or partially accessible to solvent and the side chain of a non-naturally encoded amino acid may point away from the protein surface and out into the solvent.

Exemplary positions for incorporation of one or more non-naturally encoded amino acids include sites corresponding to 35, 88, 91, 92, 94, 95, 99, 101, 103, 111, 131, 133, 134, 135, 136, 139, 140, 143, 145, and 155, or any combination thereof from SEQ ID NO: 2 or the corresponding amino acids of SEQ ID NO: 1 or 3. An examination of the crystal structure of GH, e.g., hGH and its interactions with the GH, e.g., hGH receptor indicates that the side chains of these amino acid residues are fully exposed to the solvent and the side chain of the native residue points out into the solvent.

A subset of exemplary sites for incorporation of one or more non-naturally encoded amino acids include sites corresponding to 30, 74, 103, or any combination thereof, from SEQ ID NO: 2 or the corresponding amino acids of SEQ ID NO: 1 or 3. Another subset of exemplary sites for incorporation of one or more non-naturally encoded amino acids include sites corresponding to 35, 92, 143, 145, or any combination thereof, from SEQ ID NO: 2 or the corresponding amino acids of SEQ ID NO: 1 or 3. A further subset of exemplary sites for incorporation of one or more non-naturally encoded amino acids include sites corresponding to 35, 92, 131, 134, 143, 145, or any combination thereof, from SEQ ID NO: 2 or the corresponding amino acids of SEQ ID NO: 1 or 3. Still a further subset of exemplary sites for incorporation of one or more non-naturally encoded amino acids include sites corresponding to 30, 35, 74, 92, 103, 145, or any combination thereof, from SEQ ID NO: 2 or the corresponding amino acids of SEQ ID NO: 1 or 3. Yet a further subset of exemplary sites for incorporation of one or more non-naturally encoded amino acids include sites corresponding to 35, 92, 143, 145, or any combination thereof, from SEQ ID NO: 2 or the corresponding amino acids of SEQ ID NO: 1 or 3. In certain embodiments, sites for incorporation of one or more non-naturally encoded amino acids include a site corresponding to 35 from SEQ ID NO: 2 or the corresponding amino acids of SEQ ID NO: 1 or 3.

In some embodiments, at least one of the non-naturally encoded amino acids incorporated into the GH, e.g., hGH, contains a carbonyl group, e.g., a ketone group. In certain embodiments, at least one of the non-naturally encoded amino acids incorporated into the GH, e.g., hGH is para-acetylphenylalanine. In some embodiments in which the GH, e.g., hGH contains a plurality of non-naturally-encoded amino acids, more than one of the non-naturally-encoded amino acids incorporated into the GH, e.g., hGH is para-acetylphenylalanine. In some embodiments in which the GH, e.g., hGH contains a plurality of non-naturally-encoded amino acids, substantially all of the non-naturally-encoded amino acids incorporated into the GH, e.g., hGH are para-acetylphenylalanine.

In some embodiments, the non-naturally occurring amino acid is linked to a water soluble polymer at one or more positions, including but not limited to, positions corresponding to: before position 1 (i.e. at the N-terminus), 1, 2, 3, 4, 5, 8, 9, 11, 12, 15, 16, 19, 22, 29, 30, 32, 33, 34, 35, 36, 37, 38, 39, 40, 41, 42, 43, 44, 45, 46, 47, 48, 49, 52, 55, 57, 59, 65, 66, 69, 70, 71, 74, 88, 91, 92, 94, 95, 97, 98, 99, 100, 101, 102, 103, 104, 105, 106, 107, 108, 109, 111, 112, 113, 115, 116, 119, 120, 122, 123, 126, 127, 129, 130, 131, 132, 133, 134, 135, 136, 137, 138, 139, 140, 141, 142, 143, 144, 145, 146, 147, 148, 149, 150, 151, 152, 153, 154, 155, 156, 158, 159, 161, 168, 172, 183, 184, 185, 186, 187, 188, 189, 190, 191, 192 (i.e., at the carboxyl terminus of the protein) (SEQ ID NO: 2 or the corresponding amino acids of SEQ ID NO: 1 or 3). In some embodiments, the non-naturally occurring amino acid is linked to a water soluble polymer at positions including but not limited to, positions corresponding to one or more of these positions: 30, 35, 74, 92, 103, 143, 145 (SEQ ID NO: 2 or the corresponding amino acids of SEQ ID NO: 1 or 3). In some embodiments, the non-naturally occurring amino acid is linked to a water soluble polymer at positions including but not limited to, positions corresponding to one or more of these positions: 35, 92, 143, 145 (SEQ ID NO: 2 or the corresponding amino acids of SEQ ID NO: 1 or 3). In some embodiments, the non-naturally occurring amino acid is linked to a water soluble polymer at positions including but not limited to, positions corresponding to one or more of these positions: 35, 92, 131, 134, 143, 145, or any combination thereof, from SEQ ID NO: 2 or the corresponding amino acids of SEQ ID NO: 1 or 3. In some embodiments, the non-naturally occurring amino acid is linked to a water soluble polymer at positions including but not limited to, positions corresponding to one or more of these positions: 30, 35, 74, 92, 103, 145, or any combination thereof, from SEQ ID NO: 2 or the corresponding amino acids of SEQ ID NO: 1 or 3. In some embodiments, the non-naturally occurring amino acid is linked to a water soluble polymer at positions including but not limited to, positions corresponding to one or more of these positions: 35, 92, 143, 145, or any combination thereof, from SEQ ID NO: 2 or the corresponding amino acids of SEQ ID NO: 1 or 3. In some embodiments, the non-naturally occurring amino acid is linked to a water-soluble polymer at a position corresponding to, but not limited to, position 35 from SEQ ID NO: 2 or the corresponding amino acids of SEQ ID NO: 1 or 3 is linked to a water-soluble polymer.

In some embodiments the water-soluble polymer(s) linked to the GH, e.g., hGH, include one or more polyethylene glycol molecules (PEGs). The polymer, e.g., PEG, may be linear or branched. Typically, linear polymers, e.g., PEGs, used in the invention can have a MW of about 0.1 to about 100 kDa, or about 1 to about 60 kDa, or about 20 to about 40 kDa, or about 30 kDa. Typically, branched polymers, e.g., PEGs, used in the invention can have a MW of about 1 to about 100 kDa, or about 30 to about 50 kDa, or about 40 kDa. Polymers such as PEGs are described further herein. In certain embodiments, the linkage between the GH, e.g., hGH and the water-soluble polymer, e.g., PEG, is an oxime bond.

Certain embodiments of the invention encompass compositions that include a GH, e.g., hGH, linked to at least one water-soluble polymer by a covalent bond, where the covalent bond is an oxime bond. In some embodiments, the water-soluble polymer is a PEG, e.g., a linear PEG. In some embodiments encompassing at least one linear PEG linked by an oxime bond to a GH, e.g., hGH, the PEG can have a MW of about 0.1 to about 100 kDa, or about 1 to about 60 kDa, or about 20 to about 40 kDa, or about 30 kDa. In certain embodiments encompassing a linear PEG linked by an oxime bond to a GH, e.g., hGH, the PEG has a MW of about 30 kDa. In some embodiments encompassing at least one branched PEG linked by an oxime bond to a GH, e.g., hGH, the PEG can have a MW of about 1 to about 100 kDa or about 30 to about 50 kDa, or about 40 kDa. In certain embodiments encompassing a branched PEG linked by an oxime bond to a GH, e.g., hGH, the PEG has a MW of about 40 kDa. In some embodiments, the GH is a GH, e.g., hGH and in certain of these embodiments, the GH, e.g., hGH has a sequence that is at least about 80% identical to SEQ ID NO: 2; in some embodiments the GH, e.g., hGH has a sequence that is the sequence of SEQ ID NO: 2. In some embodiments, the GH, e.g., hGH, contains at least one non-naturally-encoded amino acid; in some of these embodiments, at least one oxime bond is between the non-naturally-encoded amino acid and at least one water-soluble polymer. In some embodiments, the non-naturally-encoded amino acid contains a carbonyl group, such as a ketone group; in some embodiments, the non-naturally-encoded amino acid is para-acetylphenylalanine. In some embodiments, the para-acetylphenylalanine is substituted at a position corresponding to position 35 of SEQ ID NO: 2.

Thus, in some embodiments, the invention provides a GH, e.g., hGH, linked to at least one water-soluble polymer, e.g., a PEG, by a covalent bond, where the covalent bond is an oxime bond. In certain embodiments, the water-soluble polymer is a PEG and the PEG is a linear PEG. In these embodiments, the linear PEG has a MW of about 0.1 to about 100 kDa, or about 1 to about 60 kDa, or about 20 to about 40 kDa, or about 30 kDa. In certain embodiments encompassing a linear PEG linked by an oxime bond to a GH, e.g., hGH, the PEG has a MW of about 30 kDa. In certain embodiments, the water-soluble polymer is a PEG that is a branched PEG. In these embodiments, the branched PEG has a MW of about 1 to about 100 kDa, or about 30 to about 50 kDa, or about 40 kDa. In certain embodiments encompassing a branched PEG linked by an oxime bond to a GH, e.g., hGH, the PEG has a MW of about 40 kDa.

In some embodiments, the invention provides a GH, e.g., hGH, where the GH, e.g., hGH contains a non-naturally encoded amino acid, where the GH is linked to at least one water-soluble polymer, e.g., a PEG, by a covalent bond, and where the covalent bond is an oxime bond between the non-naturally encoded amino acid and the water-soluble polymer, e.g., PEG. In some embodiments, the non-naturally-encoded amino acid is incorporated into the GH, e.g., hGH, at a position corresponding to position 35 of SEQ ID NO: 2. In certain embodiments where the water-soluble polymer is a PEG, the PEG is a linear PEG. In these embodiments, the linear PEG has a MW of about 0.1 to about 100 kDa, or about 1 to about 60 kDa, or about 20 to about 40 kDa, or about 30 kDa. In certain embodiments encompassing a linear PEG linked by an oxime bond to a GH, e.g., hGH, the PEG has a MW of about 30 kDa. In certain embodiments where the water-soluble polymer is a PEG, the PEG is a branched PEG. In these embodiments, the branched PEG has a MW of about 1 to about 100 kDa, or about 30 to about 50 kDa, or about 40 kDa. In certain embodiments encompassing a branched PEG linked by an oxime bond to a GH, e.g., hGH, the PEG has a MW of about 40 kDa.

In some embodiments, the invention provides a GH, e.g., hGH, where the GH, e.g., hGH contains a non-naturally encoded amino acid that is a carbonyl-containing non-naturally encoded amino acid, where the GH is linked to at least one water-soluble polymer, e.g., a PEG, by a covalent bond, and where the covalent bond is an oxime bond between the non-naturally encoded carbonyl-containing amino acid and the water-soluble polymer, e.g., PEG. In some embodiments, the non-naturally-encoded carbonyl-containing amino acid is incorporated into the GH, e.g., hGH, at a position corresponding to position 35 of SEQ ID NO: 2. In certain embodiments where the water-soluble polymer is a PEG, the PEG is a linear PEG. In these embodiments, the linear PEG has a MW of about 0.1 to about 100 kDa, or about 1 to about 60 kDa, or about 20 to about 40 kDa, or about 30 kDa. In certain embodiments encompassing a linear PEG linked by an oxime bond to a GH, e.g., hGH, the PEG has a MW of about 30 kDa. In certain embodiments where the water-soluble polymer is a PEG, the PEG is a branched PEG. In these embodiments, the branched PEG has a MW of about 1 to about 100 kDa, or about 30 to about 50 kDa, or about 40 kDa. In certain embodiments encompassing a branched PEG linked by an oxime bond to a GH, e.g., hGH, the PEG has a MW of about 40 kDa.

In some embodiments, the invention provides a GH, e.g., hGH, that contains a non-naturally encoded amino acid that includes a ketone group, where the GH is linked to at least one water-soluble polymer, e.g., a PEG, by a covalent bond, and where the covalent bond is an oxime bond between the non-naturally encoded amino acid containing a ketone group and the water-soluble polymer, e.g., PEG. In some embodiments, the non-naturally-encoded amino acid containing a ketone group is incorporated into the GH, e.g., hGH, at a position corresponding to position 35 of SEQ ID NO: 2. In certain embodiments where the water-soluble polymer is a PEG, the PEG is a linear PEG. In these embodiments, the linear PEG has a MW of about 0.1 to about 100 kDa, or about 1 to about 60 kDa, or about 20 to about 40 kDa, or about 30 kDa. In certain embodiments encompassing a linear PEG linked by an oxime bond to a GH, e.g., hGH, the PEG has a MW of about 30 kDa. In certain embodiments where the water-soluble polymer is a PEG, the PEG is a branched PEG. In these embodiments, the branched PEG has a MW of about 1 to about 100 kDa, or about 30 to about 50 kDa, or about 40 kDa. In certain embodiments encompassing a branched PEG linked by an oxime bond to a GH, e.g., hGH, the PEG has a MW of about 40 kDa.

In some embodiments, the invention provides a GH, e.g., hGH, that contains a non-naturally encoded amino acid that is a para-acetylphenylalanine, where the GH linked to at least one water-soluble polymer, e.g., a PEG, by a covalent bond, and where the covalent bond is an oxime bond between the para-acetylphenylalanine and the water-soluble polymer, e.g., PEG. In some embodiments, the para-acetylphenylalanine is incorporated into the GH, e.g., hGH, at a position corresponding to position 35 of SEQ ID NO: 2. In certain embodiments where the water-soluble polymer is a PEG, the PEG is a linear PEG. In these embodiments, the linear PEG has a MW of about 0.1 to about 100 kDa, or about 1 to about 60 kDa, or about 20 to about 40 kDa, or about 30 kDa. In certain embodiments encompassing a linear PEG linked by an oxime bond to a GH, e.g., hGH, the PEG has a MW of about 30 kDa. In certain embodiments where the water-soluble polymer is a PEG, the PEG is a branched PEG. In these embodiments, the branched PEG has a MW of about 1 to about 100 kDa, or about 30 to about 50 kDa, or about 40 kDa. In certain embodiments encompassing a branched PEG linked by an oxime bond to a GH, e.g., hGH, the PEG has a MW of about 40 kDa.

In certain embodiments the invention provides a GH, e.g., hGH that includes SEQ ID NO: 2, and where the GH, e.g., hGH is substituted at a position corresponding to position 35 of SEQ ID NO: 2 with a para-acetylphenylalanine that is linked by an oxime linkage to a linear PEG of MW of about 30 kDa.

In some embodiments, the invention provides a hormone composition that includes a GH, e.g., hGH, linked via an oxime bond to at least one PEG, e.g., a linear PEG, where the GH, e.g., hGH comprises the amino acid sequence of SEQ ID NO: 2, and where the GH, e.g., hGH contains at least one non-naturally-encoded amino acid substituted at one or more positions including, but not limited to, positions corresponding to: before position 1 (i.e. at the N-terminus), 1, 2, 3, 4, 5, 8, 9, 11, 12, 15, 16, 19, 22, 29, 30, 32, 33, 34, 35, 36, 37, 38, 39, 40, 41, 42, 43, 44, 45, 46, 47, 48, 49, 52, 55, 57, 59, 65, 66, 69, 70, 71, 74, 88, 91, 92, 94, 95, 97, 98, 99, 100, 101, 102, 103, 104, 105, 106, 107, 108, 109, 111, 112, 113, 115, 116, 119, 120, 122, 123, 126, 127, 129, 130, 131, 132, 133, 134, 135, 136, 137, 138, 139, 140, 141, 142, 143, 144, 145, 146, 147, 148, 149, 150, 151, 152, 153, 154, 155, 156, 158, 159, 161, 168, 172, 183, 184, 185, 186, 187, 188, 189, 190, 191, 192 (i.e., at the carboxyl terminus of the protein) (SEQ ID NO: 2 or the corresponding amino acids of SEQ ID NO: 1 or 3). In some embodiments, the invention provides a hormone composition that includes a GH, e.g., hGH, linked via an oxime bond to at least one PEG, e.g., a linear PEG, where the GH, e.g., hGH comprises the amino acid sequence of SEQ ID NO: 2, and where the GH, e.g., hGH contains at least one non-naturally-encoded amino acid substituted at one or more positions including, but not limited to, positions corresponding to: 30, 35, 74, 92, 103, 143, 145 (SEQ ID NO: 2 or the corresponding amino acids of SEQ ID NO: 1 or 3). In some embodiments, the invention provides a hormone composition that includes a GH, e.g., hGH, linked via an oxime bond to at least one PEG, e.g., a linear PEG, where the GH, e.g., hGH comprises the amino acid sequence of SEQ ID NO: 2, and where the GH, e.g., hGH contains at least one non-naturally-encoded amino acid substituted at one or more positions including, but not limited to, positions corresponding to: 35, 92, 143, 145 (SEQ ID NO: 2 or the corresponding amino acids of SEQ ID NO: 1 or 3). In some embodiments, the invention provides a hormone composition that includes a GH, e.g., hGH, linked via an oxime bond to at least one PEG, e.g., a linear PEG, where the GH, e.g., hGH comprises the amino acid sequence of SEQ ID NO: 2, and where the GH, e.g., hGH contains at least one non-naturally-encoded amino acid substituted at one or more positions including, but not limited to, positions corresponding to: 35, 92, 131, 134, 143, 145, or any combination thereof, from SEQ ID NO: 2 or the corresponding amino acids of SEQ ID NO: 1 or 3. In some embodiments, the invention provides a hormone composition that includes a GH, e.g., hGH, linked via an oxime bond to at least one PEG, e.g., a linear PEG, where the GH, e.g., hGH comprises the amino acid sequence of SEQ ID NO: 2, and where the GH, e.g., hGH contains at least one non-naturally-encoded amino acid substituted at one or more positions including, but not limited to, positions corresponding to: 30, 35, 74, 92, 103, 145, or any combination thereof, from SEQ ID NO: 2 or the corresponding amino acids of SEQ ID NO: 1 or 3. In some embodiments, the invention provides a hormone composition that includes a GH, e.g., hGH, linked via an oxime bond to at least one PEG, e.g., a linear PEG, where the GH, e.g., hGH comprises the amino acid sequence of SEQ ID NO: 2, and where the GH, e.g., hGH contains at least one non-naturally-encoded amino acid substituted at one or more positions including, but not limited to, positions corresponding to: 35, 92, 143, 145, or any combination thereof, from SEQ ID NO: 2 or the corresponding amino acids of SEQ ID NO: 1 or 3. In some embodiments, the invention provides a hormone composition that includes a GH, e.g., hGH, linked via an oxime bond to at least one PEG, e.g., a linear PEG, where the GH, e.g., hGH comprises the amino acid sequence of SEQ ID NO: 2, and where the GH, e.g., hGH contains at least one non-naturally-encoded amino acid substituted at one or more positions including, but not limited to, positions corresponding to position 35 from SEQ ID NO: 2 or the corresponding amino acids of SEQ ID NO: 1 or 3. In embodiments in which the PEG is a linear PEG, the PEG can have a MW of about 0.1 to about 100 kDa, or about 1 to about 60 kDa, or about 20 to about 40 kDa, or about 30 kDa.

In some embodiments, the invention provides a hormone composition that includes a GH, e.g., hGH, linked via an oxime bond to at least one PEG, e.g., a linear PEG, where the GH, e.g., hGH includes the amino acid sequence of SEQ ID NO: 2, and where the GH, e.g., hGH contains at least one non-naturally-encoded amino acid that is a para-acetylphenylalanine substituted at one or more positions including, but not limited to, positions corresponding to: before position 1 (i.e. at the N-terminus), 1, 2, 3, 4, 5, 8, 9, 11, 12, 15, 16, 19, 22, 29, 30, 32, 33, 34, 35, 36, 37, 38, 39, 40, 41, 42, 43, 44, 45, 46, 47, 48, 49, 52, 55, 57, 59, 65, 66, 69, 70, 71, 74, 88, 91, 92, 94, 95, 97, 98, 99, 100, 101, 102, 103, 104, 105, 106, 107, 108, 109, 111, 112, 113, 115, 116, 119, 120, 122, 123, 126, 127, 129, 130, 131, 132, 133, 134, 135, 136, 137, 138, 139, 140, 141, 142, 143, 144, 145, 146, 147, 148, 149, 150, 151, 152, 153, 154, 155, 156, 158, 159, 161, 168, 172, 183, 184, 185, 186, 187, 188, 189, 190, 191, 192 (i.e., at the carboxyl terminus of the protein) (SEQ ID NO: 2 or the corresponding amino acids of SEQ ID NO: 1 or 3). In some embodiments, the invention provides a hormone composition that includes a GH, e.g., hGH, linked via an oxime bond to at least one PEG, e.g., a linear PEG, where the GH, e.g., hGH comprises the amino acid sequence of SEQ ID NO: 2, and where the GH, e.g., hGH contains at least one non-naturally-encoded amino acid that is a para-acetylphenylalanine substituted at one or more positions including, but not limited to, positions corresponding to: 30, 35, 74, 92, 103, 143, 145 (SEQ ID NO: 2 or the corresponding amino acids of SEQ ID NO: 1 or 3). In some embodiments, the invention provides a hormone composition that includes a GH, e.g., hGH, linked via an oxime bond to at least one PEG, e.g., a linear PEG, where the GH, e.g., hGH comprises the amino acid sequence of SEQ ID NO: 2, and where the GH, e.g., hGH contains at least one non-naturally-encoded amino acid that is a para-acetylphenylalanine substituted at one or more positions including, but not limited to, positions corresponding to: 35, 92, 143, 145 (SEQ ID NO: 2 or the corresponding amino acids of SEQ ID NO: 1 or 3). In some embodiments, the invention provides a hormone composition that includes a GH, e.g., hGH, linked via an oxime bond to at least one PEG, e.g., a linear PEG, where the GH, e.g., hGH comprises the amino acid sequence of SEQ ID NO: 2, and where the GH, e.g., hGH contains at least one non-naturally-encoded amino acid that is a para-acetylphenylalanine substituted at one or more positions including, but not limited to, positions corresponding to: 35, 92, 131, 134, 143, 145, or any combination thereof, from SEQ ID NO: 2 or the corresponding amino acids of SEQ ID NO: 1 or 3. In some embodiments, the invention provides a hormone composition that includes a GH, e.g., hGH, linked via an oxime bond to at least one PEG, e.g., a linear PEG, where the GH, e.g., hGH comprises the amino acid sequence of SEQ ID NO: 2, and where the GH, e.g., hGH contains at least one non-naturally-encoded amino acid that is a para-acetylphenylalanine substituted at one or more positions including, but not limited to, positions corresponding to: 30, 35, 74, 92, 103, 145, or any combination thereof, from SEQ ID NO: 2 or the corresponding amino acids of SEQ ID NO: 1 or 3. In some embodiments, the invention provides a hormone composition that includes a GH, e.g., hGH, linked via an oxime bond to at least one PEG, e.g., a linear PEG, where the GH, e.g., hGH comprises the amino acid sequence of SEQ ID NO: 2, and where the GH, e.g., hGH contains at least one non-naturally-encoded amino acid that is a para-acetylphenylalanine substituted at one or more positions including, but not limited to, positions corresponding to: 35, 92, 143, 145, or any combination thereof, from SEQ ID NO: 2 or the corresponding amino acids of SEQ ID NO: 1 or 3. In some embodiments, the invention provides a hormone composition that includes a GH, e.g., hGH, linked via an oxime bond to at least one PEG, e.g., a linear PEG, where the GH, e.g., hGH comprises the amino acid sequence of SEQ ID NO: 2, and where the GH, e.g., hGH contains at least one non-naturally-encoded amino acid that is a para-acetylphenylalanine substituted at one or more positions including, but not limited to, positions corresponding to position 35 from SEQ ID NO: 2 or the corresponding amino acids of SEQ ID NO: 1 or 3. In embodiments in which the PEG is a linear PEG, the PEG can have a MW of about 0.1 to about 100 kDa, or about 1 to about 60 kDa, or about 20 to about 40 kDa, or about 30 kDa.

In some embodiments, the invention provides a GH, e.g., hGH, where the GH, e.g., hGH contains at least one non-naturally encoded amino acid, where the GH is linked to a plurality of water-soluble polymers, e.g., a plurality of PEGs, by covalent bonds, where one or more of the covalent bond is an oxime bond between at least one of the non-naturally encoded amino acid and the water-soluble polymer, e.g., PEG. The GH, e.g., hGH, may be linked to about 2-100 water-soluble polymers, e.g., PEGs, or about 2-50 water-soluble polymers, e.g., PEGs, or about 2-25 water-soluble polymers, e.g., PEGs, or about 2-10 water-soluble polymers, e.g., PEGs, or about 2-5 water-soluble polymers, e.g., PEGs, or about 5-100 water-soluble polymers, e.g., PEGs, or about 5-50 water-soluble polymers, e.g., PEGs, or about 5-25 water-soluble polymers, e.g., PEGs, or about 5-10 water-soluble polymers, e.g., PEGs, or about 10-100 water-soluble polymers, e.g., PEGs, or about 10-50 water-soluble polymers, e.g., PEGs, or about 10-20 water-soluble polymers, e.g., PEGs, or about 20-100 water-soluble polymers, e.g., PEGs, or about 20-50 water-soluble polymers, e.g., PEGs, or about 50-100 water-soluble polymers, e.g., PEGs. The one or more non-naturally-encoded amino acids may be incorporated into the GH, e.g., hGH, at any position described herein. In some embodiments, at least one non-naturally-encoded amino acid is incorporated into the GH, e.g., hGH, at a position corresponding to position 35 of SEQ ID NO: 2. In some embodiments, the non-naturally encoded amino acids include at least one non-naturally encoded amino acid that is a carbonyl-containing non-naturally encoded amino acid, e.g., a ketone-containing non-naturally encoded amino acid such as a para-acetylphenylalanine. In some embodiments, the GH, e.g., hGH, includes a para-acetylphenylalanine. In some embodiments, the para-acetylphenylalanine is incorporated into the GH, e.g., hGH, at a position corresponding to position 35 of SEQ ID NO: 2, where the para-acetylphenylalanine is linked to one of the polymers, e.g., one of the PEGs, by an oxime bond. In some embodiments, at least one of the water-soluble polymers, e.g., PEGs, is linked to the GH, e.g., hGH, by a covalent bond to at least one of the non-naturally-encoded amino acids. In some embodiments, the covalent bond is an oxime bond. In some embodiments, a plurality of the water-soluble polymers, e.g., PEGs, are linked to the GH, e.g., hGH, by covalent bonds to a plurality of the non-naturally-encoded amino acids. In some embodiments, at least one the covalent bonds is an oxime bond; in some embodiments, a plurality of the covalent bonds are oxime bonds; in some embodiments, substantially all of the bonds are oxime bonds. The plurality of water-soluble polymers, e.g., PEG, may be linear, branched, or any combination thereof. In embodiments that incorporate one or more linear PEGs, the linear PEGs have a MW of about 0.1 to about 100 kDa, or about 1 to about 60 kDa, or about 20 to about 40 kDa, or about 30 kDa. In embodiments that incorporate one or more branched PEGs, the branched PEGs have a MW of about 1 to about 100 kDa, or about 30 to about 50 kDa, or about 40 kDa. It will be appreciated that embodiments employing a plurality of water-soluble polymers, e.g., PEGs, will, in general, employ such polymers at lower MWs than embodiments in which a single PEG is used. Thus, in some embodiments, the overall MW of the plurality of PEGs is about 0.1-500 kDa, or about 0.1-200 kDa, or about 0.1-100 kDa, or about 1-1000 kDa, or about 1-500 kDa, or about 1-200 kDa, or about 1-100 kDa, or about 10-1000 kDa, or about 10-500 kDa, or about 10-200 kDa, or about 10-100 kDa, or about 10-50 kDa, or about 20-1000 kDa, or about 20-500 kDa, or about 20-200 kDa, or about 20-100 kDa, or about 20-80 kDa, about 20-60 kDa, about 5-100 kDa, about 5-50 kDa, or about 5-20 kDa.

Human GH antagonists include, but are not limited to, those with substitutions at: 1, 2, 3, 4, 5, 8, 9, 11, 12, 15, 16, 19, 22, 103, 109, 112, 113, 115, 116, 119, 120, 123, and 127 or an addition at position 1 (i.e., at the N-terminus), or any combination thereof (SEQ ID NO:2, or the corresponding amino acid in SEQ ID NO: 1, 3, or any other GH sequence).

A wide variety of non-naturally encoded amino acids can be substituted for, or incorporated into, a given position in a GH, e.g., hGH polypeptide. In general, a particular non-naturally encoded amino acid is selected for incorporation based on an examination of the three dimensional crystal structure of a GH, e.g., hGH polypeptide with its receptor, a preference for conservative substitutions (i.e., aryl-based non-naturally encoded amino acids, such as p-acetylphenylalanine or O-propargyltyrosine substituting for Phe, Tyr or Trp), and the specific conjugation chemistry that one desires to introduce into the GH, e.g., hGH polypeptide (e.g., the introduction of 4-azidophenylalanine if one wants to effect a Huisgen [3+2]cycloaddition with a water soluble polymer bearing an alkyne moiety or a amide bond formation with a water soluble polymer that bears an aryl ester that, in turn, incorporates a phosphine moiety).

In one embodiment, the method further includes incorporating into the protein the unnatural amino acid, where the unnatural amino acid comprises a first reactive group; and contacting the protein with a molecule (including but not limited to, a label, a dye, a polymer, a water-soluble polymer, a derivative of polyethylene glycol, a photocrosslinker, a radionuclide, a cytotoxic compound, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, a saccharide, water-soluble dendrimer, a cyclodextrin, an inhibitory ribonucleic acid, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a photoisomerizable moiety, biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, a small molecule, a quantum dot, a nanotransmitter, a radionucleotide, a radiotransmitter, a neutron-capture agent, or any combination of the above, or any other desirable compound or substance) that comprises a second reactive group. The first reactive group reacts with the second reactive group to attach the molecule to the unnatural amino acid through a [3+2] cycloaddition. In one embodiment, the first reactive group is an alkynyl or azido moiety and the second reactive group is an azido or alkynyl moiety. For example, the first reactive group is the alkynyl moiety (including but not limited to, in unnatural amino acid p-propargyloxyphenylalanine) and the second reactive group is the azido moiety. In another example, the first reactive group is the azido moiety (including but not limited to, in the unnatural amino acid p-azido-L-phenylalanine) and the second reactive group is the alkynyl moiety.

In some cases, the non-naturally encoded amino acid substitution(s) will be combined with other additions, substitutions or deletions within the GH, e.g., hGH polypeptide to affect other biological traits of the GH, e.g., hGH polypeptide. In some cases, the other additions, substitutions or deletions may increase the stability (including but not limited to, resistance to proteolytic degradation) of the GH, e.g., hGH polypeptide or increase affinity of the GH, e.g., hGH polypeptide for its receptor. In some embodiments, the GH, e.g., hGH polypeptide comprises an amino acid substitution selected from the group consisting of F10A, F10H, F10I; M14W, M14Q, M14G; H18D; H21N; G120A; R167N; D171S; E174S; F176Y, I179T or any combination thereof in SEQ ID NO: 2. In some cases, the other additions, substitutions or deletions may increase the solubility (including but not limited to, when expressed in E. coli or other host cells) of the GH, e.g., hGH polypeptide. In some embodiments additions, substitutions or deletions may increase the polypeptide solubility following expression in E. coli or other recombinant host cells. In some embodiments sites are selected for substitution with a naturally encoded or non-natural amino acid in addition to another site for incorporation of a non-natural amino acid that results in increasing the polypeptide solubility following expression in E. coli or other recombinant host cells. In some embodiments, the GH, e.g., hGH polypeptides comprise another addition, substitution or deletion that modulates affinity for the GH, e.g., hGH polypeptide receptor, modulates (including but not limited to, increases or decreases) receptor dimerization, stabilizes receptor dimers, modulates circulating half-life, modulates release or bioavailability, facilitates purification, or improves or alters a particular route of administration. For instance, in addition to introducing one or more non-naturally encoded amino acids as set forth herein, one or more of the following substitutions are introduced: F10A, F10H or F10I; M14W, M14Q, or M14G; H18D; H21N; R167N; D171S; E174S; F176Y and I179T to increase the affinity of the GH, e.g., hGH variant for its receptor. Similarly, GH, e.g., hGH polypeptides can comprise chemical or enzyme cleavage sequences, protease cleavage sequences, reactive groups, antibody-binding domains (including but not limited to, FLAG or poly-His) or other affinity based sequences (including, but not limited to, FLAG, poly-His, GST, etc.) or linked molecules (including, but not limited to, biotin) that improve detection (including, but not limited to, GFP), purification, transport through tissues or cell membranes, prodrug release or activation, hGH size reduction, or other traits of the polypeptide.

In some embodiments, the substitution of a non-naturally encoded amino acid generates an GH, e.g., hGH antagonist. A subset of exemplary sites for incorporation of one or more non-naturally encoded amino acid include: 1, 2, 3, 4, 5, 8, 9, 11, 12, 15, 16, 19, 22, 103, 109, 112, 113, 115, 116, 119, 120, 123, 127, or an addition before position 1 (SEQ ID NO: 2, or the corresponding amino acid in SEQ ID NO: 1, 3, or any other GH sequence). In some embodiments, GH, e.g., hGH antagonists comprise at least one substitution in the regions 1-5 (N-terminus), 6-33 (A helix), 34-74 (region between A helix and B helix, the A-B loop), 75-96 (B helix), 97-105 (region between B helix and C helix, the B-C loop), 106-129 (C helix), 130-153 (region between C helix and D helix, the C-D loop), 154-183 (D helix), 184-191 (C-terminus) that cause GH to act as an antagonist. In other embodiments, the exemplary sites of incorporation of a non-naturally encoded amino acid include residues within the amino terminal region of helix A and a portion of helix C. In another embodiment, substitution of G120 with a non-naturally encoded amino acid such as p-azido-L-phenylalanine or O-propargyl-L-tyrosine. In other embodiments, the above-listed substitutions are combined with additional substitutions that cause the GH, e.g., hGH polypeptide to be an GH, e.g., hGH antagonist. For instance, a non-naturally encoded amino acid is substituted at one of the positions identified herein and a simultaneous substitution is introduced at G120 (e.g., G120R, G120K, G120W, G120Y, G120F, or G120E). In some embodiments, the GH, e.g., hGH antagonist comprises a non-naturally encoded amino acid linked to a water soluble polymer that is present in a receptor binding region of the GH, e.g., hGH molecule.

In some cases, 1, 2, 3, 4, 5, 6, 7, 8, 9, 10, or more amino acids are substituted with one or more non-naturally-encoded amino acids. In some cases, the GH, e.g., hGH polypeptide further includes 1, 2, 3, 4, 5, 6, 7, 8, 9, 10, or more substitutions of one or more non-naturally encoded amino acids for naturally-occurring amino acids. For example, in some embodiments, one or more residues in the following regions of GH, e.g., hGH are substituted with one or more non-naturally encoded amino acids: 1-5 (N-terminus); 32-46 (N-terminal end of the A-B loop); 97-105 (B-C loop); and 132-149 (C-D loop); and 184-191 (C-terminus). In some embodiments, one or more residues in the following regions of GH, e.g., hGH are substituted with one or more non-naturally encoded amino acids: 1-5 (N-terminus), 6-33 (A helix), 34-74 (region between A helix and B helix, the A-B loop), 75-96 (B helix), 97-105 (region between B helix and C helix, the B-C loop), 106-129 (C helix), 130-153 (region between C helix and D helix, the C-D loop), 154-183 (D helix), 184-191 (C-terminus). In some cases, the one or more non-naturally encoded residues are linked to one or more lower molecular weight linear or branched PEGs (approximately ~5-20 kDa in mass or less), thereby enhancing binding affinity and comparable serum half-life relative to the species attached to a single, higher molecular weight PEG.

In some embodiments, up to two of the following residues of GH, e.g., hGH are substituted with one or more non-naturally-encoded amino acids at position: 29, 30, 33, 34, 35, 37, 39, 40, 49, 57, 59, 66, 69, 70, 71, 74, 88, 91, 92, 94, 95, 98, 99, 101, 103, 107, 108, 111, 122, 126, 129, 130, 131, 133, 134, 135, 136, 137, 139, 140, 141, 142, 143, 145, 147, 154, 155, 156, 159, 183, 186, and 187. In some cases, any of the following pairs of substitutions are made: K38X* and K140X*; K41X* and K145X*; Y35X* and E88X*; Y35X* and F92X*; Y35X* and Y143X*; F92X* and Y143X* wherein X* represents a non-naturally encoded amino acid. Preferred sites for incorporation of two or more non-naturally encoded amino acids include combinations of the following residues: 29, 33, 35, 37, 39, 49, 57, 69, 70, 71, 74, 88, 91, 92, 94, 95, 98, 99, 101, 103, 107, 108, 111, 129, 130, 131, 133, 134, 135, 136, 137, 139, 140, 141, 142, 143, 145, 147, 154, 155, 156, 186, and 187. Particularly preferred sites for incorporation of two or more non-naturally encoded amino acids include combinations of the following residues: 35, 88, 91, 92, 94, 95, 99, 101, 103, 111, 131, 133, 134, 135, 136, 139, 140, 143, 145, and 155.

Preferred sites for incorporation in GH, e.g., hGH of two or more non-naturally encoded amino acids include combinations of the following residues: before position 1 (i.e. at the N-terminus), 1, 2, 3, 4, 5, 8, 9, 11, 12, 15, 16, 19, 22, 29, 30, 32, 33, 34, 35, 36, 37, 38, 39, 40, 41, 42, 43, 44, 45, 46, 47, 48, 49, 52, 55, 57, 59, 65, 66, 69, 70, 71, 74, 88, 91, 92, 94, 95, 97, 98, 99, 100, 101, 102, 103, 104, 105, 106, 107, 108, 109, 111, 112, 113, 115, 116, 119, 120, 122, 123, 126, 127, 129, 130, 131, 132, 133, 134, 135, 136, 137, 138, 139, 140, 141, 142, 143, 144, 145, 146, 147, 148, 149, 150, 151, 152, 153, 154, 155, 156, 158, 159, 161, 168, 172, 183, 184, 185, 186, 187, 188, 189, 190, 191, 192 (i.e. at the carboxyl terminus of the protein) or any combination thereof from SEQ ID NO: 2.

VIII. Measurement of hGH Polypeptide Activity and Affinity of hGH Polypeptide for the hGH Polypeptide Receptor Activity of the hGH may be measured using any of several techniques known in the art, including, but not limited to, cell binding assays or pSTAT5 assay on IM9 cells. To assess the biological activity of modified hGH polypeptides, assays monitoring the interaction between hGH and its receptor may be used. For example, an assay measuring tyrosine phosphorylation of a signal transducer and activator of transcription family member, STAT5, in the human IM-9 lymphocyte cell line (ATCC, Manassas, Va.) may be used. See, e.g., Silva et al., Mol. Endocrinol. (1996) 10(5):508-518. The IM-9 cells were starved overnight in assay media (phenol-red free RPMI, 10 mM Hepes, 1% heat inactivated charcoal/dextran treated FBS, sodium pyruvate, penicillin and streptomycin) before stimulation with a 12-point dose range of hGH polypeptides for 10 min at 37° C. Stimulated cells were fixed with 1% formaldehyde before permeabilization with 90% ice-cold methanol for 1 hour on ice. The level of STAT5 phosphorylation was detected by intra-cellular staining with a primary phospho-STAT5 antibody (Cell Signaling Technology, Beverly, Mass.) at room temperature for 30 min followed by a PE-conjugated secondary antibody. Sample acquisition was performed on the FACS Array with acquired data analyzed on the Flowjo software (Tree Star Inc., Ashland, Oreg.). $EC_{50}$ values were derived from dose response curves plotted with mean fluorescent intensity (MFI) against protein concentration utilizing SigmaPlot.

Alternatively, proliferation studies with BrdU may be done in a cell line such as BAF3 stably transfected with rat growth hormone receptor. Serum starved rat growth hormone receptor, GHR, (L43R) expressing BAF3 cell line, 2E2-2B12-F4, were plated at a density of $5 \times 10^4$ cells/well in a 96-well plate. Cells were activated with a 12-point dose range of hGH proteins and labeled at the same time with 50 uM BrdU (Sigma, St. Louis, Mo.). After 48 hours in culture, cells were fixed/permeabilized with 100 ul of BD cytofix/cytoperm solution (BD Biosciences) for 30 min at room temperature. To expose BrdU epitopes, fixed/permeablilized cells were treated with 30 ug/well of DNase (Sigma) for 1 hour at 37° C. Immunofluorescent staining with APC-conjugated anti-BrdU antibody (BD Biosciences) enabled sample analysis on the FACS Array.

The hGH receptor can be prepared as described in McFarland et al., Science, 245: 494-499 (1989) and Leung, D., et al., Nature, 330:537-543 (1987). hGH polypeptide activity can be determined using standard or known in vitro or in vivo assays. For example, cell lines that proliferate in the presence of hGH (e.g., a cell line expressing the hGH receptor or a lactogenic receptor) can be used to monitor hGH receptor binding. See, e.g., Clark, R., et al., *J. Biol. Chem.* 271(36): 21969 (1996); Wada, et al., *Mol. Endocrinol.* 12:146-156 (1998); Gout, P. W., et al. *Cancer Res.* 40, 2433-2436 (1980); WO 99/03887. For a non-PEGylated or PEGYlated hGH polypeptide comprising a non-natural amino acid, the affinity of the hormone for its receptor can be measured by using a BIAcore™ biosensor (GE Healthcare). See, e.g., U.S. Pat. No. 5,849,535; Spencer, S. A., et al., *J. Biol. Chem.*, 263: 7862-7867 (1988). In vivo animal models for testing hGH activity include those described in, e.g., Clark et al., *J. Biol. Chem.* 271(36):21969-21977 (1996). Assays for dimerization capability of hGH polypeptides comprising one or more non-naturally encoded amino acids can be conducted as described in Cunningham, B., et al., *Science,* 254:821-825 (1991) and Fuh, G., et al., *Science,* 256:1677-1680 (1992). All references and patents cited are incorporated by reference herein. The above compilation of references for assay methodologies is not exhaustive, and those of ordinary skill in the art will recognize other assays useful for testing for the desired end result.

U.S. Patent Publication No. 2005/0170404 filed Jan. 28, 2005 and entitled "Modified Growth Hormone Polypeptides and Their Uses," which is incorporated by reference herein, further details residues of hGH for incorporation of one or more non-naturally occurring amino acid, non-naturally encoded amino acids, orthogonal tRNA, orthogonal aminoacyl tRNA synthetases, and methods to characterize hGH.

IX. Measurement of Potency, Functional In Vivo Half-Life, and Pharmacokinetic Parameters An important aspect of the invention is the prolonged biological half-life that is obtained by construction of the hGH polypeptide with or without conjugation of the polypeptide to a water soluble polymer moiety. The rapid decrease of hGH polypeptide serum concentrations has made it important to evaluate biological responses to treatment with conjugated and non-conjugated hGH polypeptide and variants thereof. The conjugated and non-conjugated hGH polypeptide and variants thereof of the present invention may have prolonged serum half-lives also after subcutaneous or i.v. administration, making it possible to measure by, e.g. ELISA method or by a primary screening assay. ELISA or RIA kits from either BioSource International (Camarillo, Calif.) or Diagnostic Systems Laboratories (Webster, Tex.) may be used. Measurement of in vivo biological half-life is carried out as described herein.

The potency and functional in vivo half-life of an hGH polypeptide comprising a non-naturally encoded amino acid can be determined according to the protocol described in Clark, R., et al., *J. Biol. Chem.* 271(36): 21969-21977 (1996).

Pharmacokinetic parameters for a hGH polypeptide comprising a non-naturally encoded amino acid can be evaluated in normal Sprague-Dawley male rats (N=5 animals per treatment group). Animals will receive either a single dose of 25 ug/rat iv or 50 ug/rat sc, and approximately 5-7 blood samples will be taken according to a pre-defined time course, generally covering about 6 hours for a hGH polypeptide comprising a non-naturally encoded amino acid not conjugated to a water soluble polymer and about 4 days for a hGH polypeptide comprising a non-naturally encoded amino acid and conjugated to a water soluble polymer. Pharmacokinetic data for hGH polypeptides is well-studied in several species and can be compared directly to the data obtained for hGH polypeptides comprising a non-naturally encoded amino acid. See Mordenti J., et al., *Pharm. Res.* 8(11):1351-59 (1991) for studies related to hGH.

Pharmacokinetic parameters can also be evaluated in a primate, e.g., cynomolgus monkeys. Typically, a single injection is administered either subcutaneously or intravenously, and serum hGH levels are monitored over time.

The specific activity of hGH polypeptides in accordance with this invention can be determined by various assays known in the art. The biological activity of the hGH polypeptide muteins, or fragments thereof, obtained and purified in accordance with this invention can be tested by methods described or referenced herein or known to those of ordinary skill in the art.

X. Therapeutic Uses of hGH Polypeptides

The hGH agonist polypeptides may be useful, for example, for treating growth deficiency, immune disorders, and for stimulating heart function. Individuals with growth deficiencies include, e.g., individuals with Turner's Syndrome, GH-deficient individuals (including children), children who experience a slowing or retardation in their normal growth curve about 2-3 years before their growth plate closes (sometimes known as "short normal children"), and individuals where the insulin-like growth factor-I (IGF-I) response to GH has been blocked chemically (i.e., by glucocorticoid treatment) or by a natural condition such as in adult patients where the IGF-I response to GH is naturally reduced. The hGH polypeptides of the invention may be useful for treating individuals with the following conditions: pediatric growth hormone deficiency, idiopathic short stature, adult growth hormone deficiency of childhood onset, adult growth hormone deficiency of adult onset, or secondary growth hormone deficiency. Adults diagnosed with growth hormone deficiency in adulthood may have had a pituitary tumor or radiation. Conditions including but not limited to, metabolic syndrome, head injury, obesity, osteoporosis, or depression may result in growth hormone deficiency-like symptoms in adults.

An agonist hGH variant may act to stimulate the immune system of a mammal by increasing its immune function, whether the increase is due to antibody mediation or cell mediation, and whether the immune system is endogenous to the host treated with the hGH polypeptide or is transplanted from a donor to the host recipient given the hGH polypeptide (as in bone marrow transplants). "Immune disorders" include any condition in which the immune system of an individual has a reduced antibody or cellular response to antigens than normal, including those individuals with small spleens with reduced immunity due to drug (e.g., chemotherapeutic) treatments. Examples individuals with immune disorders include, e.g., elderly patients, individuals undergoing chemotherapy or radiation therapy, individuals recovering from a major illness, or about to undergo surgery, individuals with AIDS, Patients with congenital and acquired B-cell deficiencies such as hypogammaglobulinemia, common varied agammaglobulinemia, and selective immunoglobulin deficiencies (e.g., IgA deficiency, patients infected with a virus such as rabies with an incubation time shorter than the immune response of the patient; and individuals with hereditary disorders such as diGeorge syndrome.

hGH antagonist polypeptides may be useful for the treatment of gigantism and acromegaly, diabetes and complications (diabetic retinopathy, diabetic neuropathy) arising from diabetes, vascular eye diseases (e.g., involving proliferative neovascularization), nephropathy, and GH-responsive malignancies. Vascular eye diseases include, e.g., retinopathy (caused by, e.g., pre-maturity or sickle cell anemia) and macular degeneration. GH-responsive malignancies include, e.g., Wilm's tumor, sarcomas (e.g., osteogenic sarcoma), breast, colon, prostate, and thyroid cancer, and cancers of tissues that express GH receptor mRNA (i.e., placenta, thymus, brain, salivary gland, prostate, bone marrow, skeletal muscle, trachea, spinal cord, retina, lymph node and from Burkitt's lymphoma, colorectal carcinoma, lung carcinoma, lymphoblastic leukemia, and melanoma).

The GH, e.g., hGH agonist polypeptides of the invention may be useful, for example, for treating chronic renal failure, growth failure associated with chronic renal insufficiency (CRI), short stature associated with Turner Syndrome, pediatric Prader-Willi Syndrome (PWS), HIV patients with wasting or cachexia, children born small for gestational age (SGA), obesity, and osteoporosis.

hGH polypeptides of the invention, including PEGylated hGH, may be administered by any conventional route suitable for proteins or peptides, including, but not limited to parenterally, e.g. injections including, but not limited to, subcutaneously or intravenously or any other form of injections or infusions. Polypeptide compositions can be administered by a number of routes including, but not limited to oral, intravenous, intraperitoneal, intramuscular, transdermal, subcutaneous, topical, sublingual, or rectal means. Compositions comprising non-natural amino acid polypeptides, modified or unmodified, can also be administered via liposomes. Such administration routes and appropriate formulations are generally known to those of skill in the art. The hGH polypeptide comprising a non-natural amino acid, including PEGylated hGH, may be used alone or in combination with other suitable components such as a pharmaceutical carrier.

Average quantities of the hGH may vary and in particular should be based upon the recommendations and prescription of a qualified physician. The exact amount of hGH is a matter of preference subject to such factors as the exact type of condition being treated, the condition of the patient being treated, as well as the other ingredients in the composition. The amount to be given may be readily determined by one of ordinary skill in the art based upon therapy with hGH.

Pharmaceutical compositions of the invention may be manufactured in conventional manner.

XI. General Recombinant Nucleic Acid Methods for Use with the Invention

In numerous embodiments of the present invention, nucleic acids encoding a hGH polypeptide of interest will be isolated, cloned and often altered using recombinant methods. Such embodiments are used, including but not limited to, for protein expression or during the generation of variants, derivatives, expression cassettes, or other sequences derived from a hGH polypeptide. In some embodiments, the sequences encoding the polypeptides of the invention are operably linked to a heterologous promoter. Isolation of hGH and production of GH in host cells are described in, e.g., U.S. Pat. Nos. 4,601,980, 4,604,359, 4,634,677, 4,658,021, 4,898,830, 5,424,199, 5,795,745, 5,854,026, 5,849,535; 6,004,931; 6,022,711; 6,143,523 and 6,608,183, which are incorporated by reference herein.

A nucleotide sequence encoding a hGH polypeptide comprising a non-naturally encoded amino acid may be synthesized on the basis of the amino acid sequence of the parent polypeptide and then changing the nucleotide sequence so as to effect introduction (i.e., incorporation or substitution) or removal (i.e., deletion or substitution) of the relevant amino acid residue(s). The nucleotide sequence may be conveniently modified by site-directed mutagenesis in accordance with conventional methods. Alternatively, the nucleotide sequence may be prepared by chemical synthesis, including but not limited to, by using an oligonucleotide synthesizer, wherein oligonucleotides are designed based on the amino acid sequence of the desired polypeptide, and preferably selecting those codons that are favored in the host cell in which the recombinant polypeptide will be produced. For example, several small oligonucleotides coding for portions of the desired polypeptide may be synthesized and assembled by PCR, ligation or ligation chain reaction. See, e.g., Barany, et al., *Proc. Natl. Acad. Sci.* 88: 189-193 (1991); U.S. Pat. No. 6,521,427 which are incorporated by reference herein.

This invention utilizes routine techniques in the field of recombinant genetics. Basic texts disclosing the general methods of use in this invention include Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

General texts which describe molecular biological techniques include Berger and Kimmel, *Guide to Molecular Cloning Techniques Methods in Enzymology* volume 152 Academic Press, Inc., San Diego, Calif. (Berger); Sambrook et al., *Molecular Cloning—A Laboratory Manual* (2nd Ed.), Vol. 1-3, Cold Spring Harbor Laboratory, Cold Spring Harbor, N.Y., 1989 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 1999) ("Ausubel")). These texts describe mutagenesis, the use of vectors, promoters and many other relevant topics related to, including but not limited to, the generation of genes or polynucleotides that include selector codons for production of proteins that include unnatural amino acids, orthogonal tRNAs, orthogonal tRNA synthetases, and pairs thereof.

Various types of mutagenesis are used in the invention for a variety of purposes, including but not limited to, to produce novel synthetases or tRNAs, to mutate tRNA molecules, to mutate polynucleotides encoding synthetases, to produce libraries of tRNAs, to produce libraries of synthetases, to produce selector codons, to insert selector codons that encode unnatural amino acids in a protein or polypeptide of interest. They include but are not limited to site-directed, random point mutagenesis, homologous recombination, DNA shuffling or other recursive mutagenesis methods, chimeric construction, mutagenesis using uracil containing templates, oligonucleotide-directed mutagenesis, phosphorothioate-modified DNA mutagenesis, mutagenesis using gapped duplex DNA or the like, or any combination thereof. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, including but not limited to, involving chimeric constructs, are also included in the present invention. In one embodiment, mutagenesis can be guided by known information of the naturally occurring molecule or altered or mutated naturally occurring molecule, including but not limited to, sequence, sequence comparisons, physical properties, secondary, tertiary, or quaternary structure, crystal structure or the like.

The texts and examples found herein describe these procedures. Additional information is found in the following publications and references cited within: Ling et al., *Approaches to DNA mutagenesis: an overview, Anal Biochem.* 254(2): 157-178 (1997); Dale et al., *Oligonucleotide-directed ran-*

*dom mutagenesis using the phosphorothioate method, Methods Mol. Biol.* 57:369-374 (1996); Smith, *In vitro mutagenesis, Ann. Rev. Genet.* 19:423-462 (1985); Botstein & Shortle, *Strategies and applications of in vitro mutagenesis, Science* 229:1193-1201 (1985); Carter, *Site-directed mutagenesis, Biochem. J.* 237:1-7 (1986); Kunkel, *The efficiency of oligonucleotide directed mutagenesis*, in *Nucleic Acids & Molecular Biology* (Eckstein, F. and Lilley, D. M. J. eds., Springer Verlag, Berlin) (1987); Kunkel, *Rapid and efficient site-specific mutagenesis without phenotypic selection, Proc. Natl. Acad. Sci. USA* 82:488-492 (1985); Kunkel et al., *Rapid and efficient site-specific mutagenesis without phenotypic selection, Methods in Enzymol.* 154, 367-382 (1987); Bass et al., *Mutant Trp repressors with new DNA-binding specificities, Science* 242:240-245 (1988); Zoller & Smith, *Oligonucleotide-directed mutagenesis using M13-derived vectors: an efficient and general procedure for the production of point mutations in any DNA fragment, Nucleic Acids Res.* 10:6487-6500 (1982); Zoller & Smith, *Oligonucleotide-directed mutagenesis of DNA fragments cloned into M13 vectors, Methods in Enzymol.* 100:468-500 (1983); Zoller & Smith, *Oligonucleotide-directed mutagenesis: a simple method using two oligonucleotide primers and a single-stranded DNA template, Methods in Enzymol.* 154:329-350 (1987); Taylor et al., *The use of phosphorothioate-modified DNA in restriction enzyme reactions to prepare nicked DNA, Nucl. Acids Res.* 13: 8749-8764 (1985); Taylor et al., *The rapid generation of oligonucleotide-directed mutations at high frequency using phosphorothioate-modified DNA, Nucl. Acids Res.* 13: 8765-8785 (1985); Nakamaye & Eckstein, *Inhibition of restriction endonuclease Nci I cleavage by phosphorothioate groups and its application to oligonucleotide-directed mutagenesis, Nucl. Acids Res.* 14: 9679-9698 (1986); Sayers et al., *5'-3' Exonucleases in phosphorothioate-based oligonucleotide-directed mutagenesis, Nucl. Acids Res.* 16:791-802 (1988); Sayers et al., *Strand specific cleavage of phosphorothioate-containing DNA by reaction with restriction endonucleases in the presence of ethidium bromide,* (1988) *Nucl. Acids Res.* 16: 803-814; Kramer et al., *The gapped duplex DNA approach to oligonucleotide-directed mutation construction, Nucl. Acids Res.* 12: 9441-9456 (1984); Kramer & Fritz *Oligonucleotide-directed construction of mutations via gapped duplex DNA, Methods in Enzymol.* 154:350-367 (1987); Kramer et al., *Improved enzymatic in vitro reactions in the gapped duplex DNA approach to oligonucleotide-directed construction of mutations, Nucl. Acids Res.* 16: 7207 (1988); Fritz et al., *Oligonucleotide-directed construction of mutations: a gapped duplex DNA procedure without enzymatic reactions in vitro, Nucl. Acids Res.* 16: 6987-6999 (1988); Kramer et al., *Different base/base mismatches are corrected with different efficiencies by the methyl-directed DNA mismatch-repair system of E. coli, Cell* 38:879-887 (1984); Carter et al., *Improved oligonucleotide site-directed mutagenesis using M13 vectors, Nucl. Acids Res.* 13: 4431-4443 (1985); Carter, *Improved oligonucleotide-directed mutagenesis using M13 vectors, Methods in Enzymol.* 154: 382-403 (1987); Eghtedarzadeh & Henikoff, *Use of oligonucleotides to generate large deletions, Nucl. Acids Res.* 14: 5115 (1986); Wells et al., *Importance of hydrogen-bond formation in stabilizing the transition state of subtilisin, Phil. Trans. R. Soc. Lond. A* 317: 415-423 (1986); Nambiar et al., *Total synthesis and cloning of a gene coding for the ribonuclease S protein, Science* 223: 1299-1301 (1984); Sakmar and Khorana, *Total synthesis and expression of a gene for the alpha-subunit of bovine rod outer segment guanine nucleotide-binding protein (transducin), Nucl. Acids Res.* 14: 6361-6372 (1988); Wells et al., *Cassette mutagenesis: an efficient method for generation of multiple mutations at defined sites, Gene* 34:315-323 (1985); Grundström et al., *Oligonucleotide-directed mutagenesis by microscale 'shotgun' gene synthesis, Nucl. Acids Res.* 13: 3305-3316 (1985); Mandecki, *Oligonucleotide-directed double-strand break repair in plasmids of Escherichia coli: a method for site-specific mutagenesis, Proc. Natl. Acad. Sci. USA,* 83:7177-7181 (1986); Arnold, *Protein engineering for unusual environments, Current Opinion in Biotechnology* 4:450-455 (1993); Sieber, et al., Nature Biotechnology, 19:456-460 (2001); W. P. C. Stemmer, *Nature* 370, 389-91 (1994); and, I. A. Lorimer, I. Pastan, *Nucleic Acids Res.* 23, 3067-8 (1995). Additional details on many of the above methods can be found in *Methods in Enzymology Volume* 154, which also describes useful controls for trouble-shooting problems with various mutagenesis methods.

Oligonucleotides, e.g., for use in mutagenesis of the present invention, e.g., mutating libraries of synthetases, or altering tRNAs, are typically synthesized chemically according to the solid phase phosphoramidite triester method described by Beaucage and Caruthers, Tetrahedron Letts. 22(20):1859-1862, (1981) e.g., using an automated synthesizer, as described in Needham-VanDevanter et al., Nucleic Acids Res., 12:6159-6168 (1984).

The invention also relates to eukaryotic host cells, non-eukaryotic host cells, and organisms for the in vivo incorporation of an unnatural amino acid via orthogonal tRNA/RS pairs. Host cells are genetically engineered (including but not limited to, transformed, transduced or transfected) with the polynucleotides of the invention or constructs which include a polynucleotide of the invention, including but not limited to, a vector of the invention, which can be, for example, a cloning vector or an expression vector. For example, the coding regions for the orthogonal tRNA, the orthogonal tRNA synthetase, and the protein to be derivatized are operably linked to gene expression control elements that are functional in the desired host cell. The vector can be, for example, in the form of a plasmid, a cosmid, a phage, a bacterium, a virus, a naked polynucleotide, or a conjugated polynucleotide. The vectors are introduced into cells and/or microorganisms by standard methods including electroporation (Fromm et al., *Proc. Natl. Acad. Sci. USA* 82, 5824 (1985)), infection by viral vectors, high velocity ballistic penetration by small particles with the nucleic acid either within the matrix of small beads or particles, or on the surface (Klein et al., *Nature* 327, 70-73 (1987)), and/or the like.

The engineered host cells can be cultured in conventional nutrient media modified as appropriate for such activities as, for example, screening steps, activating promoters or selecting transformants. These cells can optionally be cultured into transgenic organisms. Other useful references, including but not limited to for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds.) (1995) *Plant Cell, Tissue and Organ Culture*; Fundamental Methods Springer Lab Manual, Springer-Verlag (Berlin Heidelberg New York) and Atlas and Parks (eds.) *The Handbook of Microbiological Media* (1993) CRC Press, Boca Raton, Fla.

Several well-known methods of introducing target nucleic acids into cells are available, any of which can be used in the invention. These include: fusion of the recipient cells with bacterial protoplasts containing the DNA, electroporation, projectile bombardment, and infection with viral vectors (discussed further, below), etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, kits are commercially available for the purification of plasmids from bacteria, (see, e.g., EasyPrep™, FlexiPrep™, both from GE Healthcare; StrataClean™ from Stratagene; and, QIAprep™ from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (including but not limited to, shuttle vectors) and selection markers for both prokaryotic and eukaryotic systems. Vectors are suitable for replication and integration in prokaryotes, eukaryotes, or both. See, Gillam & Smith, *Gene* 8:81 (1979); Roberts, et al., *Nature*, 328:731 (1987); Schneider, E., et al., *Protein Expr. Purif.* 6(1):10-14 (1995); Ausubel, Sambrook, Berger (all supra). A catalogue of bacteria and bacteriophages useful for cloning is provided, e.g., by the ATCC, e.g., *The ATCC Catalogue of Bacteria and Bacteriophage* (1992) Ghema et al. (eds) published by the ATCC. Additional basic procedures for sequencing, cloning and other aspects of molecular biology and underlying theoretical considerations are also found in Watson et al. (1992) *Recombinant DNA Second Edition* Scientific American Books, NY. In addition, essentially any nucleic acid (and virtually any labeled nucleic acid, whether standard or non-standard) can be custom or standard ordered from any of a variety of commercial sources, such as the Midland Certified Reagent Company (Midland, Tex. available on the World Wide Web at mcrc.com), The Great American Gene Company (Ramona, Calif. available on the World Wide Web at genco.com), ExpressGen Inc. (Chicago, Ill. available on the World Wide Web at expressgen.com), Operon Technologies Inc. (Alameda, Calif.) and many others.

XII. Expression in Non-Eukaryotes and Eukaryotes

To obtain high level expression of a cloned hGH polynucleotide, one typically subclones polynucleotides encoding a hGH polypeptide of the invention into an expression vector that contains a strong promoter to direct transcription, a transcription/translation terminator, and if for a nucleic acid encoding a protein, a ribosome binding site for translational initiation. Suitable bacterial promoters are known to those of ordinary skill in the art and described, e.g., in Sambrook et al. and Ausubel et al.

Bacterial expression systems for expressing hGH polypeptides of the invention are available in, including but not limited to, *E. coli, Bacillus* sp., *Pseudomonas fluorescens, Pseudomonas aeruginosa, Pseudomonas putida*, and *Salmonella* (Palva et al., *Gene* 22:229-235 (1983); Mosbach et al., *Nature* 302:543-545 (1983)). Kits for such expression systems are commercially available. Eukaryotic expression systems for mammalian cells, yeast, and insect cells are known to those of ordinary skill in the art and are also commercially available. In cases where orthogonal tRNAs and aminoacyl tRNA synthetases are used to express the hGH polypeptides of the invention, host cells for expression are selected based on their ability to use the orthogonal components. Exemplary host cells include Gram-positive bacteria (including but not limited to *B. brevis, B. subtilis,* or *Streptomyces*) and Gram-negative bacteria (*E. coli, Pseudomonas fluorescens, Pseudomonas aeruginosa, Pseudomonas putida*), as well as yeast and other eukaryotic cells. Cells comprising O-tRNA/O-RS pairs can be used as described herein.

A eukaryotic host cell or non-eukaryotic host cell of the present invention provides the ability to synthesize proteins that comprise unnatural amino acids in large useful quantities. In one aspect, the composition optionally includes, including but not limited to, at least 10 micrograms, at least 50 micrograms, at least 75 micrograms, at least 100 micrograms, at least 200 micrograms, at least 250 micrograms, at least 500 micrograms, at least 1 milligram, at least 10 milligrams, at least 100 milligrams, at least one gram, or more of the protein that comprises an unnatural amino acid, or an amount that can be achieved with in vivo protein production methods (details on recombinant protein production and purification are provided herein). In another aspect, the protein is optionally present in the composition at a concentration of, including but not limited to, at least 10 micrograms of protein per liter, at least 50 micrograms of protein per liter, at least 75 micrograms of protein per liter, at least 100 micrograms of protein per liter, at least 200 micrograms of protein per liter, at least 250 micrograms of protein per liter, at least 500 micrograms of protein per liter, at least 1 milligram of protein per liter, or at least 10 milligrams of protein per liter or more, in, including but not limited to, a cell lysate, a buffer, a pharmaceutical buffer, or other liquid suspension (including but not limited to, in a volume of, including but not limited to, anywhere from about 1 nl to about 100 L or more). The production of large quantities (including but not limited to, greater that that typically possible with other methods, including but not limited to, in vitro translation) of a protein in a eukaryotic cell or non-eukaryotic cell including at least one unnatural amino acid is a feature of the invention.

A eukaryotic host cell or non-eukaryotic host cell of the present invention provides the ability to biosynthesize proteins that comprise unnatural amino acids in large useful quantities. For example, proteins comprising an unnatural amino acid can be produced at a concentration of, including but not limited to, at least 10 µg/liter, at least 50 µg/liter, at least 75 µg/liter, at least 100 µg/liter, at least 200 µg/liter, at least 250 µg/liter, or at least 500 µg/liter, at least 1 mg/liter, at least 2 mg/liter, at least 3 mg/liter, at least 4 mg/liter, at least 5 mg/liter, at least 6 mg/liter, at least 7 mg/liter, at least 8 mg/liter, at least 9 mg/liter, at least 10 mg/liter, at least 20, 30, 40, 50, 60, 70, 80, 90, 100, 200, 300, 400, 500, 600, 700, 800, 900 mg/liter, 1 g/liter, 5 g/liter, 10 g/liter or more of protein in a cell extract, cell lysate, culture medium, a buffer, and/or the like.

Expression Systems, Culture, and Isolation hGH may be expressed in any number of suitable expression systems including, for example, yeast, insect cells, mammalian cells, and bacteria. A description of exemplary expression systems is provided below.

Yeast

As used herein, the term "yeast" includes any of the various yeasts capable of expressing a gene encoding hGH. Such yeasts include, but are not limited to, ascosporogenous yeasts (Endomycetales), basidiosporogenous yeasts and yeasts belonging to the Fungi imperfecti (Blastomycetes) group. The ascosporogenous yeasts are divided into two families, Spermophthoraceae and Saccharomycetaceae. The latter is comprised of four subfamilies, Schizosaccharomycoideae (e.g., genus *Schizosaccharomyces*), Nadsonioideae, Lipomycoideae and Saccharomycoideae (e.g., genera *Pichia*,

*Kluyveromyces* and *Saccharomyces*). The basidiosporogenous yeasts include the genera *Leucosporidium, Rhodosporidium, Sporidiobolus, Filobasidium* and *Filobasidiella*. Yeasts belonging to the Fungi Imperfecti (Blastomycetes) group are divided into two families, Sporobolomycetaceae (e.g., genera *Sporobolomyces* and *Bullera*) and Cryptococcaceae (e.g., genus *Candida*).

Of particular interest for use with the present invention are species within the genera *Pichia, Kluyveromyces, Saccharomyces, Schizosaccharomyces, Hansenula, Torulopsis* and *Candida*, including, but not limited to, *P. pastoris, P. guillerimondii, S. cerevisiae, S. carlsbergensis, S. diastaticus, S. douglasii, S. kluyveri, S, norbensis, S. oviformis, K. lactis, K. fragilis, C. albicans, C. maltosa*, and *H. polymorpha*.

The selection of suitable yeast for expression of hGH is within the skill of one of ordinary skill in the art. In selecting yeast hosts for expression, suitable hosts may include those shown to have, for example, good secretion capacity, low proteolytic activity, and overall robustness. Yeast are generally available from a variety of sources including, but not limited to, the Yeast Genetic Stock Center, Department of Biophysics and Medical Physics, University of California (Berkeley, Calif.), and the American Type Culture Collection ("ATCC") (Manassas, Va.).

The term "yeast host" or "yeast host cell" includes yeast that can be, or has been, used as a recipient for recombinant vectors or other transfer DNA. The term includes the progeny of the original yeast host cell that has received the recombinant vectors or other transfer DNA. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding an hGH, are included in the progeny intended by this definition.

Expression and transformation vectors, including extrachromosomal replicons or integrating vectors, have been developed for transformation into many yeast hosts. For example, expression vectors have been developed for *S. cerevisiae* (Sikorski et al., GENETICS (1989) 122:19; Ito et al., J. BACTERIOL. (1983) 153:163; Hinnen et al., PROC. NATL. ACAD. SCI. USA (1978) 75:1929); *C. albicans* (Kurtz et al., MOL. CELL. BIOL. (1986) 6:142); *C. maltosa* (Kunze et al., *J. BASIC MICRO*BIOL. (1985) 25:141); *H. polymorpha* (Gleeson et al., J. GEN. MICROBIOL. (1986) 132:3459; Roggenkamp et al., MOL. GENETICS AND GENOMICS (1986) 202:302); *K. fragilis* (Das et al., J. BACTERIOL. (1984) 158:1165); *K. lactis* (De Louvencourt et al., J. BACTERIOL. (1983) 154:737; Van den Berg et al., *BIO*TECHNOLOGY (NY) (1990) 8:135); *P. guillerimondii* (Kunze et al., J. BASIC MICROBIOL. (1985) 25:141); *P. pastoris* (U.S. Pat. Nos. 5,324,639; 4,929,555; and 4,837,148; Cregg et al., MOL. CELL. BIOL. (1985) 5:3376); *Schizosaccharomyces pombe* (Beach et al., NATURE (1982) 300:706); and *Y. lipolytica; A. nidulans* (Ballance et al., BIOCHEM. BIOPHYS. RES. COMMUN. (1983) 112:284-89; Tilburn et al., GENE (1983) 26:205-221; and Yelton et al., PROC. NATL. ACAD. SCI. USA (1984) 81:1470-74); *A. niger* (Kelly and Hynes, EMBO J. (1985) 4:475-479); *T. reesia* (EP 0 244 234); and filamentous fungi such as, e.g., *Neurospora, Penicillium, Tolypocladium* (WO 91/00357), each of which is incorporated by reference herein.

Control sequences for yeast vectors are known to those of ordinary skill in the art and include, but are not limited to, promoter regions from genes such as alcohol dehydrogenase (ADH) (EP 0 284 044); enolase; glucokinase; glucose-6-phosphate isomerase; glyceraldehyde-3-phosphate-dehydrogenase (GAP or GAPDH); hexokinase; phosphofructokinase; 3-phosphoglycerate mutase; and pyruvate kinase (PyK) (EP 0 329 203). The yeast PHO5 gene, encoding acid phosphatase, also may provide useful promoter sequences (Miyanohara et al., PROC. NATL. ACAD. SCI. USA (1983) 80:1). Other suitable promoter sequences for use with yeast hosts may include the promoters for 3-phosphoglycerate kinase (Hitzeman et al., J. BIOL. CHEM. (1980) 255:12073; and other glycolytic enzymes, such as pyruvate decarboxylase, triosephosphate isomerase, and phosphoglucose isomerase (Holland et al., BIOCHEMISTRY (1978) 17:4900; Hess et al., J. ADV. ENZYME REG. (1969) 7:149). Inducible yeast promoters having the additional advantage of transcription controlled by growth conditions may include the promoter regions for alcohol dehydrogenase 2; isocytochrome C; acid phosphatase; metallothionein; glyceraldehyde-3-phosphate dehydrogenase; degradative enzymes associated with nitrogen metabolism; and enzymes responsible for maltose and galactose utilization. Suitable vectors and promoters for use in yeast expression are further described in EP 0 073 657.

Yeast enhancers also may be used with yeast promoters. In addition, synthetic promoters may also function as yeast promoters. For example, the upstream activating sequences (UAS) of a yeast promoter may be joined with the transcription activation region of another yeast promoter, creating a synthetic hybrid promoter. Examples of such hybrid promoters include the ADH regulatory sequence linked to the GAP transcription activation region. See U.S. Pat. Nos. 4,880,734 and 4,876,197. Other examples of hybrid promoters include promoters that consist of the regulatory sequences of the ADH2, GAL4, GAL10, or PHO5 genes, combined with the transcriptional activation region of a glycolytic enzyme gene such as GAP or PyK. See EP 0 164 556. Furthermore, a yeast promoter may include naturally occurring promoters of non-yeast origin that have the ability to bind yeast RNA polymerase and initiate transcription.

Other control elements that may comprise part of the yeast expression vectors include terminators, for example, from GAPDH or the enolase genes (Holland et al., J. BIOL. CHEM. (1981) 256:1385). In addition, the origin of replication from the 2μ plasmid origin is suitable for yeast. A suitable selection gene for use in yeast is the trp1 gene present in the yeast plasmid. See Tschumper et al., GENE (1980) 10:157; Kingsman et al., GENE (1979) 7:141. The trp1 gene provides a selection marker for a mutant strain of yeast lacking the ability to grow in tryptophan. Similarly, Leu2-deficient yeast strains (ATCC 20,622 or 38,626) are complemented by known plasmids bearing the Leu2 gene.

Methods of introducing exogenous DNA into yeast hosts are known to those of ordinary skill in the art, and typically include, but are not limited to, either the transformation of spheroplasts or of intact yeast host cells treated with alkali cations. For example, transformation of yeast can be carried out according to the method described in Hsiao et al., PROC. NATL. ACAD. SCI. USA (1979) 76:3829 and Van Solingen et al., J. BACT. (1977) 130:946. However, other methods for introducing DNA into cells such as by nuclear injection, electroporation, or protoplast fusion may also be used as described generally in SAMBROOK ET AL., MOLECULAR CLONING: A LAB. MANUAL (2001). Yeast host cells may then be cultured using standard techniques known to those of ordinary skill in the art.

Other methods for expressing heterologous proteins in yeast host cells are known to those of ordinary skill in the art. See generally U.S. Patent Application No. 20020055169, U.S. Pat. Nos. 6,361,969; 6,312,923; 6,183,985; 6,083,723; 6,017,731; 5,674,706; 5,629,203; 5,602,034; and 5,089,398; U.S. Reexamined Patent Nos. RE37,343 and RE35,749; PCT Published Patent Applications WO 99/078621; WO 98/37208; and WO 98/26080; European Patent Applications EP 0 946 736; EP 0 732 403; EP 0 480 480; WO 90/10277; EP 0 340 986; EP 0 329 203; EP 0 324 274; and EP 0 164 556, which are incorporated by reference herein. See also Gellissen et al., ANTONIE VAN LEEUWENHOEK (1992) 62(1-2):79-93; Romanos et al., YEAST (1992) 8(6):423-488; Goeddel, METHODS IN ENZYMOLOGY (1990) 185:3-7, each is incorporated by reference herein.

The yeast host strains may be grown in fermentors during the amplification stage using standard feed batch fermentation methods known to those of ordinary skill in the art. The fermentation methods may be adapted to account for differences in a particular yeast host's carbon utilization pathway or mode of expression control. For example, fermentation of a *Saccharomyces* yeast host may require a single glucose feed, complex nitrogen source (e.g., casein hydrolysates), and multiple vitamin supplementation. In contrast, the methylotrophic yeast *P. pastoris* may require glycerol, methanol, and trace mineral feeds, but only simple ammonium (nitrogen) salts for optimal growth and expression. See, e.g., U.S. Pat. No. 5,324,639; Elliott et al., J. PROTEIN CHEM. (1990) 9:95; and Fieschko et al., BIOTECH. BIOENG. (1987) 29:1113.

Such fermentation methods, however, may have certain common features independent of the yeast host strain employed. For example, a growth limiting nutrient, typically carbon, may be added to the fermentor during the amplification phase to allow maximal growth. In addition, fermentation methods generally employ a fermentation medium designed to contain adequate amounts of carbon, nitrogen, basal salts, phosphorus, and other minor nutrients (vitamins, trace minerals and salts, etc.). Examples of fermentation media suitable for use with *Pichia* are described in U.S. Pat. Nos. 5,324,639 and 5,231,178, which are incorporated by reference herein.

Baculovirus-Infected Insect Cells

The term "insect host" or "insect host cell" refers to a insect that can be, or has been, used as a recipient for recombinant vectors or other transfer DNA. The term includes the progeny of the original insect host cell that has been transfected. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding an hGH polypeptide, are included in the progeny intended by this definition.

The selection of suitable insect cells for expression of hGH is known to those of ordinary skill in the art. Several insect species are well described in the art and are commercially available including *Aedes aegypti, Bombyx mori, Drosophila melanogaster, Spodoptera frugiperda*, and *Trichoplusia ni*. In selecting insect hosts for expression, suitable hosts may include those shown to have, inter alia, good secretion capacity, low proteolytic activity, and overall robustness. Insect are generally available from a variety of sources including, but not limited to, the Insect Genetic Stock Center, Department of Biophysics and Medical Physics, University of California (Berkeley, Calif.); and the American Type Culture Collection ("ATCC") (Manassas, Va.).

Generally, the components of a baculovirus-infected insect expression system include a transfer vector, usually a bacterial plasmid, which contains both a fragment of the baculovirus genome, and a convenient restriction site for insertion of the heterologous gene to be expressed; a wild type baculovirus with a sequences homologous to the baculovirus-specific fragment in the transfer vector (this allows for the homologous recombination of the heterologous gene in to the baculovirus genome); and appropriate insect host cells and growth media. The materials, methods and techniques used in constructing vectors, transfecting cells, picking plaques, growing cells in culture, and the like are known in the art and manuals are available describing these techniques.

After inserting the heterologous gene into the transfer vector, the vector and the wild type viral genome are transfected into an insect host cell where the vector and viral genome recombine. The packaged recombinant virus is expressed and recombinant plaques are identified and purified. Materials and methods for baculovirus/insect cell expression systems are commercially available in kit form from, for example, Invitrogen Corp. (Carlsbad, Calif.). These techniques are generally known to those of ordinary skill in the art and fully described in SUMMERS AND SMITH, TEXAS AGRICULTURAL EXPERIMENT STATION BULLETIN No. 1555 (1987), herein incorporated by reference. See also, RICHARDSON, 39 METHODS IN MOLECULAR BIOLOGY: BACULOVIRUS EXPRESSION PROTOCOLS (1995); AUSUBEL ET AL., CURRENT PROTOCOLS IN MOLECULAR BIOLOGY 16.9-16.11 (1994); KING AND POSSEE, THE BACULOVIRUS SYSTEM: A LABORATORY GUIDE (1992); and O'REILLY ET AL., BACULOVIRUS EXPRESSION VECTORS: A LABORATORY MANUAL (1992).

Indeed, the production of various heterologous proteins using baculovirus/insect cell expression systems is known to those of ordinary skill in the art. See, e.g., U.S. Pat. Nos. 6,368,825; 6,342,216; 6,338,846; 6,261,805; 6,245,528; 6,225,060; 6,183,987; 6,168,932; 6,126,944; 6,096,304; 6,013,433; 5,965,393; 5,939,285; 5,891,676; 5,871,986; 5,861,279; 5,858,368; 5,843,733; 5,762,939; 5,753,220; 5,605,827; 5,583,023; 5,571,709; 5,516,657; 5,290,686; WO 02/06305; WO 01/90390; WO 01/27301; WO 01/05956; WO 00/55345; WO 00/20032; WO 99/51721; WO 99/45130; WO 99/31257; WO 99/10515; WO 99/09193; WO 97/26332; WO 96/29400; WO 96/25496; WO 96/06161; WO 95/20672; WO 93/03173; WO 92/16619; WO 92/02628; WO 92/01801; WO 90/14428; WO 90/10078; WO 90/02566; WO 90/02186; WO 90/01556; WO 89/01038; WO 89/01037; WO 88/07082, which are incorporated by reference herein.

Vectors that are useful in baculovirus/insect cell expression systems are known in the art and include, for example, insect expression and transfer vectors derived from the baculovirus *Autographa californica* nuclear polyhedrosis virus (AcNPV), which is a helper-independent, viral expression vector. Viral expression vectors derived from this system usually use the strong viral polyhedrin gene promoter to drive expression of heterologous genes. See generally, O'Reilly ET AL., BACULOVIRUS EXPRESSION VECTORS: A LABORATORY MANUAL (1992).

Prior to inserting the foreign gene into the baculovirus genome, the above-described components, comprising a promoter, leader (if desired), coding sequence of interest, and transcription termination sequence, are typically assembled into an intermediate transplacement construct (transfer vector). Intermediate transplacement constructs are often maintained in a replicon, such as an extra chromosomal element (e.g., plasmids) capable of stable maintenance in a host, such as bacteria. The replicon will have a replication system, thus allowing it to be maintained in a suitable host for cloning and amplification. More specifically, the plasmid may contain the polyhedrin polyadenylation signal (Miller, ANN. REV. MICROBIOL. (1988) 42:177) and a prokaryotic ampicillin-resistance (amp) gene and origin of replication for selection and propagation in *E. coli*.

One commonly used transfer vector for introducing foreign genes into AcNPV is pAc373. Many other vectors, known to those of skill in the art, have also been designed including, for example, pVL985, which alters the polyhedrin start codon from ATG to ATT, and which introduces a BamHI cloning site 32 base pairs downstream from the ATT. See Luckow and Summers, VIROLOGY 170:31 (1989). Other commercially available vectors include, for example, PBlue-Bac4.5/V5-His; pBlueBacHis2; pMelBac; pBlueBac4.5 (Invitrogen Corp., Carlsbad, Calif.).

After insertion of the heterologous gene, the transfer vector and wild type baculoviral genome are co-transfected into an insect cell host. Methods for introducing heterologous DNA into the desired site in the baculovirus virus are known in the art. See SUMMERS AND SMITH, TEXAS AGRICULTURAL EXPERIMENT STATION BULLETIN No. 1555 (1987); Smith et al., MOL. CELL. BIOL. (1983) 3:2156; Luckow and Summers, VIROLOGY (1989) 170:31. For example, the insertion can be into a gene such as the polyhedrin gene, by homologous double crossover recombination; insertion can also be into a restriction enzyme site engineered into the desired baculovirus gene. See Miller et al., BIOESSAYS (1989) 11(4):91.

Transfection may be accomplished by electroporation. See TROTTER AND WOOD, 39 METHODS IN MOLECULAR BIOLOGY (1995); Mann and King, J. GEN. VIROL. (1989) 70:3501. Alternatively, liposomes may be used to transfect the insect cells with the recombinant expression vector and the baculovirus. See, e.g., Liebman et al., BIOTECHNIQUES (1999) 26(1):36; Graves et al., BIOCHEMISTRY (1998) 37:6050; Nomura et al., J. BIOL. CHEM. (1998) 273(22):13570; Schmidt et al., PROTEIN EXPRESSION AND PURIFICATION (1998) 12:323; Siffert et al., NATURE GENETICS (1998) 18:45; TILKINS ET AL., CELL BIOLOGY: A LABORATORY HANDBOOK 145-154 (1998); Cai et al., PROTEIN EXPRESSION AND PURIFICATION (1997) 10:263; Dolphin et al., NATURE GENETICS (1997) 17:491; Kost et al., GENE (1997) 190:139; Jakobsson et al., J. BIOL. CHEM. (1996) 271:22203; Rowles et al., J. BIOL. CHEM. (1996) 271(37):22376; Reverey et al., J. BIOL. CHEM. (1996) 271(39):23607-10; Stanley et al., J. BIOL. CHEM. (1995) 270:4121; Sisk et al., J. VIROL. (1994) 68(2):766; and Peng et al., BIOTECHNIQUES (1993) 14(2):274. Commercially available liposomes include, for example, Cellfectin® and Lipofectin® (Invitrogen, Corp., Carlsbad, Calif.). In addition, calcium phosphate transfection may be used. See TROTTER AND WOOD, 39 METHODS IN MOLECULAR BIOLOGY (1995); Kitts, NAR (1990) 18(19):5667; and Mann and King, J. GEN. VIROL. (1989) 70:3501.

Baculovirus expression vectors usually contain a baculovirus promoter. A baculovirus promoter is any DNA sequence capable of binding a baculovirus RNA polymerase and initiating the downstream (3') transcription of a coding sequence (e.g., structural gene) into mRNA. A promoter will have a transcription initiation region which is usually placed proximal to the 5' end of the coding sequence. This transcription initiation region typically includes an RNA polymerase binding site and a transcription initiation site. A baculovirus promoter may also have a second domain called an enhancer, which, if present, is usually distal to the structural gene. Moreover, expression may be either regulated or constitutive.

Structural genes, abundantly transcribed at late times in the infection cycle, provide particularly useful promoter sequences. Examples include sequences derived from the gene encoding the viral polyhedron protein (FRIESEN ET AL., The Regulation of Baculovirus Gene Expression in THE MOLECULAR BIOLOGY OF BACULOVIRUSES (1986); EP 0 127 839 and 0 155 476) and the gene encoding the p10 protein (Vlak et al., J. GEN. VIROL. (1988) 69:765.

The newly formed baculovirus expression vector is packaged into an infectious recombinant baculovirus and subsequently grown plaques may be purified by techniques known to those of ordinary skill in the art. See Miller et al., BIOESSAYS (1989) 11(4):91; SUMMERS AND SMITH, TEXAS AGRICULTURAL EXPERIMENT STATION BULLETIN No. 1555 (1987).

Recombinant baculovirus expression vectors have been developed for infection into several insect cells. For example, recombinant baculoviruses have been developed for, inter alia, *Aedes aegypti* (ATCC No. CCL-125), *Bombyx mori* (ATCC No. CRL-8910), *Drosophila melanogaster* (ATCC No. 1963), *Spodoptera frugiperda*, and *Trichoplusia ni*. See Wright, NATURE (1986) 321:718; Carbonell et al., J. VIROL. (1985) 56:153; Smith et al., MOL. CELL. BIOL. (1983) 3:2156. See generally, Fraser et al., IN VITRO CELL. DEV. BIOL. (1989) 25:225. More specifically, the cell lines used for baculovirus expression vector systems commonly include, but are not limited to, Sf9 (*Spodoptera frugiperda*) (ATCC No. CRL-1711), Sf21 (*Spodoptera frugiperda*) (Invitrogen Corp., Cat. No. 11497-013 (Carlsbad, Calif.)), Tri-368 (*Trichopulsia ni*), and High-Five™ BTI-TN-5B1-4 (*Trichopulsia ni*).

Cells and culture media are commercially available for both direct and fusion expression of heterologous polypeptides in a baculovirus/expression, and cell culture technology is generally known to those of ordinary skill in the art.

*E. coli, Pseudomonas* Species, and Other Prokaryotes

Bacterial expression techniques are known to those of ordinary skill in the art. A wide variety of vectors are available for use in bacterial hosts. The vectors may be single copy or low or high multicopy vectors. Vectors may serve for cloning and/or expression. In view of the ample literature concerning vectors, commercial availability of many vectors, and even manuals describing vectors and their restriction maps and characteristics, no extensive discussion is required here. As is well-known, the vectors normally involve markers allowing for selection, which markers may provide for cytotoxic agent resistance, prototrophy or immunity. Frequently, a plurality of markers are present, which provide for different characteristics.

A bacterial promoter is any DNA sequence capable of binding bacterial RNA polymerase and initiating the downstream (3') transcription of a coding sequence (e.g. structural gene) into mRNA. A promoter will have a transcription initiation region which is usually placed proximal to the 5' end of the coding sequence. This transcription initiation region typically includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*) [Raibaud et al., ANNU. REV. GENET. (1984) 18:173]. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al., NATURE (1977) 198:1056], and maltose. Additional examples include promoter sequences derived from biosynthetic enzymes such as tryptophan (trp) [Goeddel et al., NUC. ACIDS RES. (1980) 8:4057, Yelverton et al., NUCL. ACIDS RES. (1981)

9:731; U.S. Pat. No. 4,738,921; EPO Pub. Nos. 036 776 and 121 775, which are incorporated by reference herein]. The g-lactamase (bla) promoter system [Weissmann (1981) "The cloning of interferon and other mistakes." In Interferon 3 (Ed. I. Gresser)], bacteriophage lambda PL [Shimatake et al., NATURE (1981) 292:128] and T5 [U.S. Pat. No. 4,689,406] promoter systems also provide useful promoter sequences. Preferred methods of the present invention utilize strong promoters, such as the T7 promoter to induce hGH at high levels. Examples of such vectors are known those of ordinary skill in the art and include the pET29 series from Novagen, and the pPOP vectors described in WO99/05297. Such expression systems produce high levels of hGH in the host without compromising host cell viability or growth parameters. pET19 (Novagen) is another vector known in the art.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551,433, which is incorporated by reference herein]. For example, the tac promoter is a hybrid trp-lac promoter comprised of both trp promoter and lac operon sequences that is regulated by the lac repressor [Amann et al., GENE (1983) 25:167; de Boer et al., PROC. NATL. ACAD. SCI. (1983) 80:21]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system [Studier et al., J. MOL. BIOL. (1986) 189:113; Tabor et al., Proc Natl. Acad. Sci. (1985) 82:1074]. In addition, a hybrid promoter can also be comprised of a bacteriophage promoter and an *E. coli* operator region (EPO Pub. No. 267 851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence 3-9 nucleotides in length located 3-11 nucleotides upstream of the initiation codon [Shine et al., NATURE (1975) 254:34]. The SD sequence is thought to promote binding of mRNA to the ribosome by the pairing of bases between the SD sequence and the 3' and of *E. coli* 16S rRNA [Steitz et al. "Genetic signals and nucleotide sequences in messenger RNA", In Biological Regulation and Development: Gene Expression (Ed. R. F. Goldberger, 1979)]. To express eukaryotic genes and prokaryotic genes with weak ribosome-binding site [Sambrook et al. "Expression of cloned genes in *Escherichia coli*", Molecular Cloning: A Laboratory Manual, 1989].

The term "bacterial host" or "bacterial host cell" refers to a bacterial that can be, or has been, used as a recipient for recombinant vectors or other transfer DNA. The term includes the progeny of the original bacterial host cell that has been transfected. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding an hGH, are included in the progeny intended by this definition.

The selection of suitable host bacteria for expression of hGH is known to those of ordinary skill in the art. In selecting bacterial hosts for expression, suitable hosts may include those shown to have, inter alia, good inclusion body formation capacity, low proteolytic activity, and overall robustness. Bacterial hosts are generally available from a variety of sources including, but not limited to, the Bacterial Genetic Stock Center, Department of Biophysics and Medical Physics, University of California (Berkeley, Calif.); and the American Type Culture Collection ("ATCC") (Manassas, Va.). Industrial/pharmaceutical fermentation generally use bacteria derived from K strains (e.g. W3110) or bacteria derived from B strains (e.g. BL21). These strains are particularly useful because their growth parameters are extremely well known and robust. In addition, these strains are non-pathogenic, which is commercially important for safety and environmental reasons. In one embodiment, the *E. coli* host is a strain of DH10B, including but not limited to DH10B(fis). Other examples of suitable *E. coli* hosts include, but are not limited to, strains of BL21, DH10B, or derivatives thereof. In another embodiment, the *E. coli* host is a strain of W3110. Recombinant host cell strains may be modified by genetic mutation to optimize for desired characteristics. For example, host cell strains may be genetically modified to modulate the expression of metabolically important genes, such as those involved in carbon source metabolism, amino acid metabolism, or protease production. Such genes may be mutated to decrease, increase, knock-out, or knock-in expression in the desired host strain. Strain W3110, for example, may be modified to effect a genetic mutation in one or more genes involved in the metabolism of arabinose including, but not limited to, the araB gene. Strains, for example, may be modified to effect a genetic mutation or knock out other genes. Methods to mutate or knock out genes are known to one of ordinary skill in the art. Strains may also be mutated to modulate endogenous protease activity to increase the production of full length hGH and/or to minimize the need for the addition of exogenous chemical inhibitors to proteases. Other host cell strains include but are not limited to, BL21. In another embodiment of the methods of the present invention, the *E. coli* host is a protease minus strain including, but not limited to, OMP- and LON-. The host cell strain may be a species of *Pseudomonas*, including but not limited to, *Pseudomonas fluorescens*, *Pseudomonas aeruginosa*, and *Pseudomonas putida*. *Pseudomonas fluorescens* biovar 1, designated strain MB101, is known to be useful for recombinant production and is available for therapeutic protein production processes. Examples of a *Pseudomonas* expression system include the system available from The Dow Chemical Company as a host strain (Midland, Mich. available on the World Wide Web at dow.com). U.S. Pat. Nos. 4,755,465 and 4,859,600, which are incorporated by reference herein, describe the use of *Pseudomonas* strains as a host cell for hGH production.

Once a recombinant host cell strain has been established (i.e., the expression construct has been introduced into the host cell and host cells with the proper expression construct are isolated), the recombinant host cell strain is cultured under conditions appropriate for production of hGH. As will be apparent to one of skill in the art, the method of culture of the recombinant host cell strain will be dependent on the nature of the expression construct utilized and the identity of the host cell. Recombinant host strains are normally cultured using methods that are known to those of ordinary skill in the art. Recombinant host cells are typically cultured in liquid medium containing assimilatable sources of carbon, nitrogen, and inorganic salts and, optionally, containing vitamins, amino acids, growth factors, and other proteinaceous culture supplements known to those of ordinary skill in the art. Media or feed composition and/or nutrient requirements for optimal growth may differ for different recombinant host cells and/or for smaller vs. larger scale preparations. Required trace metals or vitamins, for example, may be altered as growth conditions change and/or alternative host cells are used. To optimize production of hGH polypeptide, conditions suitable for induction may be altered depending on the recombinant host cell used, the expression construct, and/or modifications such as mutations made to the host cell, including, but not limited to, alterations in arabinose levels for induction. Arabinose levels in the fermentation may be between about 0.0001% to about 0.1%, including but not limited to, 0.1%, 0.09%, 0.08%, 0.07%, 0.06%, 0.05%, 0.04%, 0.03%, 0.02%, 0.01%, 0.0095%, 0.009%, 0.0085%, 0.008%, 0.0075%, 0.007%, 0.0065%, 0.006%, 0.0055%, 0.005%, 0.0045%, 0.004%, 0.0035%, 0.003%, 0.0025%, 0.002%, 0.0015%, 0.001%, 0.00095%, 0.0009%, 0.00085%, 0.0008%, 0.00075%, 0.0007%, 0.00065%, 0.0006%, 0.00055%, 0.0005%, 0.00045%, 0.0004%, 0.00035%, 0.0003%, 0.00025%, 0.0002%, 0.00015%, 0.0001%. In some embodiments, the arabinose levels are between 0.0005% and 0.05%. In some embodiments, the arabinose levels are between 0.001% to 0.02%. Alterations to provide a higher cell density for harvest may also be performed; steps including, but not limited to, the addition of a second feed may be performed. Liquid media for culture of host cells may optionally contain antibiotics or antifungals to prevent the growth of undesirable microorganisms and/or compounds including, but not limited to, antibiotics to select for host cells containing the expression vector. Recombinant host cells may be cultured in batch or continuous formats, with either cell harvesting (in the case where the variant hGH accumulates intracellularly) or harvesting of culture supernatant in either batch or continuous formats. For production in prokaryotic host cells, batch culture and cell harvest are preferred.

Modulated suppression, continuous suppression, or induced suppression may be performed. It is readily apparent to those of skill in the art that the non-naturally encoded amino acid may be added to the cell culture at a wide variety of different times during cell growth, or may be present continuously during cell growth. The addition of one or more non-naturally encoded amino acid for incorporation into hGH may occur before induction, at the time of induction, or after induction of hGH expression by the host cells. In one embodiment, the non-naturally encoded amino acid is added before induction of hGH expression. In one embodiment, the non-naturally encoded amino acid is added approximately one hour before induction. In another embodiment, the non-naturally encoded amino acids is present throughout cell growth.

Recombinant host cells expressing hGH, whether soluble, secreted, or insoluble, may be grown in a wide variety of culture volumes. The processes of the present invention are amenable to small laboratory scale culture volumes as well as large scale commercial scale volumes. It is readily apparent to one of ordinary skill in the art that the processes of the present invention disclosed herein are scalable to larger culture volumes. Large scale commercial culture volumes may be of a wide range from, for example, one or more liters each, to hundreds of liters, thousands of liters, 5000 liters, 10,000 liters, 20,000 liters, 30,000 liters, 40,000 liters, 50,000 liters, up to 100,000 liters or more. In producing large scale volumes, modification to some steps of the process may be necessary and are readily apparent to those of ordinary skill in art.

The hGH of the invention are normally purified after expression in recombinant systems. hGH may be purified from host cells or culture medium by a variety of methods known to the art. hGH produced in bacterial host cells may be poorly soluble or insoluble (in the form of inclusion bodies). In the case of insoluble protein, the protein may be collected from host cell lysates by centrifugation and may further be followed by homogenization of the cells. In the case of poorly soluble protein, compounds including, but not limited to, polyethylene imine (PEI) may be added to induce the precipitation of partially soluble protein. The precipitated protein may then be conveniently collected by centrifugation. Recombinant host cells may be disrupted or homogenized to release the inclusion bodies from within the cells using a variety of methods known to those of ordinary skill in the art. Host cell disruption or homogenization may be performed using well known techniques including, but not limited to, enzymatic cell disruption, sonication, dounce homogenization, or high pressure release disruption. In one embodiment of the method of the present invention, the high pressure release technique is used to disrupt the E. coli host cells to release the inclusion bodies of hGH.

Insoluble or precipitated hGH may then be solubilized using any of a number of suitable solubilization agents known to the art. hGH may be solubilized with urea or guanidine hydrochloride. The volume of the solubilized hGH should be minimized so that large batches may be produced using conveniently manageable batch sizes. This factor may be significant in a large-scale commercial setting where the recombinant host may be grown in batches that are thousands of liters in volume. In addition, when manufacturing hGH in a large-scale commercial setting, in particular for human pharmaceutical uses, the avoidance of harsh chemicals that can damage the machinery and container, or the protein product itself, should be avoided, if possible. It has been shown in the method of the present invention that the milder denaturing agent urea can be used to solubilize the hGH inclusion bodies in place of the harsher denaturing agent guanidine hydrochloride. The use of urea significantly reduces the risk of damage to stainless steel equipment utilized in the manufacturing and purification process of hGH while efficiently solubilizing the hGH inclusion bodies.

In the case of soluble hGH protein, the hGH may be secreted into the periplasmic space or into the culture medium. In addition, soluble hGH may be present in the cytoplasm of the host cells. It may be desired to concentrate soluble hGH prior to performing purification steps. Standard techniques known to those of ordinary skill in the art may be used to concentrate soluble hGH from, for example, cell lysates or culture medium. In addition, standard techniques known to those of ordinary skill in the art may be used to disrupt host cells and release soluble hGH from the cytoplasm or periplasmic space of the host cells.

When hGH is produced as a fusion protein, the fusion sequence may be removed. Removal of a fusion sequence may be accomplished by enzymatic or chemical cleavage. Enzymatic removal of fusion sequences may be accomplished using methods known to those of ordinary skill in the art. The choice of enzyme for removal of the fusion sequence will be determined by the identity of the fusion, and the reaction conditions will be specified by the choice of enzyme as will be apparent to one of ordinary skill in the art. Chemical cleavage may be accomplished using reagents known to those of ordinary skill in the art, including but not limited to, cyanogen bromide, TEV protease, and other reagents. The cleaved hGH may be purified from the cleaved fusion sequence by methods known to those of ordinary skill in the art. Such methods will be determined by the identity and properties of the fusion sequence and the hGH, as will be apparent to one of ordinary skill in the art. Methods for purification may include, but are not limited to, size-exclusion chromatography, hydrophobic interaction chromatography, ion-exchange chromatography or dialysis or any combination thereof.

hGH may also be purified to remove DNA from the protein solution. DNA may be removed by any suitable method known to the art, such as precipitation or ion exchange chromatography, but may be removed by precipitation with a nucleic acid precipitating agent, such as, but not limited to, protamine sulfate. hGH may be separated from the precipitated DNA using standard well known methods including, but not limited to, centrifugation or filtration. Removal of host nucleic acid molecules is an important factor in a setting where the hGH is to be used to treat humans and the methods of the present invention reduce host cell DNA to pharmaceutically acceptable levels.

Methods for small-scale or large-scale fermentation can also be used in protein expression, including but not limited to, fermentors, shake flasks, fluidized bed bioreactors, hollow fiber bioreactors, roller bottle culture systems, and stirred tank bioreactor systems. Each of these methods can be performed in a batch, fed-batch, or continuous mode process.

Human hGH polypeptides of the invention can generally be recovered using methods standard in the art. For example, culture medium or cell lysate can be centrifuged or filtered to remove cellular debris. The supernatant may be concentrated or diluted to a desired volume or diafiltered into a suitable buffer to condition the preparation for further purification. Purification of the hGH polypeptide may include separating deamidated and clipped forms of the hGH polypeptide variant from the intact form.

Any of the following exemplary procedures can be employed for purification of hGH polypeptides of the invention: affinity chromatography; anion- or cation-exchange chromatography (using, including but not limited to, DEAE SEPHAROSE); chromatography on silica; high performance liquid chromatography (HPLC); reverse phase HPLC; gel filtration (using, including but not limited to, SEPHADEX G-75); hydrophobic interaction chromatography; size-exclusion chromatography; metal-chelate chromatography; ultrafiltration/diafiltration; ethanol precipitation; ammonium sulfate precipitation; chromatofocusing; displacement chromatography; electrophoretic procedures (including but not limited to preparative isoelectric focusing), differential solubility (including but not limited to ammonium sulfate precipitation), SDS-PAGE, or extraction.

Proteins of the present invention, including but not limited to, proteins comprising unnatural amino acids, antibodies to proteins comprising unnatural amino acids, binding partners for proteins comprising unnatural amino acids, etc., can be purified, either partially or substantially to homogeneity, according to standard procedures known to and used by those of skill in the art. Accordingly, polypeptides of the invention can be recovered and purified by any of a number of methods known to those of ordinary skill in the art, including but not limited to, ammonium sulfate or ethanol precipitation, acid or base extraction, column chromatography, affinity column chromatography, anion or cation exchange chromatography, phosphocellulose chromatography, hydrophobic interaction chromatography, hydroxylapatite chromatography, lectin chromatography, gel electrophoresis and the like. Protein refolding steps can be used, as desired, in making correctly folded mature proteins. High performance liquid chromatography (HPLC), affinity chromatography or other suitable methods can be employed in final purification steps where high purity is desired. In one embodiment, antibodies made against unnatural amino acids (or proteins comprising unnatural amino acids) are used as purification reagents, including but not limited to, for affinity-based purification of proteins comprising one or more unnatural amino acid(s). Once purified, partially or to homogeneity, as desired, the polypeptides are optionally used for a wide variety of utilities, including but not limited to, as assay components, therapeutics, prophylaxis, diagnostics, research reagents, and/or as immunogens for antibody production.

In addition to other references noted herein, a variety of purification/protein folding methods are known to those of ordinary skill in the art, including, but not limited to, those set forth in R. Scopes, *Protein Purification*, Springer-Verlag, N.Y. (1982); Deutscher, *Methods in Enzymology Vol. 182: Guide to Protein Purification*, Academic Press, Inc. N.Y. (1990); Sandana, (1997) *Bioseparation of Proteins*, Academic Press, Inc.; Bollag et al. (1996) *Protein Methods*, 2nd Edition Wiley-Liss, NY; Walker, (1996) *The Protein Protocols Handbook Humana Press, NJ, Harris and Angal*, (1990) *Protein Purification Applications: A Practical Approach* IRL Press at Oxford, Oxford, England; Harris and Angal, *Protein Purification Methods: A Practical Approach* IRL Press at Oxford, Oxford, England; Scopes, (1993) *Protein Purification: Principles and Practice 3rd Edition* Springer Verlag, NY; Janson and Ryden, (1998) *Protein Purification Principles, High Resolution Methods and Applications, Second Edition* Wiley-VCH, NY; and Walker (1998), *Protein Protocols on CD-ROM* Humana Press, NJ; and the references cited therein.

One advantage of producing a protein or polypeptide of interest with an unnatural amino acid in a eukaryotic host cell or non-eukaryotic host cell is that typically the proteins or polypeptides will be folded in their native conformations. However, in certain embodiments of the invention, those of skill in the art will recognize that, after synthesis, expression and/or purification, proteins can possess a conformation different from the desired conformations of the relevant polypeptides. In one aspect of the invention, the expressed protein is optionally denatured and then renatured. This is accomplished utilizing methods known in the art, including but not limited to, by adding a chaperonin to the protein or polypeptide of interest, by solubilizing the proteins in a chaotropic agent such as guanidine HCl, utilizing protein disulfide isomerase, etc.

In general, it is occasionally desirable to denature and reduce expressed polypeptides and then to cause the polypeptides to re-fold into the preferred conformation. For example, guanidine, urea, DTT, DTE, and/or a chaperonin can be added to a translation product of interest. Methods of reducing, denaturing and renaturing proteins are known to those of ordinary skill in the art (see, the references above, and Debinski, et al. (1993) *J. Biol. Chem.*, 268: 14065-14070; Kreitman and Pastan (1993) *Bioconjug. Chem.*, 4: 581-585; and Buchner, et al., (1992) *Anal. Biochem.*, 205: 263-270). Debinski, et al., for example, describe the denaturation and reduction of inclusion body proteins in guanidine-DTE. The proteins can be refolded in a redox buffer containing, including but not limited to, oxidized glutathione and L-arginine. Refolding reagents can be flowed or otherwise moved into contact with the one or more polypeptide or other expression product, or vice-versa.

In the case of prokaryotic production of hGH, the hGH thus produced may be misfolded and thus lack or have reduced biological activity. The bioactivity of the protein may be restored by "refolding". In general, misfolded hGH is refolded by solubilizing (where the hGH is also insoluble), unfolding and reducing the polypeptide chain using, for example, one or more chaotropic agents (e.g. urea and/or guanidine) and a reducing agent capable of reducing disulfide bonds (e.g. dithiothreitol, DTT or 2-mercaptoethanol, 2-ME). At a moderate concentration of chaotrope, an oxidizing agent is then added (e.g., oxygen, cystine or cystamine), which allows the reformation of disulfide bonds. hGH may be refolded using standard methods known in the art, such as those described in U.S. Pat. Nos. 4,511,502, 4,511,503, and 4,512,922.

After refolding, the hGH may be further purified. Purification of hGH may be accomplished using a variety of techniques known to those of ordinary skill in the art, including hydrophobic interaction chromatography, size exclusion chromatography, ion exchange chromatography, reverse-phase high performance liquid chromatography, affinity chromatography, and the like or any combination thereof. Additional purification may also include a step of drying or precipitation of the purified protein.

After purification, hGH may be exchanged into different buffers and/or concentrated by any of a variety of methods known to the art, including, but not limited to, ultrafiltration, diafiltration and dialysis. hGH that is provided as a single purified protein may be subject to aggregation and precipitation. A wide variety of materials to buffer exchange or concentrate polypeptides are known to those of ordinary skill in the art.

The purified hGH may be at least 90% pure (as measured by reverse phase high performance liquid chromatography, RP-HPLC, or sodium dodecyl sulfate-polyacrylamide gel electrophoresis, SDS-PAGE) or at least 95% pure, or at least 98% pure, or at least 99% or greater pure. Regardless of the exact numerical value of the purity of the hGH, the hGH is sufficiently pure for use as a pharmaceutical product or for further processing, such as conjugation with a water soluble polymer such as PEG.

Certain hGH molecules may be used as therapeutic agents in the absence of other active ingredients or proteins (other than excipients, carriers, and stabilizers, serum albumin and the like), or they may be complexed with another protein or a polymer.

XIII. Purification Methods

Any one of a variety of isolation steps may be performed on the cell lysate, extract, culture medium, inclusion bodies, periplasmic space of the host cells, cytoplasm of the host cells, or other material, comprising hGH or on any hGH mixtures resulting from any isolation steps including, but not limited to, affinity chromatography, ion exchange chromatography, hydrophobic interaction chromatography, gel filtration chromatography, high performance liquid chromatography ("HPLC"), reversed phase-HPLC ("RP-HPLC"), expanded bed adsorption, or any combination and/or repetition thereof and in any appropriate order.

Equipment and other necessary materials used in performing the techniques described herein are commercially available. Pumps, fraction collectors, monitors, recorders, and entire systems are available from, for example, Applied Biosystems (Foster City, Calif.), Bio-Rad Laboratories, Inc. (Hercules, Calif.), and GE Healthcare, Inc. (Piscataway, N.J.). Chromatographic materials including, but not limited to, exchange matrix materials, media, and buffers are also available from such companies.

Equilibration, and other steps in the column chromatography processes described herein such as washing and elution, may be more rapidly accomplished using specialized equipment such as a pump. Commercially available pumps include, but are not limited to, HILOAD® Pump P-50, Peristaltic Pump P-1, Pump P-901, and Pump P-903 (GE Healthcare, Piscataway, N.J.).

Examples of fraction collectors include RediFrac Fraction Collector, FRAC-100 and FRAC-200 Fraction Collectors, and SUPERFRAC® Fraction Collector (GE Healthcare, Piscataway, N.J.). Mixers are also available to form pH and linear concentration gradients. Commercially available mixers include Gradient Mixer GM-1 and In-Line Mixers (GE Healthcare, Piscataway, N.J.).

The chromatographic process may be monitored using any commercially available monitor. Such monitors may be used to gather information like UV, pH, and conductivity. Examples of detectors include Monitor UV-1, UVICORD® S II, Monitor UV-M II, Monitor UV-900, Monitor UPC-900, Monitor pH/C-900, and Conductivity Monitor (GE Healthcare, Piscataway, N.J.). Indeed, entire systems are commercially available including the various AKTA® systems from GE Healthcare (Piscataway, N.J.).

As stated herein, the pH of the first hGH mixture may be adjusted prior to performing any subsequent isolation steps. In addition, the first hGH mixture or any subsequent mixture thereof may be concentrated using techniques known in the art. Moreover, the elution buffer comprising the first hGH mixture or any subsequent mixture thereof may be exchanged for a buffer suitable for the next isolation step using techniques known to those of ordinary skill in the art.

Ion Exchange Chromatography

In one embodiment, and as an optional, additional step, ion exchange chromatography may be performed on the first hGH mixture. See generally ION EXCHANGE CHROMATOGRAPHY: PRINCIPLES AND METHODS (Cat. No. 18-1114-21, GE Healthcare (Piscataway, N.J.)). Commercially available ion exchange columns include HITRAP®, HIPREP®, and HILOAD® Columns (GE Healthcare, Piscataway, N.J.). Such columns utilize strong anion exchangers such as Q SEPHAROSE® Fast Flow, Q SEPHAROSE® High Performance, and Q SEPHAROSE® XL; strong cation exchangers such as SP SEPHAROSE® High Performance, SP SEPHAROSE® Fast Flow, and SP SEPHAROSE® XL; weak anion exchangers such as DEAE SEPHAROSE® Fast Flow; and weak cation exchangers such as CM SEPHAROSE® Fast Flow (GE Healthcare, Piscataway, N.J.). Anion or cation exchange column chromatography may be performed on the hGH at any stage of the purification process to isolate substantially purified hGH. Source 30Q and Source 30S are ion exchange media (GE Healthcare).

The cation exchange chromatography step may be performed using any suitable cation exchange matrix. Useful cation exchange matrices include, but are not limited to, fibrous, porous, non-porous, microgranular, beaded, or cross-linked cation exchange matrix materials. Such cation exchange matrix materials include, but are not limited to, cellulose, agarose, dextran, polyacrylate, polyvinyl, polystyrene, silica, polyether, or composites of any of the foregoing.

The cation exchange matrix may be any suitable cation exchanger including strong and weak cation exchangers. Strong cation exchangers may remain ionized over a wide pH range and thus, may be capable of binding hGH over a wide pH range. Weak cation exchangers, however, may lose ionization as a function of pH. For example, a weak cation exchanger may lose charge when the pH drops below about pH 4 or pH 5. Suitable strong cation exchangers include, but are not limited to, charged functional groups such as sulfopropyl (SP), methyl sulfonate (S), or sulfoethyl (SE). The cation exchange matrix may be a strong cation exchanger, having an hGH binding pH range of about 2.5 to about 6.0.

Alternatively, the strong cation exchanger may have an hGH binding pH range of about pH 2.5 to about pH 5.5. The cation exchange matrix may be a strong cation exchanger having an hGH binding pH of about 3.0. Alternatively, the cation exchange matrix may be a strong cation exchanger, having an hGH binding pH range of about 6.0 to about 8.0. The cation exchange matrix may be a strong cation exchanger having an hGH binding pH range of about 8.0 to about 12.5. Alternatively, the strong cation exchanger may have an hGH binding pH range of about pH 8.0 to about pH 12.0.

Prior to loading the hGH, the cation exchange matrix may be equilibrated, for example, using several column volumes of a dilute, weak acid, e.g., four column volumes of 20 mM acetic acid, pH 3. Following equilibration, the hGH may be added and the column may be washed one to several times, prior to elution of substantially purified hGH, also using a weak acid solution such as a weak acetic acid or phosphoric acid solution. For example, approximately 2-4 column volumes of 20 mM acetic acid, pH 3, may be used to wash the column. Additional washes using, e.g., 2-4 column volumes of 0.05 M sodium acetate, pH 5.5, or 0.05 M sodium acetate mixed with 0.1 M sodium chloride, pH 5.5, may also be used. Alternatively, using methods known in the art, the cation exchange matrix may be equilibrated using several column volumes of a dilute, weak base.

Alternatively, substantially purified hGH may be eluted by contacting the cation exchanger matrix with a buffer having a sufficiently low pH or ionic strength to displace the hGH from the matrix. The pH of the elution buffer may range from about pH 2.5 to about pH 6.0. More specifically, the pH of the elution buffer may range from about pH 2.5 to about pH 5.5, about pH 2.5 to about pH 5.0. The elution buffer may have a pH of about 3.0. In addition, the quantity of elution buffer may vary widely and will generally be in the range of about 2 to about 10 column volumes. Moreover, suitable buffers known to those of skill in the art may find use herein including, but not limited to, citrate, phosphate, formate, HEPES, and MES buffers ranging in concentration from at least about 5 mM to at least about 100 mM.

Following adsorption of the hGH to the cation exchanger matrix, substantially purified hGH may be eluted by contacting the matrix with a buffer having a sufficiently high pH or ionic strength to displace the hGH from the matrix. The pH of the elution buffer may range from about pH 8.0 to about pH 12.5. More specifically, the elution buffer may range from about pH 8.0 to about pH 12.0. Suitable buffers for use in high pH elution of substantially purified hGH include, but are not limited to, citrate, phosphate, formate, acetate, HEPES, and MES buffers ranging in concentration from at least about 5 mM to at least about 100 mM. In addition, a buffer having 0.1 M potassium borate, 0.6 M potassium chloride, 0.1 mM EDTA, pH 8.7 may be used. Substantially purified hGH may also be eluted using standard buffers, such as a bicine buffer which includes about 50 to 100 mM bicine, about 75 mM bicine; 25 to about 100 mM sodium chloride, specifically, about 50 mM sodium chloride, and about 0.05 to about 0.5 EDTA, more specifically, about 0.1 mM EDTA, pH 7.5.

Reverse-Phase Chromatography

RP-HPLC may be performed to purify proteins following suitable protocols that are known to those of ordinary skill in the art. See, e.g., Pearson et al., ANAL BIOCHEM. (1982) 124: 217-230 (1982); Rivier et al., J. CHROM. (1983) 268:112-119; Kunitani et al., J. CHROM. (1986) 359:391-402. RP-HPLC may be performed on the hGH to isolate substantially purified hGH. In this regard, silica derivatized resins with alkyl functionalities with a wide variety of lengths, including, but not limited to, at least about $C_3$ to at least about $C_{30}$, at least about $C_3$ to at least about $C_{20}$, or at least about $C_3$ to at least about $C_{18}$, resins may be used. Alternatively, a polymeric resin may be used. For example, TosoHaas Amberchrome CG1000sd resin may be used, which is a styrene polymer resin. Cyano or polymeric resins with a wide variety of alkyl chain lengths may also be used. Furthermore, the RP-HPLC column may be washed with a solvent such as ethanol. The Source RP column is another example of a RP-HPLC column.

A suitable elution buffer containing an ion pairing agent and an organic modifier such as methanol, isopropanol, tetrahydrofuran, acetonitrile or ethanol, may be used to elute the hGH from the RP-HPLC column. The most commonly used ion pairing agents include, but are not limited to, acetic acid, formic acid, perchloric acid, phosphoric acid, trifluoroacetic acid, heptafluorobutyric acid, triethylamine, tetramethylammonium, tetrabutylammonium, triethylammonium acetate. Elution may be performed using one or more gradients or isocratic conditions, with gradient conditions preferred to reduce the separation time and to decrease peak width. Generally, the gradient may be from about 5% to about 80% (v/v), about 5% to about 75% (v/v), about 5% to about 70% (v/v), about 5% to about 65% (v/v), about 5% to about 60% (v/v), about 5% to about 55% (v/v), or about 10% to about 50% (v/v) solvent in water. Another method involves the use of two gradients with different solvent concentration ranges. Examples of suitable elution buffers for use herein may include, but are not limited to, ammonium acetate and acetonitrile solutions.

The hGH derived from a recombinant *E. coli* host may be further isolated or purified by reverse-phase chromatography. The hGH may be isolated, for example, using a SOURCE RP column, with an acetonitrile gradient from about 10% to about 60% acetonitrile.

Hydrophobic Interaction Chromatography Purification Techniques

Hydrophobic interaction chromatography (HIC) may be performed on the hGH. See generally HYDROPHOBIC INTERACTION CHROMATOGRAPHY HANDBOOK: PRINCIPLES AND METHODS (Cat. No. 18-1020-90, GE Healthcare (Piscataway, N.J.) which is incorporated by reference herein. Suitable HIC matrices may include, but are not limited to, alkyl- or aryl-substituted matrices, such as butyl-, hexyl-, octyl- or phenyl-substituted matrices including agarose, cross-linked agarose, sepharose, cellulose, silica, dextran, polystyrene, poly(methacrylate) matrices, and mixed mode resins, including but not limited to, a polyethyleneamine resin or a butyl- or phenyl-substituted poly(methacrylate) matrix. Commercially available sources for hydrophobic interaction column chromatography include, but are not limited to, HITRAP®, HIPREP®, and HILOAD® columns (GE Healthcare, Piscataway, N.J.), and TSKgel Phenyl-650S and Phenyl-5PW (30 um) resins (Tosoh Bioscience).

Briefly, prior to loading, the HIC column may be equilibrated using standard buffers known to those of ordinary skill in the art, such as an acetic acid/sodium chloride solution or HEPES containing ammonium sulfate, or ammonium sulfate in a pH 6.5 sodium phosphate solution, or sodium sulfate in a pH 7-8 TRIS solution. Ammonium sulfate may be used as the buffer for loading the HIC column. After loading the hGH, the column may then washed using standard buffers and under conditions such as those described herein to remove unwanted materials but retaining the hGH on the HIC column. hGH may be eluted with about 3 to about 10 column volumes of a standard buffer, such as a HEPES buffer containing EDTA and lower ammonium sulfate concentration than the equilibrating buffer, or an acetic acid/sodium chloride buffer, among others. A decreasing linear salt gradient using, for example, a gradient of potassium phosphate, may also be used to elute the hGH molecules. Elution enhancers may also be added to the elution buffer, including but not limited to, ethylene glycol, glycerol, or urea (0.5-1.5M). The eluant may then be concentrated, for example, by filtration such as diafiltration or ultrafiltration. Diafiltration may be utilized to remove the salt used to elute hGH.

Other Purification Techniques

Yet another isolation step using, for example, gel filtration (GEL FILTRATION: PRINCIPLES AND METHODS (Cat. No. 18-1022-18, GE Healthcare, Piscataway, N.J.) which is incorporated by reference herein, hydroxyapatite chromatography (suitable matrices include, but are not limited to, HA-Ultrogel, High Resolution (Calbiochem), CHT Ceramic Hydroxyapatite (BioRad), Bio-Gel HTP Hydroxyapatite (BioRad)), HPLC, expanded bed adsorption, ultrafiltration, diafiltration, lyophilization, and the like, may be performed on the first hGH mixture or any subsequent mixture thereof, to remove any excess salts and to replace the buffer with a suitable buffer for the next isolation step or even formulation of the final drug product.

The non-naturally encoded amino acid present in the hGH molecule may also be utilized to provide separation from other cellular proteins that do not contain the non-naturally encoded amino acid. Since the non-naturally encoded amino acid may comprise unique chemical functional groups, the coupling of the unique functional group to another molecule may provide a substantial purification step. For example, the non-naturally encoded amino acid may be coupled to another molecule that facilitates separation from other proteins. Such molecules for coupling to the non-natural amino acid include, but are not limited to, PEG and other polymers.

The yield of hGH, including substantially purified hGH, may be monitored at each step described herein using techniques known to those of ordinary skill in the art. Such techniques may also be used to assess the yield of substantially purified hGH following the last isolation step. For example, the yield of hGH may be monitored using any of several reverse phase high pressure liquid chromatography columns, having a variety of alkyl chain lengths such as cyano RP-HPLC, $C_{18}$RP-HPLC; as well as cation exchange HPLC and gel filtration HPLC.

In specific embodiments of the present invention, the yield of hGH after each purification step may be at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99.9%, or at least about 99.99%, of the hGH in the starting material for each purification step.

Purity may be determined using standard techniques, such as SDS-PAGE, or by measuring hGH using Western blot and ELISA assays. For example, polyclonal antibodies may be generated against proteins isolated from a negative control yeast fermentation and the cation exchange recovery. The antibodies may also be used to probe for the presence of contaminating host cell proteins.

RP-HPLC material Vydac C4 (Vydac) consists of silica gel particles, the surfaces of which carry C4-alkyl chains. The separation of polypeptides from the proteinaceous impurities is based on differences in the strength of hydrophobic interactions. Elution is performed with an acetonitrile gradient in diluted trifluoroacetic acid. Preparative HPLC is performed using a stainless steel column (filled with 2.8 to 3.2 liter of Vydac C4 silicagel). The Hydroxyapatite Ultrogel eluate is acidified by adding trifluoroacetic acid and loaded onto the Vydac C4 column. For washing and elution an acetonitrile gradient in diluted trifluoroacetic acid is used. Fractions are collected and immediately neutralized with phosphate buffer. The polypeptide fractions which are within the IPC limits are pooled.

DEAE Sepharose (GE Healthcare) material consists of diethylaminoethyl (DEAE)-groups which are covalently bound to the surface of Sepharose beads. The binding of a polypeptide of choice to the DEAE groups is mediated by ionic interactions. Acetonitrile and trifluoroacetic acid pass through the column without being retained. After these substances have been washed off, trace impurities are removed by washing the column with acetate buffer at a low pH. Then the column is washed with neutral phosphate buffer and polypeptide is eluted with a buffer with increased ionic strength. The column is packed with DEAE Sepharose fast flow. The column volume is adjusted to assure a polypeptide load in the range of 3-10 mg polypeptide/ml gel. The column is washed with water and equilibration buffer (sodium/potassium phosphate). The pooled fractions of the HPLC eluate are loaded and the column is washed with equilibration buffer. Then the column is washed with washing buffer (sodium acetate buffer) followed by washing with equilibration buffer. Subsequently, polypeptide is eluted from the column with elution buffer (sodium chloride, sodium/potassium phosphate) and collected in a single fraction in accordance with the master elution profile. The eluate of the DEAE Sepharose column is adjusted to the specified conductivity. The resulting drug substance is sterile filtered into Teflon bottles and stored at $-70°$ C.

Methods and procedures that can be used to assess the yield and purity of hGH include, but are not limited to, the Bradford assay, SDS-PAGE, silver stained SDS-PAGE, coomassie stained SDS-PAGE, mass spectrometry (including but not limited to, MALDI-TOF) and other methods for characterizing proteins known to one of ordinary skill in the art. Additional methods include, but are not limited to: SDS-PAGE coupled with protein staining methods, immunoblotting, matrix assisted laser desorption/ionization-mass spectrometry (MALDI-MS), liquid chromatography/mass spectrometry, isoelectric focusing, analytical anion exchange, chromatofocusing, and circular dichroism.

Additional methods that may be employed include the steps to remove of endotoxins. Endotoxins are lipopoly-saccharides (LPSs) which are located on the outer membrane of Gram-negative host cells, such as, for example, *Escherichia coli*. Methods for reducing endotoxin levels are known to one of ordinary skill in the art and include, but are not limited to, purification techniques using silica supports, glass powder or hydroxyapatite, reverse-phase, affinity, size-exclusion, anion-exchange chromatography, hydrophobic interaction chromatography, filtration, a combination of these methods, and the like. Modifications or additional methods may be required to remove contaminants such as co-migrating proteins from the polypeptide of interest. Methods for measuring endotoxin levels are known to one of ordinary skill in the art and include, but are not limited to, *Limulus Amebocyte* Lysate (LAL) assays.

Although the invention has been described with reference to particular embodiments, methods, construction, and use, it will be apparent to those of ordinary skill in the art that various changes and modifications can be made without departing from the invention. Alterations to the reagents, materials, and purification conditions indicated are apparent to those of ordinary skill in the art. For example, a higher capacity resin may be substituted in a chromatography step if such capacity is desired.

XV. Expression in Alternate Systems

Several strategies have been employed to introduce unnatural amino acids into proteins in non-recombinant host cells, mutagenized host cells, or in cell-free systems. These systems are also suitable for use in making the hGH polypeptides of the present invention. Derivatization of amino acids with reactive side-chains such as Lys, Cys and Tyr resulted in the conversion of lysine to $N^2$-acetyl-lysine. Chemical synthesis also provides a straightforward method to incorporate unnatural amino acids. With the recent development of enzymatic ligation and native chemical ligation of peptide fragments, it is possible to make larger proteins. See, e.g., P. E. Dawson and S. B. H. Kent, *Annu. Rev. Biochem,* 69:923 (2000). Chemical peptide ligation and native chemical ligation are described in U.S. Pat. No. 6,184,344, U.S. Patent Publication No. 2004/0138412, U.S. Patent Publication No. 2003/0208046, WO 02/098902, and WO 03/042235, which are incorporated by reference herein. A general in vitro biosynthetic method in which a suppressor tRNA chemically acylated with the desired unnatural amino acid is added to an in vitro extract capable of supporting protein biosynthesis, has been used to site-specifically incorporate over 100 unnatural amino acids into a variety of proteins of virtually any size. See, e.g., V. W. Cornish, D. Mendel and P. G. Schultz, *Angew. Chem. Int. Ed. Engl.,* 1995, 34:621 (1995); C. J. Noren, S. J. Anthony-Cahill, M. C. Griffith, P. G. Schultz, *A general method for site-specific incorporation of unnatural amino acids into proteins, Science* 244:182-188 (1989); and, J. D. Bain, C. G. Glabe, T. A. Dix, A. R. Chamberlin, E. S. Diala, *Biosynthetic site-specific incorporation of a non-natural amino acid into a polypeptide, J. Am. Chem. Soc.* 111:8013-8014 (1989). A broad range of functional groups has been introduced into proteins for studies of protein stability, protein folding, enzyme mechanism, and signal transduction.

An in vivo method, termed selective pressure incorporation, was developed to exploit the promiscuity of wild-type synthetases. See, e.g., N. Budisa, C. Minks, S. Alefelder, W. Wenger, F. M. Dong, L. Moroder and R. Huber, *FASEB J.,* 13:41 (1999). An auxotrophic strain, in which the relevant metabolic pathway supplying the cell with a particular natural amino acid is switched off, is grown in minimal media containing limited concentrations of the natural amino acid, while transcription of the target gene is repressed. At the onset of a stationary growth phase, the natural amino acid is depleted and replaced with the unnatural amino acid analog. Induction of expression of the recombinant protein results in the accumulation of a protein containing the unnatural analog. For example, using this strategy, o, m and p-fluorophenylalanines have been incorporated into proteins, and exhibit two characteristic shoulders in the UV spectrum which can be easily identified, see, e.g., C. Minks, R. Huber, L. Moroder and N. Budisa, *Anal. Biochem.,* 284:29 (2000); trifluoromethionine has been used to replace methionine in bacteriophage T4 lysozyme to study its interaction with chitooligosaccharide ligands by $^{19}$F NMR, see, e.g., H. Duewel, E. Daub, V. Robinson and J. F. Honek, *Biochemistry,* 36:3404 (1997); and trifluoroleucine has been incorporated in place of leucine, resulting in increased thermal and chemical stability of a leucine-zipper protein. See, e.g., Y. Tang, G. Ghirlanda, W. A. Petka, T. Nakajima, W. F. DeGrado and D. A. Tirrell, *Angew. Chem. Int. Ed. Engl.,* 40:1494 (2001). Moreover, selenomethionine and telluromethionine are incorporated into various recombinant proteins to facilitate the solution of phases in X-ray crystallography. See, e.g., W. A. Hendrickson, J. R. Horton and D. M. Lemaster, *EMBO J.,* 9:1665 (1990); J. O. Boles, K. Lewinski, M. Kunkle, J. D. Odom, B. Dunlap, L. Lebioda and M. Hatada, *Nat. Struct. Biol.,* 1:283 (1994); N. Budisa, B. Steipe, P. Demange, C. Eckerskorn, J. Kellermann and R. Huber, *Eur. J. Biochem.,* 230:788 (1995); and, N. Budisa, W. Kambrock, S. Steinbacher, A. Humm, L. Prade, T. Neuefeind, L. Moroder and R. Huber, *J. Mol. Biol.,* 270:616 (1997). Methionine analogs with alkene or alkyne functionalities have also been incorporated efficiently, allowing for additional modification of proteins by chemical means. See, e.g., J. C. van Hest and D. A. Tirrell, *FEBS Lett.,* 428:68 (1998); J. C. van Hest, K. L. Kiick and D. A. Tirrell, *J. Am. Chem. Soc.,* 122:1282 (2000); and, K. L. Kiick and D. A. Tirrell, *Tetrahedron,* 56:9487 (2000); U.S. Pat. No. 6,586, 207; U.S. Patent Publication 2002/0042097, which are incorporated by reference herein.

The success of this method depends on the recognition of the unnatural amino acid analogs by aminoacyl-tRNA synthetases, which, in general, require high selectivity to insure the fidelity of protein translation. One way to expand the scope of this method is to relax the substrate specificity of aminoacyl-tRNA synthetases, which has been achieved in a limited number of cases. For example, replacement of Ala$^{294}$ by Gly in *Escherichia coli* phenylalanyl-tRNA synthetase (PheRS) increases the size of substrate binding pocket, and results in the acylation of tRNAPhe by p-Cl-phenylalanine (p-Cl-Phe). See, M. Ibba, P. Kast and H. Hennecke, *Biochemistry,* 33:7107 (1994). An *Escherichia coli* strain harboring this mutant PheRS allows the incorporation of p-Cl-phenylalanine or p-Br-phenylalanine in place of phenylalanine. See, e.g., M. Ibba and H. Hennecke, *FEBS Lett.,* 364:272 (1995); and, N. Sharma, R. Furter, P. Kast and D. A. Tirrell, *FEBS Lett.,* 467:37 (2000). Similarly, a point mutation Phe130Ser near the amino acid binding site of *Escherichia coli* tyrosyl-tRNA synthetase was shown to allow azatyrosine to be incorporated more efficiently than tyrosine. See, F. Hamano-Takaku, T. Iwama, S. Saito-Yano, K. Takaku, Y. Monden, M. Kitabatake, D. Soll and S, Nishimura, *J. Biol. Chem.,* 275: 40324 (2000).

Another strategy to incorporate unnatural amino acids into proteins in vivo is to modify synthetases that have proofreading mechanisms. These synthetases cannot discriminate and therefore activate amino acids that are structurally similar to the cognate natural amino acids. This error is corrected at a separate site, which deacylates the mischarged amino acid from the tRNA to maintain the fidelity of protein translation. If the proofreading activity of the synthetase is disabled, structural analogs that are misactivated may escape the editing function and be incorporated. This approach has been demonstrated recently with the valyl-tRNA synthetase (ValRS). See, V. Doring, H. D. Mootz, L. A. Nangle, T. L. Hendrickson, V. de Crecy-Lagard, P. Schimmel and P. Marliere, *Science,* 292:501 (2001). ValRS can misaminoacylate tRNAVal with Cys, Thr, or aminobutyrate (Abu); these noncognate amino acids are subsequently hydrolyzed by the editing domain. After random mutagenesis of the *Escherichia coli* chromosome, a mutant *Escherichia coli* strain was selected that has a mutation in the editing site of ValRS. This edit-defective ValRS incorrectly charges tRNAVal with Cys. Because Abu sterically resembles Cys (—SH group of Cys is replaced with —CH$_3$ in Abu), the mutant ValRS also incorporates Abu into proteins when this mutant *Escherichia coli* strain is grown in the presence of Abu. Mass spectrometric analysis shows that about 24% of valines are replaced by Abu at each valine position in the native protein.

Solid-phase synthesis and semisynthetic methods have also allowed for the synthesis of a number of proteins containing novel amino acids. For example, see the following publications and references cited within, which are as follows: Crick, F. H. C., Barrett, L. Brenner, S. Watts-Tobin, R. *General nature of the genetic code for proteins. Nature,* 192: 1227-1232 (1961); Hofmann, K., Bohn, H. *Studies on polypeptides. XXXVI. The effect of pyrazole-imidazole replacements on the S-protein activating potency of an S-peptide fragment, J. Am. Chem,* 88(24):5914-5919 (1966); Kaiser, E. T. *Synthetic approaches to biologically active peptides and proteins including enyzmes, Acc Chem Res,* 22:47-54 (1989); Nakatsuka, T., Sasaki, T., Kaiser, E. T. *Peptide segment coupling catalyzed by the semisynthetic enzyme thiosubtilisin, J Am Chem Soc,* 109:3808-3810 (1987); Schnolzer, M., Kent, S B H. *Constructing proteins by dovetailing unprotected synthetic peptides: backbone-engineered HIV protease, Science,* 256(5054):221-225 (1992); Chaiken, I. M. *Semisynthetic peptides and proteins, CRC Crit. Rev Biochem,* 11(3):255-301 (1981); Offord, R. E. *Protein engineering by chemical means? Protein Eng.,* 1(3):151-157 (1987); and, Jackson, D. Y., Burnier, J., Quan, C., Stanley, M., Tom, J., Wells, J. A. *A Designed Peptide Ligase for Total Synthesis of Ribonuclease A with Unnatural Catalytic Residues, Science,* 266(5183):243 (1994).

Chemical modification has been used to introduce a variety of unnatural side chains, including cofactors, spin labels and oligonucleotides into proteins in vitro. See, e.g., Corey, D. R., Schultz, P. G. *Generation of a hybrid sequence-specific single-stranded deoxyribonuclease, Science,* 238(4832): 1401-1403 (1987); Kaiser, E. T., Lawrence D. S., Rokita, S. E. *The chemical modification of enzymatic specificity, Annu Rev Biochem,* 54:565-595 (1985); Kaiser, E. T., Lawrence, D. S. *Chemical mutation of enyzme active sites, Science,* 226 (4674):505-511 (1984); Neet, K. E., Nanci A, Koshland, D. E. Properties of thiol-subtilisin, J. Biol. Chem., 243(24):6392-6401 (1968); Polgar, L. et M. L. Bender. *A new enzyme containing a synthetically formed active site. Thiol-subtilisin. J. Am. Chem Soc,* 88:3153-3154 (1966); and, Pollack, S. J., Nakayama, G. Schultz, P. G. *Introduction of nucleophiles and spectroscopic probes into antibody combining sites, Science,* 242(4881):1038-1040 (1988).

Alternatively, biosynthetic methods that employ chemically modified aminoacyl-tRNAs have been used to incorporate several biophysical probes into proteins synthesized in vitro. See the following publications and references cited within: Brunner, J. *New Photolabeling and crosslinking methods, Annu. Rev Biochem,* 62:483-514 (1993); and, Krieg, U. C., Walter, P., Hohnson, A. E. *Photocrosslinking of the signal sequence of nascent preprolactin of the 54-kilodalton polypeptide of the signal recognition particle, Proc. Natl. Acad. Sci,* 83(22):8604-8608 (1986).

Previously, it has been shown that unnatural amino acids can be site-specifically incorporated into proteins in vitro by the addition of chemically aminoacylated suppressor tRNAs to protein synthesis reactions programmed with a gene containing a desired amber nonsense mutation. Using these approaches, one can substitute a number of the common twenty amino acids with close structural homologues, e.g., fluorophenylalanine for phenylalanine, using strains auxotropic for a particular amino acid. See, e.g., Noren, C. J., Anthony-Cahill, Griffith, M. C., Schultz, P. G. *A general method for site-specific incorporation of unnatural amino acids into proteins, Science,* 244: 182-188 (1989); M. W. Nowak, et al., *Science* 268:439-42 (1995); Bain, J. D., Glabe, C. G., Dix, T. A., Chamberlin, A. R., Diala, E. S. *Biosynthetic site-specific Incorporation of a non-natural amino acid into a polypeptide, J. Am. Chem Soc,* 111:8013-8014 (1989); N. Budisa et al., *FASEB J.* 13:41-51 (1999); Ellman, J. A., Mendel, D., Anthony-Cahill, S., Noren, C. J., Schultz, P. G. *Biosynthetic method for introducing unnatural amino acids site-specifically into proteins, Methods in Enz., vol.* 202, 301-336 (1992); and, Mendel, D., Cornish, V. W. & Schultz, P. G. *Site-Directed Mutagenesis with an Expanded Genetic Code, Annu Rev Biophys. Biomol Struct.* 24, 435-62 (1995).

For example, a suppressor tRNA was prepared that recognized the stop codon UAG and was chemically aminoacylated with an unnatural amino acid. Conventional site-directed mutagenesis was used to introduce the stop codon TAG, at the site of interest in the protein gene. See, e.g., Sayers, J. R., Schmidt, W. Eckstein, F. *5'-3' Exonucleases in phosphorothioate-based olignoucleotide-directed mutagensis, Nucleic Acids Res,* 16(3):791-802 (1988). When the acylated suppressor tRNA and the mutant gene were combined in an in vitro transcription/translation system, the unnatural amino acid was incorporated in response to the UAG codon which gave a protein containing that amino acid at the specified position. Experiments using [$^3$H]-Phe and experiments with α-hydroxy acids demonstrated that only the desired amino acid is incorporated at the position specified by the UAG codon and that this amino acid is not incorporated at any other site in the protein. See, e.g., Noren, et al, supra; Kobayashi et al., (2003) Nature Structural Biology 10(6):425-432; and, Ellman, J. A., Mendel, D., Schultz, P. G. *Site-specific incorporation of novel backbone structures into proteins, Science,* 255(5041):197-200 (1992).

A tRNA may be aminoacylated with a desired amino acid by any method or technique, including but not limited to, chemical or enzymatic aminoacylation.

Aminoacylation may be accomplished by aminoacyl tRNA synthetases or by other enzymatic molecules, including but not limited to, ribozymes. The term "ribozyme" is interchangeable with "catalytic RNA." Cech and coworkers (Cech, 1987, Science, 236:15327 1539; McCorkle et al., 1987, *Concepts Biochem.* 64:221-226) demonstrated the presence of naturally occurring RNAs that can act as catalysts (ribozymes). However, although these natural RNA catalysts have only been shown to act on ribonucleic acid substrates for cleavage and splicing, the recent development of artificial evolution of ribozymes has expanded the repertoire of catalysis to various chemical reactions. Studies have identified RNA molecules that can catalyze aminoacyl-RNA bonds on their own (2')$_3$'-termini (Illangakekare et al., 1995 Science 267:643-647), and an RNA molecule which can transfer an amino acid from one RNA molecule to another (Lohse et al., 1996, Nature 381:442-444).

U.S. Patent Application Publication 2003/0228593, which is incorporated by reference herein, describes methods to construct ribozymes and their use in aminoacylation of tRNAs with naturally encoded and non-naturally encoded amino acids. Substrate-immobilized forms of enzymatic molecules that can aminoacylate tRNAs, including but not limited to, ribozymes, may enable efficient affinity purification of the aminoacylated products. Examples of suitable substrates include agarose, sepharose, and magnetic beads. The production and use of a substrate-immobilized form of ribozyme for aminoacylation is described in Chemistry and Biology 2003, 10:1077-1084 and U.S. Patent Application Publication 2003/0228593, which are incorporated by reference herein.

Chemical aminoacylation methods include, but are not limited to, those introduced by Hecht and coworkers (Hecht, S. M. Acc. Chem. Res. 1992, 25, 545; Heckler, T. G.; Roesser, J. R.; Xu, C.; Chang, P.; Hecht, S. M. Biochemistry 1988, 27, 7254; Hecht, S. M.; Alford, B. L.; Kuroda, Y.; Kitano, S. J. Biol. Chem. 1978, 253, 4517) and by Schultz, Chamberlin, Dougherty and others (Cornish, V. W.; Mendel, D.; Schultz, P. G. Angew. Chem. Int. Ed. Engl. 1995, 34, 621; Robertson, S. A.; Ellman, J. A.; Schultz, P. G. J. Am. Chem. Soc. 1991, 113, 2722; Noren, C. J.; Anthony-Cahill, S. J.; Griffith, M. C.; Schultz, P. G. Science 1989, 244, 182; Bain, J. D.; Glabe, C. G.; Dix, T. A.; Chamberlin, A. R. J. Am. Chem. Soc. 1989, 111, 8013; Bain, J. D. et al. Nature 1992, 356, 537; Gallivan, J. P.; Lester, H. A.; Dougherty, D. A. Chem. Biol. 1997, 4, 740; Turcatti, et al. J. Biol. Chem. 1996, 271, 19991; Nowak, M. W. et al. Science, 1995, 268, 439; Saks, M. E. et al. J. Biol. Chem. 1996, 271, 23169; Hohsaka, T. et al. J. Am. Chem. Soc. 1999, 121, 34), which are incorporated by reference herein, to avoid the use of synthetases in aminoacylation. Such methods or other chemical aminoacylation methods may be used to aminoacylate tRNA molecules.

Methods for generating catalytic RNA may involve generating separate pools of randomized ribozyme sequences, performing directed evolution on the pools, screening the pools for desirable aminoacylation activity, and selecting sequences of those ribozymes exhibiting desired aminoacylation activity.

Ribozymes can comprise motifs and/or regions that facilitate acylation activity, such as a GGU motif and a U-rich region. For example, it has been reported that U-rich regions can facilitate recognition of an amino acid substrate, and a GGU-motif can form base pairs with the 3' termini of a tRNA. In combination, the GGU and motif and U-rich region facilitate simultaneous recognition of both the amino acid and tRNA simultaneously, and thereby facilitate aminoacylation of the 3' terminus of the tRNA.

Ribozymes can be generated by in vitro selection using a partially randomized r24mini conjugated with tRNA$^{Asn}_{C-CCG}$, followed by systematic engineering of a consensus sequence found in the active clones. An exemplary ribozyme obtained by this method is termed "Fx3 ribozyme" and is described in U.S. Pub. App. No. 2003/0228593, the contents of which is incorporated by reference herein, acts as a versatile catalyst for the synthesis of various aminoacyl-tRNAs charged with cognate non-natural amino acids.

Immobilization on a substrate may be used to enable efficient affinity purification of the aminoacylated tRNAs. Examples of suitable substrates include, but are not limited to, agarose, sepharose, and magnetic beads. Ribozymes can be immobilized on resins by taking advantage of the chemical structure of RNA, such as the 3'-cis-diol on the ribose of RNA can be oxidized with periodate to yield the corresponding dialdehyde to facilitate immobilization of the RNA on the resin. Various types of resins can be used including inexpensive hydrazide resins wherein reductive amination makes the interaction between the resin and the ribozyme an irreversible linkage. Synthesis of aminoacyl-tRNAs can be significantly facilitated by this on-column aminoacylation technique. Kourouklis et al. Methods 2005; 36:239-4 describe a column-based aminoacylation system.

Isolation of the aminoacylated tRNAs can be accomplished in a variety of ways. One suitable method is to elute the aminoacylated tRNAs from a column with a buffer such as a sodium acetate solution with 10 mM EDTA, a buffer containing 50 mM N-(2-hydroxyethyl)piperazine-N'-(3-propanesulfonic acid), 12.5 mM KCl, pH 7.0, 10 mM EDTA, or simply an EDTA buffered water (pH 7.0).

The aminoacylated tRNAs can be added to translation reactions in order to incorporate the amino acid with which the tRNA was aminoacylated in a position of choice in a polypeptide made by the translation reaction. Examples of translation systems in which the aminoacylated tRNAs of the present invention may be used include, but are not limited to cell lysates. Cell lysates provide reaction components necessary for in vitro translation of a polypeptide from an input mRNA. Examples of such reaction components include but are not limited to ribosomal proteins, rRNA, amino acids, tRNAs, GTP, ATP, translation initiation and elongation factors and additional factors associated with translation. Additionally, translation systems may be batch translations or compartmentalized translation. Batch translation systems combine reaction components in a single compartment while compartmentalized translation systems separate the translation reaction components from reaction products that can inhibit the translation efficiency. Such translation systems are available commercially.

Further, a coupled transcription/translation system may be used. Coupled transcription/translation systems allow for both transcription of an input DNA into a corresponding mRNA, which is in turn translated by the reaction components. An example of a commercially available coupled transcription/translation is the Rapid Translation System (RTS, Roche Inc.). The system includes a mixture containing E. coli lysate for providing translational components such as ribosomes and translation factors. Additionally, an RNA polymerase is included for the transcription of the input DNA into an mRNA template for use in translation. RTS can use compartmentalization of the reaction components by way of a membrane interposed between reaction compartments, including a supply/waste compartment and a transcription/translation compartment.

Aminoacylation of tRNA may be performed by other agents, including but not limited to, transferases, polymerases, catalytic antibodies, multi-functional proteins, and the like.

Lu et al. in Mol. Cell. 2001 October; 8(4):759-69 describe a method in which a protein is chemically ligated to a synthetic peptide containing unnatural amino acids (expressed protein ligation).

Microinjection techniques have also been use incorporate unnatural amino acids into proteins. See, e.g., M. W. Nowak, P. C. Kearney, J. R. Sampson, M. E. Saks, C. G. Labarca, S. K. Silverman, W. G. Zhong, J. Thorson, J. N. Abelson, N. Davidson, P. G. Schultz, D. A. Dougherty and H. A. Lester, Science, 268:439 (1995); and, D. A. Dougherty, Curr. Opin. Chem. Biol., 4:645 (2000). A Xenopus oocyte was coinjected with two RNA species made in vitro: an mRNA encoding the target protein with a UAG stop codon at the amino acid position of interest and an amber suppressor tRNA aminoacylated with the desired unnatural amino acid. The translational machinery of the oocyte then inserts the unnatural amino acid at the position specified by UAG. This method has allowed in vivo structure-function studies of integral membrane proteins, which are generally not amenable to in vitro expression systems. Examples include the incorporation of a fluorescent amino acid into tachykinin neurokinin-2 receptor to measure distances by fluorescence resonance energy transfer, see, e.g., G. Turcatti, K. Nemeth, M. D. Edgerton, U. Meseth, F. Talabot, M. Peitsch, J. Knowles, H. Vogel and A. Chollet, J. Biol. Chem., 271:19991 (1996); the incorporation of biotinylated amino acids to identify surface-exposed residues in ion channels, see, e.g., J. P. Gallivan, H. A. Lester and D. A. Dougherty, Chem. Biol., 4:739 (1997); the use of caged tyrosine analogs to monitor conformational changes in an ion channel in real time, see, e.g., J. C. Miller, S. K. Silverman, P. M. England, D. A. Dougherty and H. A. Lester, Neuron, 20:619 (1998); and, the use of alpha hydroxy amino acids to change ion channel backbones for probing their gating mechanisms. See, e.g., P. M. England, Y. Zhang, D. A. Dougherty and H. A. Lester, *Cell,* 96:89 (1999); and, T. Lu, A. Y. Ting, J. Mainland, L. Y. Jan, P. G. Schultz and J. Yang, *Nat. Neurosci.,* 4:239 (2001).

The ability to incorporate unnatural amino acids directly into proteins in vivo offers a wide variety of advantages of including but not limited to, high yields of mutant proteins, technical ease, the potential to study the mutant proteins in cells or possibly in living organisms and the use of these mutant proteins in therapeutic treatments and diagnostic uses. The ability to include unnatural amino acids with various sizes, acidities, nucleophilicities, hydrophobicities, and other properties into proteins can greatly expand our ability to rationally and systematically manipulate the structures of proteins, both to probe protein function and create new proteins or organisms with novel properties. However, the process is difficult, because the complex nature of tRNA-synthetase interactions that are required to achieve a high degree of fidelity in protein translation.

In one attempt to site-specifically incorporate para-F-Phe, a yeast amber suppressor tRNAPheCUA/phenylalanyl-tRNA synthetase pair was used in a p-F-Phe resistant, Phe auxotrophic *Escherichia coli* strain. See, e.g., R. Furter, *Protein Sci.,* 7:419 (1998).

It may also be possible to obtain expression of a hGH polynucleotide of the present invention using a cell-free (in-vitro) translational system. Translation systems may be cellular or cell-free, and may be prokaryotic or eukaryotic. Cellular translation systems include, but are not limited to, whole cell preparations such as permeabilized cells or cell cultures wherein a desired nucleic acid sequence can be transcribed to mRNA and the mRNA translated. Cell-free translation systems are commercially available and many different types and systems are well-known. Examples of cell-free systems include, but are not limited to, prokaryotic lysates such as *Escherichia coli* lysates, and eukaryotic lysates such as wheat germ extracts, insect cell lysates, rabbit reticulocyte lysates, rabbit oocyte lysates and human cell lysates. Eukaryotic extracts or lysates may be preferred when the resulting protein is glycosylated, phosphorylated or otherwise modified because many such modifications are only possible in eukaryotic systems. Some of these extracts and lysates are available commercially (Promega; Madison, Wis.; Stratagene; La Jolla, Calif.; Amersham; Arlington Heights, Ill.; GIBCO/BRL; Grand Island, N.Y.). Membranous extracts, such as the canine pancreatic extracts containing microsomal membranes, are also available which are useful for translating secretory proteins. In these systems, which can include either mRNA as a template (in-vitro translation) or DNA as a template (combined in-vitro transcription and translation), the in vitro synthesis is directed by the ribosomes. Considerable effort has been applied to the development of cell-free protein expression systems. See, e.g., Kim, D. M. and J. R. Swartz, *Biotechnology and Bioengineering,* 74 :309-316 (2001); Kim, D. M. and J. R. Swartz, *Biotechnology Letters,* 22, 1537-1542, (2000); Kim, D. M., and J. R. Swartz, *Biotechnology Progress,* 16, 385-390, (2000); Kim, D. M., and J. R. Swartz, *Biotechnology and Bioengineering,* 66, 180-188, (1999); and Patnaik, R. and J. R. Swartz, *Biotechniques* 24, 862-868, (1998); U.S. Pat. No. 6,337,191; U.S. Patent Publication No. 2002/0081660; WO 00/55353; WO 90/05785, which are incorporated by reference herein. Another approach that may be applied to the expression of hGH polypeptides comprising a non-naturally encoded amino acid includes the mRNA-peptide fusion technique. See, e.g., R. Roberts and J. Szostak, *Proc. Natl. Acad. Sci. (USA)* 94:12297-12302 (1997); A. Frankel, et al., *Chemistry & Biology* 10:1043-1050 (2003). In this approach, an mRNA template linked to puromycin is translated into peptide on the ribosome. If one or more tRNA molecules has been modified, non-natural amino acids can be incorporated into the peptide as well. After the last mRNA codon has been read, puromycin captures the C-terminus of the peptide. If the resulting mRNA-peptide conjugate is found to have interesting properties in an in vitro assay, its identity can be easily revealed from the mRNA sequence. In this way, one may screen libraries of hGH polypeptides comprising one or more non-naturally encoded amino acids to identify polypeptides having desired properties. More recently, in vitro ribosome translations with purified components have been reported that permit the synthesis of peptides substituted with non-naturally encoded amino acids. See, e.g., A. Forster et al., *Proc. Natl. Acad. Sci.* (USA) 100:6353 (2003).

Reconstituted translation systems may also be used. Mixtures of purified translation factors have also been used successfully to translate mRNA into protein as well as combinations of lysates or lysates supplemented with purified translation factors such as initiation factor-1 (IF-1), IF-2, IF-3 ($\alpha$ or $\beta$), elongation factor T (EF-Tu), or termination factors. Cell-free systems may also be coupled transcription/translation systems wherein DNA is introduced to the system, transcribed into mRNA and the mRNA translated as described in *Current Protocols in Molecular Biology* (F. M. Ausubel et al. editors, Wiley Interscience, 1993), which is hereby specifically incorporated by reference. RNA transcribed in eukaryotic transcription system may be in the form of heteronuclear RNA (hnRNA) or 5'-end caps (7-methyl guanosine) and 3'-end poly A tailed mature mRNA, which can be an advantage in certain translation systems. For example, capped mRNAs are translated with high efficiency in the reticulocyte lysate system.

XV. Macromolecular Polymers Coupled to hGH Polypeptides

Various modifications to the non-natural amino acid polypeptides described herein can be effected using the compositions, methods, techniques and strategies described herein. These modifications include the incorporation of further functionality onto the non-natural amino acid component of the polypeptide, including but not limited to, a label; a dye; a polymer; a water-soluble polymer; a derivative of polyethylene glycol; a photocrosslinker; a radionuclide; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide; a water-soluble dendrimer; a cyclodextrin; an inhibitory ribonucleic acid; a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a photoisomerizable moiety; biotin; a derivative of biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; a quantum dot; a nanotransmitter; a radionucleotide; a radiotransmitter; a neutron-capture agent; or any combination of the above, or any other desirable compound or substance. As an illustrative, non-limiting example of the compositions, methods, techniques and strategies described herein, the following description will focus on adding macromolecular polymers to the non-natural amino acid polypeptide with the understanding that the compositions, methods, techniques and strategies described thereto are also applicable (with appropriate modifications, if necessary and for which one of skill in the art could make with the disclosures herein) to adding other functionalities, including but not limited to those listed above.

A wide variety of macromolecular polymers and other molecules can be linked to hGH polypeptides of the present invention to modulate biological properties of the hGH polypeptide, and/or provide new biological properties to the hGH molecule. These macromolecular polymers can be linked to the hGH polypeptide via a naturally encoded amino acid, via a non-naturally encoded amino acid, or any functional substituent of a natural or non-natural amino acid, or any substituent or functional group added to a natural or non-natural amino acid. The molecular weight of the polymer may be of a wide range, including but not limited to, between about 100 Da and about 100,000 Da or more. The molecular weight of the polymer may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of the polymer is between about 100 Da and 50,000 Da. In some embodiments, the molecular weight of the polymer is between about 100 Da and 40,000 Da. In some embodiments, the molecular weight of the polymer is between about 1,000 Da and 40,000 Da. In some embodiments, the molecular weight of the polymer is between about 5,000 Da and 40,000 Da. In some embodiments, the molecular weight of the polymer is between about 10,000 Da and 40,000 Da.

The present invention provides substantially homogenous preparations of polymer:protein conjugates. "Substantially homogenous" as used herein means that polymer:protein conjugate molecules are observed to be greater than half of the total protein. The polymer:protein conjugate has biological activity and the present "substantially homogenous" PEGylated hGH polypeptide preparations provided herein are those which are homogenous enough to display the advantages of a homogenous preparation, e.g., ease in clinical application in predictability of lot to lot pharmacokinetics.

One may also choose to prepare a mixture of polymer:protein conjugate molecules, and the advantage provided herein is that one may select the proportion of mono-polymer:protein conjugate to include in the mixture. Thus, if desired, one may prepare a mixture of various proteins with various numbers of polymer moieties attached (i.e., di-, tri-, tetra-, etc.) and combine said conjugates with the mono-polymer:protein conjugate prepared using the methods of the present invention, and have a mixture with a predetermined proportion of mono-polymer:protein conjugates.

The polymer selected may be water soluble so that the protein to which it is attached does not precipitate in an aqueous environment, such as a physiological environment.

The polymer may be branched or unbranched. For therapeutic use of the end-product preparation, the polymer will be pharmaceutically acceptable.

Examples of polymers include but are not limited to polyalkyl ethers and alkoxy-capped analogs thereof (e.g., polyoxyethylene glycol, polyoxyethylene/propylene glycol, and methoxy or ethoxy-capped analogs thereof, especially polyoxyethylene glycol, the latter is also known as polyethyleneglycol or PEG); polyvinylpyrrolidones; polyvinylalkyl ethers; polyoxazolines, polyalkyl oxazolines and polyhydroxyalkyl oxazolines; polyacrylamides, polyalkyl acrylamides, and polyhydroxyalkyl acrylamides (e.g., polyhydroxypropylmethacrylamide and derivatives thereof); polyhydroxyalkyl acrylates; polysialic acids and analogs thereof, hydrophilic peptide sequences; polysaccharides and their derivatives, including dextran and dextran derivatives, e.g., carboxymethyldextran, dextran sulfates, aminodextran; cellulose and its derivatives, e.g., carboxymethyl cellulose, hydroxyalkyl celluloses; chitin and its derivatives, e.g., chitosan, succinyl chitosan, carboxymethylchitin, carboxymethylchitosan; hyaluronic acid and its derivatives; starches; alginates; chondroitin sulfate; albumin; pullulan and carboxymethyl pullulan; polyaminoacids and derivatives thereof, e.g., polyglutamic acids, polylysines, polyaspartic acids, polyaspartamides; maleic anhydride copolymers such as: styrene maleic anhydride copolymer, divinylethyl ether maleic anhydride copolymer; polyvinyl alcohols; copolymers thereof; terpolymers thereof; mixtures thereof; and derivatives of the foregoing.

The proportion of polyethylene glycol molecules to protein molecules will vary, as will their concentrations in the reaction mixture. In general, the optimum ratio (in terms of efficiency of reaction in that there is minimal excess unreacted protein or polymer) may be determined by the molecular weight of the polyethylene glycol selected and on the number of available reactive groups available. As relates to molecular weight, typically the higher the molecular weight of the polymer, the fewer number of polymer molecules which may be attached to the protein. Similarly, branching of the polymer should be taken into account when optimizing these parameters. Generally, the higher the molecular weight (or the more branches) the higher the polymer:protein ratio.

As used herein, and when contemplating PEG:hGH polypeptide conjugates, the term "therapeutically effective amount" refers to an amount which gives the desired benefit to a patient. The amount will vary from one individual to another and will depend upon a number of factors, including the overall physical condition of the patient and the underlying cause of the condition to be treated. The amount of hGH polypeptide used for therapy gives an acceptable rate of change and maintains desired response at a beneficial level. A therapeutically effective amount of the present compositions may be readily ascertained by one of ordinary skill in the art using publicly available materials and procedures.

The water soluble polymer may be any structural form including but not limited to linear, forked or branched. Typically, the water soluble polymer is a poly(alkylene glycol), such as poly(ethylene glycol) (PEG), but other water soluble polymers can also be employed. By way of example, PEG is used to describe certain embodiments of this invention.

PEG is a well-known, water soluble polymer that is commercially available or can be prepared by ring-opening polymerization of ethylene glycol according to methods known to those of ordinary skill in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented as linked to the hGH polypeptide by the formula:

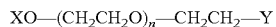

where n is 2 to 10,000 and X is H or a terminal modification, including but not limited to, a $C_{1-4}$ alkyl, a protecting group, or a terminal modification group.

In some cases, a PEG used in the invention terminates on one end with hydroxy or methoxy, i.e., X is H or $CH_3$ ("methoxy PEG"). Alternatively, the PEG can terminate with a reactive group, thereby forming a bifunctional polymer. Typical reactive groups can include those reactive groups that are commonly used to react with the functional groups found in the 20 common amino acids (including but not limited to, maleimide groups, activated carbonates (including but not limited to, p-nitrophenyl ester), activated esters (including but not limited to, N-hydroxysuccinimide, p-nitrophenyl ester) and aldehydes) as well as functional groups that are inert to the 20 common amino acids but that react specifically with complementary functional groups present in non-naturally encoded amino acids. It is noted that the other end of the PEG, which is shown in the above formula by Y, will attach either directly or indirectly to a hGH polypeptide via a naturally-occurring or non-naturally encoded amino acid. In some embodiments, a strong nucleophile (including but not limited to, hydrazine, hydrazide, hydroxylamine, semicarbazide) can be reacted with an aldehyde or ketone group present in a non-naturally encoded amino acid to form a hydrazone, oxime or semicarbazone, as applicable, which in some cases can be further reduced by treatment with an appropriate reducing agent. Alternatively, the strong nucleophile can be incorporated into the hGH polypeptide via a non-naturally encoded amino acid and used to react preferentially with a ketone or aldehyde group present in the water soluble polymer.

Any molecular mass for a PEG can be used as practically desired, including but not limited to, from about 100 Daltons (Da) to 100,000 Da or more as desired (including but not limited to, sometimes 0.1-50 kDa or 10-40 kDa). The molecular weight of PEG may be of a wide range, including but not limited to, between about 100 Da and about 100,000 Da or more. The molecular weight of PEG may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of PEG is between about 100 Da and 50,000 Da. In some embodiments, the molecular weight of PEG is between about 100 Da and 40,000 Da. In some embodiments, the molecular weight of PEG is between about 1,000 Da and 40,000 Da. In some embodiments, the molecular weight of PEG is between about 5,000 Da and 40,000 Da. In some embodiments, the molecular weight of PEG is between about 10,000 Da and 40,000 Da. Branched chain PEGs, including but not limited to, PEG molecules with each chain having a MW ranging from 1-100 kDa (including but not limited to, 1-50 kDa or 5-20 kDa) can also be used. The molecular weight of the branched chain PEG may be, including but not limited to, between about 1,000 Da and about 100,000 Da or more. The molecular weight of the branched chain PEG may be between about 1,000 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, and 1,000 Da. In some embodiments, the molecular weight of the branched chain PEG is between about 1,000 Da and 50,000 Da. In some embodiments, the molecular weight of the branched chain PEG is between about 1,000 Da and 40,000 Da. In some embodiments, the molecular weight of the branched chain PEG is between about 5,000 Da and 40,000 Da. In some embodiments, the molecular weight of the branched chain PEG is between about 5,000 Da and 20,000 Da. A wide range of PEG molecules are described in, including but not limited to, the Shearwater Polymers, Inc. catalog, Nektar Therapeutics catalog, incorporated herein by reference.

Generally, at least one terminus of the PEG molecule is available for reaction with the non-naturally-encoded amino acid. In some embodiments, the hGH polypeptide variant with a PEG derivative contains a chemical functionality that is reactive with the chemical functionality present on the side chain of the non-naturally encoded amino acid.

The polymer backbone of the water-soluble polymer can be poly(ethylene glycol). However, it should be understood that a wide variety of water soluble polymers including but not limited to poly(ethylene)glycol and other related polymers, including poly(dextran) and poly(propylene glycol), are also suitable for use in the practice of this invention and that the use of the term PEG or poly(ethylene glycol) is intended to encompass and include all such molecules. The term PEG includes, but is not limited to, poly(ethylene glycol) in any of its forms, including bifunctional PEG, multi-armed PEG, derivatized PEG, forked PEG, branched PEG, pendent PEG (i.e. PEG or related polymers having one or more functional groups pendent to the polymer backbone), or PEG with degradable linkages therein.

PEG is typically clear, colorless, odorless, soluble in water, stable to heat, inert to many chemical agents, does not hydrolyze or deteriorate, and is generally non-toxic. Poly(ethylene glycol) is considered to be biocompatible, which is to say that PEG is capable of coexistence with living tissues or organisms without causing harm. More specifically, PEG is substantially non-immunogenic, which is to say that PEG does not tend to produce an immune response in the body. When attached to a molecule having some desirable function in the body, such as a biologically active agent, the PEG tends to mask the agent and can reduce or eliminate any immune response so that an organism can tolerate the presence of the agent. PEG conjugates tend not to produce a substantial immune response or cause clotting or other undesirable effects. PEG having the formula —$CH_2CH_2O$—($CH_2CH_2O)_n$—$CH_2CH_2$—, where n is from about 3 to about 4000, typically from about 20 to about 2000, is suitable for use in the present invention. PEG having a molecular weight of from about 800 Da to about 100,000 Da are in some embodiments of the present invention particularly useful as the polymer backbone. The molecular weight of PEG may be of a wide range, including but not limited to, between about 100 Da and about 100,000 Da or more. The molecular weight of PEG may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of PEG is between about 100 Da and 50,000 Da. In some embodiments, the molecular weight of PEG is between about 100 Da and 40,000 Da. In some embodiments, the molecular weight of PEG is between about 1,000 Da and 40,000 Da. In some embodiments, the molecular weight of PEG is between about 5,000 Da and 40,000 Da. In some embodiments, the molecular weight of PEG is between about 10,000 Da and 40,000 Da.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, glycerol oligomers, pentaerythritol and sorbitol. The central branch moiety can also be derived from several amino acids, such as lysine. The branched poly(ethylene glycol) can be represented in general form as R(-PEG-OH)$_m$, in which R is derived from a core moiety, such as glycerol, glycerol oligomers, or pentaerythritol, and m represents the number of arms. Multi-armed PEG molecules, such as those described in U.S. Pat. Nos. 5,932, 462 5,643,575; 5,229,490; 4,289,872; U.S. Pat. Appl. 2003/0143596; WO 96/21469; and WO 93/21259, each of which is incorporated by reference herein in its entirety, can also be used as the polymer backbone.

Branched PEG can also be in the form of a forked PEG represented by PEG(-YCHZ$_2$)$_n$, where Y is a linking group and Z is an activated terminal group linked to CH by a chain of atoms of defined length.

Yet another branched form, the pendant PEG, has reactive groups, such as carboxyl, along the PEG backbone rather than at the end of PEG chains.

In addition to these forms of PEG, the polymer can also be prepared with weak or degradable linkages in the backbone. For example, PEG can be prepared with ester linkages in the polymer backbone that are subject to hydrolysis. As shown below, this hydrolysis results in cleavage of the polymer into fragments of lower molecular weight:

-PEG-CO$_2$-PEG-+H$_2$O—PEG-CO$_2$H+HO-PEG-

It is understood by those of ordinary skill in the art that the term poly(ethylene glycol) or PEG represents or includes all the forms known in the art including but not limited to those disclosed herein.

Many other polymers are also suitable for use in the present invention. In some embodiments, polymer backbones that are water-soluble, with from 2 to about 300 termini, are particularly useful in the invention. Examples of suitable polymers include, but are not limited to, other poly(alkylene glycols), such as poly(propylene glycol) ("PPG"), copolymers thereof (including but not limited to copolymers of ethylene glycol and propylene glycol), terpolymers thereof, mixtures thereof, and the like. Although the molecular weight of each chain of the polymer backbone can vary, it is typically in the range of from about 800 Da to about 100,000 Da, often from about 6,000 Da to about 80,000 Da. The molecular weight of each chain of the polymer backbone may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of each chain of the polymer backbone is between about 100 Da and 50,000 Da. In some embodiments, the molecular weight of each chain of the polymer backbone is between about 100 Da and 40,000 Da. In some embodiments, the molecular weight of each chain of the polymer backbone is between about 1,000 Da and 40,000 Da. In some embodiments, the molecular weight of each chain of the polymer backbone is between about 5,000 Da and 40,000 Da. In some embodiments, the molecular weight of each chain of the polymer backbone is between about 10,000 Da and 40,000 Da.

Those of ordinary skill in the art will recognize that the foregoing list for substantially water soluble backbones is by no means exhaustive and is merely illustrative, and that all polymeric materials having the qualities described above are contemplated as being suitable for use in the present invention.

In some embodiments of the present invention the polymer derivatives are "multi-functional", meaning that the polymer backbone has at least two termini, and possibly as many as about 300 termini, functionalized or activated with a functional group. Multifunctional polymer derivatives include, but are not limited to, linear polymers having two termini, each terminus being bonded to a functional group which may be the same or different.

Water soluble polymers can be linked to the hGH polypeptides of the invention. The water soluble polymers may be linked via a non-naturally encoded amino acid incorporated in the hGH polypeptide or any functional group or substituent of a non-naturally encoded or naturally encoded amino acid, or any functional group or substituent added to a non-naturally encoded or naturally encoded amino acid. Alternatively, the water soluble polymers are linked to a hGH polypeptide incorporating a non-naturally encoded amino acid via a naturally-occurring amino acid (including but not limited to, cysteine, lysine or the amine group of the N-terminal residue). In some cases, the hGH polypeptides of the invention comprise 1, 2, 3, 4, 5, 6, 7, 8, 9, non-natural amino acids, wherein one or more non-naturally-encoded amino acid(s) are linked to water soluble polymer(s) (including but not limited to, PEG and/or oligosaccharides). In some cases, the hGH polypeptides of the invention further comprise 1, 2, 3, 4, 5, 6, 7, 8, 9, 10, or more naturally-encoded amino acid(s) linked to water soluble polymers. In some cases, the hGH polypeptides of the invention comprise one or more non-naturally encoded amino acid(s) linked to water soluble polymers and one or more naturally-occurring amino acids linked to water soluble polymers. In some embodiments, the water soluble polymers used in the present invention enhance the serum half-life of the hGH polypeptide relative to the unconjugated form.

The number of water soluble polymers linked to a hGH polypeptide (i.e., the extent of PEGylation or glycosylation) of the present invention can be adjusted to provide an altered (including but not limited to, increased or decreased) pharmacologic, pharmacokinetic or pharmacodynamic characteristic such as in vivo half-life. In some embodiments, the half-life of hGH is increased at least about 10, 20, 30, 40, 50, 60, 70, 80, 90 percent, 2-fold, 5-fold, 10-fold, 50-fold, or at least about 100-fold over an unmodified polypeptide.

The degree and sites at which the water soluble polymer(s) are linked to the hGH polypeptide can modulate the binding of the hGH polypeptide to the hGH polypeptide receptor at Site 1 or binding partner. In some embodiments, the linkages are arranged such that the hGH polypeptide binds the hGH polypeptide receptor at Site 1 with a $K_d$ of about 400 nM or lower, with a $K_d$ of 150 nM or lower, and in some cases with a $K_d$ of 100 nM or lower, as measured by an equilibrium binding assay, such as that described in Spencer et al., *J. Biol. Chem.*, 263:7862-7867 (1988) for hGH.

Methods and chemistry for activation of polymers as well as for conjugation of peptides are described in the literature and are known in the art. Commonly used methods for activation of polymers include, but are not limited to, activation of functional groups with cyanogen bromide, periodate, glutaraldehyde, biepoxides, epichlorohydrin, divinylsulfone, carbodiimide, sulfonyl halides, trichlorotriazine, etc. (see, R. F. Taylor, (1991), PROTEIN IMMOBILISATION, FUNDAMENTAL AND APPLICATIONS, Marcel Dekker, N.Y.; S. S. Wong, (1992), CHEMISTRY OF PROTEIN CONJUGATION AND CROSSLINKING, CRC Press, Boca Raton; G. T. Hermanson et al., (1993), IMMOBILIZED AFFINITY LIGAND TECHNIQUES, Academic Press, N.Y.; Dunn, R. L., et al., Eds. POLYMERIC DRUGS AND DRUG DELIVERY SYSTEMS, ACS Symposium Series Vol. 469, American Chemical Society, Washington, D.C. 1991).

Several reviews and monographs on the functionalization and conjugation of PEG are available. See, for example, Harris, *Macromol. Chem. Phys.* C25: 325-373 (1985); Scouten, *Methods in Enzymology* 135: 30-65 (1987); Wong et al., *Enzyme Microb. Technol.* 14: 866-874 (1992); Delgado et al., *Critical Reviews in Therapeutic Drug Carrier Systems* 9: 249-304 (1992); Zalipsky, *Bioconjugate Chem.* 6: 150-165 (1995).

Methods for activation of polymers can also be found in WO 94/17039, U.S. Pat. No. 5,324,844, WO 94/18247, WO 94/04193, U.S. Pat. No. 5,219,564, U.S. Pat. No. 5,122,614, WO 90/13540, U.S. Pat. No. 5,281,698, and WO 93/15189, and for conjugation between activated polymers and enzymes including but not limited to Coagulation Factor VIII (WO 94/15625), hemoglobin (WO 94/09027), oxygen carrying molecule (U.S. Pat. No. 4,412,989), ribonuclease and superoxide dismutase (Veronese at al., *App. Biochem. Biotech.* 11: 141-52 (1985)). All references and patents cited are incorporated by reference herein.

The reaction products are subsequently subjected to hydrophobic interaction chromatography to separate the PEGylated hGH polypeptide variants from free PEG. Suitable conditions vary depending on the relative sizes of the cross-linked complexes versus the desired conjugates and are readily determined by those of ordinary skill in the art. The eluent containing the desired conjugates may be concentrated by ultrafiltration and desalted by diafiltration.

If necessary, the PEGylated hGH polypeptide obtained from the hydrophobic chromatography can be purified further by one or more procedures known to those of ordinary skill in the art including, but are not limited to, affinity chromatography; anion- or cation-exchange chromatography (using, including but not limited to, DEAE SEPHAROSE); chromatography on silica; reverse phase HPLC; gel filtration (using, including but not limited to, SEPHADEX G-75); hydrophobic interaction chromatography; size-exclusion chromatography, metal-chelate chromatography; ultrafiltration/diafiltration; ethanol precipitation; ammonium sulfate precipitation; chromatofocusing; displacement chromatography; electrophoretic procedures (including but not limited to preparative isoelectric focusing), differential solubility (including but not limited to ammonium sulfate precipitation), or extraction. Apparent molecular weight may be estimated by GPC by comparison to globular protein standards (Preneta, A Z in PROTEIN PURIFICATION METHODS, A PRACTICAL APPROACH (Harris & Angal, Eds.) IRL Press 1989, 293-306). The purity of the hGH-PEG conjugate can be assessed by proteolytic degradation (including but not limited to, trypsin cleavage) followed by mass spectrometry analysis. Pepinsky R B., et al., *J. Pharmcol. & Exp. Ther.* 297(3):1059-66 (2001).

A water soluble polymer linked to an amino acid of a hGH polypeptide of the invention can be further derivatized or substituted without limitation.

Other PEG Derivatives and General PEGylation Techniques

Other exemplary PEG molecules that may be linked to hGH polypeptides, as well as PEGylation methods include those described in, e.g., U.S. Patent Publication No. 2004/0001838; 2002/0052009; 2003/0162949; 2004/0013637; 2003/0228274; 2003/0220447; 2003/0158333; 2003/0143596; 2003/0114647; 2003/0105275; 2003/0105224; 2003/0023023; 2002/0156047; 2002/0099133; 2002/0086939; 2002/0082345; 2002/0072573; 2002/0052430; 2002/0040076; 2002/0037949; 2002/0002250; 2001/0056171; 2001/0044526; 2001/0021763; U.S. Pat. Nos. 6,646,110; 5,824,778; 5,476,653; 5,219,564; 5,629,384; 5,736,625; 4,902,502; 5,281,698; 5,122,614; 5,473,034; 5,516,673; 5,382,657; 6,552,167; 6,610,281; 6,515,100; 6,461,603; 6,436,386; 6,214,966; 5,990,237; 5,900,461; 5,739,208; 5,672,662; 5,446,090; 5,808,096; 5,612,460; 5,324,844; 5,252,714; 6,420,339; 6,201,072; 6,451,346; 6,306,821; 5,559,213; 5,747,646; 5,834,594; 5,849,860; 5,980,948; 6,004,573; 6,129,912; WO 97/32607, EP 229, 108, EP 402,378, WO 92/16555, WO 94/04193, WO 94/14758, WO 94/17039, WO 94/18247, WO 94/28024, WO 95/00162, WO 95/11924, WO95/13090, WO 95/33490, WO 96/00080, WO 97/18832, WO 98/41562, WO 98/48837, WO 99/32134, WO 99/32139, WO 99/32140, WO 96/40791, WO 98/32466, WO 95/06058, EP 439.508, WO 97/03106, WO 96/21469, WO 95/13312, EP 921 131, WO 98/05363, EP 809 996, WO 96/41813, WO 96/07670, EP 605 963, EP 510 356, EP 400 472, EP 183 503 and EP 154 316, which are incorporated by reference herein. Any of the PEG molecules described herein may be used in any form, including but not limited to, single chain, branched chain, multiarm chain, single functional, bi-functional, multi-functional, or any combination thereof.

Enhancing Affinity for Serum Albumin

Various molecules can also be fused to the hGH polypeptides of the invention to modulate the half-life of hGH polypeptides in serum. In some embodiments, molecules are linked or fused to hGH polypeptides of the invention to enhance affinity for endogenous serum albumin in an animal.

For example, in some cases, a recombinant fusion of a hGH polypeptide and an albumin binding sequence is made. Exemplary albumin binding sequences include, but are not limited to, the albumin binding domain from streptococcal protein G (see. e.g., Makrides et al., *J. Pharmacol. Exp. Ther.* 277:534-542 (1996) and Sjolander et al., *J. Immunol. Methods* 201:115-123 (1997)), or albumin-binding peptides such as those described in, e.g., Dennis, et al., *J. Biol. Chem.* 277:35035-35043 (2002).

In other embodiments, the hGH polypeptides of the present invention are acylated with fatty acids. In some cases, the fatty acids promote binding to serum albumin. See, e.g., Kurtzhals, et al., *Biochem. J.* 312:725-731 (1995).

In other embodiments, the hGH polypeptides of the invention are fused directly with serum albumin (including but not limited to, human serum albumin). Those of skill in the art will recognize that a wide variety of other molecules can also be linked to hGH in the present invention to modulate binding to serum albumin or other serum components.

XVI. Glycosylation of hGH Polypeptides

The invention includes hGH polypeptides incorporating one or more non-naturally encoded amino acids bearing saccharide residues. The saccharide residues may be either natural (including but not limited to, N-acetylglucosamine) or non-natural (including but not limited to, 3-fluorogalactose). The saccharides may be linked to the non-naturally encoded amino acids either by an N- or O-linked glycosidic linkage (including but not limited to, N-acetylgalactose-L-serine) or a non-natural linkage (including but not limited to, an oxime or the corresponding C- or S-linked glycoside).

The saccharide (including but not limited to, glycosyl) moieties can be added to hGH polypeptides either in vivo or in vitro. In some embodiments of the invention, a hGH polypeptide comprising a carbonyl-containing non-naturally encoded amino acid is modified with a saccharide derivatized with an aminooxy group to generate the corresponding glycosylated polypeptide linked via an oxime linkage. Once attached to the non-naturally encoded amino acid, the saccharide may be further elaborated by treatment with glycosyltransferases and other enzymes to generate an oligosaccharide bound to the hGH polypeptide. See, e.g., H. Liu, et al. *J. Am. Chem. Soc.* 125: 1702-1703 (2003).

XVII. GH Supergene Family Member Dimers and Multimers

The present invention also provides for GH supergene family member combinations (including but not limited to hGH and hGH analogs) such as homodimers, heterodimers, homomultimers, or heteromultimers (i.e., trimers, tetramers, etc.) where a GH supergene family member polypeptide such as hGH containing one or more non-naturally encoded amino acids is bound to another GH supergene family member or variant thereof or any other polypeptide that is a non-GH supergene family member or variant thereof, either directly to the polypeptide backbone or via a linker. Due to its increased molecular weight compared to monomers, the GH supergene family member, such as hGH, dimer or multimer conjugates may exhibit new or desirable properties, including but not limited to different pharmacological, pharmacokinetic, pharmacodynamic, modulated therapeutic half-life, or modulated plasma half-life relative to the monomeric GH supergene family member. In some embodiments, the GH supergene family member, such as hGH, dimers of the invention will modulate the dimerization of the GH supergene family member receptor. In other embodiments, the GH supergene family member dimers or multimers of the present invention will act as a GH supergene family member receptor antagonist, agonist, or modulator.

In some embodiments, one or more of the hGH molecules present in a hGH containing dimer or multimer comprises a non-naturally encoded amino acid linked to a water soluble polymer that is present within the Site II binding region. As such, each of the hGH molecules of the dimer or multimer are accessible for binding to the hGH polypeptide receptor via the Site I interface but are unavailable for binding to a second hGH polypeptide receptor via the Site II interface. Thus, the hGH polypeptide dimer or multimer can engage the Site I binding sites of each of two distinct hGH polypeptide receptors but, as the hGH molecules have a water soluble polymer attached to a non-genetically encoded amino acid present in the Site II region, the hGH polypeptide receptors cannot engage the Site II region of the hGH polypeptide ligand and the dimer or multimer acts as a hGH polypeptide antagonist. In some embodiments, one or more of the hGH molecules present in a hGH polypeptide containing dimer or multimer comprises a non-naturally encoded amino acid linked to a water soluble polymer that is present within the Site I binding region, allowing binding to the Site II region. Alternatively, in some embodiments one or more of the hGH molecules present in a hGH polypeptide containing dimer or multimer comprises a non-naturally encoded amino acid linked to a water soluble polymer that is present at a site that is not within the Site I or Site II binding region, such that both are available for binding. In some embodiments a combination of hGH molecules is used having Site I, Site II, or both available for binding. A combination of hGH molecules wherein at least one has Site I available for binding, and at least one has Site II available for binding may provide molecules having a desired activity or property. In addition, a combination of hGH molecules having both Site I and Site II available for binding may produce a super-agonist hGH molecule.

In some embodiments, the GH supergene family member polypeptides are linked directly, including but not limited to, via an Asn-Lys amide linkage or Cys-Cys disulfide linkage. In some embodiments, the linked GH supergene family member polypeptides, and/or the linked non-GH supergene family member, will comprise different non-naturally encoded amino acids to facilitate dimerization.

Alternatively, the two GH supergene family member polypeptides, and/or the linked non-GH supergene family member, are linked via a linker. Any hetero- or homo-bifunctional linker can be used to link the two GH supergene family members, and/or the linked non-GH supergene family member, polypeptides, which can have the same or different primary sequence. In some cases, the linker used to tether the GH supergene family member, and/or the linked non-GH supergene family member, polypeptides together can be a bifunctional PEG reagent. The linker may have a wide range of molecular weight or molecular length. Larger or smaller molecular weight linkers may be used to provide a desired spatial relationship or conformation between the hGH and the linked entity.

In some embodiments, the invention provides water-soluble bifunctional linkers that have a dumbbell structure that includes: a) a first functional group on at least a first end of a polymer backbone; and b) at least a second functional group on a second end of the polymer backbone. The second functional group can be the same or different as the first functional group. The second functional group, in some embodiments, is not reactive with the first functional group. The invention provides, in some embodiments, water-soluble compounds that comprise at least one arm of a branched molecular structure. For example, the branched molecular structure can be dendritic. In some embodiments, the invention provides multimers comprising one or more GH supergene family member, such as hGH, formed by reactions with water soluble activated polymers.

XVIII. Administration and Pharmaceutical Compositions

The polypeptides or proteins of the invention (including but not limited to, hGH, synthetases, proteins comprising one or more unnatural amino acid, etc.) are optionally employed for therapeutic uses, including but not limited to, in combination with a suitable pharmaceutical carrier. Such compositions, for example, comprise a therapeutically effective amount of the compound, and a pharmaceutically acceptable carrier or excipient. Such a carrier or excipient includes, but is not limited to, saline, buffered saline, dextrose, water, glycerol, ethanol, and/or combinations thereof. The formulation is made to suit the mode of administration. In general, methods of administering proteins are known to those of ordinary skill in the art and can be applied to administration of the polypeptides of the invention.

Therapeutic compositions comprising one or more polypeptide of the invention are optionally tested in one or more appropriate in vitro and/or in vivo animal models of disease, to confirm efficacy, tissue metabolism, and to estimate dosages, according to methods known to those of ordinary skill in the art. In particular, dosages can be initially determined by activity, stability or other suitable measures of unnatural herein to natural amino acid homologues (including but not limited to, comparison of a hGH polypeptide modified to include one or more unnatural amino acids to a natural amino acid hGH polypeptide), i.e., in a relevant assay.

Administration is by any of the routes normally used for introducing a molecule into ultimate contact with blood or tissue cells. The unnatural amino acid polypeptides of the invention are administered in any suitable manner, optionally with one or more pharmaceutically acceptable carriers. Suitable methods of administering such polypeptides in the context of the present invention to a patient are available, and, although more than one route can be used to administer a particular composition, a particular route can often provide a more immediate and more effective action or reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

hGH polypeptides of the invention may be administered by any conventional route suitable for proteins or peptides, including, but not limited to parenterally, e.g. injections including, but not limited to, subcutaneously or intravenously or any other form of injections or infusions. Polypeptide compositions can be administered by a number of routes including, but not limited to oral, intravenous, intraperitoneal, intramuscular, transdermal, subcutaneous, topical, sublingual, or rectal means. Compositions comprising non-natural amino acid polypeptides, modified or unmodified, can also be administered via liposomes. Such administration routes and appropriate formulations are generally known to those of skill in the art. The hGH polypeptide comprising a non-naturally encoded amino acid, may be used alone or in combination with other suitable components such as a pharmaceutical carrier.

The hGH polypeptide comprising a non-natural amino acid, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations of hGH can be presented in unit-dose or multi-dose sealed containers, such as ampules and vials.

Parenteral administration and intravenous administration are preferred methods of administration. In particular, the routes of administration already in use for natural amino acid homologue therapeutics (including but not limited to, those typically used for EPO, GH, G-CSF, GM-CSF, IFNs, interleukins, antibodies, and/or any other pharmaceutically delivered protein), along with formulations in current use, provide preferred routes of administration and formulation for the polypeptides of the invention.

The dose administered to a patient, in the context of the present invention, is sufficient to have a beneficial therapeutic response in the patient over time, or other appropriate activity, depending on the application. The dose is determined by the efficacy of the particular vector, or formulation, and the activity, stability or serum half-life of the unnatural amino acid polypeptide employed and the condition of the patient, as well as the body weight or surface area of the patient to be treated. The size of the dose is also determined by the existence, nature, and extent of any adverse side-effects that accompany the administration of a particular vector, formulation, or the like in a particular patient.

In determining the effective amount of the vector or formulation to be administered in the treatment or prophylaxis of disease (including but not limited to, cancers, inherited diseases, diabetes, AIDS, or the like), the physician evaluates circulating plasma levels, formulation toxicities, progression of the disease, and/or where relevant, the production of anti-unnatural amino acid polypeptide antibodies.

The dose administered, for example, to a 70 kilogram patient, is typically in the range equivalent to dosages of currently-used therapeutic proteins, adjusted for the altered activity or serum half-life of the relevant composition. The vectors or pharmaceutical formulations of this invention can supplement treatment conditions by any known conventional therapy, including antibody administration, vaccine administration, administration of cytotoxic agents, natural amino acid polypeptides, nucleic acids, nucleotide analogues, biologic response modifiers, and the like.

For administration, formulations of the present invention are administered at a rate determined by the LD-50 or ED-50 of the relevant formulation, and/or observation of any side-effects of the unnatural amino acid polypeptides at various concentrations, including but not limited to, as applied to the mass and overall health of the patient. Administration can be accomplished via single or divided doses.

If a patient undergoing infusion of a formulation develops fevers, chills, or muscle aches, he/she receives the appropriate dose of aspirin, ibuprofen, acetaminophen or other pain/fever controlling drug. Patients who experience reactions to the infusion such as fever, muscle aches, and chills are premedicated 30 minutes prior to the future infusions with either aspirin, acetaminophen, or, including but not limited to, diphenhydramine. Meperidine is used for more severe chills and muscle aches that do not quickly respond to antipyretics and antihistamines. Cell infusion is slowed or discontinued depending upon the severity of the reaction.

Human hGH polypeptides of the invention can be administered directly to a mammalian subject. Administration is by any of the routes normally used for introducing hGH polypeptide to a subject. The hGH polypeptide compositions according to embodiments of the present invention include those suitable for oral, rectal, topical, inhalation (including but not limited to, via an aerosol), buccal (including but not limited to, sub-lingual), vaginal, parenteral (including but not limited to, subcutaneous, intramuscular, intradermal, intraarticular, intrapleural, intraperitoneal, intracerebral, intraarterial, or intravenous), topical (i.e., both skin and mucosal surfaces, including airway surfaces) and transdermal administration, although the most suitable route in any given case will depend on the nature and severity of the condition being treated. Administration can be either local or systemic. The formulations of compounds can be presented in unit-dose or multi-dose sealed containers, such as ampoules and vials. hGH polypeptides of the invention can be prepared in a mixture in a unit dosage injectable form (including but not limited to, solution, suspension, or emulsion) with a pharmaceutically acceptable carrier. hGH polypeptides of the invention can also be administered by continuous infusion (using, including but not limited to, minipumps such as osmotic pumps), single bolus or slow-release depot formulations.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. Solutions and suspensions can be prepared from sterile powders, granules, and tablets of the kind previously described.

Freeze-drying is a commonly employed technique for presenting proteins which serves to remove water from the protein preparation of interest. Freeze-drying, or lyophilization, is a process by which the material to be dried is first frozen and then the ice or frozen solvent is removed by sublimation in a vacuum environment. An excipient may be included in pre-lyophilized formulations to enhance stability during the freeze-drying process and/or to improve stability of the lyophilized product upon storage. Pikal, M. Biopharm. 3(9)26-30 (1990) and Arakawa et al. Pharm. Res. 8(3):285-291 (1991).

The spray drying of pharmaceuticals is also known to those of ordinary skill in the art. For example, see Broadhead, J. et al., "The Spray Drying of Pharmaceuticals," in Drug Dev. Ind. Pharm, 18 (11 & 12), 1169-1206 (1992). In addition to small molecule pharmaceuticals, a variety of biological materials have been spray dried and these include: enzymes, sera, plasma, micro-organisms and yeasts. Spray drying is a useful technique because it can convert a liquid pharmaceutical preparation into a fine, dustless or agglomerated powder in a one-step process. The basic technique comprises the following four steps: a) atomization of the feed solution into a spray; b) spray-air contact; c) drying of the spray; and d) separation of the dried product from the drying air. U.S. Pat. Nos. 6,235,710 and 6,001,800, which are incorporated by reference herein, describe the preparation of recombinant erythropoietin by spray drying.

The pharmaceutical compositions and formulations of the invention may comprise a pharmaceutically acceptable carrier, excipient, or stabilizer. Pharmaceutically acceptable carriers are determined in part by the particular composition being administered, as well as by the particular method used to administer the composition. Accordingly, there is a wide variety of suitable formulations of pharmaceutical compositions (including optional pharmaceutically acceptable carriers, excipients, or stabilizers) of the present invention (see, e.g., *Remington's Pharmaceutical Sciences*, 17$^{th}$ ed. 1985)).

Suitable carriers include, but are not limited to, buffers containing succinate, phosphate, borate, HEPES, citrate, histidine or histidine derivatives, imidazole, acetate, bicarbonate, and other organic acids; antioxidants including but not limited to, ascorbic acid; low molecular weight polypeptides including but not limited to those less than about 10 residues; proteins, including but not limited to, serum albumin, gelatin, or immunoglobulins; hydrophilic polymers including but not limited to, polyvinylpyrrolidone; amino acids including but not limited to, glycine, glutamine, histidine or histidine derivatives, methionine, asparagine, arginine, glutamate, or lysine; monosaccharides, disaccharides, and other carbohydrates, including but not limited to, trehalose, sucrose, glucose, mannose, or dextrins; chelating agents including but not limited to, EDTA; divalent metal ions including but not limited to, zinc, cobalt, or copper; sugar alcohols including but not limited to, mannitol or sorbitol; salt-forming counter ions including but not limited to, sodium; and/or nonionic surfactants including but not limited to Tween™ (including but not limited to, Tween 80 (polysorbate 80) and Tween 20 (polysorbate 20; PS20)), Pluronics™ and other pluronic acids, including but not limited to, pluronic acid F68 (poloxamer 188), or PEG. Suitable surfactants include for example but are not limited to polyethers based upon poly(ethylene oxide)-poly(propylene oxide)-poly(ethylene oxide), i.e., (PEO-PPO-PEO), or poly(propylene oxide)-poly(ethylene oxide)-poly(propylene oxide), i.e., (PPO-PEO-PPO), or a combination thereof. PEO-PPO-PEO and PPO-PEO-PPO are commercially available under the trade names Pluronics™, R-Pluronics™, Tetronics™ and R-Tetronics™ (BASF Wyandotte Corp., Wyandotte, Mich.) and are further described in U.S. Pat. No. 4,820,352 incorporated herein in its entirety by reference. Other ethylene/polypropylene block polymers may be suitable surfactants. A surfactant or a combination of surfactants may be used to stabilize PEGylated hGH against one or more stresses including but not limited to stress that results from agitation. Some of the above may be referred to as "bulking agents." Some may also be referred to as "tonicity modifiers."

hGH polypeptides of the invention, including those linked to water soluble polymers such as PEG can also be administered by or as part of sustained-release systems. Sustained-release compositions include, including but not limited to, semi-permeable polymer matrices in the form of shaped articles, including but not limited to, films, or microcapsules. Sustained-release matrices include from biocompatible materials such as poly(2-hydroxyethyl methacrylate) (Langer et al., *J. Biomed. Mater. Res.*, 15: 267-277 (1981); Langer, *Chem. Tech.*, 12: 98-105 (1982), ethylene vinyl acetate (Langer et al., supra) or poly-D-(−)-3-hydroxybutyric acid (EP 133,988), polylactides (polylactic acid) (U.S. Pat. No. 3,773,919; EP 58,481), polyglycolide (polymer of glycolic acid), polylactide co-glycolide (copolymers of lactic acid and glycolic acid) polyanhydrides, copolymers of L-glutamic acid and gamma-ethyl-L-glutamate (Sidman et al., *Biopolymers*, 22, 547-556 (1983), poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Sustained-release compositions also include a liposomally entrapped compound. Liposomes containing the compound are prepared by methods known per se: DE 3,218,121; Eppstein et al., *Proc. Natl. Acad. Sci. U.S.A.*, 82: 3688-3692 (1985); Hwang et al., *Proc. Natl. Acad. Sci. U.S.A.*, 77: 4030-4034 (1980); EP 52,322; EP 36,676; U.S. Pat. No. 4,619,794; EP 143,949; U.S. Pat. No. 5,021,234; Japanese Pat. Appln. 83-118008; U.S. Pat. Nos. 4,485,045 and 4,544,545; and EP 102,324. All references and patents cited are incorporated by reference herein.

Liposomally entrapped hGH polypeptides can be prepared by methods described in, e.g., DE 3,218,121; Eppstein et al., *Proc. Natl. Acad. Sci. U.S.A.*, 82: 3688-3692 (1985); Hwang et al., *Proc. Natl. Acad. Sci. U.S.A.*, 77: 4030-4034 (1980); EP 52,322; EP 36,676; U.S. Pat. No. 4,619,794; EP 143,949; U.S. Pat. No. 5,021,234; Japanese Pat. Appln. 83-118008; U.S. Pat. Nos. 4,485,045 and 4,544,545; and EP 102,324. Composition and size of liposomes are well known or able to be readily determined empirically by one of ordinary skill in the art. Some examples of liposomes as described in, e.g., Park J W, et al., *Proc. Natl. Acad. Sci. USA* 92:1327-1331 (1995); Lasic D and Papahadjopoulos D (eds): MEDICAL APPLICATIONS OF LIPOSOMES (1998); Drummond D C, et al., Liposomal drug delivery systems for cancer therapy, in Teicher B (ed): CANCER DRUG DISCOVERY AND DEVELOPMENT (2002); Park J W, et al., *Clin. Cancer Res.* 8:1172-1181 (2002); Nielsen U B, et al., *Biochim. Biophys. Acta* 1591(1-3):109-118 (2002); Mamot C, et al., *Cancer Res.* 63: 3154-3161 (2003). All references and patents cited are incorporated by reference herein.

The dose administered to a patient in the context of the present invention should be sufficient to cause a beneficial response in the subject over time. Generally, the total pharmaceutically effective amount of the hGH polypeptide of the present invention administered parenterally per dose is in the range of about 0.01 μg/kg/day to about 100 μg/kg, or about 0.05 mg/kg to about 1 mg/kg, of patient body weight, although this is subject to therapeutic discretion. The frequency of dosing is also subject to therapeutic discretion, and may be more frequent or less frequent than the commercially available hGH polypeptide products approved for use in humans. Generally, a PEGylated hGH polypeptide of the invention can be administered by any of the routes of administration described above.

It is believed that one of ordinary skill in the art, using the preceding description, may utilize the present invention to the fullest extent. The following examples are illustrative only, and not limiting of the claims or the present disclosure, in any way whatsoever.

EXAMPLES

The following examples are offered to illustrate, but not to limit the claimed invention.

Example 1

8 Liter Fermentation

This example describes expression methods used for hGH polypeptides comprising a non-natural amino acid. Host cells were transformed with constructs for orthogonal tRNA, orthogonal aminoacyl tRNA synthetase, and a polynucleotide encoding hGH polypeptide comprising a selector codon.

Preparation

Sterile base, 5.5 M potassium carbonate (0.5 L), was prepared and sterilized by steam or filtration. Sterile 25% v/v polyalkylene defoamer, such as Struktol J673 (0.1 L), was prepared and sterilized by steam. No acid was required. Concentrated feed medium (4 L, defined) was prepared and filter sterilized into a sterile feed tank or bioprocess bag.

The fermentor was set-up. It was sterilized with 3.91 L Base Salts solution. The fermentor was brought to the following conditions: temperature=37° C., pH=6.9, 1 VVM air. 0.092 L concentrated feed medium was added to the fermentor. 4 mL of 50 mg/mL kanamycin was added.

Solutions of glycerol and arabinose (an optionally yeast extract) as well as the following reagents were prepared:

| Trace metals (steam sterilized or filter sterilized) | |
| --- | --- |
| Component | g/l |
| $Na_3$citrate | 74 |
| $FeCl_3 \cdot 6H_2O$ | 27 |
| $CoCl_2 \cdot 6H_2O$ | 2 |
| $Na_2MoO_4 \cdot 2H_2O$ | 2 |
| $ZnSO_4 \cdot 7H_2O$ | 3 |
| $MnSO_4 \cdot nH_2O$ | 2 |
| $CuCl_2 \cdot 2H_2O$ | 1.3 |
| $CaCl_2 \cdot 2H_2O$ | 1 |
| $H_3BO_3$ | 0.5 |

| Vitamins (filter sterilized) | |
| --- | --- |
| Component | g/l |
| Niacin | 6.1 |
| Pantothenic acid | 5.4 |
| Pyridoxine•HCl | 1.4 |
| Thiamine•HCl | 1 |
| Riboflavin | 0.42 |
| Biotin | 0.06 |
| Folic acid | 0.04 |

| Glucose (steam sterilized or filter sterilized) | | |
| --- | --- | --- |
| Component | g/l | l |
| Glucose | 600 | 1.8-2 |

| 1 M $MgSO_4$ (steam sterilized or filter sterilized) | |
| --- | --- |
| Component | g/l |
| $MgSO_4 \cdot 7H_2O$ | 246 |

| Ammonium sulfate, 400 g/l (steam sterilized or filter sterilized) | |
| --- | --- |
| Component | g/l |
| Ammonium sulfate | 400 |

| 5.5 M $K_2CO_3$ (steam sterilized or filter sterilized) | |
| --- | --- |
| Component | g/l or l/l |
| $K_2CO_3$ | 760 |
| $H_2O$ | 0.76 |

| 1M L-leucine (filter sterilized) | |
| --- | --- |
| Component | g/l or l/l |
| L-leucine | 131 |
| Conc. HCl | 0.1 |

| 1M L-isoleucine (filter sterilized) | |
| --- | --- |
| Component | g/l or l/l |
| L-isoleucine | 131 |
| Conc. HCl | 0.1 |

| Base salts, 1X (steam sterilized or filter sterilized) | |
| --- | --- |
| Component | g/l or l/l |
| $Na_2HPO_4 \cdot 7H_2O$ | 15.4 |
| $KH_2PO_4$ | 6.8 |
| $NH_4Cl$ | 4 |

| Concentrated feed | |
| --- | --- |
| Component | l/l |
| Ammonium sulfate solution | 0.194 |
| Glucose solution | 0.537 |
| Magnesium solution | 0.029 |
| Trace metals concentrate solution | 0.045 |
| Vitamins concentrate solution | 0.045 |
| L-isoleucine | 0.054 |
| L-leucine | 0.096 |

| Batch medium | |
| --- | --- |
| Component | g/l or l/l |
| Base salts solution, 1X | 0.977 |
| Concentrated feed medium | 0.023 |

Process

The process performed is described as indicated in Table 2.

TABLE 2

| Day | Clock | Time (hr) | Action |
| --- | --- | --- | --- |
| −2 | 0800 | −46 | 2 mL starter culture was begun with a 1 μL glycerol stock. The culture was shaken at 37° C., 250 rpm until $OD_{600}$ = 2-6. |
| −1 | 0800 | −22 | 150 μL of starter culture was transferred to 150 mL of defined medium in a shake flask. The culture was incubated at 28-37° C. with aeration until $OD_{600}$ = 2-5. |
| 1 | 0600 | 0 | 100 mL of the seed culture was transferred to the fermentor. |
| 1 | 1400 | 8 | The feed pump was started. The exact timing of this was dictated by when the culture depleted the batch nutrients. Approximately |

TABLE 2-continued

| Day | Clock | Time (hr) | Action |
| --- | --- | --- | --- |
| | | | 2.6 L of concentrated feed medium was fed to the culture over 19.5 hours using a preset feed schedule. The minimum feed rate was 0.31 mL/minute, and the maximum feed rate was 6 mL/minute. If needed, the DO (dissolved oxygen) was controlled with cascade of agitation and $O_2$ supplementation. |
| 2 | 0830 | 26.5 | 200 mL bolus of 80% glycerol was added to the culture while maintaining the feed schedule of concentrated feed. |
| 2 | 0930 | 27.5 | The concentrated feed was turned off. The feed was changed to a 40% glycerol solution, and the feed line was purged. The feed was stopped. The non-natural amino acid pAF was added to a final concentration of 4 mM. The culture was induced with a 8 mL bolus of 20% arabinose. |
| 2 | 1130 | 29.5 | The 40% glycerol feed was turned on. |
| 2 | 1930 | 37.5 | Cells were harvested. Tight wet cell densities were from 0.2-0.3 kg/L. The cell paste at was frozen at −80° C. |

Figure 2:
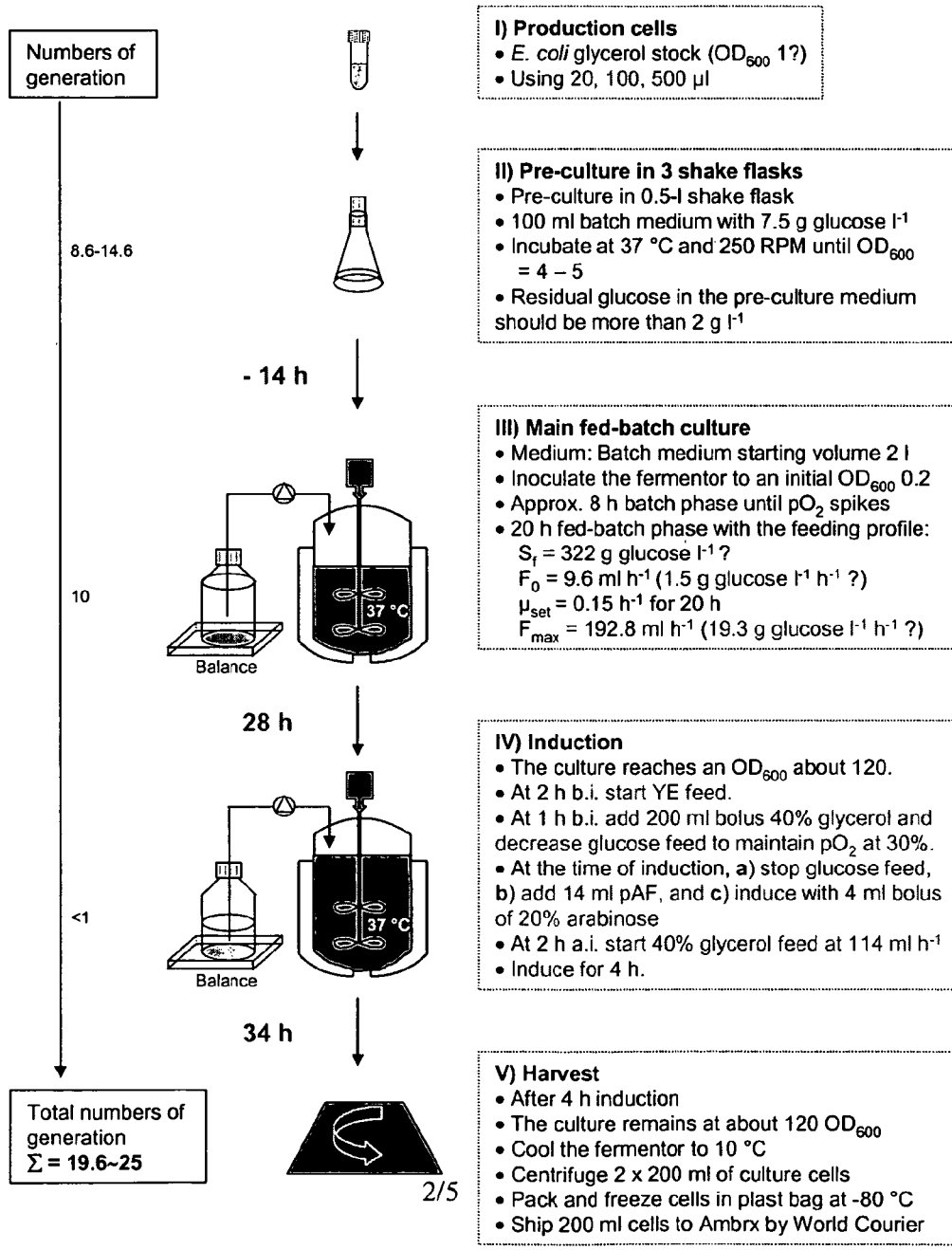
FIG. 2 shows a fermentation process on a 5 liter scale.

The feed schedule was as indicated in Table 3, and the fermentation feed flow rate is shown as FIG. 1. See also FIG. 2.

TABLE 3

| Approximate time (h) | Flow rate (ml/mm) | Notes |
| --- | --- | --- |
| 0 | 0 | Times indicated are post inoculation. |
| 8 | 0 | |
| 8 | 0.31 | Flow rates increased linearly from one set point to the next. |
| 10 | 0.42 | |
| 12 | 0.57 | |
| 14 | 0.77 | |
| 16 | 1.04 | |
| 18 | 1.40 | |
| 20 | 1.90 | |
| 22 | 2.57 | |
| 24 | 3.47 | |
| 26 | 4.69 | |
| 27.5 | 6.00 | Flow was turned off at 27.5 hours after purging the line with 40% glycerol. |
| 27.5 | 0.00 | |
| 29.5 | 0 | |
| 29.5 | 1.90 | 40% glycerol feed was turned on at 29.5 hours. |
| 37.5 | 1.90 | |
| 37.5 | 0 | Fermentation was harvested. |

Modifications to this scheme have been completed at the induction step (step TV) and harvest step (step V). After the culture reached an $OD_{600}$ of about 100 to about 120, a) the glycerol bolus was delivered 1.5 hours before induction; b) the pAF was added and a switch to yeast extract/glycerol feed was performed 1 hour before induction; 3) arabinose was added 0 hours before induction; 4) the induction was completed for 8 hours.

Example 2 hGH Purification, PEGylation, and hGH-PEG Purification Process Cytoplasmic Preparation from *E. coli*

1. Cell Lysis & hGH Oxidation

An 850 gram bacterial cell pellet was resuspended in 2550 ml (3 volumes) of 20 mM TRIS, pH 8.5 lysis buffer to obtain a mixture that is 25% solid. Approximately four liters of culture in fermentation broth will yield this 850 gram bacterial pellet. The mixture was stirred at room temperature for 30-60 minutes, and the suspension was passed through the Microfluidizer processor twice with cooling at 15,000 psi. The lysate was centrifuged at 13,500×g for 45 minutes in a JA10 rotor at 4° C., and the supernatant was collected. Freshly prepared 0.1 M GSSG (FW 612.6) was added so that the molar ratio of GSSG to hGH was approximately 16. The combination was stirred to mix well, and the pH was adjusted to 7.2-7.4 with 1 M NaOH. After the mixture was stirred overnight at 4° C., it was diluted until its conductivity is 1.6-1.9 mS/cm with water. The sample was designated as GHQFFload with the lot number.

2. Column 1—Q Sepharose FF Chromatography

The column dimension was as indicated: INdEX100/500, 100 mmI.D.×21.5 cm=1688 ml. GHQFF Buffer A consisted of 10 mM Bis-TRIS, pH 6.5 with a conductivity of 0.5 mS/cm, and GHQFF Buffer B consisted of 10 mM Bis-TRIS, 1 M NaCl, pH 6.5 with a conductivity of 90 mS/cm. The flow rate was 90 ml/min for processing the sample, and 40 ml/min for cleaning.

The AKTA system was depyrogenated. To depyrogenate and equilibrate the QFF column, the "QFF depy equi" program was used: the column was washed with 2 column volumes of MilliQ water, 2 column volumes of 1 M NaOH/1M NaCl, incubated for 30 minutes, washed with 3 column volumes of GHQFF Buffer B, then equilibrated with 4 column volumes of GHQFF Buffer A.

The sample GHQFFload was loaded onto the anion exchange column. The column was washed with 5 column volumes of GHQFF Buffer A, and eluted with 4 column volumes of 6% GHQFF Buffer B in A. The major peak was collected. Sample collection was initiated at approximately 0.85 mS/cm and 166 niAU and was ended at approx. 220 mAU. The collected eluate was designated as GHQFFpool with the lot number, and it was brownish orange in color. The pool was stored at 4° C. overnight. The average step yield from 3 batches was 84.7%.

The column was washed with 2-3 column volumes of GHQFF Buffer B. 2 column volumes of 1 M NaOH/1M NaCl was pumped in, and the column was incubated for 1-6 days. If the column was not used within 6 days, it was rinsed with 1 column volume of 1 M NaOH/1M NaCl, 3 column volumes of Buffer B, 2 column volumes of MilliQ water, and 2.5 column volumes of 20% EtOH.

An extensive cleaning of the column was done every 3-5 cycles. Following the 1 M NaOH/1 M NaCl incubation, the following was performed: washed upflow with 2.5 column volumes of Q Column Cleaning Buffer, incubated for 60-80 hours, washed with 1.5 column volumes of MilliQ water, 1 column volume from 0 to 70% EtOH, 5 column volumes of 70% EtOH, 2.5 column volumes of 20% EtOH. The Q Column Cleaning Buffer consisted of 0.5% Triton X-100, 0.1 M acetic acid.

3. UF/DF (Ultrafiltration/Diafiltration) I

The following filter was used for this procedure: Sartorius Sartocon Slice 10K Hydrosart cassette, 1000 cm². The GHQFFpool sample was concentrated down to ~450 ml (or ~200 ml in the retentate flask). It was then diafiltrated with 2.7 L (6-volume) of GHCHT Buffer A which consists of 10 mM Bis-TRIS, 1 mM $MgCl_2$, pH 6.3. After collecting the retentate, the system was rinsed with 300 ml of the buffer and the rinse solution was combined with the retentate. The retentate was centrifuged at 4,000 rpm (2,862×g) for 5 minutes, and the supernatant was collected. The supernatant was designated as GHCHTload with the lot number. This sample was either processed within 2 hours or was stored at 4° C. overnight.

4. Column 2—Ceramic Hydroxyapatite (CHT) Chromatography (Type I CHT, 40 μm)

The column dimension was as follows: INdEX100/500, 100 mmI.D.×10.5 cm=824 ml. GHCHT Buffer A consisted of 10 mM Bis-TRIS, 1 mM $MgCl_2$, pH 6.3 with a conductivity of 0.94 mS/cm. GHCHT Buffer B consisted of 10 mM Bis-TRIS, 0.5 M $MgCl_2$, pH 6.3 with a conductivity of 80.5 mS/cm. The flow rate was 90 ml/min for processing, and 40 m/min for cleaning.

The AKTA system was depyrogenated. To depyrogenate and equilibrate the CHT column, the "CHT depy equi" program was run: the CHT column was washed with 2 column volumes of MilliQ water, 2 column volumes of 1 M NaOH/1 M NaCl, incubated for 30 minutes, washed with 3 column volumes of 0.5 M $NaPO_4$/pH 7.0, and then equilibrated with 4 column volumes of GHCHT Buffer A. The GHCHTload sample was then loaded onto the column. The column was washed with 5 column volumes of GHCHT Buffer A.

Elution was performed with a linear gradient of 0-40% GHCHT Buffer B over 5 column volumes, a step gradient of 40% GHCHT Buffer B over 3 column volumes, and washed with 100% GHCHT Buffer B over 2 column volumes. The main peak was collected. The collection was started at approximately 26 mAU, 20 mS/cm, 28% GHCHT Buffer B and was ended at approx. 86 mAU, 34 mS/cm, 40% GHCHT Buffer B. The collected eluate was designated as GHCHTpool with the lot #. The pool was stored at 4° C. overnight. The average step yield from 3 batches was 96.3%.

The CHT column was washed with 3 column volumes of 0.5 M $NaPO_4$/pH 7.0. The column was left in this phosphate buffer, or the following was performed: washed the column upflow with 2 column volumes of 1 M NaOH/1 M NaCl, 3 column volumes of 0.5 M $NaPO_4$/pH 7.0, 2.5 column volumes of MilliQ water, and 2.5 column volumes of 20% EtOH.

5. Column 3—Phenyl Sepharose HP Chromatography

The column dimension was as follows: INdEX100/500, 100 mmI.D.×9.7 cm=761 ml. The GHPhe Buffer A consisted of 20 mM $NaPO_4$, 2 M NaCl, pH 7.0 with a conductivity of 163 mS/cm, and the GHPhe Buffer B consisted of 20 mM $NaPO_4$, pH 7.0 with a conductivity of 3.2 mS/cm. The flow rate was 90 ml/min for processing, and 40 ml/min for cleaning.

The AKTA system was depyrogenated. To depyrogenate and equilibrate the Phe column, the "PheHP depy equi" program was run: the column was washed with 2 column volumes of MilliQ water, 2 column volumes of 1 M NaOH/1 M NaCl, incubated for 30 minutes, then equilibrated with 4 column volumes of GHPhe Buffer A.

Solid NaCl was added to the GHCHTpool to 2 M. The mixture was stirred at room temperature for 1-2 hours to dissolve, and the solution was warmed to approximately 20° C. To calculate the amount of NaCl needed (Z g): (V+Z/4000)×2×58.44=Z, or Z=116.88V/(1-116.88/4000), where V is the volume of GHCHTpool in liters.

The GHCHTpool+NaCl mixture was loaded onto the column. The column was washed with 3 column volumes of GHPhe Buffer A. Elution was performed with the following complex gradient: 10% step of GHPhe Buffer B over 3 column volumes, 10-80% GHPhe Buffer B gradient over 7 column volumes, 80% GHPhe Buffer B step over 2 column volumes, and 100% GHPhe Buffer B step over 3 column volumes. The main peak was collected. The collection was initiated at approximately 17.3 mAU, 111 mS/cm, 46.7% GHPhe Buffer B and was ended at approx. 43 mAU, 54 mS/cm, 80% GHPhe Buffer B. The collected eluate was designated as GHPhe pool with the lot number, and it was a colorless solution. The next step was either performed within 2 hours, or the pool was stored at 4° C. overnight. The average step yield from 3 batches is 94.6%.

The Phe column was washed upflow with 2 column volumes of 1 M NaOH, incubated for 30 min, washed with 3 column volumes of GHPhe Buffer A, 3 column volumes of MilliQ water, and 2.5 column volumes of 20% EtOH. After 3-5 cycles, the Phe column was washed upflow with 2 column volumes of 1 M NaOH, incubated for 30 min, washed with 3 column volumes of GHPhe Buffer A, 3 column volumes of MilliQ water, 0-70% EtOH over 1 column volume, 3 column volumes of 70% EtOH, and stored in 20% EtOH.

6. UF/DF (Ultrafiltration/Diafiltration) II

The following filter was used for this procedure: Sartorius Sartocon Slice 10K Hydrosart cassette, 1000 cm$^2$. The GHPhe pool was concentrated down to ~450 ml (or ~200 ml in the retentate flask). It was then diafiltrated with 2.7 L (6-volumes) of GH Formulation Buffer which consisted of 20 mM Sodium Citrate, 20 g/L Glycine, 5 g/L Mannitol, pH 6.0. The sample was concentrated down to ~360 ml. The retentate was collected. The system was rinsed with 300 ml of the GH Formulation Buffer, and the rinse solution was combined with the retentate. The retentate was centrifuged at 4,000 rpm (2,862×g) for 5 minutes, and the supernatant was collected. The supernatant was designated as Y35pAF-cBx, and was also referred to as "in-process bulk". The in-process bulk was aliquoted and stored at −80° C.

The overall yield of Y35pAF was 435 mg per liter of fermentation broth. The purity was >90% based on 3 HPLC methods (RP-HPLC, SEC-HPLC, IEX-HPLC) and SDS-PAGE analysis.

7. UF/DF (Ultrafiltration/Diafiltration) IIa

The following concentrator/filter was used for this procedure: Amicon Stirred Cell (200 ml) with a YM10 membrane (63.5 mm). Reaction Buffer consisted of 20 mM Sodium Acetate, 20 g/L Glycine, 5 g/L Mannitol, 1 mM EDTA, pH 4.0. A portion of in-process bulk from step 6 was used, such as 250 mg of Y35pAF, and the pH was adjusted to approximately 4 by adding 10-12% (v/v) of 10% acetic acid. The sample was concentrated down to 25-50 ml, and Reaction Buffer was added to approximately 180 ml. The process was repeated until a total of >500-fold of buffer exchange was achieved. The sample was concentrated to approximately 25 ml. The retentate was collected, and centrifuged at 2,000×g for 3 minutes to remove any precipitate. The supernatant was designated as Y35pAF-cBx/pH4 with the date.

The protein concentration of Y35pAF-cBx/pH4 was determined by measuring $A_{276}$ of a 20-fold diluted sample, using $A_{276}^{1\ mg/ml}=0.818$. The concentration of Y35pAF-cBx/pH4 was adjusted to 8 mg/ml by diluting with the Reaction Buffer.

8. PEGylation Reaction

The amount of 30K MPEG-Oxyamine required was calculated using the molar ratio of PEG:Y35pAF=10. The PEG powder was weighed and added to the 8 mg/ml Y35pAF solution at room temperature slowly, and mixed with a spatula after each addition. The reaction mixture was placed at 28° C. with gentle shaking for 18-48 hours. PEGylation was confirmed by running a SDS gel. The reaction formed an oxime bond between hGH and PEG.

9. Column 4—Source Q Chromatography (30 μm)

The column dimension was as follows: XK26/20, 26 mmI.D.×17 cm=90 ml. SourceQ Buffer A consisted of 10 mM TRIS, pH 7.0 with a conductivity of 0.9 mS/cm. SourceQ Buffer B consisted of 10 mM TRIS, 1 M NaCl, pH 7.0 with a conductivity of 93 mS/cm. The flow rate was 6 ml/min.

The AKTA system was depyrogenated. To depyrogenate and equilibrate the SourceQ column, the "SourceQ depy equi" was run: washed the SourceQ column with 2 column volumes of MilliQ water, 2 column volumes of 1 M NaOH/1M NaCl, incubated for 30 min, washed with 5 column volumes of SourceQ Buffer B, then equilibrated with 5 column volumes of SourceQ Buffer A.

20% (v/v) of 0.5 M TRIS base was added to the reaction mixture from Step 8. A twenty-fold dilution was performed with 9-volumes of SourceQ Buffer A and 10-volumes of MilliQ water. The mixture was then loaded onto the column. The column was washed with 5 column volumes of SourceQ Buffer A. Elution was performed with a linear gradient of 0-10% SourceQ Buffer B over 20 column volumes. The 1$^{st}$ major peak was collected. The collected eluate was designated as SourceQ pool with the lot number. The pool was stored at 4° C. overnight.

10. UF/DF (Ultrafiltration/Diafiltration) III

The following concentrator/filter was used for this procedure: Amicon Stirred Cell (200 ml) with a YM10 membrane (63.5 mm). WHO Buffer consisted of 2.5 g/L NaHCO$_3$, 20 g/L Glycine, 2 g/L Mannitol, 2 g/L Lactose, pH 7.3.

The SourceQ pool was concentrated to 20-30 ml, and the WHO Buffer was added to approximately 180 ml. The process was repeated until a total of >600-fold of buffer exchange had been achieved. The sample was then concentrated to 2 mg/ml or the desired concentration. The retentate was collected, and filter sterilized with a 0.2 μm membrane in a hood. The sterile sample was designated as PEG30-cY35pAF with the lot number.

The equivalent hGH concentration of PEG30-cY35pAF was determined by measuring the $A_{276}$ of diluted sample by using $A_{276}^{1\ mg/ml}=0.818$ with triplicate dilutions and measurements. The overall yield from Step 7 is approximately 20%. The PEG-Y35pAF purity was >95% based on HPLC and SDS-PAGE analysis.

Example 3 hGH Purification, PEGylation, and hGH-PEG Purification Process Periplasmic Preparation from *E. coli*

1. Periplasmic Release of hGH

An 800 gram bacterial cell pellet obtained from approximately 4 liters of fermentation broth was resuspended in 3200 ml (4-volumes) of 4-6° C. PR Buffer (50 mM TRIS, 2 mM EDTA, 0.07% Triton X-100, pH 8.0; conductivity=3 mS/cm) to obtain 20% solid. After stirring the suspension at 4-6° C. for 1 hour, 150 ml of 8M urea was added to obtain a final urea concentration of 0.3 M. This suspension was then stirred at 4-6° C. for 1 hour. The suspension was centrifuged at 15,000×g for 25 minutes in a J20 rotor (Avanti J20 XP centrifuge—Beckman Coulter) at 4° C. The supernatant was collected, and its volume measured (approximately 3.4 L). The sample was designated as PRS with the date and lot number.

2. UF/DF (Ultrafiltration/Diaflltration) I

The following filter was used for this procedure: Sartorius Sartocon Slice 10K Hydrosart cassette, 1000 cm$^2$. Additional parameters include: filtrate flow rate of 80 ml/minute and TMP of approximately 14 psi.

The system was depyrogenated with 1N NaOH, and circulation allowed for 30-45 minutes. The system was rinsed with approximately 2 liters of MilliQ water until the pH dropped to below 8. Equilibration was completed with QFF Buffer A (10 mM Bis-TRIS, pH 6.5) for at least 5 minutes. PRS was concentrated down to approximately 1.6 liters (or approximately 1.4 liters in the retentate container). It was then diafiltrated with 5-volumes (~7 liters) of QFF Buffer A. After collecting the retentate, the system was rinsed with 300 ml of the buffer, and the rinse solution was combined with the retentate. The combined sample was designated as QFFload with the lot number. It was a brownish color. This sample was either processed within 2 hours or stored at 4° C. overnight.

The system was rinsed with MilliQ water and cleaned with 1 N NaOH by circulating for 30-45 minutes. Rinsing was then completed with MilliQ water until the pH was less than 8. The cassette was stored in 0.1N NaOH.

3. Column 1—Q Sepharose FF Chromatography

The column dimension was as follows: 50 mm I.D.×6.3 cm=123 ml (XK26/20 column). The flow rate was 35 ml/min. QFF Buffer A consisted of 10 mM Bis-TRIS, pH 6.5 with a conductivity of 0.6 mS/cm. The High Salt Buffer consisted of 10 mM TRIS, 2 M NaCl, pH 7.0 with a conductivity of 156 mS/cm. QFF Buffer B consisted of 10 mM Bis-TRIS, 0.1 M NaCl, pH 6.5 with a conductivity of 11.5 mS/cm.

The AKTA system was depyrogenated. To accomplish this, the "AKTA depy" program was run three times: all buffer lines were placed in MilliQ water for the first run of the program, and then in 1 N NaOH for the second run. An incubation was completed for 30 minutes, and the buffer lines were placed in MilliQ water again for the third run. The program "QFF depy equi" was run to depyrogenate and equilibrate the QFF column: the QFF column was washed with 2 column volumes of MilliQ $H_2O$, 2 column volumes of 1 N NaOH/1M NaCl, incubated for 30 min, washed with three column volumes of High Salt Buffer, then equilibrated with 4 column volumes of QFF Buffer A.

The QFFload was then loaded onto the column. The column was washed with 5 column volumes of QFF Buffer A, and 5.5 column volumes of 15% QFF Buffer B in A. Elution was performed with 4.5 column volumes of 60% QFF Buffer B in A, and the elution peak was collected. The collected eluate was designated as QFFpool with the lot number, and it was a light yellow color. The pool was stored at 4° C. overnight.

The column was washed with 3 column volumes of High Salt Buffer. Then 3 column volumes of 1 N NaOH/1M NaCl was pumped in, and an incubation done for 1-6 days. If the column was not used within 6 days, it was rinsed with 1 column volume of 1 N NaOH/1M NaCl, 3 column volumes of High Salt Buffer, 3 column volumes of MilliQ $H_2O$, and 2.5 column volumes of 20% EtOH or 10 mM NaOH. An extensive cleaning of the column was done every 3-5 cycles such that following the 1 N NaOH/1 M NaCl incubation, it was washed upflow with 3 column volumes of Q Column Cleaning Buffer (0.5% Triton X-100, 0.1 M acetic acid), incubated for 60-80 hours, washed with 1.5 column volumes of MilliQ $H_2O$, 1 column volume from 0 to 70% EtOH, 5 column volumes of 70% EtOH, and 2.5 column volumes of 20% EtOH.

4. Column 2—Phenyl Sepharose HP Chromatography

The column dimension was as follows: 50 mm I.D.×7.5 cm=147 ml (XK26/20 column). The flow rate was 35 ml/minute. Phe Buffer A consisted of 10 mM TRIS, 2 M NaCl, pH 7.0 with a conductivity of 156 mS/cm. Phe Buffer B consisted of 10 mM TRIS, pH 7.0 with a conductivity of 0.9 mS/cm.

The AKTA system was depyrogenated. The "AKTA depy" program was run 3 times: all buffer lines were placed in MilliQ water for the $1^{st}$ run and then in 1 N NaOH for the $2^{nd}$ run. An incubation was completed for 30 minutes, and then all buffer lines were placed in MilliQ water again for the $3^{rd}$ run. The "PheHP depy equi" program was run to depyrogenate and equilibrate the Phe column: it was washed with 2 column volumes of MilliQ $H_2O$, 2 column volumes of 1 M NaOH/1 M NaCl, incubated for 30 min, then equilibrated with 4 column volumes of Phe Buffer A.

Solid NaCl was added to the QFFpool to 2 M. The mixture was stirred at room temperature for 1-2 hours to dissolve the NaCl, and the solution was warmed to approximately 20° C. To calculate the amount of NaCl needed (Z g): (V+Z/4000)× 2×58.44=Z, or Z=116.88V/(1-116.88/4000); where V is the volume of QFFpool in liters.

The QFFpool+NaCl was loaded onto the column. The column was washed with 5 column volumes of Phe Buffer A. Elution was performed with the following complex gradient: 0-45% B linear gradient over 10 column volumes, 45% B step over 2 column volumes, and 100% B step over 3 column volumes. The main peak was collected during the gradient elution. The collected eluate was designated as Phe pool with the lot number, and it was a colorless solution. The next step was performed, or the pool was stored at 4° C.

The Phe column was washed upflow with 2 column volumes of 1 M NaOH, incubated for 30 min, washed with 3 column volumes of Phe Buffer A, 3 column volumes of $H_2O$, and 2.5 column volumes of 20% EtOH or 10 mM NaOH. After 3-5 cycles, the Phe column was washed upflow with 2 column volumes of 1 M NaOH, incubated for 30 min, washed with 3 column volumes of GH Phe Buffer A, 3 column volumes of $H_2O$, 0-70% EtOH over 1 column volume, 3 column volumes of 70% EtOH, and finally, stored in 20% EtOH.

5. UF/DF (Ultrafiltration/Diafiltration) II

The following filter was used for this procedure: Sartorius Sartocon Slice 10K Hydrosart cassette, 200 cm². Additional parameters include: filtrate flow rate of 15 ml/min and TMP of 14 psi. The preliminary formulation buffer consisted of 20 mM Sodium Citrate, 20 g/L Glycine, 5 g/L Mannitol, pH 6.0 with a conductivity of 4.7 mS/cm.

The system was depyrogenated with 1N NaOH, and circulation allowed for 30-45 minutes. The system was rinsed with approximately 2 liters of MilliQ water until the pH dropped to below 8. Equilibration was completed with Preliminary Formulation Buffer for at least 5 minutes.

The GH Phe pool was concentrated down to approximately 350 ml (or approximately 200 ml in the retentate flask). Diafiltration was completed with 2.1 liters (6-volumes) of the Preliminary Formulation Buffer. Then the sample was concentrated down to approximately 350 ml, and the retentate collected. The system was rinsed with 300 ml of the buffer, and the rinse solution was combined with the retentate. The retentate was centrifuged at 4,000 rpm (2,862×g) for 5 minutes, and the supernatant was collected. The supernatant was designated as Y35pAF-pBx, and was also referred to as "in-process bulk".

The protein concentration of Y35pAF-pBx was determined by measuring $A_{276}$ of diluted sample, using $A_{276}^{1\ mg/ml}$=0.818. The in-process bulk can be stored at 4° C. For long term storage, it was aliquoted and kept at −80° C.

The system was rinsed with MilliQ water and cleaned with 1 N NaOH by circulating for 30-45 minutes. Then it was rinsed with MilliQ water until the pH was below 8. The cassette was stored in 0.1 N NaOH.

6. UF/DF (Ultrafiltration/Diaflltration) IIa

The following concentrator/filter was used: Amicon Stirred Cell (350 ml) with a YM10 membrane (76 mm). Reaction Buffer consisted of: 20 mM Sodium Acetate, 20 g/L Glycine, 5 g/L Mannitol, 1 mM EDTA, pH 4.0 with a conductivity of 2.6 mS/cm.

The system was depyrogenated with Pyroclean. All components were incubated in Pyroclean for 30 minutes. Rinsing with MilliQ water was completed until $A_{205}$ was less then 0.01.

The pH of a portion of the in-process bulk, such as 300 mg, is adjusted to approximately 4 by adding 10-12% (v/v) of 10% acetic acid. This sample was concentrated down to 25-50 ml, and Reaction Buffer was added to approximately 350 ml. The process was repeated until a total of >500-fold of buffer exchange was achieved. The sample was then concentrated to approximately 30 ml. The retentate was collected and centrifuged at 2,000×g for 3 minutes to remove any precipitate. The supernatant was designated as Y35pAF-pBx/pH4 with the date. For long term storage, it was aliquoted and kept at −80° C.

The protein concentration of Y35pAF-pBx/pH4 was determined by measuring $A_{276}$ of a 20-fold diluted sample by using $A_{276}^{1\ mg/ml}$=0.818. The concentration of Y35pAF-pBx/pH4 was adjusted to 8 mg/ml by dilution with the Reaction Buffer.

7. PEGylation Reaction

The amount of 30K MPEG-Oxyamine required was calculated using the molar ratio of PEG:Y35pAF=5. The PEG powder was weighed and added to the 8 mg/ml Y35pAF-pBx/pH4 solution at room temperature slowly while stirring. The reaction mixture was placed at 28° C. with gentle stirring for 39-50 hours. The PEGylation was confirmed by performing SDS-PAGE. The reaction formed an oxime bond between hGH and PEG.

8. Column 3—Source Q Chromatography (30 μm)

The column dimension was as follows: XK26/20, 26 mm I.D.×17 cm=90 ml. The flow rate was 8 ml/minute. SourceQ Buffer A consisted of 10 mM TRIS, pH 7.0 with a conductivity of 0.9 mS/cm. SourceQ Buffer B consisted of 10 mM TRIS, 1 M NaCl, pH 7.0 with a conductivity of 87 mS/cm.

To depyrogenate the AKTA system, the program "AKTA depy" was run 3 times: all buffer lines were placed in MilliQ water for the $1^{st}$ run and in 1 N NaOH for the $2^{nd}$ run. An incubation was completed for 30 minutes, and all buffer lines were placed in MilliQ water again for the $3^{rd}$ run. To depyrogenate and equilibrate the SourceQ column, the program "SourceQ depy equi" was run: the SourceQ column was washed with 2 column volumes of MilliQ $H_2O$, 2 column volumes of 1 M NaOH/1M NaCl, incubated for 30 minutes, washed with 5 column volumes of SourceQ Buffer B, then equilibrated with 5 column volumes of SourceQ Buffer A.

20% (v/v) of 0.5 M TRIS base was added to the reaction mixture from the previous step. A 20-fold dilution was performed with 9-volumes of SourceQ Buffer A and 10-volumes of MilliQ $H_2O$. The diluted material was passed through a 0.45 μm filter. The filtrate was then loaded onto the column. The column was washed with 5 column volumes of SourceQ Buffer A. Elution was performed with a linear gradient of 0-10% SourceQ Buffer B over 20 column volumes. The Frac-950 was used to collect elution fractions at 13 ml/fraction. SDS-PAGE was run on the $1^{st}$ major peak to determine the pool. The pooled fractions were designated as SourceQ pool with the lot number. The pool was stored at 4° C. overnight.

9. UF/DF (Ultrafiltration/Diafiltration) III

The following concentrator/filter was used: Amicon Stirred Cell (350 ml) with an YM10 membrane (76 mm). Preliminary Formulation Buffer consisted of 20 mM Sodium Citrate, 20 g/L Glycine, 5 g/L Mannitol, pH 6.0 with a conductivity of 4.7 mS/cm.

The system was depyrogenated with Pyroclean. All components were incubated in Pyroclean for 30 minutes. Rinsing with MilliQ water was completed until $A_{205}$<0.01.

The SourceQ pool was concentrated to 20-40 ml, and the Preliminary Formulation Buffer was added to approximately 350 ml. The process was repeated until a total of >600-fold of buffer exchange was achieved. The sample was concentrated to 2 mg/ml or the desired concentration. The retentate was collected, and filter sterilized with a 0.2 μm membrane in a hood. The sterile sample was designated as PEG30-pY35pAF with the lot number.

The equivalent hGH concentration of PEG30-pY35pAF was determined by measuring $A_{276}$ of diluted sample by using $A_{276}^{1\ mg/ml}$=0.818, and triplicate dilutions and measurements were done. The PEG30-pY35pAF can be stored at 4° C. For long term storage, it was aliquoted and kept at −80° C.

Periplasmic release preparations have been completed with strains of DH10B(fis) and W3110 with the araB gene knocked out. Both strains were transformed with orthogonal tRNA, orthogonal aminoacyl tRNA synthetase, and hGH constructs. The PEG-Y35pAF purity was >95% based on HPLC and SDS-PAGE analysis.

Example 4

Comparison of hGH Preparations

Periplasmic Release vs. Cytoplasmic (Homogenization)

Figure 3:
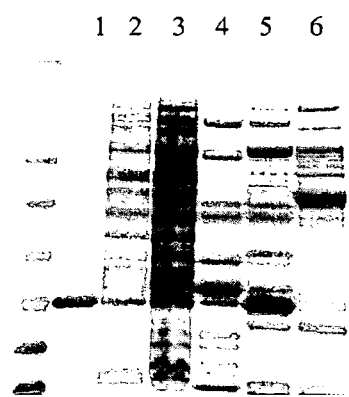
FIG. 3, Panels A and B show SDS-PAGE analysis of hGH polypeptide prepared by periplasmic release and homogenization.
Figure 3:
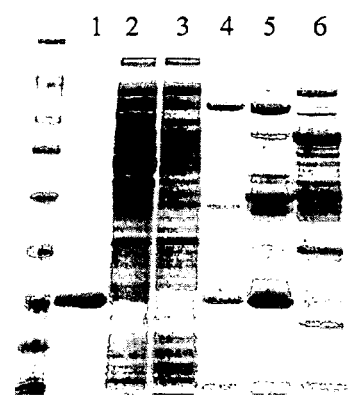

FIG. 3, Panels A and B show SDS-PAGE analysis of hGH produced in E. coli. A periplasmic release batch (fermentation lot 050425B2; 800 grams of cell paste) and a cytoplasmic batch (lysed by microfluidizer; fermentation lot 050414B1; 60 grams of cell paste) were made. Each batch was run over a 123 ml Q FF column with QFF Buffer A consisting of 10 mM Bis-TRIS, pH 6.5 and QFF Buffer B consisting of 10 mM Bis-TRIS, pH 6.5, 0.1M NaCl. Three cuts were performed during elution: 15, 60, and 100% Buffer B (15 mM NaCl, 60 mM NaCl, and 100 mM NaCl respectively). Aliquots from the separation were analyzed by SDS-PAGE. The lanes for Panel A and B are as follows: lane 1=WHO hGH standard; lane 2=Load; lane 3=BE/FT; lane 4=15% Buffer B; lane 5=60% Buffer B; and lane 6=100% Buffer B.

Example 5

5 Liter Fermentation Process

Figure 4:
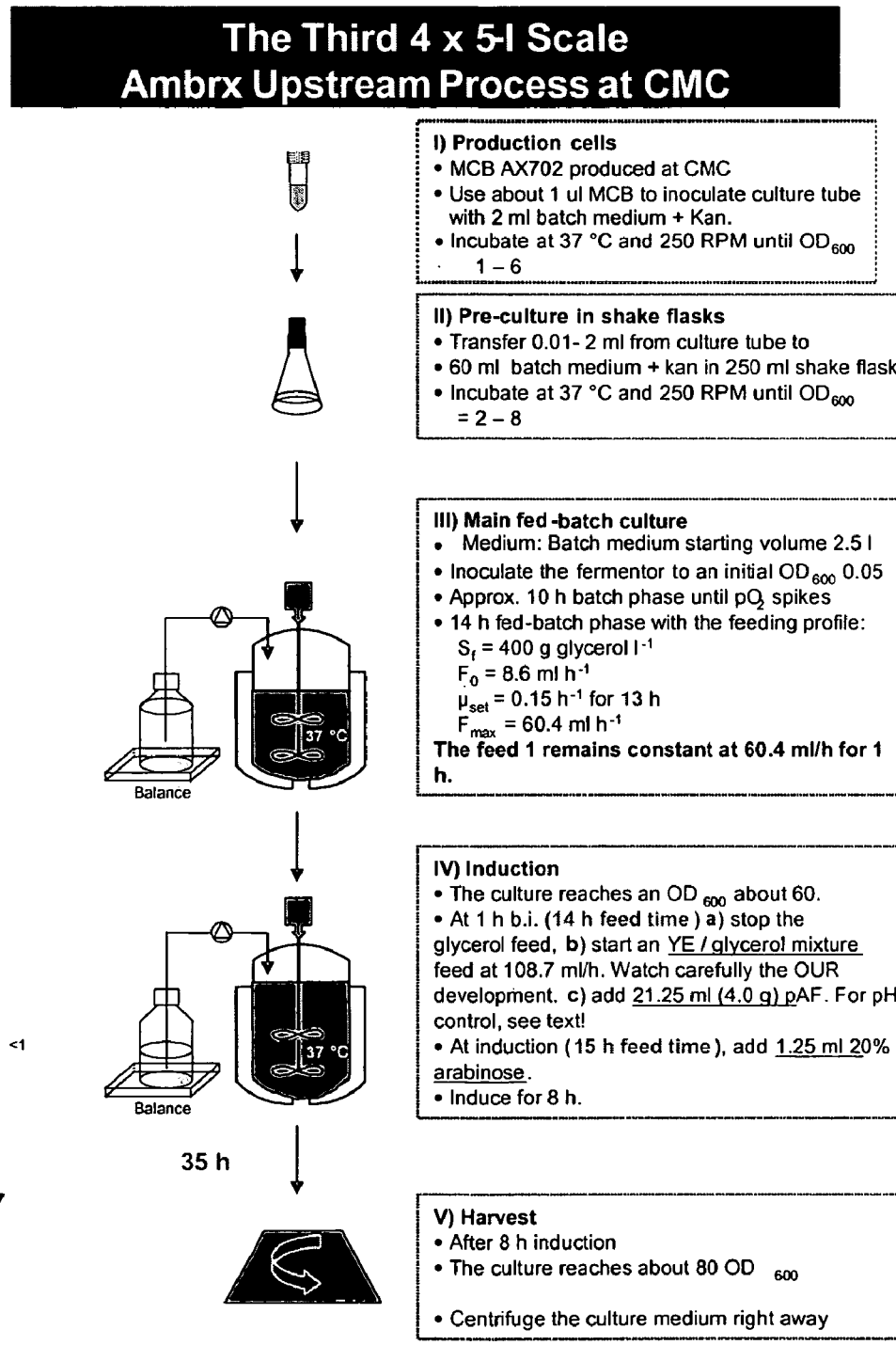
FIG. 4 shows a process flow for a 5 liter fermentation.

This example describes expression methods used for hGH polypeptides comprising a non-natural amino acid. The strain of host cells used was a modified W3110 cell line. The host cells were transformed with constructs for orthogonal tRNA, orthogonal aminoacyl tRNA synthetase, and a polynucleotide encoding hGH polypeptide comprising a selector codon. The process flow is shown as FIG. 4.

Preparation

The following reagents were prepared:

| Trace Elements (Steam sterilized) | |
|---|---|
| Component | g/l |
| $Na_3$citrate | 74 |
| $FeCl_3 \cdot 6H_2O$ | 27 |
| $CoCl_2 \cdot 6H_2O$ | 2 |
| $Na_2MoO_4 \cdot 2H_2O$ | 2 |
| $ZnSO_4 \cdot 7H_2O$ | 3 |
| $MnSO_4 \cdot nH_2O$ | 2 |
| $CuCl_2 \cdot 2H_2O$ | 1.3 |
| $CaCl_2 \cdot 2H_2O$ | 1 |
| $H_3BO_3$ | 0.5 |

| Vitamins (filter sterilized) | |
| --- | --- |
| Component | g/l |
| Niacin | 6.1 |
| Pantothenic acid | 5.4 |
| Pyridoxine•HCl | 1.4 |
| Thiamine•HCl | 1 |
| Riboflavin | 0.42 |
| Biotin | 0.06 |
| Folic acid | 0.04 |

| 1 M MgSO$_4$ (Steam sterilized) | |
| --- | --- |
| Component | g/l |
| MgSO$_4$•7H$_2$O | 246 |

| Ammonium hydroxide, 15% as NH$_3$* for all | |
| --- | --- |
| Component | l/l |
| 15% ammonium hydroxide | 1 |

| Base salts, 1X, for all (steam sterilized) | |
| --- | --- |
| Component | g/l |
| Na$_2$HPO$_4$•7H$_2$O | 15.4 |
| KH$_2$PO$_4$ | 6.8 |
| NH$_4$Cl | 4 |

| Concentrated feed (aseptically mixed sterile components) | |
| --- | --- |
| Component | g or l per l |
| Concentrated glycerol, 100% (w/v) | 0.4 l |
| 1 M Magnesium sulfate solution* | 0.05 l |
| Vitamins | 0.05 l |
| Trace Elements | 0.05 l |
| Water | 0.45 l |

*Added after steam sterilization.

| Batch medium | |
| --- | --- |
| Component | l/l |
| Base salts solution, 1X | 0.98 |
| Concentrated feed | 0.02 |
| Kanamycin stock 50 mg/ml | 0.001 |

* Added after steam sterilization.

| Marcor Yeast extract/Glycerol mixture (Steam sterilized) | |
| --- | --- |
| Component | g/l or l/l |
| Yeast extract powder | 200 g |
| Concentrated glycerol 100% (w/v) | 0.171 |

| Kanamycin stock for all (Filter sterilized) | | |
| --- | --- | --- |
| Component | mg/ml | ml |
| Kanamycin | 50 | 3 |

| p-Acetyl Phenylalanine (pAF)* for all (Filter sterilized) | |
| --- | --- |
| Component | g or ml |
| p-Acetyl Phenylalanine | 4 g |
| 1 M HCl | 6.25 ml |
| Water | 12.5 ml |

*The final volume became 21.25 ml. Used all of the resulting solution after filtration.

| L-(+)-Arabinose 20% for all (Filter sterilized) | | |
| --- | --- | --- |
| Component | g/l | ml |
| L-(+)-Arabinose | 200 | 1.25 |

* Used all of the resulting solution after filtration.

For each fermentation, the following was performed. 25% Struktol J 673 (0.1 L) was prepared and sterilized by steam. 15% NH$_3$*H$_2$O (0.3 L) was prepared for pH control and as nitrogen source. 10% H$_3$PO$_4$ (0.2 L) was prepared for pH control. Concentrated feed, 1 L, was prepared in feeding container 1. YE/glycerol mixture, 2 L each, was prepared in feeding container 2.

The fermenter was set-up. It was sterilized with 2.5 L Base Salts solution. The fermentor was brought to the following conditions: temperature=37° C., pH=6.9, 1.0 VVM air based on 5 L working volume (Air flow can be increased up to 2 VVM).

The concentrated feed was added to the fermentor, and 2.5 ml of 50 mg/mL kanamycin was added.

Process Schedule

Day 1 (Stage I):

About 1 ul from the E. coli MCB (master cell bank, glycerol stock) was stabbed, and 1 μl of the glycerol stock was transferred into 2 ml batch medium+kanamycin in a culture tube. The composition of the batch medium was described above.

Day 2 (Stages II and III):

Stage II:

The culture tube contained a cell density of about 1-6 (OD$_{600}$). 0.01-2 ml of culture tube culture was transferred into 60 ml batch medium+kanamycin in a 250 ml shake flask. Only healthy cells that were not subjected to any carbon starvation were used. The composition of the batch medium was described above.

Stage III:

The fermentor was inoculated to an initial $OD_{600}$ of about 0.05. The amount of the cells (in L) needed from Stage II is $$\frac{2.5L \times 0.05}{4} = 0.031 \ L \ (if \ flask \ OD600 = 4)$$

The cells were allowed to grow batch-wise for approximately 10 hours. The specific time was dictated by the depletion of glycerol by the culture. Glycerol depletion is indicated by a sudden decrease in STIRR speed followed by increase in $pO_2$ signal. The concentrated glycerol feed was started. The feed rate was based on Formula I:

$$F(0) = \frac{\mu_{set}}{Y_{x/s}} \times X(0) \times V(0) \times Exp(\mu_{set} \times 0) \times \frac{1}{S_f}$$

$\mu_{set} = 0.15 \ h^{-1}$;

$X(0) = Yx/s * 8.0 \ g/l$ $V(0) = 2.5 \ l$;

$Exp(\mu_{set} * 0) = 1$;

$S_f = 400 \ g/l$.

The above values were inserted into the equation, F(0)=7.5 ml/h. A scaling factor was used, so the real F(0)' will be 8.6 ml/h.

$F(t)'=F(0)'*Exp(\mu_{set}*t)$. For t=13 hours, F(t)'=60.4 ml/hour.

The flow rate was held at 60.4 ml/hour for 1 hour.

For the run, pAF was added at the start of feed 2. Arabinose induction was added 1 hour after pAF addition. The final feed2 flow rate was maintained until harvest.

Day 3 (Stages 1V and V)

Stage IV.

The culture $OD_{600}$ reached about 50 to 60. At 1 hour before induction (feed time=14 hours), 1) the concentrated feed (rate=60.4 ml/hour at this time) was stopped. 2) YE/glycerol (200 g YE and 170 g glycerol per liter) feed was started at 108.7 ml/hour. 3) A 21.25 ml bolus that contained 4.0 g pAF was added. Control of the pH was continued at pH 6.9, using 15% ammonium hydroxide and 10% phosphoric acid to adjust pH when needed. 3a) The feed 2 rate was linearly increased for 3 hours, reaching 141.3 ml/hour at feed time=17 hours. The culture OUR should remain at about 250 mmol/l/hour. 3b) The carbon source transition was continued for 1 hour. 3c) An adequate amount of cells ($OD_{600}$*ml=2) was saved for SDS-PAGE analysis.

At the time of induction (feed time=15 hours), induction was done with 1.25 ml 20% (w/v or 200 g/l) L-(+)-arabinose. Adequate amounts of cells ($OD_{600}$*ml=2) were saved at 4 hours, 6 hours, and 8 hours after induction for SDS-PAGE analysis. The induction lasted 8 hours.

Stage V:

The culture $OD_{600}$ was checked at the end of induction. An adequate amount of cells ($OD_{600}$*ml=2) was saved for SDS-PAGE analysis. 2×200 ml culture were collected by centrifugation for evaluation by ELISA. The cells were harvested using bucket centrifugation at 15,000 g for 22 minutes, and the cells were frozen at −80° C.

This procedure has been scaled to a 100 liter culture.

Example 6 hGH Purification, PEGylation, and hGH-PEG Purification Process Periplasmic Preparation from *E. coli*

1. Periplasmic Release of hGH

A 1.9 kilogram bacterial cell paste was resuspended in approximately 7.6 liters (4-volumes) of 4° C. PR Buffer (50 mM TRIS, 10 mM EDTA, 0.07% Triton X-100, pH 8.0) to obtain 20% solid. After stirring the suspension at 4° C. for 1 hour, 8M urea was added to obtain a final urea concentration of 0.3 M. The 8M urea solution was used within 48 hours of preparation. This suspension was then stirred at 4° C. for 1 hour. The suspension was centrifuged at 15,000×g for 45 minutes in a fixed angle J20 rotor (Avanti J20 XP centrifuge—Beckman Coulter) at 4° C. The supernatant was collected, and its volume measured (approximately 7.7 L). The sample was designated as PRS with the date and lot number.

The PRS was filtered through a prefilter, Sartopure GF2 1.2 μm capsule (1000 cm²) (Part # 5571303P800B). The filtrate flow rate was 0.86 L/min at pump setting 1 (MasterFlex I/P Model 7529-10). The filtrate was collected and designated as PRSF with the date and lot number. The volume of PRSF was measured.

The PRSF was filtered through a Sartopore 2 0.8+0.45 μm filter capsule (500 cm²) (Part # 5441306G700B). The filtrate was collected and designated as PRSFF with the date and lot #. The volume of PRSFF was measured.

In-process analysis includes non-reduced SDS-PAGE analysis to confirm the presence of hGH in the correct form as compared with a reference standard, measurement of $A_{276}$, and ELISA for quantitation.

2. UF/DF (Ultrafiltration/Diafiltration) I—Buffer Exchange for QFF

The following filter was used for this procedure: Sartorius Sartocon Slice 10K Hydrosart cassette, 2×1000 cm². Additional parameters include: filtrate (permeate) flow rate of 100-160 ml/minute, feed pressure of 24-26 psi, and retentate pressure of 5-6 psi.

The system was depyrogenated with 1N NaOH, and circulation allowed for 30-45 minutes. The system was rinsed with approximately 4 liters of MilliQ water until the pH dropped to below 8. Equilibration was completed with QFF Buffer A (10 mM Bis-TRIS, pH 6.5) for at least 5 minutes. PRSFF was concentrated down to approximately one tenth of its volume. It was then diafiltrated with 8-volumes of QFF Buffer A. The retentate was recirculated for 3-5 minutes. After collecting the retentate, the system was flushed with 300-350 ml of QFF Buffer A, and the rinse solution was combined with the retentate. The combined sample was filtered through a Sartopore 2 0.8+0.45 μm capsule (500 cm²) (Part # 5441306G700B), and the filtrate collected was designated as QFF Load with the date and lot number. It was a brownish color. The volume of QFF Load was measured, and QFF Load was either processed within 2 hours or stored at 4° C. overnight.

The system was rinsed with MilliQ water and cleaned with 1 N NaOH by circulating for 30-45 minutes. Rinsing was then completed with MilliQ water until the pH was less than 8. The cassette was stored in 0.1N NaOH.

In-process analysis includes measurement of $A_{276}$ to quantify total protein and determine the amount of QFF Load for the next step, ELISA, LAL, and non-reduced SDS-PAGE analysis.

3. Column 1—Q Sepharose FF Chromatography

Q Sepharose Fast Flow was obtained from GE Healthcare. The column dimension was as follows: 70 mm I.D.×16 cm=616 ml (INdEX70/500 column). The operating capacity was 150 mg total protein (140-160 mg, based on $A_{276}$) or 10 mg GH (based on ELISA) per ml QFF. The flow rate was 100 ml/min (linear velocity: 156 cm/h). QFF Buffer A consisted of 10 mM Bis-TRIS, pH 6.5 with a conductivity of 0.6 mS/cm. QFF Buffer B consisted of 10 mM Bis-TRIS, 0.1 M NaCl, pH 6.5 with a conductivity of 11.5 mS/cm.

The AKTA explorer system was depyrogenated. To accomplish this, the "AKTA depy" program was run three times: all buffer lines were placed in MilliQ water for the first run of the program, and then in 1 N NaOH for the second run. An incubation was completed for 30 minutes, and the buffer lines were placed in MilliQ water again for the third run. The program "QFF depy equi" was run to depyrogenate and equilibrate the QFF column at 30 cm/h linear velocity: the QFF column was washed with 2 column volumes of MilliQ $H_2O$, 2 column volumes of 1 N NaOH/1M NaCl, incubated for 30 min, washed with three column volumes of Q Buffer C (10 mM TRIS, 2 M NaCl, pH 7.0 with a conductivity of 156 mS/cm), then equilibrated with 4 column volumes of QFF Buffer A.

The QFF Load was then loaded onto the column. The column was washed with 4 column volumes of QFF Buffer A, and 7 column volumes of 10% QFF Buffer B in A. Elution was performed with 6 column volumes of 60% QFF Buffer B in A. The column may be washed with 3 column volumes of QFF Buffer B. The elution peak was collected. The collected eluate was designated as QFF Pool with the date and lot number. The pool was processed within 2 hours or stored at 4° C. overnight.

The column was washed with 3 column volumes of Q Buffer C. Then 3 column volumes of 1 N NaOH/1M NaCl was pumped in, and an incubation done for 1-6 days. If the column was not used within 6 days, it was rinsed with 1 column volume of 1 N NaOH/1M NaCl, 3 column volumes of Q Buffer C, 3 column volumes of MilliQ $H_2O$, and 2.5 column volumes of 20% EtOH or 10 mM NaOH. An extensive cleaning of the column was done every 3-5 cycles such that following the 1 N NaOH/1 M NaCl incubation, it was washed upflow with 3 column volumes of Q Column Cleaning Buffer (0.5% Triton X-100, 0.1 M acetic acid), incubated for 60-80 hours, washed with 1.5 column volumes of MilliQ $H_2O$, 1 column volume from 0 to 70% EtOH, 5 column volumes of 70% EtOH, and 2.5 column volumes of 20% EtOH.

4M NaCl was added to the QFF Pool to reach a final 0.1 M concentration. The product was filtered through a Sartobind Q100x filter (Part #Q100X), pre-equilibrated with QFF Buffer B, to remove endotoxin. The filtrate was collected and labeled as QFF PoolQ with the date and lot #. The filtrate was processed within 2 hours or stored at 4° C. overnight.

The QFF PoolQ was passed through a Sartobran 0.45+0.2 μm filter capsule (300 cm$^2$) (Part # 5231307H500B) and the filtrate collected. The filtrate was designated QFF PoolQF with the date and lot number. The QFF PoolQF was processed within 2 hours or stored at 4° C. overnight.

In-process analysis includes measurement of $A_{276}$, ELISA, LAL, and non-reduced SDS-PAGE analysis.

4. Column 2—Phenyl Sepharose HP Chromatography

Phenyl Sepharose High Performance was obtained from GE Healthcare. The column dimension was as follows: 100 mm I.D.×9.7 cm=761 ml (INdEX100/500 column). The operating capacity was 4.5-9 mg total protein, preferably 6-8 mg total protein (based on $A_{276}$), per ml of Phenyl HP. The flow rate was 100 ml/minute (linear velocity: 76.4 cm/h). Phe Buffer A consisted of 20 mM TRIS, 0.4 M sodium citrate pH 7.0. Phe Buffer B consisted of 10 mM TRIS, pH 7.0 with a conductivity of 0.9 mS/cm.

The AKTA explorer system was depyrogenated. The "AKTA depy" program was run 3 times: all buffer lines were placed in MilliQ water for the 1$^{st}$ run and then in 1 N NaOH for the 2$^{nd}$ run. An incubation was completed for 30 minutes, and then all buffer lines were placed in MilliQ water again for the 3$^{rd}$ run. The "PheHP depy equi" program was run to depyrogenate and equilibrate the Phe column at 30 cm/h linear velocity: it was washed with 2 column volumes of MilliQ $H_2O$, 2 column volumes of 1 M NaOH/1 M NaCl, incubated for 30 minutes, then equilibrated with 4 column volumes of Phe Buffer A.

1.4 M sodium citrate was added to the QFF PoolQF to a final concentration of 0.4 M. The mixture was stirred at room temperature for approximately 1 hour to dissolve the sodium citrate, and the solution was warmed to >16° C. The QFF PoolQF+NaCitrate was loaded onto the column. The column was washed with 4 column volumes of Phe Buffer A, then 9-17 column volumes of 27% Phe Buffer B in A. The length of the 27% Phe Buffer B wash was dependent on total protein amount loaded onto the column. The more protein was loaded, the less column volume of 27% Phe Buffer B was required. Elution was performed with 8-10 column volumes of 48% Phe Buffer B in A. The column was washed again with 100% Phe Buffer B. The 48% B elution peak was collected and designated as Phe Pool with the lot number. The next step was performed within 2 hours, or the pool was stored at 4° C. overnight.

The Phe column was washed upflow with 2 column volumes of 1 M NaOH, incubated for 30 minutes, washed with 3 column volumes of Phe Buffer A, 3 column volumes of $H_2O$, and 2.5 column volumes of 20% EtOH or 10 mM NaOH. After 3-5 cycles, the Phe column was washed upflow with 2 column volumes of 1 M NaOH, incubated for 30 minutes, washed with 3 column volumes of Phe Buffer A, 3 column volumes of $H_2O$, 0-70% EtOH over I column volume, 3 column volumes of 70% EtOH, and finally, stored in 20% EtOH or 10 mM NaOH.

In-process analysis includes measurement of $A_{276}$, ELISA, LAL, and non-reduced SDS-PAGE analysis.

5. UF/DF II—Formulation of In-Process Bulk GH

The following filter was used for this procedure: Sartorius Sartocon Slice 10K Hydrosart cassette, 1000 cm$^2$. Additional parameters include: filtrate (permeate) flow rate of 50-90 ml/min, feed pressure of 20-27 psi, and retentate pressure of 3-4 psi. The UF/DF II Buffer consisted of 10 mM Sodium Phosphate, 20 g/L Glycine, and 5 g/L Mannitol, pH 7.0.

The system was depyrogenated with 1N NaOH, and circulation allowed for 30-45 minutes. The system was rinsed with approximately 4 liters of MilliQ water until the pH dropped to below 8. Equilibration was completed with UF/DF II Buffer for at least 5 minutes.

The Phe Pool was concentrated down to approximately 700-900 ml (or approximately 500-700 ml in the retentate flask). Diafiltration was completed with 4.2-5.4 liters (6-volumes) of the UF/DF II Buffer. The retentate was recirculated for 3-5 minutes, and the retentate was collected. The system was flushed with 100-200 ml of UF/DF II Buffer, and the rinse solution was combined with the retentate. The combined sample was filtered with a Sartobran 0.45+0.2 μm capsule (150 cm$^2$) (Part # 5231307H400B), and the filtrate was designated as Y35pAF-pBx and was also referred to as "in-process bulk."

The protein concentration of Y35pAF-pBx was determined by measuring $A_{276}$ of a diluted sample, using $A_{276}^{1\ mg/ml}=1.037$. The in-process bulk can be stored at 4° C. for up to 1 week. For long term storage, it was aliquoted and kept at −80° C.

The system was rinsed with MilliQ water and cleaned with 1 N NaOH by circulating for 30-45 minutes. Then it was rinsed with MilliQ water until the pH was below 8. The cassette was stored in 0.1 N NaOH.

In-process analysis includes RP-HPLC, measurement of $A_{276}$, ELISA, LAL, and non-reduced SDS-PAGE analysis.

6. UF/DF IIa—Concentration and Buffer Exchange for PEGylation

The following filter was used for this procedure: Sartorius Sartocon Slice 10K Hydrosart cassette, 200 cm². Additional parameters include: filtrate (permeate) flow rate of 12-14 ml/min, feed pressure of approximately 25 psi, and retentate pressure of 0-0.5 psi. The Reaction Buffer consisted of 20 mM Sodium Acetate, 20 g/L Glycine, 5 g/L Mannitol, 1 mM EDTA, pH 4.0 with a conductivity of 2.6 mS/cm.

The system was depyrogenated with 1N NaOH and circulation allowed for 30-45 minutes. The system was rinsed with approximately 2 liters of MilliQ water until the pH dropped to below 8. Equilibration was performed with Reaction Buffer for at least 5 minutes.

The pH of an amount of the in-process bulk from step 5 was adjusted to approximately 4 by adding 3.7% (v/v) of 10% acetic acid. Then it was concentrated down to the target volume with 8 mg/ml concentration based on the amount of starting hGH used. The sample was then diafiltered with 5 volumes of Reaction Buffer. The retentate was recirculated for 3-5 minutes, and then retentate was collected. The system was flushed with 80-120 ml of Reaction Buffer and combined with the retentate. The combined retentate was filtered through a Sartobran 0.45+0.2 μm capsule (150 cm²) (Part # 5231307H400B). The filtrate was designated as Y35pAF-pBx/pH4 with the date. The sample can be stored at 4° C. overnight.

The protein concentration of Y35pAF-pBx/pH4 was determined by measuring $A_{276}$ of a 20-fold diluted sample using $A_{276}^{1\ mg/ml}=1.037$. The concentration of Y35pAF-pBx/pH4 was adjusted to 7 mg/ml (5-9 mg/ml) by dilution with the Reaction Buffer.

7. PEGylation Reaction

Figure 5:
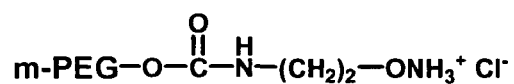
FIG. 5 shows a chemical structure of a linear, 30 kDa PEG.

The molecular weight of hGH with the p-acetyl-phenylalanine substituted for the tyrosine at position 35 (Y35pAF) was 22,149 Da, and the molecular weight of lot of mPEG-oxyamine was 30,961 Da. See SEQ ID NO: 2 of US Patent Publication No. 2005/0170404 for the sequence of wild-type mature hGH. FIG. 5 shows the chemical structure of the PEG used. Using the molar ratio of PEG:Y35pAF=5, the amount of 30K MPEG-Oxyamine required was calculated. The PEG powder was weighed and added to the 7 mg/ml Y35pAF solution at 25-28° C. slowly while stirring. Large pieces of solid PEG were manually broken up. Following the last addition, the reaction mixture was placed at 28° C. with gentle stirring for 39-50 hours. The reaction formed an oxime bond between hGH and PEG.

In-process analysis includes non-reduced SDS-PAGE analysis to confirm the PEGylation.

8. Column 3—Source 30Q Chromatography

Source 30Q was obtained from GE Healthcare. The column dimension was as follows: 70 mm I.D.×17.5 cm=673 ml (INdEX 70/500 column). The operating capacity was 2.4 mg (1-2.8 mg) GH per ml SourceQ. The flow rate was 80 ml/minute (linear velocity: 125 cm/h). SourceQ Buffer A consisted of 5 mM TRIS, pH 7.0. SourceQ Buffer B consisted of 5 mM TRIS, 0.1 M NaCl, pH 7.0.

To depyrogenate the AKTA explorer system, the program "AKTA depy" was run 3 times: all buffer lines were placed in MilliQ water for the 1$^{st}$ run and in 1 N NaOH for the 2$^{nd}$ run. An incubation was completed for 30 minutes, and all buffer lines were placed in MilliQ water again for the 3$^{rd}$ run. To depyrogenate and equilibrate the SourceQ column, the program "SourceQ depy equi" was run: the SourceQ column was washed with 2 column volumes of MilliQ $H_2O$, 2 column volumes of 1 M NaOH/1M NaCl, incubated for 30 minutes, washed with 5 column volumes of SourceQ Buffer B, then equilibrated with 5 column volumes of SourceQ Buffer A.

20% (v/v) of 0.5 M TRIS base was added to the reaction mixture from the previous step (step 7). The sample was then passed through a Sartobran 0.45+0.2 μm filter capsule (150 cm²) (Part # 5231307H400B). A 20-fold dilution was performed with 9-volumes of SourceQ Buffer A and 10-volumes of MilliQ $H_2O$. The diluted sample was then loaded onto the column. The column was washed with 5 column volumes of SourceQ Buffer A. Elution was performed with a linear gradient of 0-50% SourceQ Buffer B over 10 column volumes. Fractions were collected at approximately ⅕ column volume/ fraction. SE-HPLC and non-reduced SDS-PAGE analysis were performed on the 1$^{st}$ major peak to determine the pool. The pooled fractions were designated as SourceQ pool with the date and lot number. The pool was stored at 4° C. overnight.

9. UF/DF (Ultrafiltration/Diafiltration) III—Concentrate and Buffer Exchange for Formulated Bulk The following filter was used: Sartorius Sartocon Slice 10K Hydrosart cassette, 200 cm². Additional parameters include: filtrate (permeate) flow rate of 12-14 ml/min, feed pressure of approximately 25 psi, and retentate pressure of approximately 0-0.5 psi.

The system was depyrogenated with 1 N NaOH, and circulation was allowed for 30-45 minutes. The system was rinsed with approximately 2 liters of MilliQ water until the pH dropped to below 8. Equilibration was then performed with Formulation Buffer for at least 5 minutes.

The SourceQ pool (step 3.6) was concentrated to the target volume of 8 mg/ml concentration based on the amount of starting material used. Diafiltration was performed with 6-volumes of Formulation Buffer. The retentate was recirculated for 3-5 minutes, and the retentate was collected. The system was flushed with 50-100 mls of Formulation Buffer and combined with the retentate. The combined retentate was sterile filtered with a Sartobran 0.45+0.2 μm capsule (150 cm²) (Part # 5231307H400B) using sterile technique in a biosafety hood or a Class 100 hood. The sterile sample was designated as PEG30-pY35pAF with the lot number.

The equivalent hGH concentration of PEG30-pY35pAF was determined by measuring $A_{276}$ of a diluted sample by using $A_{276}^{1\ mg/ml}=1.145$ with triplicate dilutions and measurements. The PEG30-pY35pAF can be stored at 4° C. for up to 3 days. For long term storage, it was aliquoted and kept at −80° C.

Material from a strain of W3110 has been processed with this protocol. The strain used was transformed with orthogonal tRNA, orthogonal aminoacyl tRNA synthetase, and hGH constructs. The PEG-Y35pAF purity was >95% based on HPLC and SDS-PAGE analysis.

Full release assays include, but are not limited to, assays that evaluate attributes of PEG30-pY35pAF such as appearance, dissolve time, identity and purity, potency, safety, and other attributes including, but not limited to, pH. Test methods for evaluation include, but are not limited to, reduced and non-reduced SDS-PAGE, SE-HPLC, RP-HPLC, IEX-HPLC, CEX-HPLC, measurement of host cell protein, measurement of residual DNA, $A_{276}$ for concentration, cell proliferation assays, LAL, pyrogen, sterility, bioburden (microbial limit), Karl Fisher (water content), content uniformity, and osmolality.

The buffer used in the buffer exchange of UF/DF III may be any suitable buffer. Additional steps after UF/DFIII include, but are not limited to, lyophilization. Lyophilization can be done using standard techniques known to those of ordinary skill in the art.

This method has been performed with a bacterial cell pellet of about 2.7 kg.

Example 7

Additional Methods

Purity Analysis by SDS-PAGE

The following method was used to evaluate the purity of in-process and final bulk recombinant hGH and PEG-recombinant hGH conjugates by SDS-PAGE, followed by total protein staining. Any charged molecule such as a protein will migrate when placed in an electric field. The velocity of migration of a protein in an electric field depends on the strength of the electric field, the net electric charge on the protein, and the frictional resistance. The frictional resistance is the function of the size and shape of the protein. When denatured in the presence of excess SDS, most proteins bind SDS in a constant weight ratio such that they have essentially identical charge densities and migrate in polyacrylamide gels according to protein size. Proteins separated by gel electrophoresis can be detected by Coomassie Brilliant Blue staining.

Equipment for this procedure included, the following or equivalents thereof: XCell Surelock Mini-Cell (Invitrogen), heat block set to +70-80° C., power supply (up to 200V), microcentrifuge (such as Beckman Coulter Microfuge 18 or 22R), and reciprocal shaker. Reagents included NuPAGE MOPS SDS Running Buffer (20×, Invitrogen PN NP0001); NuPAGE MES SDS Running Buffer (20×, Invitrogen PN NP0002); NuPAGE LDS Sample Buffer (4×, Invitrogen PN NP0007); NuPAGE Sample Reducing Agent (10×, Invitrogen PN NP0009); 12% Bis-Tris NuPAGE precast gel, 1.0mm× 10-well (Invitrogen PN NP0341BOX); 4-12% Bis-Tris NuPAGE precast gel, 1.0 mm×10-well (Invitrogen PN NP0321BOX); Pre-Stained Molecular Weight Marker (SeeBlue Plus2, Invitrogen PN LC5925); MilliQ-quality $H_2O$ or equivalent; SimplyBlue SafeStain (Invitrogen PN LC6065) or equivalent; reference standard (WHO rhGH standard; calibration solutions for rhGH (Y35pAF-pB2/pB3, 2 mg/ml); calibration solutions for the pEG-rhGH conjugate (PEG30-pY35pAF-01, 2 mg/mL). Protein concentrations of the standards and the test article were measured using standard techniques known in the art.

Analysis of pre-PEGylation Purification Step Samples

3 µg reference standard (RS, e.g. calibration solution Y35pAF-pB2/pB3) were prepared under non-reducing conditions. 3 µg of reference standard was added to 4×LDS and MilliQ $H_2O$ to obtain a 28 µl sample in 1×LDS. Similarly, the rhGH test article was prepared under non-reducing conditions. Both the rhGH test article and reference standards were heated at +70-80° C. for 8-10 minutes and centrifuged prior to loading onto the gel. The 12% Bis-Tris NuPAGE precast gel was prepared with 1×MOPS SDS Running Buffer according to manufacturer's instructions. The gel was loaded as follows: Pre-Stained Molecular Weight Marker, 3 µg reference standard, test articles and run with a maximum setting of 200V for 50 minutes. The gel was incubated in di-$H_2O$, stained with shaking using SimplyBlue or an equivalent, and destained with water. The major band position of the rhGH test article is compared to that of the 3 µg reference standard.

Analysis of the Purified In-Process Bulk rhGH

20 µg and 1 µg of the reference standard (RS, e.g. WHO rhGH) were prepared under non-reducing and reducing conditions. For non-reduced conditions, 20 or 1 µg of reference standard was added to 4×LDS and MilliQ $H_2O$ to obtain a 28 µl sample in 1×LDS. For reduced conditions, 20 or 1 µg of reference standard was added to 4×LDS, 10× Reducing Agent, and MilliQ $H_2O$ to obtain a 28 µl sample in 1×LDS and 1× Reducing Agent. Both the rhGH test articles and reference standards were heated at +70-80° C. for 8-10 minutes and centrifuged prior to loading onto the gel. 12% Bis-Tris NuPAGE precast gels were run in 1×MOPS SDS Running Buffer according to manufacturer's instructions with one unit for the non-reducing condition and the other unit for the reducing condition. The gels were loaded as follows: PreStained Molecular Weight Marker, 1 µg reference standard, 20 µg reference standard, blank lane, followed by the test articles at a maximum setting of 200V for 50 minutes. The gels were incubated in di-$H_2O$, stained with shaking using SimplyBlue or an equivalent, and destained with water. The major band position of the rhGH test article is compared to the 20 µg reference standard. In the lane of the rhGH test article, no band apart from the major band should be more intense than the major band in the lane of the 1 µg reference standard (5%).

Analysis of PEGylation of rhGH and Purification of PEGrhGH

The reference standard (RS, e.g. calibration solution PEG30-pY35pAF-01) was prepared under non-reducing conditions. 5 µg of PEG30-pY35pAF-01 was added to 4×LDS and MilliQ $H_2O$ to obtain a final 28 µl sample in 1×LDS. 5-20 µg of the test article, depending on the procedure being analyzed, was added to 4×LDS and MilliQ $H_2O$ to obtain a final 28 µl sample in 1×LDS. For the PEGylation reaction mixtures, 15-20 µg of the test article was used. For the analysis of the PEGylation reaction mixture, a comparison was made between: a) serial concentrations of the rhGH prior to the additional of PEG at pH 4 to allow estimation of the relative percent of non-PEGylated rhGH remaining in the PEGylation reaction mixture; b) 10 µL of a 1/10 dilution of the reaction mixture. 5-20 µg of the test article was used from column fractions during the purification post PEGylation. For the analysis of the PEG-rhGH column fractions, column fractions were compared by using fixed volumes of each column fraction (typically 21 µL of each column fraction).

PEG-rhGH test articles or PEG-rhGH reference standard samples were not heated. Samples were centrifuged and loaded onto a 4-12% Bis-Tris NuPAGE precast gel prepared with 1×MES SDS Running Buffer according to manufacturer's instructions. The gel was loaded as follows: Pre-Stained Molecular Weight Marker, 5 µg reference standard, followed by the test articles and run with a maximum setting of 200V for 35 minutes. The gels were incubated in di-$H_2O$, stained with shaking using SimplyBlue or an equivalent, and destained with water.

The electropherogram of the PEG-rhGH test article should conform to the electropherogram obtained with the PEG-rhGH reference standard.

Analysis of Final PEGylated rhGH Product

10 µg of the reference standard (RS, e.g. calibration solution PEG30-pY35pAF-01) was prepared under non-reducing and reducing conditions. 10 ug of PEG30-pY35pAF-01 (2 mg/mL) was added to 4×LDS and MilliQ $H_2O$ to obtain a final 28 µl sample in 1×LDS. For reduced conditions, 10 µg of reference standard was added to 4×LDS, 10× Reducing Agent, and MilliQ $H_2O$ to obtain a 28 µl sample in 1×LDS and 1× Reducing Agent. Similarly, 10 µg of pegylated rhGH test articles were also prepared under non-reduced and reduced conditions. The PEG-rhGH test articles and PEG-rhGH reference standards were not heated, but were snap centrifuged prior to loading on 4-12% Bis-Tris NuPAGE precast gels prepared with 1×MES SDS Running Buffer according to manufacturer's instructions. The gels were loaded in the order of Pre-Stained Molecular Weight Marker, 10 µg reference standard, blank lane (recommended to minimize potential carryover effects), followed by the test articles with a maximum setting of 200V for 35 minutes. The gels were incubated in di-$H_2O$, stained with shaking using SimplyBlue or an equivalent, and destained with water.

The electropherogram of the PEG-rhGH test article should conform to the electropherogram obtained with the PEG-rhGH reference standard. The electropherogram of the PEG-rhGH test article should conform to the electropherogram obtained with the PEG-rhGH reference standard. Any bands that do not match the reference standard may be degradation products or aggregates. Higher molecular weight bands may represent aggregates, and lower molecular weight bands may represent polypeptide that is no longer conjugated to PEG.

Purity and Chemical Degradation Analysis of rhGH by CEX-HPLC/IEX-HPLC

The following method was used to assess relative purity and potential chemical degradation (i.e. deamidation) of PEGylated recombinant human growth hormone (rhGH) by cation-exchange high performance liquid chromatography (CEX-HPLC). CEX-HPLC is a technique that relies on charge-charge interactions between a protein and the charges immobilized on the resin. Cation exchange chromatography takes advantage of the positively charged ions of a protein that bind to the negatively charged resin. A common structural modification of rhGH deamidation of asparagine (Asn) residues, and this CEX-HPLC method permits the separation of deamidated and deamidation intermediates of PEGylated and nonPEGylated rhGH. This method was used to support identification and purity assessment of PEGylated rhGH. Some partial degradation products of rhGH are observable using this technique.

Equipment for this procedure included, the following or equivalents thereof: UV/Vis Spectrophotometer (Agilent 8453 or equivalent); 50 µl quartz cuvette; 0.5 mL Vivaspin concentrators (if needed; Vivascience 10,000 MWCO, PES, VS0102 or equivalent); PD-10, NAP-10, or NAP-5 column (GE Healthcare, Cat. #17-0851-01, 17-0853-01, 17-0854-01); HPLC vials and caps (Alltech 100 µl screw cap polypropylene vials #12962, TFE liner caps #73048, open hole screw caps #73044, or equivalent); clean 1 and 2 L glass bottles; column—PolyCAT A 4.6×200 mm, 5µ, 1000 Å (PolyLC, 204CT0510) and PolyCAT A guard column, 4.6×10 mm, 5µ, 1000 Å (PolyLC, JGCCT0510); high-pressure liquid chromatography instrument capable of performing linear gradients (such as Agilent 1100 HPLC equipped with a vacuum degasser, quaternary pump, thermostatted autosampler, thermostatted column compartment, diode array detector (DAD), and Chemstation chromatography software).

Reagents for this procedure included water (Milli-Q quality or equivalent) and solid chemicals are analytical grade or better and solvents are HPLC grade or better, unless otherwise noted. Storage of reagents and procedural steps occurred at room temperature, unless otherwise indicated. Examples of such chemicals include Ammonium Acetate, Spectrum A2149, HPLC grade, or equivalent; Acetonitrile, Fisher A998; HPLC grade, or equivalent; Ammonium Bicarbonate, Fluka # 09830, Ultra >99.5%, or equivalent; Glacial Acetic Acid, Fisher # 64-19-7, HPLC grade, or equivalent; Sodium Citrate Dihydrate, Spectrum S0165, USP grade, or equivalent; Glycine, Spectrum AM125 or equivalent; Mannitol, Spectrum MA165, or equivalent; 6N HCl, Mallinckrodt 2662-46, or equivalent.

Mobile phase A buffer was 50 mM Ammonium Acetate, pH 4.25, 40% Acetonitrile (AcCN), and Mobile Phase B buffer was 500 mM Ammonium Acetate, pH 4.25, 40% AcCN. Additional reagents prepared were 10% acetic acid; Buffer for Deamidation: 30 mM Ammonium Bicarbonate, pH 9.0; and Sample Dilution Buffer: 20 mM Sodium Citrate, 20 g/L Glycine, 5 g/L Mannitol, pH 6.0, each sterile filtered using 0.22 µm PES filters (Corning #431098, or equivalent).

World Health Organization (WHO) rhGH (Cat. # 98/574) was used as a non-PEGylated hGH standard. It was reconstituted in 1.0 ml of water and diluted to 1.1 mg/ml using dilution buffer. 10% (v/v) of 10% acetic acid was added to bring the pH between pH 3.8-4.3 with a final concentration of 1.0 mg/ml (acceptable range 0.9-1.1 mg/ml). Another non-PEGylated hGH standard, the calibration solution Y35pAF-pB2/pB3, was prepared in a similar fashion. A PEGylated hGH standard, calibration solution PEG30-pY35pAF-01, was also prepared in a similar fashion.

For the PEGylated Resolution Solution, the PEG30-pY35pAF-01 calibration solution was buffer exchanged into 30 mM Ammonium Bicarbonate, pH 9.0 buffer using a PD-10, Nap-10, or Nap-5 desalting column. The standard was concentrated using a 0.5 mL Vivaspin concentrator to approximately 2 mg/ml (acceptable range 1.9-2.1 mg/ml), and the sample was incubated at 37° C. for 24 hours. The sample or portion of the sample needed was diluted to 1.1 mg/ml using dilution buffer, and 10% (v/v) of 10% acetic acid was added to bring pH between pH 3.8-4.3 with a final concentration of 1.0 mg/ml (acceptable range 0.9-1.1 mg/ml).

The test article was diluted to 1.1 mg/ml using dilution buffer and 10% (v/v) of 10% acetic acid was added to bring pH between pH 3.8-4.3 with a final concentration of 1.0 mg/ml (acceptable range 0.9-1.0 mg/ml). Protein concentrations of the standards and the test article were measured using standard techniques known in the art.

Procedure

The instrument was set-up with the following conditions: 1) Column: PolyCAT A 204CT0510 and JGCCT0510; 2) Auto sampler Temperature: room temperature; 3) Pump Setup: step gradient: 81.5-108.5 mM Ammonium Acetate pH 4.25 (7-13% B), followed by 108.5-500 mM Ammonium Acetate pH 4.25 (13-100% B); 4) Table 4;

TABLE 4

| Time | Mobile Phase A | Mobile Phase B | Flow (ml/min) | Pressure (bar) |
|---|---|---|---|---|
| 0 | 100 | 0 | 1.0 | 140 |
| 10 | 100 | 0 | 1.0 | 140 |
| 11 | 93 | 7 | 1.0 | 140 |
| 91 | 87 | 13 | 1.0 | 140 |
| 102 | 0 | 100 | 1.0 | 140 |
| 118 | 0 | 100 | 1.0 | 140 |
| 119 | 100 | 0 | 1.0 | 140 |
| 151 | 100 | 10 | 1 | 140 |

5) Injector Setup—Injection: Standard Injection; Injection Volume: 25 µl; Draw Speed: 50 µl/min; Injection Speed: 50 µl/min; Needle wash: 15 µl $H_2O$; Stop Time: As pump; 6) DAD signals; Table 5;

TABLE 5

| Sample | Bw | Reference | Bw | Units |
|--------|----|-----------|----|----|
| 280 | 4 | 600 | 100 | nm |
| 276 | 4 | 600 | 100 | nm |
| 214 | 8 | 600 | 100 | nm |
| 220 | 4 | 600 | 100 | nm |
| 250 | 8 | 600 | 100 | nm |

Peak Width: >0.1 min; Slit: 4 nm; Stop Time: as pump; 7) Column Thermostat: Temperature: 30° C.; record the temperature.

The column was equilibrated with 10-15 column volumes of 100% mobile phase A. 25-50 µl of the PEGylated calibration solution PEG30-pY35pAF-01 was injected. The main PEGylated peak eluted at a retention time of 56.97 min (±0.5 min). Next, 25-50 µl of the WHO or calibration solution Y35pAF-pB2/pB3 was injected and the HPLC program was run. The main non-PEGylated peak eluted at a retention time of 98.54 min (±0.5 min), a relative retention time of 1.73±0.01 to the main PEGylated peak.

25-50 µl of the PEGylated resolution solution was then injected. In the chromatogram obtained, the main PEGylated peak eluted at a retention time of 56.97 min (±0.5 min), and the PEGylated deamidated peak eluted at a retention time of 0.79±0.02 relative to the main peak (45.23±0.3 min; (current conditions result in a resolution of 2.3±0.02).

25-50 µl of the PEGylated test article was then injected, and the HPLC program was run. The samples were run in triplicate, and average retention times were noted. Chromatograms were generated with absorbance (280 nm).

Data Analysis

The retention time of the PEGylated rhGH test article was compared with the calibration solution PEG30-pY35pAF-01. The average purity of the test article was calculated using: (Integration area of the main peak/integration areas of all peaks)×100%. Any peak(s) due to the solvent were disregarded.

Purity Determination of rhGH by SEC-HPLC

This procedure was used to assess the purity of recombinant human growth hormone (rhGH) including in-process material and PEGylated rhGH by size-exclusion high performance liquid chromatography (SEC-HPLC). This test separates monomer from dimer and other related substances of higher molecular weight in the sample, as well as PEGylated and nonPEGylated samples. SEC-HPLC is a technique using the stationary phase as a porous matrix which is permeated by mobile phase molecules. Sample molecules small enough to enter the pore structure are retarded, while larger molecules are excluded and therefore rapidly carried through the column. Thus, size exclusion chromatography means separation of molecules by size and the chromatographic elution time is characteristic for a particular molecule. This procedure is used to determine the percentage of monomer (PEGylated and unPEGylated) rhGH. Dimer and other high molecular weight proteins are observable using this technique.

References for this technique include European Pharmacopoeia 2002, p. 193; British Pharmacopoeia 2001, p. 1941; "High-Performance Size-Exclusion Chromatographic Determination of the Potency of Biosynthetic Human Growth Hormone Products" by R. M. Riggin et al. Journal of Chromatography 435 (1988), p. 307-318.

Equipment for this procedure included, the following or equivalents thereof: UV/Vis Spectrophotometer (Agilent 8453 or equivalent); 50 ul quartz cuvette; 0.5 mL Vivaspin concentrators (if needed; Vivascience 10,000 MWCO, PES, VS0102 or equivalent); HPLC vials and caps (Alltech 100 ul screw cap polypropylene vials #12962, TFE liner caps #73048, open hole screw caps #73044, or equivalent); clean 1 and 2 L glass bottles; Column—Tosohaas TSK Super SW3000 18675 and Super SW Guard Column 18762, a silica-based size exclusion HPLC column with a dimension of 4.6×300 mm, particle size of 4 µm and pore size of 250 Å along with a guard column having a dimension of 4.6×35 mm and 4µ particle size; High-pressure liquid chromatography instrument capable of performing linear gradients (such as Agilent 1100 HPLC equipped with a vacuum degasser, quaternary pump, thermostatted autosampler, thermostatted column compartment, diode array detector (DAD), Refractive Index detector (RID) and Chemstation chromatography software).

Reagents for this procedure included water (Milli-Q quality or equivalent) and solid chemicals are analytical grade or better and solvents are HPLC grade or better, unless otherwise noted. The storage of reagents and procedural steps occurred at room temperature, unless otherwise indicated. Examples of such chemicals included Monobasic Monohydrate Sodium Phosphate, Spectrum U.S.P. grade S0130, or equivalent; Dibasic Heptahydrate Sodium Phosphate, Spectrum U.S.P. grade S0140, or equivalent; 2-propanol, Fisher HPLC grade A451-4, or equivalent.

Mobile phase buffer was 97% of 63 mM sodium phosphate pH 7.0, 3% of 2-propanol. Solution A was 25 mM Sodium Phosphate, pH 7.0. Both were sterile filtered using 0.22 µm PES filters (Corning #431098, or equivalent).

World Health Organization (WHO) rhGH (Cat. # 98/574) was used as a nonPEGylated hGH standard. It was reconstituted with 1.0 ml of water and diluted to 1 mg/ml concentration (acceptable range 0.9-1.1 mg/ml) in WHO buffer. Another non-PEGylated hGH standard, calibration solution Y35pAF-pB2/pB3, was prepared in a similar fashion and diluted with 20 mM sodium citrate, 2% glycine, 0.5% mannitol, pH 6. A PEGylated hGH standard, calibration solution PEG30-pY35pAF-01, was also prepared in a similar fashion and diluted with 20 mM sodium citrate, 2% glycine, 0.5% mannitol, pH 6. For the Resolution Solution, the PEG30-pY35pAF-02 higher molecular weight standard was brought to 1 mg/ml concentration (acceptable range 0.9-1.1 mg/ml). This solution contains approximately 33% PEG-PEG-GH, 66.5% PEG-GH). Test material was diluted to approximately 1.0 mg/ml with Solution A (acceptable range 0.9-1.1 mg/ml). All sample concentrations were measured using standard techniques known in the art. The dilution of samples may be performed with any suitable buffer.

Procedure

The instrument was set-up with the following conditions: 1) Column: TSK Super SW3000 18675 and Guard Column 18762; 2) Pump Setup—gradient: isocratic; flow rate: 0.3 ml/min; duration: 25 min; Max Pressure: 120 bar; 3) Injector Setup—Injection: Standard Injection; Injection Volume: 10 µl; Draw Speed: 100 µl/min; Injection Speed: 100 µl/min; Needle wash: 100 ul $H_2O$; Stop Time: As pump; 4) DAD Signals: Table 6;

TABLE 6

| Sample | Bw | Reference | Bw | Units |
|--------|----|-----------|----|----|
| 214 | 4 | 600 | 100 | nm |
| 276 | 4 | 600 | 100 | nm |
| 220 | 8 | 600 | 100 | nm |
| 280 | 4 | 600 | 100 | nm |
| 250 | 8 | 600 | 100 | nm |

Peak Width: >0.05 min; Slit: 2 nm; Stop Time: as pump; 5) RID Signal—Temperature: 35° C.; Response Time: >0.2 min 4 s, standard; 6) Column Thermostat: Temperature: 23° C.; record the temperature.

The column was equilibrated with 10 column volumes (50 ml=166 min at 0.3 ml/min) of the mobile phase, and the RID was purged for at least 20 minutes before injecting samples. DAD and R1 detectors were autobalanced before sample runs.

20 µl of the calibration solution Y35pAF-pB2/pB3 (or WHO standard) was injected, and the HPLC program was run. In the chromatogram obtained, the main unPEGylated peak eluted at a retention time of approximately 12.96 (±0.05) min. The higher molecular weight unPEGylated rhGH dimer eluted at a retention time of 0.94±0.02 relative to the main peak. Higher molecular weight aggregates eluted at retention times of 7.3-8.0 min.

20 µl of the calibration solution PEG30-pY35pAF-01 was injected. The main pegylated peak eluted at a retention time of approximately 8.33 (±0.08) min (relative retention time of 0.64 to the unPEGylated rhGH). Higher molecular weight PEGylated rhGH aggregates eluted at times greater than 8.0 min.

20 µl of the resolution solution was injected, and the HPLC program was run. The main PEGylated peak elutes at a retention time of 8.28 min, and the higher molecular weight species eluted at 7.54 min, a relative retention time of 0.9 (±0.05) relative to the main PEGylated peak.

20 µl of the test article was injected, and the HPLC program was run. Samples were run in triplicate and average retention times were noted. The retention time of the rhGH test article was compared with the rhGH standard(s).

The SEC-HPLC data from the test article was compared to data obtained from the reference standards. To determine the purity of non-PEGylated rhGH, the integrated main peak areas of the rhGH test article was compared with the total peak area, and the percentage of monomer in the rhGH test article was calculated by: (main peak area of rhGH sample/total peak area)×100%. The percentage of dimer and/or higher aggregates were calculated in the hGH test article. Any peak(s) due to the solvent were disregarded. To determine the purity of PEGylated rhGH, the integrated main peak areas of the PEGylated rhGH sample was compared with the total peak area, and the percentage of PEGylated monomer in PEG-rhGH sample was calculated by: (main peak area of PEG-rhGH sample/total peak area)×100%. The percentage of PEGylated dimer, higher aggregates, and nonPEGylated monomer were calculated in the PEGylated hGH test article. Any peak(s) due to the solvent were disregarded. Peaks eluting in the chromatogram prior to the main PEGylated hGH peak represent higher molecular weight species. Such higher molecular weight species may include but are not limited to dimers (such as PEG-PEG-hGH and other possible dimers) or soluble aggregates. Peaks eluting after the main PEGylated hGH peak represent lower molecular weight species. Such lower molecular weight species may include but are not limited to non-PEGylated monomer and clipped forms of PEGylated hGH.

Purity and Chemical Degradation Analysis of rhGH by RP-HPLC

The following method was used to assess relative purity and potential chemical degradation (deamidation and oxidation) of recombinant human growth hormone (rhGH) by C4 reverse phase high performance liquid chromatography (RP-HPLC). RP-HPLC is a technique that separates molecules on the basis of relative hydrophobicities. Samples are passed over a stationary phase of silica covalently bonded to hydrocarbon chains. The molecules of interest are retarded by the stationary phase and eluted with an isocratic solvent. The chromatographic elution time is characteristic for a particular molecule. This method separates rhGH based on subtle differences in hydrophobicity and retention behavior associated with structural modifications such as deamidation. This method was used to support identification and purity assessment of rhGH. Some partial degradation products of rhGH are observable using this technique.

References for this technique include European Pharmacopoeia 2002, p. 193; British Pharmacopoeia 2001, p. 1938-1939; A Reversed-Phase High Performance Liquid Chromatographic Method for Characterization of Biosynthetic Human Growth Hormone" by R. M. Riggin et al. Analytical Biochemistry 167, 199-209 (1987).

Equipment for this procedure included, the following or equivalents thereof: UV/Vis Spectrophotometer (Agilent 8453 or equivalent); 50 ul quartz cuvette; PD-10, Nap-10, or Nap 5 (depending on sample volume; GE Healthcare Nap5 column 17-0853-02 or equivalent); 0.5 mL Vivaspin concentrators (if needed; Vivascience 10,000 MWCO, PES, VS0102 or equivalent); HPLC vials and caps (Alltech 100 ul screw cap polypropylene vials #12962, TFE liner caps #73048, open hole screw caps #73044, or equivalent; Clean 1 and 2 L glass bottles; Column—Vydac C4 214ATP54, a C4-silica reversed phase HPLC column with a dimension of 4.6×250 mm, particle size of 5µ and pore size of 300 Å; High-pressure liquid chromatography instrument capable of performing linear gradients (such as Agilent 1100 HPLC equipped with a vacuum degasser, quaternary pump, thermostatted autosampler, thermostatted column compartment, diode array detector (DAD), and Chemstation chromatography software).

Reagents for this procedure included water (Milli-Q quality or equivalent) and solid chemicals are analytical grade or better and solvents are HPLC grade or better, unless otherwise noted. The storage of reagents and procedural steps occurred at room temperature, unless otherwise indicated. Examples of such chemicals included TRIS—Tromethamine, U.S.P. grade, Spectrum TR149, or equivalent; N-propanol, HPLC grade, 99.9%, Sigma Aldrich 34871, or equivalent; Ammonium Bicarbonate, Ultra >99.5%, Fluka # 09830, or equivalent.

The Buffer for Deamidation Control was 30 mM Ammonium Bicarbonate, pH 9.0. The Buffer for Oxidation Control was 50 mM TRIS, pH 7.5. Each of these solutions were sterile filtered using 0.22 µm PES filters (Corning #431098, or equivalent). Mobile phase: 710 ml 50 mM TRIS-HCl pH 7.5; 290 ml n-propanol (or other appropriate volume with 71% 50 mM Tris-HCl, pH 7.5 and 29% n-propanol). 6.05 g Tromethamine (USP grade, Spectrum # TR149, or equivalent) was dissolved in 0.95 L Milli-Q $H_2O$. The solution was brought to pH 7.5 with HCl and the volume brought up to 1 L with Milli-Q $H_2O$. After the mixing of the two solvents (TRIS and propanol), the mixture was sterile filtered using 0.22 µm PES filters (Corning #431098, or equivalent). The Conditioning Solution was 50% AcCN:$H_2O$, 0.1% TFA.

Samples used as standards included World Health, Organization (WHO) rhGH (Cat. # 98/574) reconstituted to 1.9-2.1 mg/ml with 1.0 ml of water and a rhGH reference standard at 1.9-2.1 mg/ml concentration. The Deamidation Resolution Solution was made by buffer exchanging the WHO standard into 30 mM Ammonium Bicarbonate, pH 9.0 buffer using a PD-10, Nap-10, or Nap-5 desalting column (depending on sample volume). The standard was concentrated using a 0.5 mL Vivaspin concentrator to 1.9-2.1 mg/ml, and the sample was incubated at 37° C. for 24 hours. For the Oxidation Resolution Solution, the WHO standard was buffer exchanged into 50 mM TRIS, pH 7.5 buffer using a PD-10, Nap-10, or Nap-5 desalting column (depending on sample volume). The standard was concentrated using a 0.5 mL Vivaspin concentrator to 1.9-2.1 mg/ml and $H_2O_2$ added to a final concentration of 0.015%. The reaction was incubated at 4° C. for 24 hrs. The reaction was stopped by adding 0.5-1 µl if 20 mg/ml catalase. For the test sample, the test material was diluted to 2.0 mg/ml protein concentration.

Procedure

The instrument was set-up with the following conditions: I) Column: Vydac C4 214ATP54 column; 2) Pump Setup—gradient: isocratic; flow rate: 0.5 m/min; duration: 60 min; Max Pressure: 200 bar; 3) Autosampler Temperature: 4° C.; 4) Injector Setup—Injection: Standard Injection; Injection Volume: 20 µl; Draw Speed: 100 µl/min; Needle Wash: 100 ul with water; Injection Speed: 100 µl/min; Stop Time: As pump; 5) DAD Signals (Table 7);

TABLE 7

| Sample | Bw | Reference | Bw | Units |
|---|---|---|---|---|
| 220 | 4 | 600 | 100 | nm |
| 276 | 4 | 600 | 100 | nm |
| 214 | 8 | 600 | 100 | nm |
| 220 | 4 | 600 | 100 | nm |

Peak Width: >0.1 min; Slit: 4 nm; Stop Time: 60 min; 6) Column Thermostat: Temperature: 45° C.; record the temperature; 7) Preliminary Integration Events (Chemstation Software, Agilent): Slope Sensitivity: 0.1; Peak Width: 0.5; Area Reject: 1.0; Height Reject: 1.0; Integration ON 10 min.

The column was pre-conditioned with 300 mL of conditioning solution (50% AcCN, $H_2O$, 0.1% TFA) at a flow rate between 0.5 and 1.5 ml/min. Pre-equilibration should be performed before a column has been used, or if peaks are broadening, re-condition the column with the conditioning solution (200-300 mL). The column was equilibrated with 10 column volumes (41.5 ml=83 min at 0.5 ml/min) of the mobile phase.

20 µl of the standard was injected using the autosampler, and the HPLC program was run. If the retention time of the WHO standard was not between 32.5-35 min, the mobile phase composition was adjusted, the column re-equilibrated, and the standard was re-run. Suggested adjustments included adding less than 5 ml of 50 mM Tris-HCl pH 7.5 per liter of mobile phase if retention time is less than 32.5 min, and less than 2 ml of n-propanol if retention time greater than 35. Since evaporation of the propanol may occur, a standard was run each day samples were to be tested and buffers were adjusted accordingly.

20 µl of the deamidation resolution solution was injected, and the HPLC program was run. Desamido-hGH appears as a small peak at a retention time of about 0.88±0.03 relative to the principal peak. The resolution between the peaks corresponding to hGH and desamido-hGH was at least 1.0 (current conditions result in a resolution of 1.29±0.04) and the symmetry factor of the hGH peak is 0.8 to 1.8 (current conditions result in a resolution of 1.26±0.06).

20 µl of the oxidation resolution solution was injected, and the HPLC program was run. Oxidized-hGH appears as a small peak at a retention time of about 0.8 relative to the principal peak.

20 µl of the test article was injected, and the HPLC program was run. Samples were run in triplicate. Average retention times were noted.

Data Analysis

The average retention time of the test article was compared with the rhGH reference standard or the WHO standard. The average purity of the test article was calculated: (Integration area of the main peak/integration areas of all peaks)×100%. Any peak(s) due to the solvent were disregarded. Chromatograms showed absorbance (220 nm).

It is understood that the examples and embodiments described herein are for illustrative purposes only and that various modifications or changes in light thereof will be suggested to persons of ordinary skill in the art and are to be included within the spirit and purview of this application and scope of the appended claims. All publications, patents, and patent applications cited herein are hereby incorporated by reference herein in their entirety for all purposes.

TABLE 8

SEQUENCES CITED.

| SEQ ID # | Sequence Name |
|---|---|
| 1 | Full-length amino acid sequence of hGH |
| 2 | The mature amino acid sequence of hGH (isoform 1) |
| 3 | The 20-kDa hGH variant in which residues 32-46 of hGH are deleted |

What is claimed is:

1. A process comprising: a) culturing *Escherichia coli* host cells comprising an O-tRNA/O-RS pair and capable of producing human growth hormone (hGH) comprising a non-naturally encoded amino acid in culture medium; b) producing the hGH comprising the non-naturally encoded amino acid wherein the non-naturally encoded amino acid is at a position corresponding to 35, 92, 143, or 145 of SEQ ID NO: 2, or the corresponding amino acid positions in SEQ ID NO: 1 or 3; c) coupling the non-naturally encoded amino acid to a water soluble polymer; and d) purifying the coupled hGH comprising the non-naturally encoded amino acid with one or more steps, wherein at least about 100 mg substantially purified hGH is produced per liter of recombinant host cell culture medium.

2. The method of claim 1, wherein the coupling of hGH to a water soluble polymer produces a substantially purified hGH polypeptide.

3. The method of claim 1, wherein step d) comprises contacting the coupled hGH with an anion exchange chromatography matrix under conditions that allow binding of the coupled hGH to the matrix followed by elution and collection of the coupled hGH.

4. The method of claim 3 further comprising contacting the eluted coupled hGH with a hydroxyapatite chromatography matrix under conditions that allow binding of the coupled hGH to the matrix.

* * * * *